US012378556B2

(12) United States Patent
Gottesman et al.

(10) Patent No.: US 12,378,556 B2
(45) Date of Patent: *Aug. 5, 2025

(54) TREATMENT OF ANGIOPOIETIN LIKE 7 (ANGPTL7) RELATED DISEASES

(71) Applicant: EMPIRICO INC., San Diego, CA (US)

(72) Inventors: Omri Gottesman, San Diego, CA (US); Shannon Bruse, San Diego, CA (US); Paul Buske, Madison, WI (US); Brian Cajes, San Diego, CA (US); David Lewis, Madison, WI (US); David Rozema, Cross Plains, WI (US)

(73) Assignee: EMPIRICO INC., San Diego, CA (US)

(*) Notice: Subject to any disclaimer, the term of this patent is extended or adjusted under 35 U.S.C. 154(b) by 1168 days.

This patent is subject to a terminal disclaimer.

(21) Appl. No.: 17/156,421

(22) Filed: Jan. 22, 2021

(65) Prior Publication Data
US 2021/0163950 A1  Jun. 3, 2021

Related U.S. Application Data

(63) Continuation of application No. 17/012,524, filed on Sep. 4, 2020, now Pat. No. 10,941,404, which is a continuation of application No. PCT/US2020/034063, filed on May 21, 2020.

(60) Provisional application No. 62/881,906, filed on Aug. 1, 2019, provisional application No. 62/852,813, filed on May 24, 2019.

(51) Int. Cl.
C12N 15/113 (2010.01)
A61P 27/06 (2006.01)

(52) U.S. Cl.
CPC .......... C12N 15/1136 (2013.01); A61P 27/06 (2018.01); C12N 2310/14 (2013.01); C12N 2310/315 (2013.01); C12N 2310/321 (2013.01); C12N 2310/322 (2013.01); C12N 2310/3515 (2013.01)

(58) Field of Classification Search
CPC ............ C12N 15/1136; C12N 2310/14; C12N 2310/315; C12N 2310/321; C12N 2310/322; C12N 2310/3515; C12N 2310/346; C12N 2310/3533; C12N 2310/3521; A61P 27/06; A61K 48/00; A61K 31/713
See application file for complete search history.

(56) References Cited

U.S. PATENT DOCUMENTS

| 543,227 A | 7/1895 | Benner |
|---|---|---|
| 7,691,997 B2 | 4/2010 | Khvorova et al. |
| 8,090,542 B2 * | 1/2012 | Khvorova .......... C12N 15/1135 435/6.1 |
| 9,206,423 B2 | 12/2015 | Russell et al. |
| 9,796,974 B2 | 10/2017 | Rajeev et al. |
| 9,920,320 B2 | 3/2018 | Russell et al. |
| 10,053,694 B2 | 8/2018 | Lee et al. |
| 10,668,170 B2 | 6/2020 | Rajeev et al. |
| 10,941,404 B2 | 3/2021 | Gottesman et al. |
| 2004/0198640 A1 | 10/2004 | Leake et al. |
| 2005/0080246 A1 | 4/2005 | Allerson et al. |
| 2006/0148743 A1 | 7/2006 | Jadhav et al. |
| 2008/0038202 A1 | 2/2008 | Zhao et al. |
| 2009/0137507 A1 | 5/2009 | McSwiggen et al. |
| 2011/0150897 A1 | 6/2011 | Meyer et al. |
| 2015/0174203 A1 | 6/2015 | Chen et al. |
| 2016/0264969 A1 | 9/2016 | Patel et al. |
| 2018/0105563 A1 | 4/2018 | Usui et al. |
| 2018/0177847 A1 | 6/2018 | Chen et al. |
| 2020/0399640 A1 | 12/2020 | Gottesman et al. |
| 2022/0089664 A1 | 3/2022 | Praveen et al. |
| 2023/0357774 A1 | 11/2023 | Gottesman et al. |

FOREIGN PATENT DOCUMENTS

| EP | 2213738 A2 | 8/2010 |
|---|---|---|
| WO | WO-9302093 A1 | 2/1993 |
| WO | WO-2010093816 A2 | 8/2010 |
| WO | WO-2011051276 A1 | 5/2011 |
| WO | WO-2014167529 A1 | 10/2014 |
| WO | WO-2015106128 A2 | 7/2015 |
| WO | WO-2018201090 A1 | 11/2018 |
| WO | WO-2019161213 A1 | 8/2019 |
| WO | WO-2020142693 A1 | 7/2020 |
| WO | WO-2020154268 A2 | 7/2020 |
| WO | WO-2020242896 A2 | 12/2020 |
| WO | WO-2022031433 A1 | 2/2022 |

(Continued)

OTHER PUBLICATIONS

Praveen, K., Patel, G.C., Gurski, L. et al. ANGPTL7, a therapeutic target for increased intraocular pressure and glaucoma. Commun Biol 5, 1051 (2022). https://doi.org/10.1038/s42003-022-03932-6 (Year: 2022).*
Fitzpatrick et al., Developmental eye disorders, Current Opinion in Genetics & Development 2005, 15:348-353 (Year: 2005).*
Vicentini et al., Delivery systems and local administration routes for therapeutic siRNA, 2013, Pharm. Res., 30, 915-931. (Year: 2013).*
Battacharya et al.: Proteomics Reveal Cochlin Deposits Associated with Glaucomatous Trabecular Meshwork. J. Biol. Chem. 280(7):6080-6084 (2005).
Comes et al.: Individual molecule response to elevated intraocular pressure in perfused postmortem human eyes. Physiol. Genomics 38:205-225 (2009).
Comes et al., Evidence for a role of angiopoietin-like 7 (ANGPTL7) in extracellular matrix formation of the human trabecular meshwork: implications for glaucoma. Genes to Cells 16(2):243-259 (2011).

(Continued)

Primary Examiner — Jennifer Dunston
Assistant Examiner — Keyur A Vyas
(74) Attorney, Agent, or Firm — Wilson Sonsini Goodrich & Rosati

(57) ABSTRACT

Provided herein are oligonucleotide compositions that inhibit ANGPTL7 and reduce intraocular pressure when administered to an eye. The oligonucleotide compositions contain nucleoside modifications.

19 Claims, 12 Drawing Sheets
Specification includes a Sequence Listing.

(56) References Cited

FOREIGN PATENT DOCUMENTS

WO  WO-2022072356 A1  4/2022
WO  WO-2023192828 A2  10/2023

OTHER PUBLICATIONS

Kuchtey et al., Angiopoietin-like 7 secretion is induced by glaucoma stimuli and its concentration is elevated in glaucomatous aqueous humor. Investigative Ophthalmology and Visual Science 49(8):3438-3448 (2008).
PCT/US2020/034063 International Search Report and Written Opinion dated Dec. 9, 2020.
PCT/US2020/034063 Invitation to Pay Additional Fees dated Aug. 21, 2020.
Rozsa et al.: Gene expression profile of human trabecular meshwork cells in response to long-term dexamethasone exposure. Molecular Vision. 125-141 (2006).
Santa Cruz Biotechnology, Inc.: Angptl7 siRNA (h): sc-88201 (1 page) https://datasheets.scbt.com/sc-88201.pdf (2019).
Toyono et al.: Angiopoietin-Like 7 Is an Anti-Angiogenic Protein Required to Prevent Vascularization of the Cornea. PLoS One. DOI: 10.1371/journal.pone.0116838 (2015).
U.S. Appl. No. 17/012,524 First Action Interview dated Nov. 10, 2020.
PCT/US2021/052424 International Invitation to Pay Additional Fees dated Dec. 13, 2021.
PCT/US2021/052424 International Search Report and Written Opinion dated Feb. 17, 2022.
Tanigawa et al.: Rare protein-altering variants in ANGPTL7 lower intraocular pressure and protect against glaucoma. PLoS Genet. 16(5):e1008682 (2020).
Buie et al.: Angiopoietin-like 7 (ANGPTL7) Modulates DEX Induction and Fibronectin (FN1) Fibrils Formation in the Human Trabecular Meshwork (HTM)—ARVO Annual Meeting Abstract. Investigative Ophthalmology & Visual Science. 52(14):4622 (2011).
EP20813437.9 Partial European Search Report dated Nov. 17, 2023.
PCT/US2023/064997 Invitation to Pay Additional Fees dated Jul. 17, 2023.
Chemical Abstracts Service. CAS Registry: 114616-27-2. MMT-Hexylaminolinker Phosphoramidite: pp. 1-9. STN Entry Date Sep. 25, 2006. Retrieved Oct. 11, 2024. Retrieved from: https://pubchem.ncbi.nlm.nih.gov/compound/9873234.
Chemical Abstracts Service. CAS Registry: 178925-21-8. Amino-Modifier C6 dT: pp. 1-4. STN Entry Date Feb. 18, 2024. Retrieved Oct. 11, 2024. Retrieved from :https://pubchem.ncbi.nlm.nih.gov/substance/488407216.
Cheng, Angie et al. Stem-loop RT-PCR quantification of siRNAs in vitro and in vivo. Oligonucleotides 19(2):203-208 (2009).
Database Accession No. HD836236. Sequence 712952 from EP2213738 (2010).
EP20813437.9 European Search Report dated Aug. 13, 2024.
PCT/US2023/064997 International Preliminary Report on Patentability dated Oct. 10, 2024.
PCT/US2023/064997 International Search Report and Written Opinion dated Sep. 29, 2023.

\* cited by examiner

TREATMENT OF ANGIOPOIETIN LIKE 7 (ANGPTL7) RELATED DISEASES

CROSS-REFERENCE TO RELATED APPLICATIONS

This application is a continuation of U.S. application Ser. No. 17/012,524, filed Sep. 4, 2020, now issued as U.S. Pat. No. 10,941,404, which is a continuation of International Application No. PCT/US20/34063, filed May 21, 2020, which claims the benefit of U.S. Provisional Application No. 62/852,813, filed May 24, 2019, and of U.S. Provisional Application No. 62/881,906, filed Aug. 1, 2019, which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on May 15, 2020 and updated on Jan. 21, 2021, is named 54462-709_302_SL.txt and is 3,368,664 bytes in size.

BACKGROUND

Large-scale human genetic data provides a mechanism for improving the success rate of pharmaceutical discovery and development by leveraging experiments of nature.

The Genome Wide Association Study (GWAS) is an experimental design to detect associations between genetic variants and traits in a population sample. The purpose is to better understand the biology of disease and to develop treatments based on this understanding. GWAS can utilize genotyping and/or sequencing data and often involves evaluation of millions of genetic variants that are relatively evenly distributed across the genome. The most common GWAS design is the case-control study, which involves comparing variant frequencies in cases versus controls. If a variant has a significantly different frequency in cases versus controls, that variant is said to be associated with disease. The commonly reported association statistics for GWAS are p-values, as a measure of statistical significance and odds ratios (OR) or beta coefficients (beta), as a measure of effect size. Researchers often assume an additive genetic model and calculate an allelic odds ratio, which is the increased (or decreased) risk of disease conferred by each additional copy of an allele (compared to carrying no copies of that allele). An additional and important concept in design and interpretation of GWAS is that of linkage disequilibrium, which is the non-random association of alleles. The presence of linkage disequilibrium can obfuscate which is the "causal" variant.

Functional annotation of variants and/or wet lab experimentation can identify the causal genetic variant identified via GWAS, and in many cases, this has led to the identification of disease-causing genes. In particular, understanding the functional effect of a causal genetic variant (e.g. loss or gain of protein function, increase or decrease in gene expression) allows that variant to be used as a proxy for therapeutic modulation of the target gene and to gain an insight into the potential therapeutic efficacy and safety of a therapeutic that modulates that target.

Identification of such gene-disease associations has provided fundamental insights into disease biology and is rapidly becoming an essential means of identifying novel therapeutic targets for the pharmaceutical industry. In order to translate the therapeutic insights derived from human genetics, disease biology in patients must be exogenously 'programmed' into replicating the observation from human genetics. Today, the potential options for therapeutic modality that could be brought to bear in translating therapeutic targets identified via human genetics into novel medicines are greater than ever before. These include well established therapeutic modalities such as small molecules and monoclonal antibodies, maturing modalities such as oligonucleotides and emerging modalities such as gene therapy and gene editing. The choice of therapeutic modality depends on several factors including the location of the target (e.g. intracellular, extracellular or secreted), the relevant tissue (e.g. lung, liver) and the relevant indication.

SUMMARY

Glaucoma is a heterogenous group of diseases, affecting greater than 70 million people worldwide, that is characterized by optic nerve damage resulting in a progressive loss of retinal ganglion cells and leading to loss of vision. The different subtypes of glaucoma are generally stratified by the iridocorneal angle, with open-angle glaucoma accounting for approximately 75% of cases. Though the pathophysiology of glaucoma remains poorly understood, a primary causal feature and risk factor is elevated intraocular pressure (IOP). IOP is determined by the balance between aqueous humor secretion from the ciliary body and its drainage through the trabecular meshwork and uveoscleral outflow pathways. Reducing IOP is the only strategy that has been proven to prevent the development or slow the progression of glaucoma and consequently, treatment is focused on lowering IOP to target levels by increasing aqueous outflow or decreasing aqueous production. Several classes of IOP-lowering medication are used, including prostaglandin analogues, beta-adrenergic blockers, alpha-adrenergic agonists, carbonic anhydrase inhibitors and most-recently rho kinase inhibitors. Surgical methods, such as laser trabeculoplasty to improve drainage of aqueous humor through the trabecular meshwork, are also employed. Despite the availability of medical and surgical therapies for glaucoma, it is the leading cause of irreversible blindness worldwide and there remains a need for novel therapeutic strategies that may further reduce the risk of the significant morbidity and reduction in quality of life associated with loss of vision.

In one aspect, provided is a composition comprising an inhibitor or modulator of ANGPTL7 that is efficacious in treating glaucoma and ocular hypertension. In some embodiments, the inhibitor or modulator of ANGPTL7 is an RNAi. In some embodiments, the RNAi is siRNA. In some embodiments, the siRNA comprises one or more sense strand and antisense strand sequences selected from SEQ ID NOS: 1-4412. In some embodiments, the siRNA comprises a sequence comprising the reverse complement of a sequence selected from SEQ ID NOS: 1-4412. In some embodiments, the siRNA comprises a sequence having at least about 85%, 90%, or 95% homology to a sequence selected from SEQ ID NOS: 1-4412. In some embodiments, the siRNA comprises a sequence having at least about 85%, 90%, or 95% identity to a sequence selected from SEQ ID NOS: 1-4412. In some embodiments, the RNAi is miRNA. In some embodiments, the RNAi is an antisense oligonucleotide (ASO). In some embodiments, the ASO is double-stranded or single-stranded. In some embodiments, the inhibitor of ANGPTL7 is a small molecule. In some embodiments, the inhibitor of ANGPTL7 is an aptamer. In some embodiments, the aptamer is an oligonucleotide aptamer. In some embodiments, the aptamer is a peptide aptamer. In some embodiments, the inhibitor of ANGPTL7 is an antibody. In some embodiments, the antibody is a monoclonal antibody.

In another aspect, provided herein are molecules for inhibition or modulation of angiopoietin-like 7 (ANGPTL7) gene products, including dsRNA (dsRNA) agents such as small interfering RNAs (siRNAs), or antisense oligonucleotides for therapeutic use. Further provided are methods of inhibiting the expression of a target gene by administering a dsRNA agent, or antisense oligonucleotide, e.g., for the treatment of various diseases involving ANGPTL7 gene products. Also provided is a method of modulating the expression of a target gene in a cell, comprising providing to said cell a dsRNA agent, or antisense oligonucleotide. In some embodiments, the target gene is ANGPTL7.

In another aspect, provided is a method of treating one or more disorders of the eye in a subject in need thereof comprising editing an ANGPTL7 gene in the subject wherein the one or more disorders of the eye comprises glaucoma or ocular hypertension. In some embodiments, the editing of the ANGPTL7 gene comprises administering CRISPR/cas9 to the subject. In some embodiments, the CRISPR/cas9 targets the ANGPTL7 gene. In some embodiments, the CRISPR/cas9 edits the ANGPTL7 gene to a loss of function mutation. In some embodiments, the loss of function mutation comprises a premature stop mutation. In some embodiments, the premature stop mutation occurs at amino acid position 177 according to the human protein sequence numbering. In some embodiments, the CRISPR/cas9 edits the ANGPTL7 gene to a missense mutation. In some embodiments, the missense mutation comprises a glutamine to histidine mutation. In some embodiments, the glutamine to histidine mutation occurs at amino acid position 175 according to the human protein sequence numbering. In some embodiments, the CRISPR/cas9 is delivered systemically to the subject. In some embodiments, the CRISPR/cas9 is delivered locally to the subject. In some embodiments, the CRISPR/cas9 is delivered locally to the eye of the subject. In some embodiments, the CRISPR/cas9 is delivered locally to the eye of the subject via intraocular injection. In some embodiments, the CRISPR/cas9 is delivered locally to the eye of the subject via topical solution. In some embodiments, the editing of the ANGPTL7 gene is efficacious in treating the one or more disorders of the eye. In some embodiments, the one or more disorders of the eye is glaucoma. In some embodiments, the subject has ocular hypertension. In some embodiments, the subject has received a first line treatment comprising topical ocular prostaglandin analogues, beta-adrenergic blockers, alpha-adrenergic agonists, and carbonic anhydrase inhibitors for the one or more disorders of the upper and eye. In some embodiments, the editing of the ANGPTL7 gene causes a reduction in or modulation of the production of the gene product of ANGPTL7. In some embodiments, the editing of the ANGPTL7 gene causes a reduction in the subject of intraocular pressure.

In another aspect, provided is a composition comprising CRISPR/cas9 that targets ANGPTL7 that is efficacious in treating glaucoma or ocular hypertension. In some embodiments, the CRISPR/cas9 edits the ANGPTL7 gene to a loss of function mutation. In some embodiments, the loss of function mutation comprises a premature stop mutation. In some embodiments, the premature stop mutation occurs at amino acid position 177 according to the human protein sequence numbering. In some embodiments, the CRISPR/cas9 edits the ANGPTL7 gene to a missense mutation. In some embodiments, the missense mutation comprises a glutamine to histidine mutation. In some embodiments, the glutamine to histidine mutation occurs at amino acid position 175 according to the human protein sequence numbering.

A non-limiting example of a therapeutic molecule for inhibiting or modulating ANGPTL7 is RNA interference (RNAi), where double-stranded RNAi (dsRNA) can be utilized to block gene expression. Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 21 nucleotides) derived from the double-stranded RNA trigger, but the protein components of this activity remained unknown.

Another non-limiting example of a therapeutic molecule for inhibiting or modulating ANGPTL7 is antisense oligonucleotides. DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H (RNaseH), an activity that is present in most cell types. Antisense molecules can be delivered into cells, as is the case for oligodeoxynucleotides (ODNs), or they can be expressed from endogenous genes as RNA molecules.

Another non-limiting example of a therapeutic molecule for inhibiting or modulating ANGPTL7 is splice switching antisense oligonucleotides (SSOs). These are short, synthetic, antisense, modified nucleic acids that hybridize with a pre-mRNA and disrupt the normal splicing repertoire of the transcript by blocking the RNA-RNA base-pairing or protein-RNA binding interactions that occur between components of the splicing machinery and the pre-mRNA. Splicing of pre-mRNA is required for the proper expression of the vast majority of protein-coding genes, and thus, targeting the process offers a means to manipulate protein production from a gene. As an example, the splicing of a pre-mRNA can also be used to alter the reading frame downstream of the splice site leading to a truncated protein with impaired function.

Splice switching antisense oligonucleotides differ from mRNA cleaving antisense oligonucleotides in that they do not recruit RNaseH to degrade the pre-mRNA-SSO complex and are strictly steric blocking. This is accomplished through the use of fully, or nearly fully, 2'-modified antisense oligonucleotides that therefore lack the necessary DNA-RNA hybrid region that is recognized by RNaseH. Other types of modified oligonucleotides for modifying splicing are phosphoramidite morpholinos (PMOs). PMOs have a morpholine ring in place of the furanose ring found in natural nucleic acids and a neutral phosphorodiamidate backbone in place of the negatively charged phosphodiester backbone.

In some embodiments, the present disclosure provides methods for inhibiting or modulating the action of a natural transcript by using antisense oligonucleotide(s) targeted to any region of the natural transcript. It is also contemplated herein that inhibition or modulation of the natural transcript can be achieved by siRNA, ribozymes and small molecules. In an exemplary embodiment, the natural transcript encodes for ANGPTL7.

One embodiment provides a method of modulating function and/or expression of an ANGPTL7 polynucleotide in patient cells or tissues, in vivo or in vitro, the method comprising contacting said cells or tissues with an antisense oligonucleotide 5 to 30 nucleotides in length, wherein said antisense oligonucleotide has at least 50% sequence identity to a reverse complement of a polynucleotide comprising 5 to 30 consecutive nucleotides within nucleotides 1 to 6333 of SEQ ID NO: 11086, and any variants, alleles, homologs, mutants, derivatives, fragments and complementary sequences thereof, thereby modulating function and/or expression of the ANGPTL7 polynucleotide in patient cells or tissues, in vivo or in vitro. In some embodiments, the oligonucleotide comprises SEQ ID NO: 11087. In some embodiments, the oligonucleotide comprises a sequence selected from SEQ ID NOS: 4413-11084. In some embodiments, the oligonucleotide comprises a sequence at least about 80%, 85%, 90%, or 95% identical to a sequence selected from SEQ ID NOS: 4413-11084.

In some embodiments, an oligonucleotide targets a natural sequence of ANGPTL7 polynucleotides, for example, nucleotides set forth in SEQ ID NO: 11085, and any variants, alleles, homologs, mutants, derivatives, fragments and complementary sequences thereto. In some embodiments, the oligonucleotide comprises a sequence selected from SEQ ID NOS: 4413-11084. In some embodiments, the oligonucleotide comprises a sequence at least about 80%, 85%, 90%, or 95% identical to a sequence selected from SEQ ID NOS: 4413-11084.

In some embodiments, an oligonucleotide targets a natural sequence of ANGPTL7 polynucleotides, for example, nucleotides set forth in SEQ ID NO: 11086, and any variants, alleles, homologs, mutants, derivatives, fragments and complementary sequences thereto. In some embodiments, the oligonucleotide comprises a sequence selected from SEQ ID NOS: 4413-11084. In some embodiments, the oligonucleotide comprises a sequence at least about 80%, 85%, 90%, or 95% identical to a sequence selected from SEQ ID NOS: 4413-11084.

In some embodiments, a composition comprises one or more antisense oligonucleotides which bind to sense ANGPTL7 polynucleotides. In some embodiments, the oligonucleotide comprises a sequence selected from SEQ ID NOS: 4413-11084. In some embodiments, the oligonucleotide comprises a sequence at least about 80%, 85%, 90%, or 95% identical to a sequence selected from SEQ ID NOS: 4413-11084. In some embodiments, the oligonucleotide comprises SEQ ID NO: 11087.

In some embodiments, the oligonucleotides comprise one or more modified or substituted nucleotides. In some embodiments, the oligonucleotides comprise one or more modified bonds. In some embodiments, the modified nucleotides comprise modified bases comprising phosphorothioate, methylphosphonate, peptide nucleic acids, 2'-0-methyl, methoxyethly, fluoro- or carbon, methylene or other locked nucleic acid (LNA) molecules. In some embodiments, the modified nucleotides are locked nucleic acid molecules, including a-L-LNA.

In some embodiments, the oligonucleotides are administered to a patient by topical application, inhalation, intranasally, subcutaneously, intramuscularly, intravenously, intraocularly or intraperitoneally.

In some embodiments, the oligonucleotides are administered in a pharmaceutical composition. A treatment regimen comprises administering the antisense compounds at least once to a patient; however, this treatment can be modified to include multiple doses over a period of time. The treatment can be combined with one or more other types of therapies.

In some embodiments, the oligonucleotides are encapsulated in a liposome or attached to a carrier molecule (e.g. cholesterol, TAT peptide).

In one aspect, provided herein is an RNA interference (RNAi) agent capable of inhibiting or modulating the expression of angiopoietin like 7 (ANGPTL7), wherein the RNAi agent comprises a double-stranded RNA (dsRNA) comprising a sense strand and an antisense strand, each strand having 14 to 30 nucleotides. In some embodiments, the dsRNA has a length of 17-30 nucleotide pairs. In some embodiments, the sense strand and antisense strand each have 17-30 nucleotides. In some embodiments, the sense strand comprises a sequence at least about 80%, 85%, 90%, 95%, or 100% identical to a sequence selected from SEQ ID NOS: 1-4412. In some embodiments, the antisense strand comprises a sequence at least about 80%, 85%, 90%, 95%, or 100% identical to the reverse complement of the sense strand. In some embodiments, the antisense strand comprises a sequence at least about 80%, 85%, 90%, 95%, or 100% identical to a sequence selected from SEQ ID NOS: 1-4412. In some embodiments, the sequence of the sense strand comprises SEQ ID NO: 11089 and the sequence of the antisense strand comprises SEQ ID NO: 11090. In some embodiments, the RNAi agent comprises one or more nucleotide modifications selected from the group consisting of LNA, HNA, CeNA, 2'-methoxyethyl, 2'-0-alkyl, 2'-0-allyl, 2'-C-allyl, 2'-fluoro, and 2'-deoxy. In some embodiments, the nucleotides are modified with either 2'-OCH$_3$ or 2'-F. In some embodiments, the RNAi agent further comprises at least one ligand. In some embodiments, the RNAi agent comprises one or more nucleotide modifications selected from the group consisting of 2'-0-methyl nucleotide, 2'-deoxyfluoro nucleotide, 2'-0-N-methylacetamido (2'-0-NMA) nucleotide, a 2'-0-dimethylaminoethoxyethyl (2'-0-DMAEOE) nucleotide, 2'-0-aminopropyl (2'-0-AP) nucleotide, and 2'-ara-F. In some embodiments, the RNAi agent comprises at least one phosphorothioate or methylphosphonate internucleotide linkage. In some embodiments, the nucleotide at the 1 position of the 5'-end of the antisense strand of the dsRNA is selected from the group consisting of A, dA, dU, U, and dT. In some embodiments, the base pair at the 1 position of the 5'-end of the dsRNA is an AU base pair.

In one aspect, provided herein is an RNA interference (RNAi) agent capable of inhibiting or modulating the expression of ANGPTL7, wherein the RNAi agent comprises a double-stranded RNA (dsRNA) comprising a sense strand and an antisense strand, each of the strands having 14 to 30 nucleotides, wherein the sense strand contains at least two motifs of three identical modifications on three consecutive nucleotides, a first of said sense strand motifs occurring at a cleavage site in the sense strand and a second of said sense strand motifs occurring at a different region of the sense strand that is separated from the first sense strand motif by at least one nucleotide; and wherein the antisense strand contains at least two motifs of three identical modifications on three consecutive nucleotides, a first of said antisense strand motifs occurring at or near the cleavage site in the antisense strand and a second of said antisense strand motifs occurring at a different region of the antisense strand that is separated from the first antisense strand motif by at least one nucleotide; wherein the modification in the first antisense strand motif is different than the modification in the second antisense strand motif. In some embodiments, at least one of the nucleotides occurring in the first sense strand motif forms a base pair with one of the nucleotides in the first antisense strand motif. In some embodiments, the dsRNA has 17-30 nucleotide base pairs. In some embodiments, the dsRNA has 17-19 nucleotide base pairs. In some embodiments, each strand has 17-23 nucleotides. In some embodiments, the modifications on the nucleotides of the sense strand and/or antisense strand are selected from the group consisting of LNA, HNA, CeNA, 2'-methoxyethyl, 2'-0-alkyl, 2'-0-allyl, 2'-C-allyl, 2'-fluoro, 2'-deoxy, and combinations thereof. In some embodiments, the modifications on the nucleotides of the sense strand and/or antisense strand are 2'-OCH3 or 2'-F. In some embodiments, the RNAi agent further comprises a ligand attached to the 3' end of the sense strand.

In one aspect, provided herein is an RNA interference (RNAi) agent capable of inhibiting or modulating the expression of ANGPTL7, wherein the RNAi agent comprises a double-stranded RNA (dsRNA) comprising a sense strand and an antisense strand, each of the strands having 14 to 30 nucleotides, wherein the sense strand contains at least one motif of three 2'-F modifications on three consecutive nucleotides, one of said motifs occurring at or near the cleavage site in the sense strand; and wherein the antisense strand contains at least one motif of three 2'-0-methyl modifications on three consecutive nucleotides, one of said motifs occurring at or near the cleavage site in the antisense strand. In some embodiments, the sense strand comprises a sequence at least about 80%, 85%, 90%, 95%, or 100% identical to a sequence selected from SEQ ID NOS: 1-4412. In some embodiments, the antisense strand comprises a sequence at least about 80%, 85%, 90%, 95%, or 100% identical to the reverse complement of the sense strand. In some embodiments, the antisense strand comprises a sequence at least about 80%, 85%, 90%, 95%, or 100% identical to a sequence selected from SEQ ID NOS: 1-4412.

In one aspect, provided herein is a method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least 50% sequence identity to a reverse complement of a polynucleotide comprising 5 to 30 consecutive nucleotides within nucleotides 1 to 2224 of SEQ ID NO: 11085; thereby modulating a function of and/or the expression of the angiopoietin like 7 (ANGPTL7) polynucleotide in patient cells or tissues, in vivo or in vitro.

In one aspect, provided herein is a method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length, wherein said antisense oligonucleotide has at least 50% sequence identity to an antisense oligonucleotide to the angiopoietin like 7 (ANGPTL7) polynucleotide; thereby modulating a function of and/or the expression of the angiopoietin like 7 (ANGPTL7) polynucleotide in patient cells or tissues, in vivo or in vitro.

In one aspect, provided herein is a method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide that targets a region of a natural antisense oligonucleotide of the angiopoietin like 7 (ANGPTL7) polynucleotide; thereby modulating a function of and/or the expression of the angiopoietin like 7 (ANGPTL7) polynucleotide in patient cells or tissues, in vivo or in vitro.

In one aspect, provided herein is a method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length; thereby modulating a function of and/or the expression of the ANGPTL7 polynucleotide in patient cells or tissues, in vivo or in vitro.

In some embodiments, the at least one antisense oligonucleotide comprises SEQ ID NO: 11087. In some embodiments, the at least one antisense oligonucleotide comprises SEQ ID NO: 11087. In some embodiments, the at least one antisense oligonucleotide comprises a sequence at least about 80%, 85%, 90%, 95% identical to SEQ ID NO: 11087. In some embodiments, a function of and/or the expression of the angiopoietin like 7 (ANGPTL7) is increased in vivo or in vitro with respect to a control oligonucleotide that does not target or specifically hybridize to ANGPTL7. In some embodiments, a function of and/or the expression of the angiopoietin like 7 (ANGPTL7) is decreased in vivo or in vitro with respect to a control oligonucleotide that does not target or specifically hybridize to ANGPTL7. In some embodiments, the at least one antisense oligonucleotide targets a natural antisense sequence of an angiopoietin like 7 (ANGPTL7) polynucleotide. In some embodiments, the at least one antisense oligonucleotide targets a nucleic acid sequence comprising coding and/or non-coding nucleic acid sequences of an angiopoietin like 7 (ANGPTL7) polynucleotide. In some embodiments, the at least one antisense oligonucleotide targets overlapping and/or non-overlapping sequences of an angiopoietin like 7 (ANGPTL7) polynucleotide. In some embodiments, the at least one antisense oligonucleotide comprises one or more modifications. In some embodiments, the one or more modifications is selected from: at least one modified sugar moiety, at least one modified internucleoside linkage, at least one modified nucleotide, and combinations thereof. In some embodiments, the one or more modifications comprise at least one modified sugar moiety selected from: a 2'-0-methoxyethyl modified sugar moiety, a 2'-methoxy modified sugar moiety, a 2'-0-alkyl modified sugar moiety, a bicyclic sugar moiety, and combinations thereof. In some embodiments, the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof. In some embodiments, the one or more modifications comprise at least one modified nucleotide selected from: a peptide nucleic acid (PNA), a locked nucleic acid (LNA), an arabin-nucleic acid (FANA), an analogue, a derivative, and combinations thereof.

In one aspect, provided herein is a method of modulating a function of and/or the expression of an angiopoietin like 7 (ANGPTL7) gene in mammalian cells or tissues, in vivo or in vitro, the method comprising: contacting said cells or tissues with at least one short interfering RNA (siRNA) oligonucleotide 5 to 30 nucleotides in length, said at least one siRNA oligonucleotide being specific for an antisense polynucleotide of an angiopoietin like 7 (ANGPTL7) polynucleotide, wherein said at least one siRNA oligonucleotide has at least 50% sequence identity to a complementary sequence of at least about five consecutive nucleic acids of the antisense and/or sense nucleic acid molecule of the angiopoietin like 7 (ANGPTL7) polynucleotide; thereby modulating a function of and or the expression of angiopoietin like 7, (ANGPTL7) in mammalian cells or tissues in vivo or in vitro. In some embodiments, said oligonucleotide has at least 80% sequence identity to a sequence of at least about five consecutive nucleic acids that is complementary to the antisense and/or sense nucleic acid molecule of the angiopoietin like 7 (ANGPTL7) polynucleotide. In some embodiments, the at least one siRNA oligonucleotide comprises a sequence selected from SEQ ID NOS: 1-4412. In some embodiments, the at least one siRNA oligonucleotide comprises a sequence at least about 80%, 85%, 90%, 95%, or 100% identical to a sequence selected from SEQ ID NOS: 1-4412.

In one aspect, provided herein is a method of modulating a function of and/or the expression of angiopoietin like 7, (ANGPTL7) in mammalian cells or tissues, in vivo or in vitro, the method comprising: contacting said cells or tissues with at least one antisense oligonucleotide of about 5 to 30 nucleotides in length, the antisense oligonucleotide specific for noncoding and/or coding sequences of a sense and/or natural antisense strand of an angiopoietin like 7 (ANGPTL7) polynucleotide, wherein said at least one antisense oligonucleotide has at least 50% sequence identity to at least one nucleic acid sequence set forth as 1 to 2224 of SEQ ID NO: 11085 or its complement; thereby modulating the function and/or expression of the angiopoietin like 7 (AGNPTL7) in mammalian cells or tissues, in vivo or in vitro. In some embodiments, the at least one antisense oligonucleotide comprises SEQ ID NO: 11087. In some embodiments, the at least one antisense oligonucleotide comprises a sequence at least about 80%, 85%, 90%, 95% identical to SEQ ID NO:11087.

In one aspect, provided herein is a synthetic, modified oligonucleotide comprising at least one modification wherein the at least one modification is selected from: at least one modified sugar moiety; at least one modified internucleotide linkage; at least one modified nucleotide, and combinations thereof; wherein said oligonucleotide is an antisense compound which hybridizes to and modulates the function and/or expression of an angiopoietin like 7 (ANGPTL7) polynucleotide in vivo or in vitro as compared to a control oligonucleotide that does not specifically hybridize to the ANGPTL7 polynucleotide. In some embodiments, the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof. In some embodiments, said oligonucleotide comprises at least one phosphorothioate internucleotide linkage. In some embodiments, said oligonucleotide comprises a backbone of phosphorothioate internucleotide linkages. In some embodiments, the oligonucleotide comprises at least one modified nucleotide, said modified nucleotide selected from: a peptide nucleic acid, a locked nucleic acid (LNA), and an analogue, derivative, and a combination thereof. In some embodiments, the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof. In some embodiments, the oligonucleotide comprises a plurality of modifications, wherein said modifications comprise modified nucleotides selected from: peptide nucleic acids, locked nucleic acids (LNA), and analogues, derivatives, and a combination thereof. In some embodiments, the oligonucleotide comprises at least one modified sugar moiety selected from: a 2'-O-methoxyethyl modified sugar moiety, a 2'-methoxy modified sugar moiety, a 2-0-alkyl modified sugar moiety, a bicyclic sugar moiety, and a combination thereof. In some embodiments, the oligonucleotide comprises a plurality of modifications, wherein said modifications comprise modified sugar moieties selected from: a 2'-0-methoxyethyl modified sugar moiety, a 2-methoxy modified sugar moiety, a 2'-0-alkyl modified sugar moiety, a bicyclic sugar moiety, and a combination thereof. In some embodiments, the oligonucleotide is of at least about 5 to 30 nucleotides in length and hybridizes to an antisense and/or sense strand of an angiopoietin like 7 (ANGPTL7) polynucleotide, wherein said oligonucleotide has at least about 20% sequence identity to a complementary sequence of at least about five consecutive nucleic acids of the antisense and/or sense coding and/or noncoding nucleic acid sequences of the angiopoietin like 7 (ANGPTL7) polynucleotide. In some embodiments, the oligonucleotide has at least about 80% sequence identity to a complementary sequence of at least about five consecutive nucleic acids of the antisense and or sense coding and/or noncoding nucleic acid sequence of the angiopoietin like 7 (ANGPTL7) polynucleotide. In some embodiments, said oligonucleotide hybridizes to and modulates expression and/or function of at least one angiopoietin like 7 (ANGPTL7) polynucleotide, in vivo or in vitro, as compared to the control oligonucleotide. In some embodiments, the oligonucleotide comprises the sequence set forth as SEQ ID NO: 11087. In some embodiments, the at least one antisense oligonucleotide comprises SEQ ID NO: 11087. In some embodiments, the at least one antisense oligonucleotide comprises a sequence at least about 80%, 85%, 90%, or 95% identical to SEQ ID NO: 11087.

In one aspect, provided herein is a composition comprising one or more oligonucleotides specific for one or more angiopoietin like 7 (ANGPTL7) polynucleotides, said one or more oligonucleotides comprising an antisense sequence, complementary sequence, allele, homolog, isoform, variant, derivative, mutant, or fragment of the ANGPTL7 polynucleotide, or a combination thereof. In some embodiments, the one or more oligonucleotides have at least about 40% sequence identity as compared to the nucleotide sequence set forth as SEQ ID NO: 11087. In some embodiments, the oligonucleotide comprises the nucleotide sequence set forth as SEQ ID NO: 11087. In some embodiments, the one or more oligonucleotides comprises a sequence selected from SEQ ID NOS: 1-4412. In some embodiments, the one or more oligonucleotides comprises a sequence at least about 80%, 85%, 90%, 95%, or 100% identical to a sequence selected from SEQ ID NOS: 1-4412. In some embodiments, the one or more oligonucleotides comprises one or more modifications or substitutions. In some embodiments, the one or more modifications are selected from: phosphorothioate, methylphosphonate, peptide nucleic acid, locked nucleic acid (LNA) molecules, and combinations thereof.

In one aspect, provided herein is a method of preventing or treating a disease associated with at least one angiopoietin like 7 (ANGPTL7) polynucleotide and/or at least one encoded product thereof, the method comprising: administering to a subject in need thereof a therapeutically effective dose of at least one antisense oligonucleotide that binds to a natural antisense sequence of said at least one angiopoietin like 7 (ANGPTL7) polynucleotide and modulates expression of said at least one angiopoietin like 7 (ANGPTL7)

polynucleotide; thereby preventing or treating the disease associated with the at least one angiopoietin like 7 (ANGPTL7) polynucleotide and or at least one encoded product thereof.

In one aspect, provided herein is a method of preventing or treating a disease associated with at least one angiopoietin like 7 (ANGPTL7) polynucleotide and/or at least one encoded product thereof, the method comprising: administering to a subject in need thereof a therapeutically effective dose of at least one antisense oligonucleotide that binds to a natural sense sequence of said at least one angiopoietin like 7 (ANGPTL7) polynucleotide and modulates expression of said at least one angiopoietin like 7 (ANGPTL7) polynucleotide; thereby preventing or treating the disease associated with the at least one angiopoietin like 7 (ANGPTL7) polynucleotide and or at least one encoded product thereof.

In some embodiments, a disease associated with the at least one angiopoietin like 7 (ANGPTL7) polynucleotide is selected from: a disease or disorder associated with abnormal function and/or expression of ANGPTL7, a disease or disorder associated with optic nerve damage, a disease or disorder associated with intraocular pressure, a degenerative retinal disease or disorder, an inflammatory eye disease or disorder, an allergic eye disease or disorder, a disease or disorder associated with degeneration or inflammation of the joints, a disease or disorder associated with abnormal lipid metabolism, cancer, Alzheimer's disease, dementia, stroke and brain ischemia. In some embodiments, the disease or disorder associated with optic nerve damage comprises primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma, absolute glaucoma, ocular hypertension, or a combination thereof. In some embodiments, the disease or disorder associated with degeneration or inflammation of the joints comprises osteoarthritis, osteoarthrosis or a combination thereof. In some embodiments, the cancer is selected from lung cancer, epidermoid carcinoma, breast cancer, or a combination thereof.

In one aspect, provided herein is a method of identifying and selecting at least one oligonucleotide for in vivo administration comprising: identifying at least one oligonucleotide comprising at least five consecutive nucleotides which are complementary to ANGPTL7 or to a polynucleotide that is antisense to ANGPTL7; measuring the thermal melting point of a hybrid of an antisense oligonucleotide and the ANGPTL7 or the polynucleotide that is antisense to the ANGPTL7 under stringent hybridization conditions; and selecting at least one oligonucleotide for in vivo administration based on the information obtained.

In one aspect, provided herein is a method of treating a disease or condition mediated by ANGPTL7, the method comprising administering to a subject in need thereof an oligonucleotide comprising a sequence at least about 80%, 85%, 90%, 95%, or 100% identical to a sequence selected from SEQ ID NOS: 1-4412. In some embodiments, the oligonucleotide comprises a sequence selected from SEQ ID NOS: 1-4412. In some embodiments, the target is ANGPTL7. In some embodiments, the disease or condition comprises glaucoma (including, primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma and absolute glaucoma), ocular hypertension, optic neuropathy or a combination thereof. In some embodiments, the oligonucleotide comprises dsRNA. In some embodiments, the oligonucleotide comprises a sequence at least about 80%, 85%, 90%, 95%, or 100% identical to a sequence selected from SEQ ID NOS: 1-4412. In some embodiments, the oligonucleotide comprises a sequence at least about 80%, 85%, 90%, 95%, or 100% identical to SEQ ID NO: 11087.

In one aspect, provided herein is a method of treating one or more disorders of the eye in a subject in need thereof comprising editing an ANGPTL7 gene in the subject wherein the one or more disorders of the eye comprises glaucoma or ocular hypertension. In some embodiments, the editing of the ANGPTL7 gene comprises administering CRISPR/cas9 to the subject. In some embodiments, the CRISPR/cas9 targets the ANGPTL7 gene. In some embodiments, the CRISPR/cas9 edits the ANGPTL7 gene to a loss of function mutation. In some embodiments, the loss of function mutation comprises a premature stop mutation. In some embodiments, the premature stop mutation occurs at amino acid position 177 according to the human protein sequence numbering. In some embodiments, the CRISPR/cas9 edits the ANGPTL7 gene to a missense mutation. In some embodiments, the missense mutation comprises a glutamine to histidine mutation. In some embodiments, the glutamine to histidine mutation occurs at amino acid position 175 according to the human protein sequence numbering. In some embodiments, the CRISPR/cas9 is delivered systemically to the subject. In some embodiments, the CRISPR/cas9 is delivered locally to the subject. In some embodiments, the CRISPR/cas9 is delivered locally to the eye of the subject. In some embodiments, the editing of the ANGPTL7 gene is efficacious in treating the one or more disorders of the eye. In some embodiments, the one or more disorders of the eye is glaucoma. In some embodiments, the subject has ocular hypertension. In some embodiments, imaging from the subject ocular hypertension demonstrates optic nerve damage. In some embodiments, the subject has received a first line treatment comprising topical ocular prostaglandin analogues, beta-adrenergic blockers, alpha-adrenergic agonists, and carbonic anhydrase inhibitors for the one or more disorders of the eye. In some embodiments, the editing of the ANGPTL7 gene causes a reduction in or modulation of the production of the gene product of ANGPTL7 in the subject. In some embodiments, the editing of the ANGPTL7 gene causes a reduction in the subject of intraocular pressure.

In one aspect, provided herein is a composition comprising CRISPR/cas9 that targets ANGPTL7 that is efficacious in treating glaucoma or ocular hypertension. In some embodiments, the CRISPR/cas9 edits the ANGPTL7 gene to a loss of function mutation. In some embodiments, the loss of function mutation comprises a premature stop mutation. In some embodiments, the premature stop mutation occurs at amino acid position 177 according to the human protein sequence numbering. In some embodiments, the CRISPR/cas9 edits the ANGPTL7 gene to a missense mutation. In some embodiments, the missense mutation comprises a glutamine to histidine mutation. In some embodiments, the glutamine to histidine mutation occurs at amino acid position 175 according to the human protein sequence numbering.

Disclosed herein, in some embodiments, are compositions comprising an oligonucleotide that targets Angiopoietin like 7 (ANGPTL7) and when administered to a subject in an effective amount decreases intraocular pressure, wherein the oligonucleotide comprises a small interfering RNA (siRNA) comprising a sense strand and an antisense strand, the antisense strand being complementary to a portion of a nucleic acid having the nucleoside sequence of SEQ ID NO: 11085, and each strand having 14 to 30 nucleotides. In some embodiments, the intraocular pressure is decreased by about 10% or more, as compared to prior to administration. Disclosed herein, in some embodiments, are compositions comprising an oligonucleotide that targets Angiopoietin like 7 (ANGPTL7) and when administered to a cell decreases expression of ANGPTL7, wherein the oligonucleotide comprises a small interfering RNA (siRNA) comprising a sense strand and an antisense strand, the antisense strand being complementary to a portion of a nucleic acid having the nucleoside sequence of SEQ ID NO: 11085, and each strand having 14 to 30 nucleotides. In some embodiments, the composition decreases expression of ANGPTL7 as compared to a baseline ANGPTL7 measurement. In some embodiments, the baseline ANGPLT7 measurement is measured before the composition is administered to the cell. In some embodiments, the composition decreases expression of ANGPLT7 by at least 10% relative to the baseline ANGPTL7 measurement. In some embodiments, the composition decreases expression of ANGPLT7 by at least 20% relative to the baseline ANGPTL7 measurement. In some embodiments, the composition decreases expression of ANGPLT7 by at least 30% relative to the baseline ANGPTL7 measurement. In some embodiments, the composition decreases expression of ANGPLT7 by at least 40% relative to the baseline ANGPTL7 measurement. In some embodiments, the composition decreases expression of ANGPLT7 by at least 50% relative to the baseline ANGPTL7 measurement. In some embodiments, the composition decreases expression of ANGPLT7 by at least 25% to 75% relative to the baseline ANGPTL7 measurement. In some embodiments, the baseline measurement is an ANGPLT7 protein measurement. In some embodiments, the baseline measurement is an ANGPLT7 mRNA measurement. In some embodiments, the expression of ANGPLT7 comprises ANGPTL7 mRNA expression. In some embodiments, the expression of ANGPLT7 comprises ANGPTL7 protein expression. In some embodiments, the siRNA binds with a human ANGPTL7 mRNA with no more than 2 mismatches in the antisense strand. In some embodiments, the siRNA binds with a human ANGPTL7 mRNA target site that does not harbor an SNP, with a minor allele frequency (MAF) greater or equal to 1% (pos. 2-18). In some embodiments, the sense strand and the antisense strand each comprise a seed region that is not identical to a seed region of a human miRNA. In some embodiments, the sense strand comprises a nucleoside sequence at least 85% identical to any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the sense strand comprises the nucleoside sequence of any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192, or a sense strand sequence thereof having 1 or 2 nucleoside substitutions, additions, or deletions. In some embodiments, the sense strand comprises the nucleoside sequence of any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the antisense strand comprises a nucleoside sequence at least 85% identical to any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the antisense strand comprises the nucleoside sequence of any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398, or an antisense strand sequence thereof having 1 or 2 nucleoside substitutions, additions, or deletions. In some embodiments, the antisense strand comprises the nucleoside sequence of any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the oligonucleotide comprises one or more modified internucleoside linkages. In some embodiments, the one or more modified internucleoside linkages comprise alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the one or more modified internucleoside linkages comprise a phosphorothioate linkage. In some embodiments, the oligonucleotide comprises 2-6 modified internucleoside linkages. In some embodiments, the oligonucleotide comprises one or more modified nucleosides. In some embodiments, the one or more modified nucleosides comprise a locked nucleic acid (LNA), hexitol nucleic acid (HLA), cyclohexene nucleic acid (CeNA), a 2',4' constrained ethyl, 2'-methoxyethyl, 2'-O-alkyl, 2'-O-allyl, 2'-O-allyl, 2'-fluoro, or 2'-deoxy, a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, 2'-ara-F, or a combination thereof. In some embodiments, the one or more modified nucleosides comprise a 2' fluoro modified nucleoside. In some embodiments, the one or more modified nucleosides comprise a 2' O-methyl modified nucleoside. In some embodiments, the oligonucleotide comprises 15-23 modified nucleosides. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholyl, docosanoyl, docosahexaenoyl, myristyl, palmityl stearyl, or α-tocopherol, or a combination thereof. In some embodiments, the lipid comprises cholesterol. In some embodiments, the oligonucleotide comprises an arginineglycine-aspartic acid (RGD) peptide attached at a 3' or 5' terminus of the oligonucleotide. In some embodiments, the RGD peptide comprises Cyclo(-Arg-Gly-Asp-D-Phe-Cys), Cyclo(-Arg-Gly-Asp-D-Phe-Lys), Cyclo(-Arg-Gly-Asp-D-Phe-azido), an amino benzoic acid derived RGD, or a combination thereof. In some embodiments, the oligonucleotide comprises an RGD peptide and a lipid attached at a 3' or 5' terminus of the oligonucleotide. In some embodiments, the sense strand comprises modification pattern 1S: 5'-NfsnsNfnNfnNfnNfnNfnNfnNfnNfnNfnNfnNfsnsn-3' (SEQ ID NO: 11381), modification pattern 2S: 5'-nsnsnnNfnNfnNfnNfnnnnnnnnnnnsnsn-3' (SEQ ID NO: 11382), modification pattern 3S: 5'-nsnsnnNfnNfnNfnnnnnnnnnnnnsnsn-3' (SEQ ID NO: 11383), modification pattern 4S: 5'-NfsnsNfnNfnNfnNfnNfnNfnNfnNfnNfnNfnNfsnsnN-Lipid-3' (SEQ ID NO: 11384), or modification pattern 5S: 5'-nsnsnnNfnNfnNfnNfnnnnnnnnnnnnsnsnN-Lipid-3' (SEQ ID NO: 11385); wherein "Nf" is a 2' fluoro-modified nucleoside, "n" is a 2' 0-methyl modified nucleoside, "s" is a phosphorothioate linkage, and N comprises a nucleoside. In some embodiments, the antisense strand comprises modification pattern 1AS: 5'-nsNfsnNfnNfnNfnNfnNfnnnNfnNfnNfsnsn-3' (SEQ ID NO: 11386), modification pattern 2AS: 5'-nsNfsnnnNfnNfnNfnnnnNfnNfnnnsnsn-3' (SEQ ID NO: 11387), modification pattern 3AS: 5'-nsNfsnnnNfnnnnnnnnNfnNfnnnsnsn-3' (SEQ ID NO: 11388), or modification pattern 4AS: 5'-nsNfsnNfnNfnnnnnnnnnNfnNfnnnsnsn-3' (SEQ ID NO: 11389); wherein "Nf" is a 2' fluoro-modified nucleoside, "n" is a 2' O-methyl modified nucleoside, and "s" is a phosphorothioate linkage. In some embodiments, the sense strand comprises a nucleoside sequence at least 85% identical the sense strand sequence of an siRNA in any of Tables 5-13. In some embodiments, the sense strand comprises the sense strand sequence of an siRNA in any of Tables 5-13. In some embodiments, the sense strand comprises the nucleoside sequence of any one of SEQ ID NOS: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212, or a sense strand sequence thereof having 1 or 2 nucleoside substitutions, additions, or deletions. In some embodiments, the sense strand comprises the nucleoside sequence of any one of SEQ ID NOS: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212. In some embodiments, the antisense strand comprises a nucleoside sequence at least 85% identical the antisense strand sequence of an siRNA in any of Tables 5-13. In some embodiments, the antisense strand comprises the antisense strand sequence of an siRNA in any of Tables 5-13. In some embodiments, the antisense strand comprises the nucleoside sequence of any one of SEQ ID NOS: 11214, 11215, 11216, 11217, 11218, 11219, 11220, 11221, 11222, 11223, 11224, 11225, 11226, 11229, 11230, 11233, 11236, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332, or an antisense strand sequence thereof having 1 or 2 nucleoside substitutions, additions, or deletions. In some embodiments, the antisense strand comprises the nucleoside sequence of any one of SEQ ID NOS: 11214, 11215, 11216, 11217, 11218, 11219, 11220, 11221, 11222, 11223, 11224, 11225, 11226, 11229, 11230, 11233, 11236, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332. In some embodiments, the sense strand or the antisense strand comprises a 3' overhang of at least 2 nucleotides. In some embodiments, the composition is a pharmaceutical composition. In some embodiments, the composition is sterile. Some embodiments include a pharmaceutically acceptable carrier. In some embodiments, the pharmaceutically acceptable carrier comprises water, a buffer, or a saline solution.

Disclosed herein, in some embodiments, are methods of treating an ocular disorder in a subject in need thereof, the method comprising administering to the subject a composition comprising an oligonucleotide that targets ANGPTL7. In some embodiments, the ocular disorder comprises a glaucoma. In some embodiments, the composition decreases intraocular pressure in an eye of the subject relative to a baseline intraocular pressure measurement obtained from the subject prior to administering the composition to the subject. In some embodiments, the sense strand comprises a nucleoside sequence at least 85% identical to any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the sense strand comprises the nucleoside sequence of any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192, or a sense strand sequence thereof having 1 or 2 nucleoside substitutions, additions, or deletions. In some embodiments, the sense strand comprises the nucleoside sequence of any one of SEQ ID NOS: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the antisense strand comprises a nucleoside sequence at least 85% identical to any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the antisense strand comprises the nucleoside sequence of any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398, or an antisense strand sequence thereof having 1 or 2 nucleoside substitutions, additions, or deletions. In some embodiments, the antisense strand comprises the nucleoside sequence of any one of SEQ ID NOS: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the sense strand comprises modification pattern 1S: 5'-NfsnsNfnNfnNfNfNfnNfnNfnNfnNfnNfsnsn-3' (SEQ ID NO: 11381), modification pattern 2S: 5'-nsnsnnNfnNfNfNfnnnnnnnnnnnsnsn-3' (SEQ ID NO: 11382), modification pattern 3S: 5'-nsnsnnNfnNfnNfnNfnnnnnnnnnnnsnsn-3' (SEQ ID NO: 11383), modification pattern 4S: 5'-NfsnsNfnNfnNfnNfNfnNfnNfnNfnNfnNfsnsnN-Lipid-3' (SEQ ID NO: 11384), or modification pattern 5S: 5'-nsnsnnNfnNfNfNfnnnnnnnnnnnsnsnN-Lipid-3' (SEQ ID NO: 11385); wherein "Nf" is a 2' fluoro-modified nucleoside, "n" is a 2' 0-methyl modified nucleoside, "s" is a phosphorothioate linkage, and N comprises a nucleoside. In some embodiments, the antisense strand comprises modification pattern 1AS: 5'-nsNfsnNfnNfnNfnNfnNfnnnNfnNfnNfnsnsn-3' (SEQ ID NO: 11386), modification pattern 2AS: 5'-nsNfsnnnNfnNfnNfnnnnNfnNfnnnsnsn-3' (SEQ ID NO: 11387), modification pattern 3AS: 5'-nsNfsnnnNfnnnnnnnnNfnNfnnnsnsn-3' (SEQ ID NO: 11388), or modification pattern 4AS: 5'-nsNfsnNfnNfnNfnnnnnnnnNfnNfnnnsnsn-3' (SEQ ID NO: 11389); wherein "Nf" is a 2' fluoro-modified nucleoside, "n" is a 2' O-methyl modified nucleoside, and "s" is a phosphorothioate linkage. In some embodiments, the sense strand comprises a nucleoside sequence at least 85% identical the sense strand sequence of an siRNA in any of Tables 5-13. In some embodiments, the sense strand comprises the sense strand sequence of an siRNA in any of Tables 5-13. In some embodiments, the sense strand comprises the nucleoside sequence of any one of SEQ ID NOS: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212, or a sense strand sequence thereof having 1 or 2 nucleoside substitutions, additions, or deletions. In some embodiments, the sense strand comprises the nucleoside sequence of any one of SEQ ID NOS: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212. In some embodiments, the antisense strand comprises a nucleoside sequence at least 85% identical the antisense strand sequence of an siRNA in any of Tables 5-13. In some embodiments, the antisense strand comprises the antisense strand sequence of an siRNA in any of Tables 5-13. In some embodiments, the antisense strand comprises the nucleoside sequence of any one of SEQ ID NOS: 11214, 11215, 11216, 11217, 11218, 11219, 11220, 11221, 11222, 11223, 11224, 11225, 11226, 11229, 11230, 11233, 11236, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332, or an antisense strand sequence thereof having 1 or 2 nucleoside substitutions, additions, or deletions. In some embodiments, the antisense strand comprises the nucleoside sequence of any one of SEQ ID NOS: 11214, 11215, 11216, 11217, 11218, 11219, 11220, 11221, 11222, 11223, 11224, 11225, 11226, 11229, 11230, 11233, 11236, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332. In some embodiments, the oligonucleotide comprises a cholesterol moiety attached at a 3' or 5' terminus of the oligonucleotide. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof. In some embodiments, the lipid comprises cholesterol. In some embodiments, the oligonucleotide comprises an arginine-glycine-aspartic acid (RGD) peptide attached at a 3' or 5' terminus of the oligonucleotide. In some embodiments, the RGD peptide comprises Cyclo(-Arg-Gly-Asp-D-Phe-Cys), Cyclo(-Arg-Gly-Asp-D-Phe-Lys), Cyclo(-Arg-Gly-Asp-D-Phe-azido), an amino benzoic acid derived RGD, or a combination thereof.

DETAILED DESCRIPTION

Figure 1A:
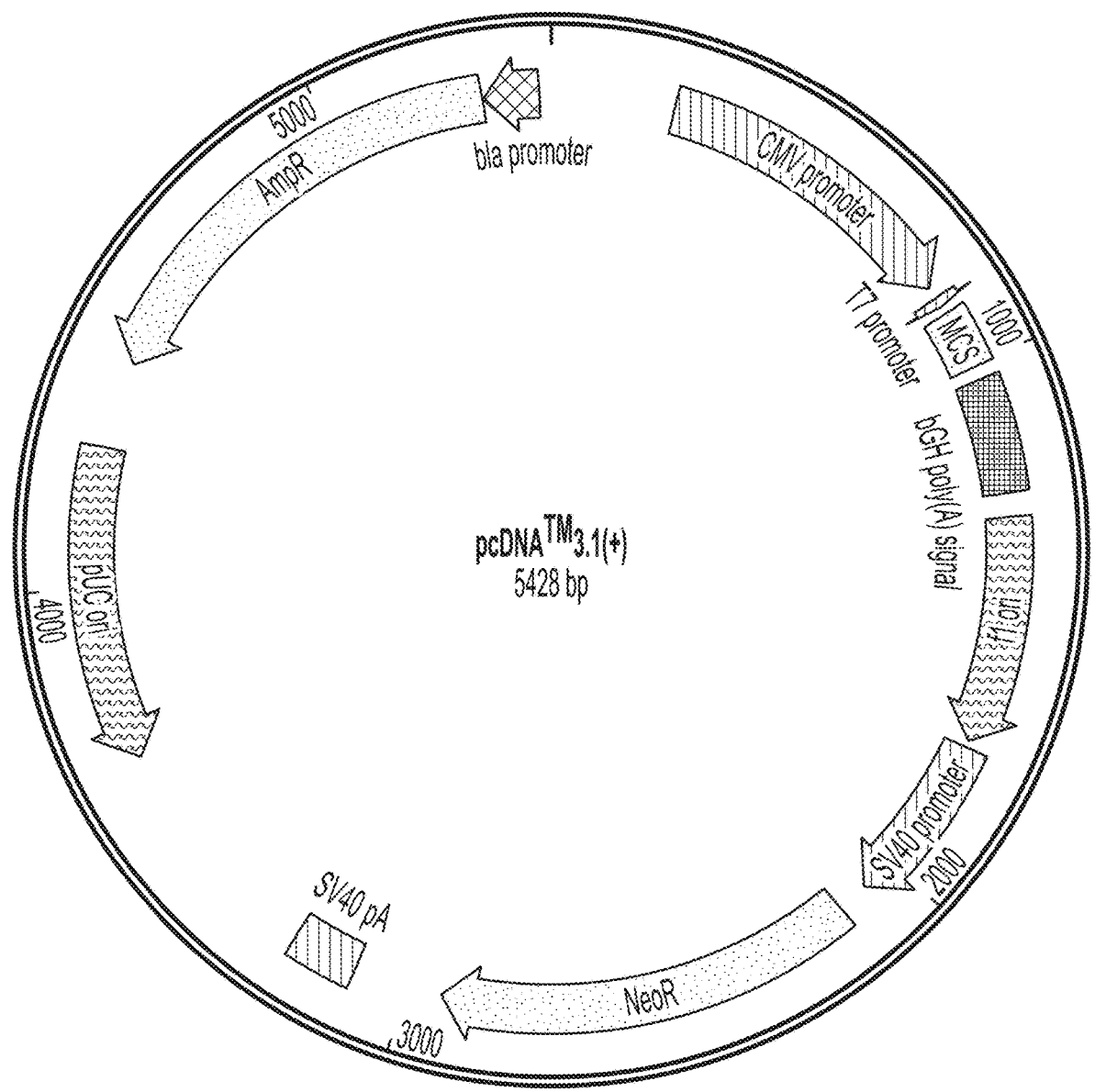
FIGS. 1A-1D show an empty plasmid construct (FIG. 1A) used in accordance with some embodiments, GFP tagged plasmid construct (FIG. 1B), a representative ANGPTL7 pre-mRNA encoding construct (FIG. 1C) and a representative ANGPTL7 CDS encoding construct (FIG. 1D).
Figure 1B:
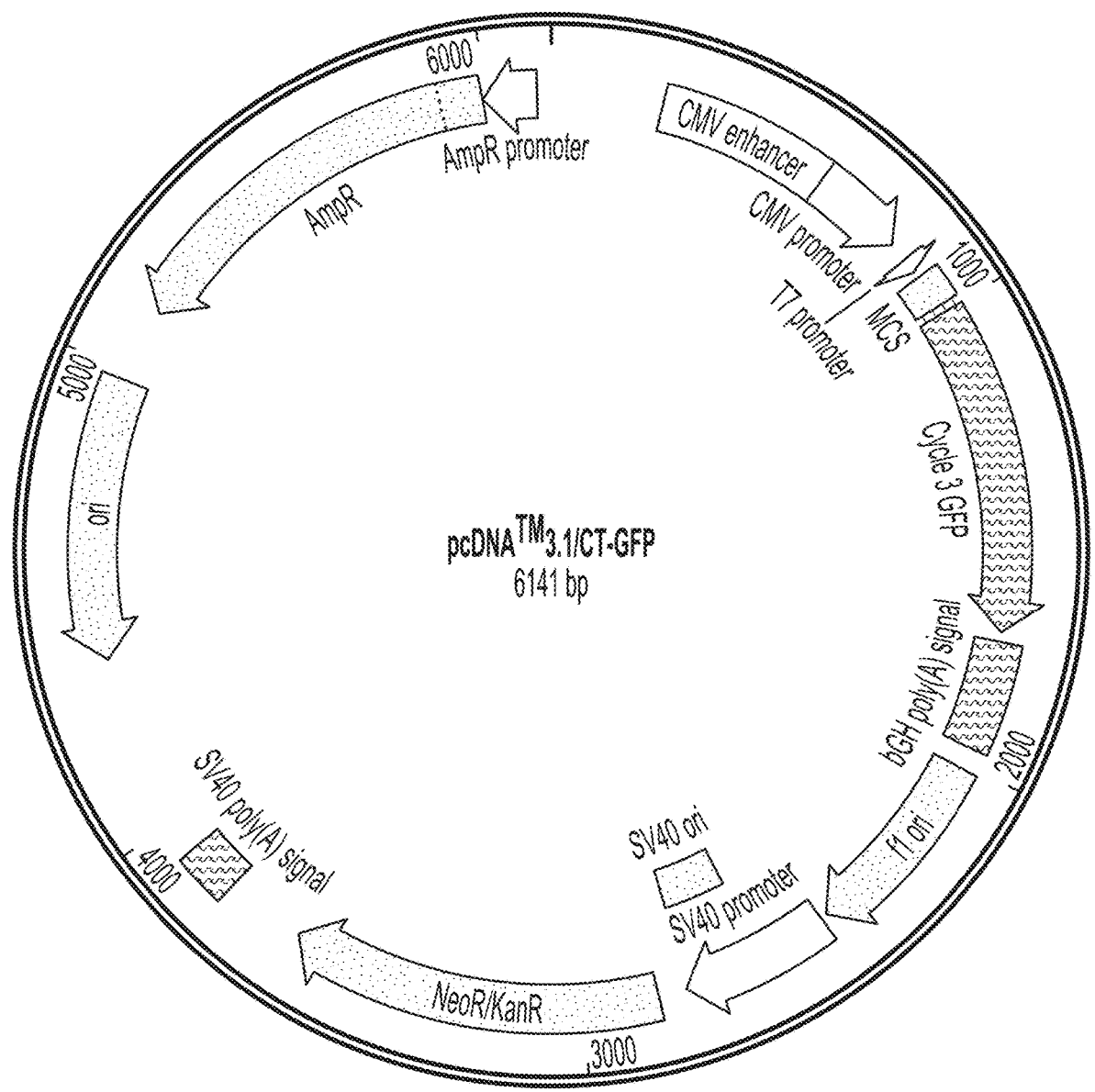
Figure 1C:
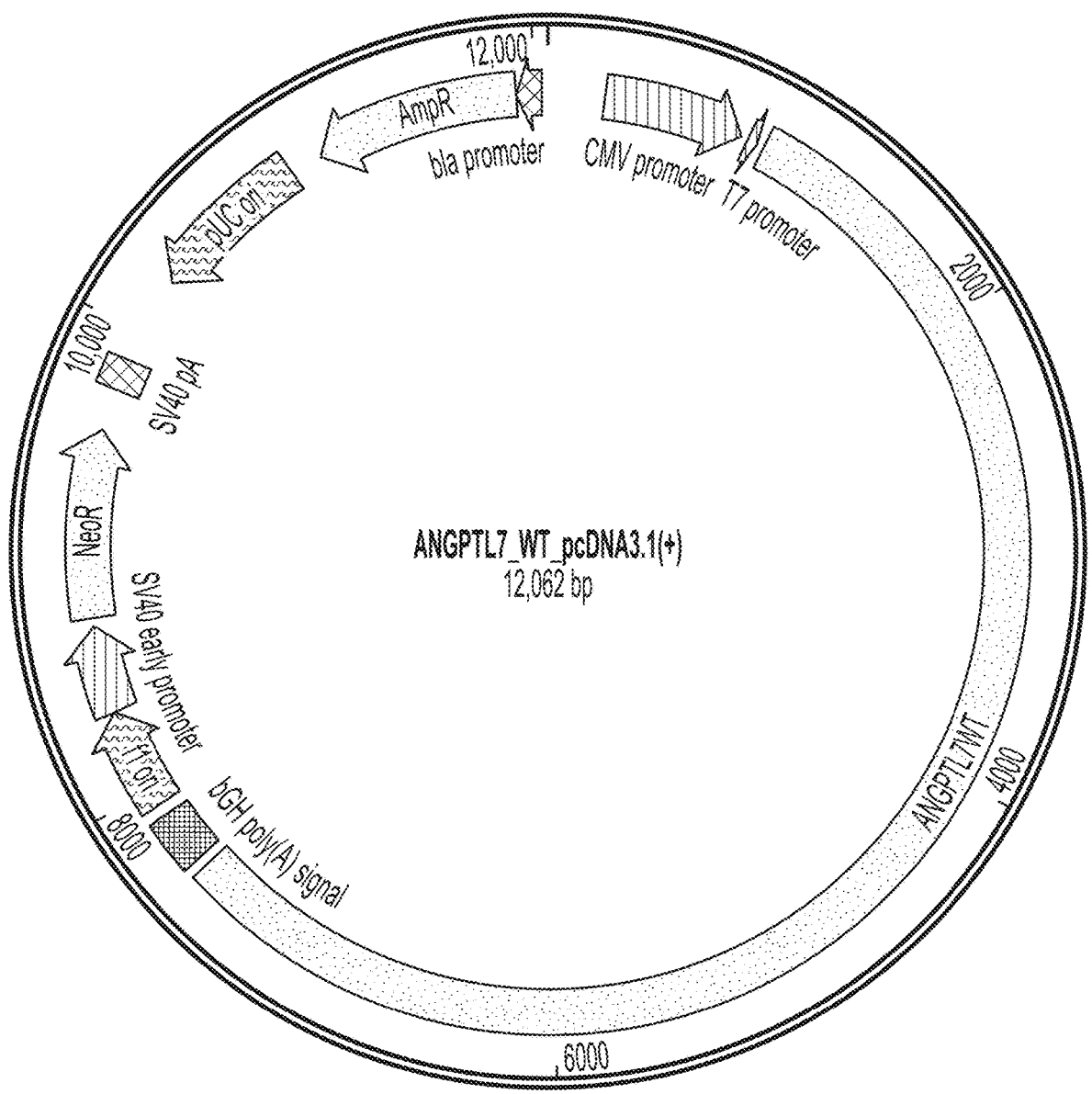
Figure 1D:
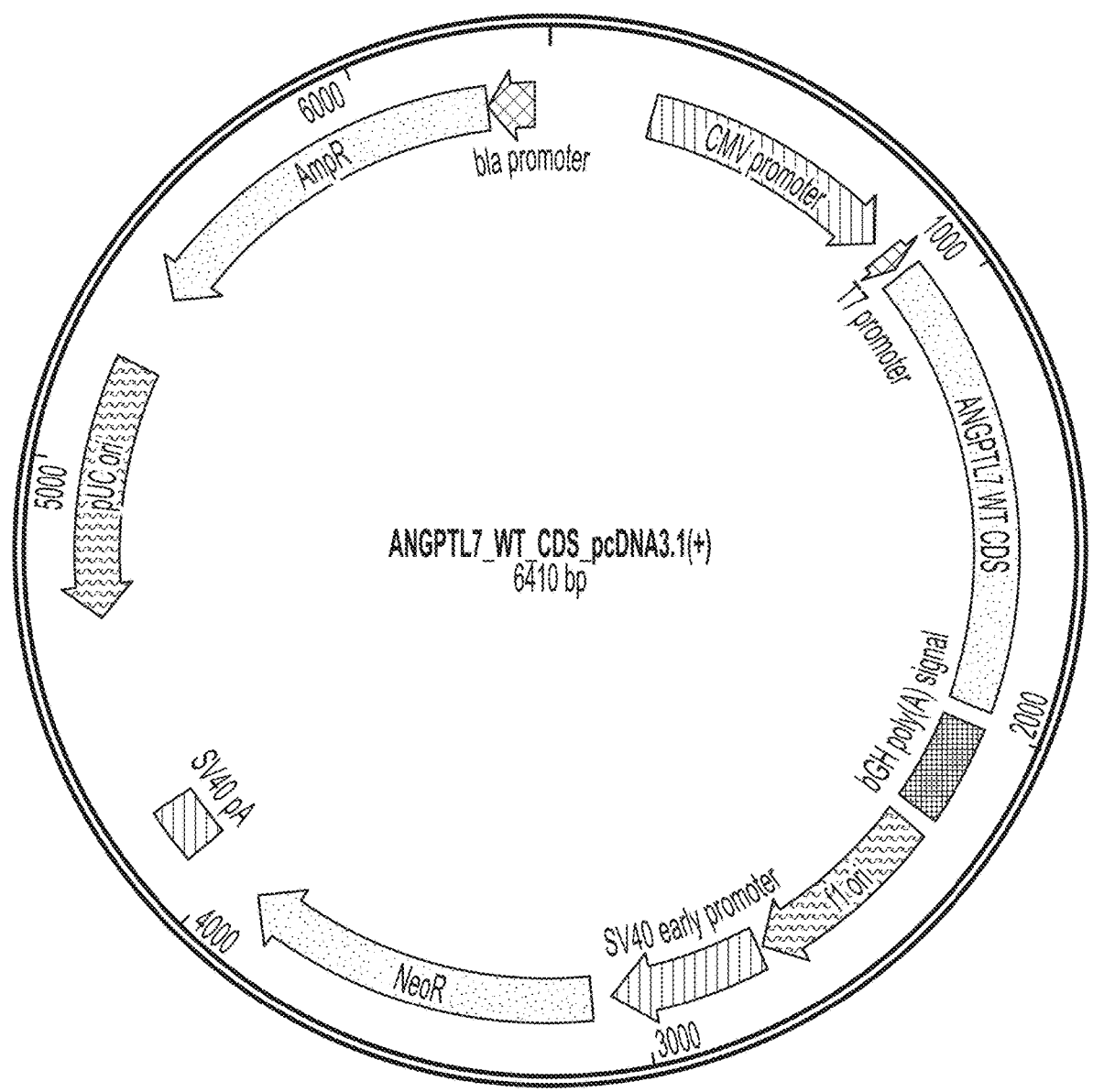

Glaucoma is the leading cause of irreversible blindness in the world, with an approximate 1-2% prevalence worldwide in individuals >40 years of age. There are several subtypes of glaucoma, but two subtypes are dominant primary open angle glaucoma (POAG) and primary angle closure glaucoma (PACG). POAG accounts for about 90% of glaucoma cases in the US and the majority of these cases occur in the context of ocular hypertension (OHT). In some populations (i.e. Asian populations) the majority of glaucoma occurs in the context of normal intraocular pressure (normal-tension glaucoma, NTG).

Glaucoma is generally characterized by blocked outflow of the aqueous humor through the conventional outflow pathway. The conventional outflow pathway is comprised of the trabecular meshwork (TM) and Schlemm's canal at the base of the cornea. There is also a non-conventional outflow pathway which involves uveoscleral drainage and accounts for a fraction of the aqueous humor outflow from the anterior compartment of the eye. Blockage of the TM/Schlemm's canal (conventional pathway) restricts aqueous humor outflow leading to increased pressure in the anterior chamber which translates to increased pressure in the posterior chamber and optic nerve degeneration and damage.

Treatments for glaucoma aim to lower intraocular pressure (IOP) to target levels (generally a 20-50% reduction in IOP). Despite normal IOP, treatment of NTG also revolves around lowering IOP. Several classes of IOP-lowering medication are used, including prostaglandin analogues (typically the first-line therapy), beta-adrenergic blockers, alpha-adrenergic agonists, and carbonic anhydrase inhibitors. These drugs are often ineffective and surgical methods (trabeculoplasty/trabeculotomy) are employed. However, the beneficial effects of trabeculoplasty/trabeculotomy decrease over time such that there is an approximate 10% failure rate per year.

Angiopoietin-like proteins (ANGPTLs) are a family of eight proteins with structural and functional similarities to angiopoietins, comprised of an N-terminal coiled-coil domain which mediates homo-oligomerization and a C-terminal fibrinogen domain. ANGPTLs are widely expressed in the liver, vasculature and hematopoietic systems, and serve important roles in inflammation, lipid metabolism, angiogenesis and extracellular matrix (ECM) formation.

ANGPTL7 was originally discovered in human corneal cDNA libraries and named cornea-derived transcript 6 (CDT6) Immunohistochemistry reveals ANGPTL7 staining in multiple tissues in the eye. ANGPTL7 is overexpressed in the aqueous humor of patients with glaucoma and is upregulated by glaucomatous conditions such as TGFβ and dexamethasone exposure. Nonetheless, the molecular function of ANGPTL7 in eye health and disease is not well understood.

The terminology used herein is for the purpose of describing particular embodiments only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. In some cases, "about" can mean a range of up to 20%, up to 10%, up to 5%, and up to 1% of a given value. In some cases, particularly with respect to biological systems or processes, the term can mean within an order of magnitude, e.g., within 5-fold, or within 2-fold, of a value. Where particular values are described in the application and claims, unless otherwise stated the term "about" meaning within an acceptable error range for the particular value should be assumed.

In some embodiments, the term "mRNA" means the presently known mRNA transcript(s) of a targeted gene, and any further transcripts which may be elucidated.

In some embodiments, "dsRNA", "siRNA", and "siRNA agent" are used interchangeably as agents that can mediate silencing of a target RNA, e.g., mRNA, e.g., a transcript of a gene that encodes a protein. In some cases, the target RNA is ANGPTL7. Such mRNA may also be referred to herein as mRNA to be silenced. Such a gene is also referred to as a target gene. In some cases, the RNA to be silenced is an endogenous gene or a pathogen gene. In addition, RNAs other than mRNA, e.g., tRNAs, and viral RNAs, can also be targeted.

In some embodiments, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent.

In some embodiments, "specifically hybridizable" and "complementary" are terms which are used to indicate a sufficient degree of complementarity such that stable and specific binding occurs between a compound described herein and a target RNA molecule.

Specific binding may require a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences may differ by at least 5 nucleotides.

In some embodiments, a dsRNA agent is "sufficiently complementary" to a target RNA, e.g., a target mRNA, such that the dsRNA agent silences production of protein encoded by the target mRNA. In some embodiments, the dsRNA agent is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent specifically discriminates a single-nucleotide difference. In this case, the dsRNA agent only mediates RNAi if exact complementarity is found in the region (e.g., within 7 nucleotides of) the single-nucleotide difference.

In some embodiments, the term "oligonucleotide" refers to a nucleic acid molecule (RNA or DNA) for example of length less than 100, 200, 300, or 400 nucleotides.

In some embodiments, "antisense oligonucleotides" or "antisense compound" is meant as an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA and DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In some embodiments, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

In some embodiments, the oligonucleotide is "chimeric", that is, composed of different regions. "Chimeric" oligonucleotides contain two or more chemical regions, for example, DNA region(s), RNA region(s), PNA region(s), etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. Chimeric oligonucleotides can be formed as mixed structures of two or more oligonucleotides, modified oligonucleotides, oligonucleosides and/or oligonucleotide analogs.

The oligonucleotide can comprise or be composed of regions that can be linked in "register", that is, when the monomers are linked consecutively, as in native DNA, or linked via spacers. The spacers are intended to constitute a covalent "bridge" between the regions and have, in some cases, a length not exceeding about 100 carbon atoms. The spacers may carry different functionalities, for example, having positive or negative charge, carry special nucleic acid binding properties (intercalators, groove binders, toxins, fluorophores etc.), being lipophilic, inducing special secondary structures like, for example, alanine containing peptides that induce alpha-helices.

In some embodiments, "ANGPTL7" and "angiopoietin like 7" are inclusive of all family members, mutants, alleles, fragments, species, coding and noncoding sequences, sense and antisense polynucleotide strands, etc. of the ANGPTL7 transcript (NM_021146; SEQ ID NO: 11085). In some embodiments, "ANGPTL7" and "angiopoietin like 7" are used interchangeably in the present application.

In some embodiments, "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays.

In some embodiments, the term "target nucleic acid" encompasses DNA, RNA (including pre-mRNA and mRNA) transcribed from such DNA, and also cDNA derived from such RNA, coding, noncoding sequences, sense and antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA that are modulated include, for example, replication and transcription. The functions of RNA that are modulated, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs can be synthesized and used. Small interfering RNAs for use in the methods herein suitably comprise between about 1 to about 50 nucleotides (nt). In examples of non-limiting embodiments, siRNAs can comprise about 5 to about 40 nt, about 5 to about 30 nt, about 10 to about 30 nt, about 15 to about 25 nt, or about 20-25 nucleotides.

In some embodiments, selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes.

In some embodiments, "enzymatic RNA" is meant an RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

In some embodiments, "decoy RNA" is meant an RNA molecule that mimics the natural binding domain for a ligand. The decoy RNA therefore competes with natural binding target for the binding of a specific ligand. For example, over-expression of HIV trans-activation response (TAR) RNA can act as a "decoy" and efficiently binds HIV tat protein, thereby preventing it from binding to TAR sequences encoded in the HIV RNA. This is meant to be a specific example Those in the art will recognize that this is but one example, and some embodiments can be readily generated using techniques generally known in the art.

In some embodiments, "monomers" typically indicates monomers linked by phosphodiester bonds or analogs thereof to form oligonucleotides ranging in size from a few monomelic units, e.g., from about 3-4, to about several hundreds of monomelic units. Analogs of phosphodiester linkages include: phosphorothioate, phosphorodithioate, methylphosphornates, phosphoroselenoate, phosphoramidate, and the like, as more fully described below.

In some embodiments, "nucleotide" covers naturally occurring nucleotides as well as non-naturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, ˆaminopurine, 8-oxo-N6-memyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-memyl-4-triazolopvridin, isocytosine, isoguanin, inosine and the "non-naturally occurring" nucleotides described in Benner et al, U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, as well as their analogs.

In some embodiments, "analogs" in reference to nucleotides includes synthetic nucleotides having modified base moieties and/or modified sugar moieties. Such analogs include synthetic nucleotides designed to enhance binding properties, e.g., duplex or triplex stability, specificity, or the like.

In some embodiments, "hybridization" means the pairing of at least substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

In some embodiments, an antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In some embodiments, "stringent hybridization conditions" or "stringent conditions" refers to conditions under which a compound will hybridize to its target sequence, but to a minimal number of other sequences. Stringent conditions are sequence-dependent and will be different in different circumstances and "stringent conditions" under which oligomeric compounds hybridize to a target sequence are determined by the nature and composition of the oligomeric compounds and the assays in which they are being investigated. In some cases, stringent hybridization conditions comprise low concentrations (<0.15M) of salts with inorganic cations such as Na+ or K+ (i.e., low ionic strength), temperature higher than about 20° C. to 25° C. and below the Tm of the oligomeric compound/target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

In some embodiments, "complementary" refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid may be considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which may be used to indicate a sufficient degree of precise pairing or complementarity over a sufficient number of nucleotides such that stable and specific binding occurs between the oligomeric compound and a target nucleic acid.

The sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). In some embodiments, oligomeric compounds disclosed herein comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present disclosure. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman.

In some embodiments, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

In some embodiments, "modulation" means either an increase (stimulation) or a decrease (inhibition) in the expression of a gene.

In some embodiments, the term "variant", when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, co factors, inhibitors, magnetic particles, and the like.

In some embodiments, a "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals) Examples include feline, canine, equine, bovine, and human, as well as just human.

"Treating" or "treatment" includes the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.). The term "treatment" is intended to encompass also prophylaxis, therapy and cure. The patient receiving this treatment is any animal in need, including primates, in particular humans, and other mammals such as equines, cattle, swine and sheep; and poultry and pets in general.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In some embodiments, the genes or nucleic acid sequences are human.

In some embodiments, the term "halo" refers to any radical of fluorine, chlorine, bromine or iodine. In some embodiments, the term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, Ci-Cio indicates that the group may have from 1 to 10 (inclusive) carbon atoms in it. The term "alkoxy" refers to an —O-alkyl radical. In some embodiments, the term "alkylene" refers to a divalent alkyl (i.e., —R—). The term "alkylenedioxo" refers to a divalent species of the structure -0-R-0-, in which R represents an alkylene. The term "aminoalkyl" refers to an alkyl substituted with an amino. In some embodiments, the term "mercapto" refers to an —SH radical. The term "thioalkoxy" refers to an —S-alkyl radical.

In some embodiments, the term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. In some embodiments, the term "arylalkyl" or the term "aralkyl" refers to alkyl substituted with an aryl. In some embodiments, the term "arylalkoxy" refers to an alkoxy substituted with aryl.

In some embodiments, the term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

In some embodiments, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. In some embodiments, the term "heteroarylalkyl" or the term "heteroaralkyl" refers to an alkyl substituted with a heteroaryl. In some embodiments, the term "heteroarylalkoxy" refers to an alkoxy substituted with heteroaryl.

In some embodiments, the term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

In some embodiments, the term "oxo" refers to an oxygen atom, which forms a carbonyl when attached to carbon, an N-oxide when attached to nitrogen, and a sulfoxide or sulfone when attached to sulfur.

In some embodiments, the term "acyl" refers to an alkylcarbonyl, cycloalkylcarbonyl, arylcarbonyl, heterocyclylcarbonyl, or heteroarylcarbonyl substituent, any of which may be further substituted by substituents.

In some embodiments, the term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylamino carbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Oligonucleotide Compounds and Compositions

Some embodiments refer to nucleic acid sequence information. In some embodiments, any uracil (U) may be interchanged with any thymine (T), and vice versa. For example, in an siRNA with a nucleic acid sequence comprising one or more Us, in some embodiments any of the Us may be replaced with Ts. Similarly, in an siRNA with a nucleic acid sequence comprising one or more Ts, in some embodiments any of the Ts may be replaced with Us. In some embodiments, an oligonucleotide such as an siRNA disclosed herein comprises or consists of RNA. In some embodiments, the oligonucleotide may comprise or consist of DNA.

Some embodiments refer to a particular nucleic acid sequence comprising modified nucleic acids. In some embodiments, an oligonucleotide described herein comprises or consists of a nucleic acid sequence comprising an unmodified version of the nucleic acid sequence comprising modified nucleic acids. In some embodiments, an oligonucleotide described herein comprises or consists of a nucleic acid sequence comprising the nucleic acid sequence comprising modified nucleic acids, but with any one or more additional modifications or different modifications.

In some embodiments, provided herein are oligonucleotide compounds that target a nucleic acid sequence of angiopoietin like 7 (ANGPTL7), including, without limitation, sense and/or antisense noncoding and/or coding sequences associated with ANGPTL7. In some embodiments, the target nucleic acid molecule is not limited to ANGPTL7 polynucleotides alone but extends to any of the isoforms, receptors, homologs, non-coding regions and the like of ANGPTL7.

In some embodiments, provided is a composition comprising one or more antisense oligonucleotides or dsRNA agents targeted to a first nucleic acid and one or more additional antisense compounds targeted to a second nucleic acid target. For example, the first target may be a particular sequence of angiopoietin like 7 (ANGPTL7), and the second target may be a region from another nucleotide sequence. In some embodiments, compositions may contain two or more antisense oligonucleotide or dsRNA compounds targeted to different regions of the same ANGPTL7 nucleic acid target. Numerous examples of antisense oligonucleotide or dsRNA compounds are illustrated herein and others may be selected from among suitable compounds known in the art. Two or more combined compounds may be used together or sequentially.

In some embodiments, a composition is provided that includes a plurality of antisense oligonucleotide or dsRNA agent species. In some embodiments, the antisense oligonucleotide or dsRNA agent species has sequences that are non-overlapping and non-adjacent to another species with respect to a naturally occurring target sequence. In some embodiments, the plurality of antisense oligonucleotide or dsRNA agent species is specific for different naturally occurring target genes. In some embodiments, the dsRNA agent is allele specific.

The disclosure provides methods, compositions, and kits, for administration and delivery of antisense oligonucleotide or dsRNA agents described herein.

Compositions

Disclosed herein, in some embodiments, are compositions comprising an oligonucleotide. In some embodiments, the composition comprises an oligonucleotide that targets ANGPTL7. In some embodiments, the composition consists of an oligonucleotide that targets ANGPTL7. In some embodiments, a composition described herein is used in a method of treating a disorder in a subject in need thereof. Some embodiments relate to a composition comprising an oligonucleotide for use in a method of treating a disorder as described herein. Some embodiments relate to use of a composition comprising an oligonucleotide, in a method of treating a disorder as described herein. The composition (e.g. oligonucleotide composition) may comprise or consist of a dsRNA agent described herein. The composition (e.g. oligonucleotide composition) may comprise or consist of an siRNA described herein. The composition (e.g. oligonucleotide composition) may comprise or consist of an antisense oligonucleotide described herein.

In some embodiments, the composition comprises an oligonucleotide that targets ANGPTL7 and when administered to a subject in an effective amount decreases ANGPTL7 mRNA levels in a cell or tissue. In some embodiments, the cell is a ANGPTL7. In some embodiments, the tissue is ANGPTL7 tissue. In some embodiments, the ANGPTL7 mRNA levels are decreased by about 2.5% or more, about 5% or more, or about 7.5% or more, as compared to prior to administration. In some embodiments, the ANGPTL7 mRNA levels are decreased by about 10% or more, as compared to prior to administration. In some embodiments, the ANGPTL7 mRNA levels are decreased by about 20% or more, about 30% or more, about 40% or more, about 50% or more, about 60% or more, about 70% or more, about 80% or more, about 90% or more, or about 100% or more as compared to prior to administration. In some embodiments, the ANGPTL7 mRNA levels are decreased by about 200% or more, about 300% or more, about 400% or more, about 500% or more, about 600% or more, about 700% or more, about 800% or more, about 900% or more, or about 1000% or more, as compared to prior to administration. In some embodiments, the ANGPTL7 mRNA levels are decreased by no more than about 2.5%, no more than about 5%, or no more than about 7.5%, as compared to prior to administration. In some embodiments, the ANGPTL7 mRNA levels are decreased by no more than about 10%, as compared to prior to administration. In some embodiments, the ANGPTL7 mRNA levels are decreased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the ANGPTL7 mRNA levels are decreased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the ANGPTL7 mRNA levels are decreased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the composition comprises an oligonucleotide that targets ANGPTL7 and when administered to a subject in an effective amount decreases circulating ANGPTL7 protein levels. In some embodiments, the ANGPTL7 protein levels are decreased by about 2.5% or more, about 5% or more, or about 7.5% or more, as compared to prior to administration. In some embodiments, the ANGPTL7 protein levels are decreased by about 10% or more, as compared to prior to administration. In some embodiments, the ANGPTL7 protein levels are decreased by about 20% or more, about 30% or more, about 40% or more, about 50% or more, about 60% or more, about 70% or more, about 80% or more, about 90% or more, or about 100% or more as compared to prior to administration. In some embodiments, the ANGPTL7 protein levels are decreased by about 200% or more, about 300% or more, about 400% or more, about 500% or more, about 600% or more, about 700% or more, about 800% or more, about 900% or more, or about 1000% or more, as compared to prior to administration. In some embodiments, the ANGPTL7 protein levels are decreased by no more than about 2.5%, no more than about 5%, or no more than about 7.5%, as compared to prior to administration. In some embodiments, the ANGPTL7 protein levels are decreased by no more than about 10%, as compared to prior to administration. In some embodiments, the ANGPTL7 protein levels are decreased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the ANGPTL7 protein levels are decreased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the ANGPTL7 protein levels are decreased by 2.5%, 5%, 7.5%, 10%, 20%, 30%, 40%, 50%, 60%, 70%, 80%, 90%, 100%, 200% 300%, 400%, 500%, 600%, 700%, 800%, 900%, 1000%, or by a range defined by any of the two aforementioned percentages.

In some embodiments, the composition comprises an oligonucleotide that targets ANGPTL7 and when administered to a subject in an effective amount decreases a symptom of glaucoma. In some embodiments, the glaucoma symptom is decreased by about 2.5% or more, about 5% or more, or about 7.5% or more, as compared to prior to administration. In some embodiments, the glaucoma symptom is decreased by about 10% or more, as compared to prior to administration. In some embodiments, the glaucoma symptom is decreased by about 20% or more, about 30% or more, about 40% or more, about 50% or more, about 60% or more, about 70% or more, about 80% or more, about 90% or more, or about 100% or more as compared to prior to administration. In some embodiments, the glaucoma symptom is decreased by no more than about 2.5%, no more than about 5%, or no more than about 7.5%, as compared to prior to administration. In some embodiments, the glaucoma symptom is decreased by no more than about 10%, as compared to prior to administration. In some embodiments, the glaucoma symptom is decreased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the glaucoma symptom is decreased by 2.5%, 5%, 7.5%, 10%, 20%, 30%, 40%, 50%, 60%, 70%, 80%, 90%, or 100%, or by a range defined by any of the two aforementioned percentages. In some embodiments, the glaucoma symptom is incidence of glaucoma, or of a glaucoma subtype. In some embodiments, the glaucoma symptom is severity of glaucoma, or of a glaucoma subtype. Examples of glaucoma subtypes include non-specific glaucoma, primary open angle glaucoma (POAG), and primary angle closure glaucoma (PACG).

In some embodiments, the composition comprises an oligonucleotide that targets ANGPTL7 and when administered to a subject in an effective amount decreases intraocular pressure. In some embodiments, the intraocular pressure is decreased by about 2.5% or more, about 5% or more, or about 7.5% or more, as compared to prior to administration. In some embodiments, the intraocular pressure is decreased by about 10% or more, as compared to prior to administration. In some embodiments, the intraocular pressure is decreased by about 20% or more, about 30% or more, about 40% or more, about 50% or more, about 60% or more, about 70% or more, about 80% or more, about 90% or more, or about 100% or more as compared to prior to administration. In some embodiments, the intraocular pressure is decreased by no more than about 2.5%, no more than about 5%, or no more than about 7.5%, as compared to prior to administration. In some embodiments, the intraocular pressure is decreased by no more than about 10%, as compared to prior to administration. In some embodiments, the intraocular pressure is decreased by no more than about 20%, no more than about 30%, no more than about 40%, no more than about 50%, no more than about 60%, no more than about 70%, no more than about 80%, no more than about 90%, or no more than about 100% as compared to prior to administration. In some embodiments, the intraocular pressure is decreased by 2.5%, 5%, 7.5%, 10%, 20%, 30%, 40%, 50%, 60%, 70%, 80%, 90%, or 100%, or by a range defined by any of the two aforementioned percentages.

Modification Patterns

In some embodiments, the composition comprises an oligonucleotide that inhibits the expression of ANGPTL7, wherein the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. Benefits of the modified internucleoside linkage may include decreased toxicity or improved pharmacokinetics. The composition (e.g. oligonucleotide composition) may comprise or consist of a dsRNA agent described herein. The composition (e.g. oligonucleotide composition) may comprise or consist of an siRNA described herein. The composition (e.g. oligonucleotide composition) may comprise or consist of an antisense oligonucleotide described herein.

In some embodiments, the composition comprises an oligonucleotide that inhibits the expression of ANGPTL7, wherein the oligonucleotide comprises a modified internucleoside linkage, wherein the oligonucleotide comprises 1, 2, 3, 4, 5, 6, 7, 8, 9, 10, 11, 12, 13, 14, 15, 16, 17, 18, 19, or 20 modified internucleoside linkages, or a range of modified internucleoside linkages defined by any two of the aforementioned numbers. In some embodiments, the oligonucleotide comprises no more than 18 modified internucleoside linkages. In some embodiments, the oligonucleotide comprises no more than 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

In some embodiments, the composition comprises an oligonucleotide that inhibits the expression of ANGPTL7, wherein the oligonucleotide comprises the modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises HLA. In some embodiments, the modified nucleoside comprises CeNA. In some embodiments, the modified nucleoside comprises a 2'-methoxyethyl group. In some embodiments, the modified nucleoside comprises a 2'-O-alkyl group. In some embodiments, the modified nucleoside comprises a 2'-O-allyl group. In some embodiments, the modified nucleoside comprises a 2'-fluoro group. In some embodiments, the modified nucleoside comprises a 2'-deoxy group. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises a 2'-O-methyl nucleoside. In some embodiments, the modified nucleoside comprises a 2'-deoxyfluoro nucleoside. In some embodiments, the modified nucleoside comprises a 2'-O-NMA nucleoside. In some embodiments, the modified nucleoside comprises a 2'-O-DMAEOE nucleoside. In some embodiments, the modified nucleoside comprises a 2'-O-aminopropyl (2'-O-AP) nucleoside. In some embodiments, the modified nucleoside comprises 2'-ara-F. In some embodiments, the modified nucleoside comprises one or more 2'fluoro modified nucleosides. In some embodiments, the modified nucleoside comprises a 2' O-alkyl modified nucleoside. Benefits of the modified nucleoside may include decreased toxicity or improved pharmacokinetics.

In some embodiments, the oligonucleotide comprises 1, 2, 3, 4, 5, 6, 7, 8, 9, 10, 11, 12, 13, 14, 15, 16, 17, 18, 19, 20, or 21 modified nucleosides, or a range of nucleosides defined by any two of the aforementioned numbers. In some embodiments, the oligonucleotide comprises no more than 19 modified nucleosides. In some embodiments, the oligonucleotide comprises no more than 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

In some embodiments, a hydrophobic moiety is attached to the oligonucleotide (e.g. a sense strand and/or an antisense strand of an siRNA, or an ASO). In some embodiments, a hydrophobic moiety is attached at a 3' terminus of the oligonucleotide. In some embodiments, a hydrophobic moiety is attached at a 5' terminus of the oligonucleotide. In some embodiments, the hydrophobic moiety comprises cholesterol.

In some embodiments, the composition comprises an oligonucleotide that inhibits the expression of ANGPTL7, wherein the oligonucleotide comprises a lipid attached at a 3' or 5' terminus of the oligonucleotide. In some embodiments, a lipid is attached at a 3' terminus of the oligonucleotide. In some embodiments, a lipid is attached at a 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof. In some embodiments, the lipid comprises cholesterol.

In some embodiments, the composition comprises an arginine-glycine-aspartic acid (RGD) peptide. In some embodiments, the RGD peptide is attached at a 3' terminus of the oligonucleotide. In some embodiments, the RGD peptide is attached at a 5' terminus of the oligonucleotide. In some embodiments, the composition comprises a sense strand, and the RGD peptide is attached to the sense strand (e.g. attached to a 5' end of the sense strand, or attached to a 3' end of the sense strand). In some embodiments, the composition comprises an antisense strand, and the RGD peptide is attached to the antisense strand (e.g. attached to a 5' end of the antisense strand, or attached to a 3' end of the antisense strand). In some embodiments, the composition comprises an RGD peptide attached at a 3' or 5' terminus of the oligonucleotide. In some embodiments, the oligonucleotide comprises an RGD peptide and a lipid attached at a 3' or 5' terminus of the oligonucleotide. In some embodiments, the RGD peptide comprises Cyclo(-Arg-Gly-Asp-D-Phe-Cys). In some embodiments, the RGD peptide comprises Cyclo(-Arg-Gly-Asp-D-Phe-Lys). In some embodiments, the RGD peptide comprises Cyclo(-Arg-Gly-Asp-D-Phe-azido). In some embodiments, the RGD peptide comprises an amino benzoic acid derived RGD. In some embodiments, the RGD peptide comprises Cyclo(-Arg-Gly-Asp-D-Phe-Cys), Cyclo(-Arg-Gly-Asp-D-Phe-Lys), Cyclo(-Arg-Gly-Asp-D-Phe-azido), an amino benzoic acid derived RGD, or a combination thereof. In some embodiments, the RGD peptide comprises multiple of such RGD peptides. For example, the RGD peptide may include 2, 3, or 4 RGD peptides.

In some embodiments, the oligonucleotide comprises a dsRNA agent described herein. In some embodiments, the oligonucleotide comprises an siRNA described herein. In some embodiments, the oligonucleotide comprises an antisense oligonucleotide described herein. In some embodiments, one or more nucleotides in the sense and/or antisense strand of an antisense oligonucleotide, dsRNA agent, or siRNA, is modified in accordance with any of the modifications or modification patterns described herein.

In some embodiments, a modification or modification pattern disclosed herein includes a cholesterol moiety.

dsRNA Agent

In some embodiments, the composition comprises a double-stranded RNAi (dsRNA) agent. In one aspect, provided herein is a dsRNA agent capable of inhibiting the expression of ANGPTL7. The dsRNA agent comprises a sense strand and an antisense strand. In some cases, the sense strand comprises a sequence at least about 80%, 85%, 90%, 95%, or 100% identical to a sequence selected from SEQ ID NOS: 1-4412. In some cases, the antisense strand comprises a sequence at least about 80%, 85%, 90%, 95%, or 100% identical to the reverse complement of the sense strand. In some cases, the antisense strand comprises a sequence at least about 80%, 85%, 90%, 95%, or 100% identical to a sequence selected from SEQ ID NOS: 1-4412.

In some cases, each strand of the dsRNA agent can range from 12-30 nucleotides in length. For example, each strand can be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex dsRNA. The duplex region of a dsRNA agent may be 12-30 nucleotide pairs in length. For example, the duplex region can be between 14-30 nucleotide pairs in length, 17-30 nucleotide pairs in length, 25-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region has a length of about 15, 16, 17, 18, 19, 20, 21, 22, 23, 24, 25, 26, and 27.

In some embodiments, the dsRNA agent comprises one or more overhang regions and/or capping groups at the 3'-end, or 5'-end, or both ends of a strand. In some cases, the overhang is about 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhang can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

Described herein, in some embodiments, are compositions comprising an RNA interference (RNAi) agent. In some embodiments, the RNAi agent is capable of inhibiting or modulating the expression of angiopoietin like 7 (ANGPTL7). In some embodiments, the RNAi agent comprises a siRNA described herein. In some embodiments, the RNAi agent comprises a double-stranded RNA (dsRNA). In some embodiments, the dsRNA comprises a sense strand and an antisense strand (such as a sense strand and/or an antisense strand described herein) In some embodiments, the antisense strand is complementary to a portion of a nucleic acid having the nucleoside sequence of SEQ ID NO: 11085. In some embodiments, the antisense strand is complementary to a portion of a nucleic acid having the nucleoside sequence of SEQ ID NO: 11086. In some embodiments, each strand has 14 to 30 nucleotides.

Described herein, in some embodiments, are compositions comprising an RNA interference (RNAi) agent capable of inhibiting or modulating the expression of angiopoietin like 7 (ANGPTL7); wherein the RNAi agent comprises a double-stranded RNA (dsRNA) comprising a sense strand and an antisense strand, the antisense strand being complementary to a portion of a nucleic acid having the nucleoside sequence of SEQ ID NO: 11085, and each strand having 14 to 30 nucleotides.

Described herein, in some embodiments, are compositions comprising an RNA interference (RNAi) agent capable of inhibiting or modulating the expression of angiopoietin like 7 (ANGPTL7); wherein the RNAi agent comprises a double-stranded RNA (dsRNA) comprising a sense strand and an antisense strand, the antisense strand being complementary to a portion of a nucleic acid having the nucleoside sequence of SEQ ID NO: 11086, and each strand having 14 to 30 nucleotides.

In some embodiments, the one or more modifications confers nuclease resistance upon the oligonucleotide (e.g. siRNA or antisense oligonucleotide). In some embodiments, the modification pattern confers nuclease resistance upon the oligonucleotide (e.g. siRNA or antisense oligonucleotide). For example, modification pattern 1S, 2S, 3S, 4S, 5S, 1AS, 2AS, 3AS, 4AS, or ASO1 may confer nuclease resistance.

dsRNA Modifications

The modifications described herein in reference to dsRNA agents may be applicable to antisense oligonucleotides described elsewhere herein. The modifications described herein in reference to dsRNA agents may be applicable to siRNA oligonucleotides described elsewhere herein.

In some embodiments, one or more nucleotides in the sense and/or antisense strand of a dsRNA agent is modified. In some cases, every nucleotide in the sense strand and antisense strand of the dsRNA is modified. The modifications on sense strand and antisense strand may each independently comprises at least two different modifications. In some cases, not every nucleotide in the sense and antisense strand is modified. In some cases, no nucleotide in the sense and/or antisense strand is modified.

In some cases, the sense strand contains at least one motif of three identical modifications on three consecutive nucleotides, where at least one of the motifs occurs at or near the cleavage site in the antisense strand. In some cases, the antisense strand contains at least one motif of three identical modifications on three consecutive nucleotides. The modification pattern of the antisense strand may be shifted by one or more nucleotides relative to the modification pattern of the sense strand.

In some cases, the sense strand contains at least two motifs of three identical modifications on three consecutive nucleotides, when at least one of the motifs occurs at the cleavage site in the strand and at least one of the motifs occurs at another portion of the strand that is separated from the motif at the cleavage site by at least one nucleotide. In some cases, the antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide.

In some cases, the sense strand contains at least two motifs of three identical modifications on three consecutive nucleotides, where at least one of the motifs occurs at the cleavage site in the strand and at least one of the motifs occurs at another portion of the strand that is separated from the motif at the cleavage site by at least one nucleotide. In some cases, the antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide. In some cases, the modification in the motif occurring at the cleavage site in the sense strand is different than the modification in the motif occurring at or near the cleavage site in the antisense strand.

In some cases, the sense strand contains at least one motif of three 2'-F modifications on three consecutive nucleotides, where at least one of the motifs occurs at the cleavage site in the strand. In some cases, the antisense strand contains at least one motif of three 2'-0-methyl modifications on three consecutive nucleotides.

In some cases, the sense strand comprises one or more motifs of three identical modifications on three consecutive nucleotides, where the one or more additional motifs occur at another portion of the strand that is separated from the three 2'-F modifications at the cleavage site by at least one nucleotide. The antisense strand may comprise one or more motifs of three identical modifications on three consecutive nucleotides, where the one or more additional motifs occur at another portion of the strand that is separated from the three 2'-0-methyl modifications by at least one nucleotide. In some cases at least one of the nucleotides having a 2'-F modification may form a base pair with one of the nucleotides having a 2'-0-methyl modification.

In some embodiments, if the dsRNA agent comprises an overhang, the nucleotides in the overhang region of the dsRNA agent can each independently be a modified or unmodified nucleotide. Non-limiting examples of modifications include, but are not limited to, a 2'-sugar modification, such as, 2-F 2'-Omethyl, thymidine (T), 2'-0-methoxyethyl-5-methyluridine (Teo), 2'-0-methoxyethyladenosine (Aeo), 2'-0-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

In some embodiments, if the dsRNA agent comprises an overhang, the 5'- and/or 3'-overhang at the sense strand, antisense strand or both strands of the dsRNA agent may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

In some embodiments, the modified dsRNA agent comprises one or more modified nucleotides including, but not limited to, 2'OMe nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, or combinations thereof. In some embodiments, the modified dsRNA agent comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, or combinations thereof. In certain instances, the modified dsRNA agent does not comprise 2'OMe-cytosine nucleotides. In some embodiments, the modified dsRNA agent comprises a hairpin loop structure.

In certain aspects, the modified dsRNA agent has an IC50 less than or equal to ten-fold that of the corresponding unmodified dsRNA (e.g., the modified dsRNA agent has an IC50 that is less than or equal to ten-times the IC50 of the corresponding unmodified dsRNA agent). In some embodiments, the modified dsRNA agent has an IC50 less than or equal to three-fold that of the corresponding unmodified dsRNA agent. In some embodiments, the modified dsRNA agent has an IC50 less than or equal to two-fold that of the corresponding unmodified dsRNA agent. It will be readily apparent to those of skill in the art that a dose response curve can be generated and the IC50 values for the modified dsRNA agent and the corresponding unmodified dsRNA agent can be readily determined using methods known to those of skill in the art.

The modified dsRNA agent may have 3' overhangs of one, two, three, four, or more nucleotides on one or both sides of the double-stranded region, or may lack overhangs (i.e., have blunt ends). In some cases, the modified dsRNA agent has 3' overhangs of two nucleotides on each side of the double-stranded region. In certain instances, the 3' overhang on the antisense strand has complementarity to the target sequence and the 3' overhang on the sense strand has complementarity to the complementary strand of the target sequence. In some cases, the 3' overhangs do not have complementarity to the target sequence or the complementary strand thereof. In some embodiments, the 3' overhangs comprise one, two, three, four, or more nucleotides such as 2'-deoxy(2'H) nucleotides. In some cases, the 3' overhangs comprise deoxythymidine (dT) nucleotides.

In some embodiments, the modified dsRNA agent comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region of the dsRNA agent. In some embodiments, less than about 30% (e.g., less than about 30%, 25%, 20%, 15%, 10%, or 5%) or from about 1% to about 30% (e.g., from about 1%-30%, 5%-30%, 10%-30%, 15%-30%, 20%-30%, or 25%-30%) of the nucleotides in the double-stranded region of the dsRNA agent comprise modified nucleotides.

In some embodiments, the dsRNA agent does not comprise phosphate backbone modifications, e.g., in the sense and/or antisense strand of the double-stranded region. In some embodiments, the modified dsRNA agent does not comprise 2'-deoxy nucleotides, e.g., in the sense and/or antisense strand of the double-stranded region. In certain instances, the nucleotide at the 3'-end of the double-stranded region in the sense and/or antisense strand is not a modified nucleotide. In certain instances, the nucleotides near the 3'-end (e.g., within one, two, three, or four nucleotides of the 3'-end) of the double-stranded region in the sense and/or antisense strand are not modified nucleotides.

The dsRNA agent may have 3' overhangs of one, two, three, four, or more nucleotides on one or both sides of the double-stranded region, or may lack overhangs (i.e., have blunt ends). In some cases, the dsRNA agent has 3' overhangs of two nucleotides on each side of the double-stranded region. In some embodiments, the 3' overhangs comprise one, two, three, four, or more nucleotides such as 2'-deoxy (2'H) nucleotides. In some cases, the 3' overhangs comprise deoxythymidine (dT) nucleotides.

The dsRNA agent may also have a blunt end, located at the 5'-end of the antisense strand (or the 3'-end of the sense strand) or vice versa. In some cases, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand may favor the guide strand loading into RISC process.

In some embodiments, the dsRNA agent may also have two blunt ends, at both ends of the dsRNA duplex.

In some embodiments, every nucleotide in the sense strand and antisense strand of the dsRNA agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone. In some embodiments, fewer than all nucleotides in the sense and antisense strand are modified.

As nucleic acids are polymers of subunits, in some cases, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in other cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a R A or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, purine nucleotides may be included in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-0-methyl modified instead of the ribosugar of the nucleobase, and modifications in the phosphate group, e.g., phosphorothioate modifications. In some cases, overhangs need not be homologous with the target sequence.

In some embodiments, each residue of the sense strand and antisense strand is independently modified with LNA, HNA, CeNA, 2'-methoxyethyl, 2'-O-methyl, 2'-0-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro.

In some embodiments, at least two different modifications are present on the sense strand and antisense strand. Those two modifications may be the 2'-O-methyl or 2'-fluoro modifications, or others.

In some embodiments, the sense strand and antisense strand each contains two differently modified nucleotides selected from 2'-0-methyl or 2'-fluoro.

In some embodiments, each residue of the sense strand and antisense strand is independently modified with 2'-0-methyl nucleotide, 2'-deoxyfluoro nucleotide, 2-O—N-methylacetamido (2'-0-NMA) nucleotide, a 2'-0-dimethylaminoethoxyethyl (2'-0-DMAEOE) nucleotide, 2'-0-aminopropyl (2'-0-AP) nucleotide, or 2'-ara-F nucleotide.

The type of modifications contained in an alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "AC AC AC . . . " "BDBDBD . . . " or "CDCDCD," etc.

In some embodiments, the dsRNA agent comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5 of the strand within the duplex region. As another example, the alternating motif in the sense strand may start with "AABBAABB" from 5'-3' of the strand and the alternating motif in the antisense strand may start with "BBAABBAA" from 3'-5 Of the strand within the duplex region, so that there is a complete or partial shift of the modification patterns between the sense strand and the antisense strand.

In some embodiments, the dsRNA agent comprises the pattern of the alternating motif of 2'-0-methyl modification and 2'-F modification on the sense strand initially has a shift relative to the pattern of the alternating motif of 2'-0-methyl modification and 2'-F modification on the antisense strand initially, i.e., the 2'-0-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification. The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand may enhance the gene silencing activity to the target gene.

The dsRNA agent may comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. In some cases, these terminal three nucleotides may be at the 3'-end of the antisense strand.

In some embodiments the sense strand of the dsRNA agent comprises 1-10 blocks of two to ten phosphorothioate or methylphosphonate internucleotide linkages separated by about 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of two phosphorothioate or methylphosphonate internucleotide linkages separated by about 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of three phosphorothioate or methylphosphonate internucleotide linkages separated by about 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of four phosphorothioate or methylphosphonate internucleotide linkages separated by about 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of five phosphorothioate or methylphosphonate internucleotide linkages separated by about 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of six phosphorothioate or methylphosphonate internucleotide linkages separated by about 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of seven phosphorothioate or methylphosphonate internucleotide linkages separated by about 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of eight phosphorothioate or methylphosphonate internucleotide linkages separated by about 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments the antisense strand of the dsRNA agent comprises two blocks of nine phosphorothioate or methylphosphonate internucleotide linkages separated by about 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In some embodiments, the dsRNA agent comprises one or more phosphorothioate or methylphosphonate internucleotide linkage modification within 1-10 of the termini position(s) of the sense and/or antisense strand. For example, at least about 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA agent comprises one or more phosphorothioate or methylphosphonate internucleotide linkage modification within 1-10 of the internal region of the duplex of each of the sense and/or antisense strand. For example, at least about 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA can optionally further comprise one or more phosphorothioate or methylphosphonate internucleotide linkage modification within 1-10 of the termini position(s).

In some embodiments, the dsRNA agent comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA agent comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end). In some embodiments, the dsRNA agent comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA agent comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA agent comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA agent comprises one phosphorothioate internucleotide linkage modification within position 1-5 (counting from the 5'-end), and two phosphorothioateinternucleotide linkage modifications at positions 1 and 2 and one phosphorothioate internucleotide linkage modification within positions 18-23 of the antisense strand (counting from the 5'-end).

In some embodiments, the dsRNA agent comprises two phosphorothioate internucleotide linkage modifications within position 1-5 (counting from the 5'-end), and one phosphorothioateinternucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA agent comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA agent comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, the dsRNA agent comprises mismatch(es) with the target, within the duplex, or combinations thereof. The mismatch can occur in an overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In some cases, in terms of promoting dissociation: A:U is preferred over G:C; G:U is preferred over G:C; and I:C is preferred over G:C (I=inosine). In some cases, mismatches, e.g., non-canonical or other than canonical pairings (as described elsewhere herein) are preferred over canonical (A:T, A:U, G:C) pairings; and pairings which include a universal base are preferred over canonical pairings. In some embodiments, the dsRNA agent comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. In some embodiments, at least one of the first 1, 2 or 3 base pair within the duplex region from the 5'-end of the antisense strand is an AU base pair. For example, the first base pair within the duplex region from the 5'-end of the antisense strand is an AU base pair.

In some embodiments, the dsRNA agent is conjugated to one or more carbohydrate moieties, which may optimize one or more properties of the dsRNA agent. In some cases, the carbohydrate moiety is attached to a modified subunit of the dsRNA agent. For example, the ribose sugar of one or more ribonucleotide subunits of a dsRNA agent can be replaced with another moiety, e.g., a non-carbohydrate (e.g., cyclic) carrier to which is attached a carbohydrate ligand. A ribonucleotide subunit in which the ribose sugar of the subunit is so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

In some embodiments, a ligand is attached to the dsRNA via a carrier. In some cases, the carriers include (i) at least one "backbone attachment point" or two "backbone attachment points" and (ii) at least one "tethering attachment point." In some cases, a "backbone attachment point" refers to a functional group, e.g. a hydroxy 1 group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP), in some embodiments, refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier may include a functional group, e.g., an amino group, or generally, provide a bond, that is suitable for incorporation or tethering of another chemical entity, e.g., a ligand to the constituent ring.

In some embodiments the dsRNA agent is conjugated to a ligand via a carrier, wherein the carrier can be cyclic group or acyclic group; e.g., the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; e.g., the acyclic group is selected from serinol backbone or diethanolamine backbone. The dsRNA agent may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments, the dsRNA is modified to promote stability. Stabilization of synthetic siRNA, such as a dsRNA herein, against rapid nuclease degradation may be regarded as a prerequisite for in vivo and therapeutic applications. This can be achieved using a variety of stabilization chemistries previously developed for other nucleic acid drugs, such as ribozymes and antisense molecules. These include chemical modifications to the native 2'-OH group in the ribose sugar backbone, such as 2'-O-methyl (2'OMe) and 2'-Fluoro (2'F) substitutions that can be readily introduced into siRNA as 2'-modified nucleotides during RNA synthesis. In some cases, the introduction of chemical modifications to native siRNA duplexes can have a negative impact on RNAi activity, therefore the design of chemically modified siRNA may require a stochastic screening approach to identify duplexes that retain potent gene silencing activity.

In some cases, when cleavage of the sense strand is inhibited, the endonucleolytic cleavage of target mRNA is impaired. In some cases, incorporation of a 2'-0-Me ribose to the Ago2 cleavage site in the sense strand inhibits RNAi. In some cases, with regard to phosphorothioate modifications, cleavage of the sense strand may be required for efficient RNAi.

In some cases, the dsRNA agent comprises 2'-F modified residues, e.g., at the Ago2 cleavage site. The modification may or may not be motif specific, e.g., one modification includes 2'-F modifications on all pyrimidines on both sense and antisense strands as long as pyrimidine residue is present, without any selectivity.

In some cases, the dsRNA agent comprises two 2'-F modified residues, e.g., at the Ago2 cleavage site, on the sense and/or antisense strand. In some cases, for each particular strand, either all pyrimidines or all purines are modified.

In some cases, the dsRNA agent comprises 2'-OMe modifications or various combinations of 2'-F, 2'-OMe and phosphorothioate modifications to stabilize the siRNA. In some cases, the residues at the cleavage site of the antisense strand are not be modified with 2'-OMe in order to increase the stability of the siRNA.

siRNAs

In some embodiments, the composition comprises an oligonucleotide that targets ANGPTL7, wherein the oligonucleotide comprises a small interfering RNA (siRNA). In some embodiments, the composition comprises an oligonucleotide that targets ANGPTL7, wherein the oligonucleotide comprises an siRNA comprising a sense strand and an antisense strand. In some embodiments, the siRNA comprises a double stranded agent described herein.

In some embodiments, the composition comprises an oligonucleotide that inhibits the expression of ANGPTL7, wherein the oligonucleotide comprises a siRNA comprising a sense strand and an antisense strand, wherein the sense strand is 14-30 nucleosides in length. In some embodiments, the composition comprises a sense strange that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the composition comprises an antisense strand is 14-30 nucleosides in length. In some embodiments, the composition comprises an antisense strange that is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers.

In some embodiments, the composition comprises an oligonucleotide that inhibits the expression of ANGPTL7, wherein the oligonucleotide comprises a siRNA comprising a sense strand and an antisense strand, each strand is independently about 14-30 nucleosides in length, and at least one of the sense strand and the antisense strand comprises a nucleoside sequence comprising about 14-30 contiguous nucleosides of a full-length human ANGPTL7 mRNA sequence such as SEQ ID NO: 11085. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 11085.

In some embodiments, the composition comprises an oligonucleotide that inhibits the expression of ANGPTL7, wherein the oligonucleotide comprises a siRNA comprising a sense strand and an antisense strand, each strand is independently about 14-30 nucleosides in length, and at least one of the sense strand and the antisense strand comprises a nucleoside sequence comprising about 14-30 contiguous nucleosides of a full-length human ANGPTL7 mRNA sequence such as SEQ ID NO: 11086. In some embodiments, at least one of the sense strand and the antisense strand comprise a nucleoside sequence comprising at least about 10, 11, 12, 13, 14, 15, 15, 17, 18, 19, 20, 21, 22, 23, 24, 25, 26, 27, 28, 29, 30, or more contiguous nucleosides of one of SEQ ID NO: 11086.

In some embodiments, the composition comprises an oligonucleotide that inhibits the expression of ANGPTL7, wherein the oligonucleotide comprises a siRNA comprising a sense strand and an antisense strand, wherein the sense strand and the antisense strand form a double-stranded RNA duplex. In some embodiments, the first base pair of the double-stranded RNA duplex is an AU base pair.

In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the composition comprises an oligonucleotide that inhibits the expression of ANGPTL7, wherein the oligonucleotide comprises a siRNA comprising a sense strand and an antisense strand, wherein the siRNA binds with a 19mer in a human ANGPTL7 mRNA. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a human ANGPTL7 mRNA.

In some embodiments, the composition comprises an oligonucleotide that inhibits the expression of ANGPTL7, wherein the oligonucleotide comprises a siRNA comprising a sense strand and an antisense strand, wherein the siRNA binds with a 17mer in a non-human primate ANGPTL7 mRNA. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a non-human primate ANGPTL7 mRNA.

In some embodiments, the composition comprises an oligonucleotide that inhibits the expression of ANGPTL7, wherein the oligonucleotide comprises a siRNA comprising a sense strand and an antisense strand, wherein the siRNA binds with a 19mer in a human ANGPTL7 mRNA, or a combination thereof. In some embodiments, the siRNA binds with a 12mer, a 13mer, a 14mer, a 15mer, a 16mer, a 17mer, and 18mer, a 19mer, a 20mer, a 21mer, a 22mer, a 23mer, a 24mer, or a 25mer in a human ANGPTL7 mRNA.

In some embodiments, the composition comprises an oligonucleotide that inhibits the expression of ANGPTL7, wherein the oligonucleotide comprises a siRNA comprising a sense strand and an antisense strand, wherein the siRNA binds with a human ANGPTL7 mRNA and less than or equal to 20 human off-targets, with no more than 2 mismatches in the antisense strand. In some embodiments, the siRNA binds with a human ANGPTL7 mRNA and less than or equal to 10 human off-targets, with no more than 2 mismatches in the antisense strand. In some embodiments, the siRNA binds with a human ANGPTL7 mRNA and less than or equal to 30 human off-targets, with no more than 2 mismatches in the antisense strand. In some embodiments, the siRNA binds with a human ANGPTL7 mRNA and less than or equal to 40 human off-targets, with no more than 2 mismatches in the antisense strand. In some embodiments, the siRNA binds with a human ANGPTL7 mRNA and less than or equal to 50 human off-targets, with no more than 2 mismatches in the antisense strand. In some embodiments, the siRNA binds with a human ANGPTL7 mRNA and less than or equal to 10 human off-targets, with no more than 3 mismatches in the antisense strand. In some embodiments, the siRNA binds with a human ANGPTL7 mRNA and less than or equal to 20 human off-targets, with no more than 3 mismatches in the antisense strand. In some embodiments, the siRNA binds with a human ANGPTL7 mRNA and less than or equal to 30 human off-targets, with no more than 3 mismatches in the antisense strand. In some embodiments, the siRNA binds with a human ANGPTL7 mRNA and less than or equal to 40 human off-targets, with no more than 3 mismatches in the antisense strand. In some embodiments, the siRNA binds with a human ANGPTL7 mRNA and less than or equal to 50 human off-targets, with no more than 3 mismatches in the antisense strand.

In some embodiments, the composition comprises an oligonucleotide that inhibits the expression of ANGPTL7, wherein the oligonucleotide comprises a siRNA comprising a sense strand and an antisense strand. In some embodiments, the siRNA binds with a human ANGPTL7 mRNA target site that does not harbor an SNP, with a minor allele frequency (MAF) greater or equal to 1% (pos. 2-18). In some embodiments, the MAF is greater or equal to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, the siRNA binds with a human ANGPTL7 mRNA with no more than 2 mismatches in the antisense strand. In some embodiments, the siRNA binds with a human ANGPTL7 mRNA target site that does not harbor an SNP, with a minor allele frequency (MAF) greater or equal to 1% (pos. 2-18). In some embodiments, the sense strand and the antisense strand each comprise a seed region that is not identical to a seed region of a human miRNA. In some embodiments, the sense strand comprises a seed region that is not identical to a seed region of a human miRNA. In some embodiments, the antisense strand comprises a seed region that is not identical to a seed region of a human miRNA.

In some embodiments, the composition comprises an oligonucleotide that inhibits the expression of ANGPTL7, wherein the oligonucleotide comprises a siRNA comprising a sense strand and an antisense strand. In some embodiments, the oligonucleotide comprises a nucleic acid sequence (e.g. a sense strand sequence or an antisense strand sequence). In some embodiments, the sense strand comprises a sense strand sequence. In some embodiments, the antisense strand comprises an antisense strand sequence. In some embodiments, the nucleic acid sequence comprises or consists of sequence at least 75% identical to of any one of SEQ ID NOs: 1-4412, at least 80% identical to of any one of SEQ ID NOs: 1-4412, at least 85% identical to of any one of SEQ ID NOs: 1-4412, at least 90% identical to of any one of SEQ ID NOs: 1-4412, or at least 95% identical to of any one of SEQ ID NOs: 1-4412. In some embodiments, the nucleic acid sequence comprises or consists of the sequence of any one of SEQ ID NOs: 1-4412, or a nucleic acid sequence thereof having 1, 2, 3, or 4 nucleoside substitutions, additions, or deletions. In some embodiments, the nucleic acid sequence comprises or consists of the sequence of any one of SEQ ID NOs: 1-4412, or a nucleic acid sequence thereof having 1 or 2 nucleoside substitutions, additions, or deletions. In some embodiments, the nucleic acid sequence comprises or consists of the sequence of any one of SEQ ID NOs: 1-4412. In some embodiments, the oligonucleotide comprises an overhang described herein. In some embodiments, the oligonucleotide comprises on or more modifications or modification patterns described herein.

In some embodiments, the oligonucleotide comprises or consists of any one of the siRNAs of siRNA subset A, or an siRNA thereof having 1 or 2 nucleoside substitutions, additions, or deletions. In some embodiments, the oligonucleotide comprises or consists of any one of the siRNAs of siRNA subset A. In some embodiments, the oligonucleotide comprises or consists of any one of the siRNAs of siRNA subset B, or an siRNA thereof having 1 or 2 nucleoside substitutions, additions, or deletions. In some embodiments, the oligonucleotide comprises or consists of any one of the siRNAs of siRNA subset B. In some embodiments, the oligonucleotide comprises or consists of any one of the siRNAs of siRNA subset C, or an siRNA thereof having 1 or 2 nucleoside substitutions, additions, or deletions. In some embodiments, the oligonucleotide comprises or consists of any one of the siRNAs of siRNA subset C. In some embodiments, the oligonucleotide comprises or consists of any one of the siRNAs of siRNA subset D, or an siRNA thereof having 1 or 2 nucleoside substitutions, additions, or deletions. In some embodiments, the oligonucleotide comprises or consists of any one of the siRNAs of siRNA subset D. In some embodiments, the oligonucleotide comprises or consists of any one of the siRNAs of siRNA subset E, or an siRNA thereof having 1 or 2 nucleoside substitutions, additions, or deletions. In some embodiments, the oligonucleotide comprises or consists of any one of the siRNAs of siRNA subset E.

In some embodiments, the sense strand sequence comprises or consists of sequence at least 75% identical to of any one of SEQ ID NOs: 1-2206, at least 80% identical to of any one of SEQ ID NOs: 1-2206, at least 85% identical to of any one of SEQ ID NOs: 1-2206, at least 90% identical to of any one of SEQ ID NOs: 1-2206, or at least 95% identical to of any one of SEQ ID NOs: 1-2206. In some embodiments, the sense strand sequence comprises or consists of the sequence of any one of SEQ ID NOs: 1-2206, or a sense strand sequence thereof having 1, 2, 3, or 4 nucleoside substitutions, additions, or deletions. In some embodiments, the sense strand sequence comprises or consists of the sequence of any one of SEQ ID NOs: 1-2206, or a sense strand sequence thereof having 1 or 2 nucleoside substitutions, additions, or deletions. In some embodiments, the sense strand sequence comprises or consists of the sequence of any one of SEQ ID NOs: 1-2206. In some embodiments, the sense strand comprises an overhang described herein. In some embodiments, the sense strand comprises on or more modifications or modification patterns described herein.

In some embodiments, the sense strand sequence comprises or consists of sequence at least 75% identical, at least 80% identical, at least 85% identical, at least 90% identical, or at least 95% identical to of any one of SEQ ID NOs: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the sense strand sequence comprises or consists of the sequence of any one of SEQ ID NOs: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192, or a sense strand sequence thereof having 1, 2, 3, or 4 nucleoside substitutions, additions, or deletions. In some embodiments, the sense strand sequence comprises or consists of the sequence of any one of SEQ ID NOs: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192, or a sense strand sequence thereof having 1 or 2 nucleoside substitutions, additions, or deletions. In some embodiments, the sense strand sequence comprises or consists of the sequence of any one of SEQ ID NOs: 7, 92, 93, 94, 115, 117, 118, 120, 206, 207, 256, 645, 646, 657, 740, 741, 743, 923, 943, 948, 1021, 1092, 1094, 1097, 1105, 1107, 1132, 1198, 1201, 1424, 1425, 1429, 1434, 1436, 1438, 1537, 1541, 1639, 1654, 1691, 1693, 1762, 1764, 1765, 1794, 1796, 1797, 1968, 1969, 2030, 2085, 2087, 2091, 2095, 2099, or 2192. In some embodiments, the sense strand comprises an overhang described herein.

In some embodiments, the sense strand comprises or consists of a sense strand of any one of the siRNAs of siRNA subset A, or a sense strand thereof having 1 or 2 nucleoside substitutions, additions, or deletions. In some embodiments, the sense strand comprises or consists of a sense strand of any one of the siRNAs of siRNA subset A. In some embodiments, the sense strand comprises or consists of a sense strand of any one of the siRNAs of siRNA subset B, or a sense strand thereof having 1 or 2 nucleoside substitutions, additions, or deletions. In some embodiments, the sense strand comprises or consists of a sense strand of any one of the siRNAs of siRNA subset B. In some embodiments, the sense strand comprises or consists of a sense strand of any one of the siRNAs of siRNA subset C, or a sense strand thereof having 1 or 2 nucleoside substitutions, additions, or deletions. In some embodiments, the sense strand comprises or consists of a sense strand of any one of the siRNAs of siRNA subset C. In some embodiments, the sense strand comprises or consists of a sense strand of any one of the siRNAs of siRNA subset D, or a sense strand thereof having 1 or 2 nucleoside substitutions, additions, or deletions. In some embodiments, the sense strand comprises or consists of a sense strand of any one of the siRNAs of siRNA subset D. In some embodiments, the sense strand comprises or consists of a sense strand of any one of the siRNAs of siRNA subset E, or a sense strand thereof having 1 or 2 nucleoside substitutions, additions, or deletions. In some embodiments, the sense strand comprises or consists of a sense strand of any one of the siRNAs of siRNA subset E.

In some embodiments, the sense strand sequence comprises or consists of the sequence of SEQ ID NO: 11089, or a sense strand sequence thereof having 1 or 2 nucleoside substitutions, additions, or deletions. In some embodiments, the sense strand sequence comprises or consists of the sequence of SEQ ID NO: 11089.

In some embodiments, the antisense strand sequence comprises or consists of sequence at least 75% identical to of any one of SEQ ID NOs: 2207-4412, at least 80% identical to of any one of SEQ ID NOs: 2207-4412, at least 85% identical to of any one of SEQ ID NOs: 2207-4412, at least 90% identical to of any one of SEQ ID NOs: 2207-4412, or at least 95% identical to of any one of SEQ ID NOs: 2207-4412. In some embodiments, the antisense strand sequence comprises or consists of the sequence of any one of SEQ ID NOs: 2207-4412, or an antisense strand sequence thereof having 1, 2, 3, or 4 nucleoside substitutions, additions, or deletions. In some embodiments, the antisense strand sequence comprises or consists of the sequence of any one of SEQ ID NOs: 2207-4412, or an antisense strand sequence thereof having 1 or 2 nucleoside substitutions, additions, or deletions. In some embodiments, the antisense strand sequence comprises or consists of the sequence of any one of SEQ ID NOs: 2207-4412. In some embodiments, the antisense strand comprises an overhang described herein. In some embodiments, the antisense strand comprises on or more modifications or modification patterns described herein.

In some embodiments, the antisense strand sequence comprises or consists of sequence at least 75% identical, at least 80% identical, at least 85% identical, at least 90% identical, or at least 95% identical to of any one of SEQ ID NOs: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the antisense strand sequence comprises or consists of the sequence of any one of SEQ ID NOs: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398, or an antisense strand sequence thereof having 1, 2, 3, or 4 nucleoside substitutions, additions, or deletions. In some embodiments, the antisense strand sequence comprises or consists of the sequence of any one of SEQ ID NOs: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398, or an antisense strand sequence thereof having 1 or 2 nucleoside substitutions, additions, or deletions. In some embodiments, the antisense strand sequence comprises or consists of the sequence of any one of SEQ ID NOs: 2213, 2298, 2299, 2300, 2321, 2323, 2324, 2326, 2412, 2413, 2462, 2851, 2852, 2863, 2946, 2947, 2949, 3129, 3149, 3154, 3227, 3298, 3300, 3303, 3311, 3313, 3338, 3404, 3407, 3630, 3631, 3635, 3640, 3642, 3644, 3743, 3747, 3845, 3860, 3897, 3899, 3968, 3970, 3971, 4000, 4002, 4003, 4174, 4175, 4236, 4291, 4293, 4297, 4301, 4305, or 4398. In some embodiments, the antisense strand comprises an overhang described herein. In some embodiments, the antisense strand comprises on or more modifications or modification patterns described herein.

In some embodiments, the antisense strand comprises or consists of an antisense strand of any one of the siRNAs of siRNA subset A, or an antisense strand thereof having 1 or 2 nucleoside substitutions, additions, or deletions. In some embodiments, the antisense strand comprises or consists of an antisense strand of any one of the siRNAs of siRNA subset A. In some embodiments, the antisense strand comprises or consists of an antisense strand of any one of the siRNAs of siRNA subset B, or an antisense strand thereof having 1 or 2 nucleoside substitutions, additions, or deletions. In some embodiments, the antisense strand comprises or consists of an antisense strand of any one of the siRNAs of siRNA subset B. In some embodiments, the antisense strand comprises or consists of an antisense strand of any one of the siRNAs of siRNA subset C, or an antisense strand thereof having 1 or 2 nucleoside substitutions, additions, or deletions. In some embodiments, the antisense strand comprises or consists of an antisense strand of any one of the siRNAs of siRNA subset C. In some embodiments, the antisense strand comprises or consists of an antisense strand of any one of the siRNAs of siRNA subset D, or an antisense strand thereof having 1 or 2 nucleoside substitutions, additions, or deletions. In some embodiments, the antisense strand comprises or consists of an antisense strand of any one of the siRNAs of siRNA subset D. In some embodiments, the antisense strand comprises or consists of an antisense strand of any one of the siRNAs of siRNA subset E, or an antisense strand thereof having 1 or 2 nucleoside substitutions, additions, or deletions. In some embodiments, the antisense strand comprises or consists of an antisense strand of any one of the siRNAs of siRNA subset E.

In some embodiments, the antisense strand sequence comprises or consists of the sequence of SEQ ID NO: 11090, or an antisense strand sequence thereof having 1 or 2 nucleoside substitutions, additions, or deletions. In some embodiments, the antisense strand sequence comprises or consists of the sequence of SEQ ID NO: 11090.

siRNA Modification Patterns

The oligonucleotides described herein (e.g. siRNAs, antisense oligonucleotides, sense strands, antisense strands, siRNA agents, or dsRNA agents) may include any modification pattern disclosed herein, including but not limited to any one or more of modification patterns 1S-5S, 1AS-4AS, or ASO1.

In some embodiments, the composition comprises an oligonucleotide that inhibits the expression of ANGPTL7 wherein the oligonucleotide comprises a siRNA comprising a sense strand and an antisense strand, wherein the sense strand comprises modification pattern 1S: 5' NfsnsNfnNfnNfNfNfnNfnNfnNfnNfnNfsnsn-3' (SEQ ID NO: 11381), wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5' nsnsnnNfnNfNfNfnnnnnnnnnnsnsn-3' (SEQ ID NO: 11382), wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5' nsnsnnNfnNfnNfnnnnnnnnnnsnsn-3' (SEQ ID NO: 11383), wherein "Nf" is a 2' fluoro-modified nucleoside, "n" is a 2' 0-methyl modified nucleoside, and "s" is a phosphorothioate linkage. In some embodiments, the sense strand comprises modification pattern 4S: 5' NfsnsNfnNfnNfNfNfnNfnNfnNfnNfnNfsnsnN-Lipid-3' (SEQ ID NO: 11384), wherein "Nf" is a 2' fluoro-modified nucleoside, "n" is a 2' O-methyl modified nucleoside, "s" is a phosphorothioate linkage, and N comprises a nucleoside. In some embodiments, the sense strand comprises modification pattern 5S: 5'-nsnsnnNfnNfNfNfnnnnnnnnnnsnsnN-Lipid-3' (SEQ ID NO: 11385), wherein "Nf" is a 2' fluoro-modified nucleoside, "n" is a 2' 0-methyl modified nucleoside, "s" is a phosphorothioate linkage, and N comprises a nucleoside.

In some embodiments, the composition comprises an oligonucleotide that inhibits the expression of ANGPTL7 wherein the oligonucleotide comprises a siRNA comprising a sense strand and an antisense strand, wherein the antisense strand comprises modification pattern 1AS: 5'-nsNfsnNfnNfnNfnNfnNfnnnNfnNfnNfsnsn-3' (SEQ ID NO: 11386), wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5' nsNfsnnnNfnNfNfnnnnNfnNfnnnsnsn-3' (SEQ ID NO: 11387), wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5' nsNfsnnnNfnnnnnnNfnNfnnnsnsn-3' (SEQ ID NO: 11388), wherein "Nf" is a 2' fluoro-modified nucleoside, "n" is a 2' O-methyl modified nucleoside, and "s" is a phosphorothioate linkage. In some embodiments, the antisense strand comprises modification pattern 4AS: 5' nsNfsnNfnNfnnnnnnnnNfnNfnnnsnsn 3' (SEQ ID NO: 11389), wherein "Nf" is a 2' fluoro-modified nucleoside, "n" is a 2' O-methyl modified nucleoside, and "s" is a phosphorothioate linkage.

In some embodiments, the composition comprises an oligonucleotide that inhibits the expression of ANGPTL7 wherein the oligonucleotide comprises a siRNA comprising a sense strand and an antisense strand, wherein the sense strand comprises pattern 1S and the antisense strand comprises pattern 1AS, 2AS, 3AS, or 4AS. In some embodiments, the sense strand comprises pattern 2S and the antisense strand comprises pattern 1AS, 2AS, 3AS, or 4AS. In some embodiments, the sense strand comprises pattern 3S and the antisense strand comprises pattern 1AS, 2AS, 3AS, or 4AS. In some embodiments, the sense strand comprises pattern 4S and the antisense strand comprises pattern 1AS, 2AS, 3AS, or 4AS. In some embodiments, the sense strand comprises modification pattern 1AS, 2AS, 3AS, or 4AS. In some embodiments, the antisense strand comprises modification pattern 1S, 2S, 3S, 4S, or 5S. In some embodiments, the sense strand or the antisense strand comprises modification pattern ASO1.

In some embodiments, the composition comprises an oligonucleotide that inhibits the expression of ANGPTL7, wherein the oligonucleotide comprises a siRNA comprising a sense strand and an antisense strand, wherein the sense strand and/or the antisense strand comprises one or more modifications or modification patterns. In some embodiments, the oligonucleotide comprises a nucleic acid sequence (e.g. a sense strand sequence or an antisense strand sequence) with one or more modifications or modification patterns.

In some embodiments, the nucleic acid sequence comprises or consists of sequence at least 75% identical to of any one of SEQ ID NOs: 11093-11332, at least 80% identical to of any one of SEQ ID NOs: 11093-11332, at least 85% identical to of any one of SEQ ID NOs: 11093-11332, at least 90% identical to of any one of SEQ ID NOs: 11093-11332, or at least 95% identical to of any one of SEQ ID NOs: 11093-11332. In some embodiments, the nucleic acid sequence comprises or consists of the sequence of any one of SEQ ID NOs: 11093-11332, or a sequence thereof having 1, 2, 3, or 4 nucleoside substitutions, additions, or deletions. In some embodiments, the nucleic acid sequence comprises or consists of the sequence of any one of SEQ ID NOs: 11093-11332, or a sequence thereof having 1 or 2 nucleoside substitutions, additions, or deletions. In some embodiments, the nucleic acid sequence comprises or consists of the sequence of any one of SEQ ID NOs: 11093-11332. In some embodiments, the nucleic acid sequence is an unmodified version of a nucleic acid sequence described herein. In some embodiments, the nucleic acid sequence has more or different sequence modifications than a nucleic acid sequence described herein.

In some embodiments, the nucleic acid sequence comprises or consists of sequence at least 75% identical to of any one of SEQ ID NOs: 11333-11376, at least 80% identical to of any one of SEQ ID NOs: 11333-11376, at least 85% identical to of any one of SEQ ID NOs: 11333-11376, at least 90% identical to of any one of SEQ ID NOs: 11333-11376, or at least 95% identical to of any one of SEQ ID NOs: 11333-11376. In some embodiments, the nucleic acid sequence comprises or consists of the sequence of any one of SEQ ID NOs: 11333-11376, or a sequence thereof having 1, 2, 3, or 4 nucleoside substitutions, additions, or deletions. In some embodiments, the nucleic acid sequence comprises or consists of the sequence of any one of SEQ ID NOs: 11333-11376, or a sequence thereof having 1 or 2 nucleoside substitutions, additions, or deletions. In some embodiments, the nucleic acid sequence comprises or consists of the sequence of any one of SEQ ID NOs: 11333-11376. In some embodiments, the nucleic acid sequence lacks the sequence modifications, or has different or additional sequence modifications, but otherwise is similar to a sequence described herein.

In some embodiments, the oligonucleotide comprises or consists of any one of the siRNAs disclosed in any of Tables 5-13, or an siRNA thereof having 1 or 2 nucleoside substitutions, additions, or deletions. In some embodiments, the oligonucleotide comprises or consists of any one of the siRNAs disclosed in any of Tables 5-13. In some embodiments, the oligonucleotide comprises a nucleoside sequence at least 85% identical the sense strand sequence of an siRNA in any of Tables 5-13.

In some embodiments, the oligonucleotide comprises or consists of any one of the siRNAs disclosed in any of Tables 5-10, or an siRNA thereof having 1 or 2 nucleoside substitutions, additions, or deletions. In some embodiments, the oligonucleotide comprises or consists of any one of the siRNAs disclosed in any of Tables 5-10. In some embodiments, the oligonucleotide comprises or consists of any one of the siRNAs disclosed in any of Tables 5-10 where a relative ANGPTL expression in the table is below 1, or an siRNA thereof having 1 or 2 nucleoside substitutions, additions, or deletions. In some embodiments, the oligonucleotide comprises or consists of any one of the siRNAs disclosed in any of Tables 5-10 where a relative ANGPTL expression in the table is below 1. In some embodiments, the oligonucleotide comprises or consists of any one of the siRNAs disclosed in any of Tables 5-10 where a relative ANGPTL expression of the siRNA in the table is below the expression of a negative control in the table, or an siRNA thereof having 1 or 2 nucleoside substitutions, additions, or deletions. In some embodiments, the oligonucleotide comprises or consists of any one of the siRNAs disclosed in any of Tables 5-10 where a relative ANGPTL expression of the siRNA in the table is below the expression of a negative control in the table. In some embodiments, the oligonucleotide comprises or consists of any one of the siRNAs disclosed in any of Tables 5-10 where a relative ANGPTL expression in the table is below 0.5, or an siRNA thereof having 1 or 2 nucleoside substitutions, additions, or deletions. In some embodiments, the oligonucleotide comprises or consists of any one of the siRNAs disclosed in any of Tables 5-10 where a relative ANGPTL expression in the table is below 0.5. In some embodiments, the oligonucleotide comprises or consists of any one of the siRNAs disclosed in any of Tables 5-10 where a relative ANGPTL expression in the table is below 0.25, or an siRNA thereof having 1 or 2 nucleoside substitutions, additions, or deletions. In some embodiments, the oligonucleotide comprises or consists of any one of the siRNAs disclosed in any of Tables 5-10 where a relative ANGPTL expression in the table is below 0.25. In some embodiments, the oligonucleotide comprises or consists of an unmodified version of any one of the siRNAs disclosed in any of Tables 5-10. In some embodiments, the oligonucleotide comprises or consists of an siRNA with the nucleic acid sequence of any one of the siRNAs disclosed in any of Tables 5-10, but with one or more additional or different modifications, or with a different modification pattern. In some embodiments, the nucleic acid sequence lacks the sequence modifications, or has different or additional sequence modifications, but otherwise is similar to a sequence described herein.

In some embodiments, the sense strand comprises a sense strand sequence with one or more modifications or modification patterns. In some embodiments, the sense strand sequence comprises or consists of sequence at least 75% identical to of any one of SEQ ID NOs: 11093-11212, at least 80% identical to of any one of SEQ ID NOs: 11093-11212, at least 85% identical to of any one of SEQ ID NOs: 11093-11212, at least 90% identical to of any one of SEQ ID NOs: 11093-11212, or at least 95% identical to of any one of SEQ ID NOs: 11093-11212. In some embodiments, the sense strand sequence comprises or consists of the sequence of any one of SEQ ID NOs: 11093-11212, or a sequence thereof having 1, 2, 3, or 4 nucleoside substitutions, additions, or deletions. In some embodiments, the sense strand sequence comprises or consists of the sequence of any one of SEQ ID NOs: 11093-11212, or a sequence thereof having 1 or 2 nucleoside substitutions, additions, or deletions. In some embodiments, the sense strand sequence comprises or consists of the sequence of any one of SEQ ID NOs: 11093-11212. In some embodiments, the sense strand sequence is an unmodified version of a sense strand sequence described herein. In some embodiments, the sense strand sequence has more or different sequence modifications than a sense strand sequence described herein.

In some embodiments, the sense strand sequence comprises or consists of sequence at least 75% identical to of any one of SEQ ID NOs: 11333-11354, at least 80% identical to of any one of SEQ ID NOs: 11333-11354, at least 85% identical to of any one of SEQ ID NOs: 11333-11354, at least 90% identical to of any one of SEQ ID NOs: 11333-11354, or at least 95% identical to of any one of SEQ ID NOs: 11333-11354. In some embodiments, the sense strand sequence comprises or consists of the sequence of any one of SEQ ID NOs: 11333-11354, or a sequence thereof having 1, 2, 3, or 4 nucleoside substitutions, additions, or deletions. In some embodiments, the sense strand sequence comprises or consists of the sequence of any one of SEQ ID NOs: 11333-11354, or a sequence thereof having 1 or 2 nucleoside substitutions, additions, or deletions. In some embodiments, the sense strand sequence comprises or consists of the sequence of any one of SEQ ID NOs: 11333-11354. In some embodiments, the sense strand sequence lacks the sequence modifications, or has different or additional sequence modifications, but otherwise is similar to a sequence described herein.

In some embodiments, the sense strand sequence comprises or consists of a sense strand sequence of a sense strand sequence of any one of the siRNAs disclosed in any of Tables 5-13, or an siRNA thereof having 1 or 2 nucleoside substitutions, additions, or deletions. In some embodiments, the sense strand sequence comprises or consists of a sense strand sequence of a sense strand sequence of any one of the siRNAs disclosed in any of Tables 5-13. In some embodiments, the sense strand sequence comprises or consists of a sequence at least 75% identical, at least 80% identical, at least 85% identical, at least 90% identical, or at least 95% identical to a sense strand sequence of an siRNA in any of Tables 5-13.

In some embodiments, the sense strand sequence comprises or consists of a sense strand sequence of a sense strand sequence of any one of the siRNAs disclosed in any of Tables 5-10, or an siRNA thereof having 1 or 2 nucleoside substitutions, additions, or deletions. In some embodiments, the sense strand sequence comprises or consists of a sense strand sequence of any one of the siRNAs disclosed in any of Tables 5-10. In some embodiments, the sense strand sequence comprises or consists of a sense strand sequence of any one of the siRNAs disclosed in any of Tables 5-10 where a relative ANGPTL expression in the table is below 1, or an siRNA thereof having 1 or 2 nucleoside substitutions, additions, or deletions. In some embodiments, the sense strand sequence comprises or consists of a sense strand sequence of any one of the siRNAs disclosed in any of Tables 5-10 where a relative ANGPTL expression in the table is below 1. In some embodiments, the sense strand sequence comprises or consists of a sense strand sequence of any one of the siRNAs disclosed in any of Tables 5-10 where a relative ANGPTL expression of the siRNA in the table is below the expression of a negative control in the table, or an siRNA thereof having 1 or 2 nucleoside substitutions, additions, or deletions. In some embodiments, the sense strand sequence comprises or consists of a sense strand sequence of any one of the siRNAs disclosed in any of Tables 5-10 where a relative ANGPTL expression of the siRNA in the table is below the expression of a negative control in the table. In some embodiments, the sense strand sequence comprises or consists of a sense strand sequence of any one of the siRNAs disclosed in any of Tables 5-10 where a relative ANGPTL expression in the table is below 0.5, or an siRNA thereof having 1 or 2 nucleoside substitutions, additions, or deletions. In some embodiments, the sense strand sequence comprises or consists of a sense strand sequence of any one of the siRNAs disclosed in any of Tables 5-10 where a relative ANGPTL expression in the table is below 0.5. In some embodiments, the sense strand sequence comprises or consists of a sense strand sequence of any one of the siRNAs disclosed in any of Tables 5-10 where a relative ANGPTL expression in the table is below 0.25, or an siRNA thereof having 1 or 2 nucleoside substitutions, additions, or deletions. In some embodiments, the sense strand sequence comprises or consists of a sense strand sequence of any one of the siRNAs disclosed in any of Tables 5-10 where a relative ANGPTL expression in the table is below 0.25. In some embodiments, the sense strand sequence comprises or consists of an unmodified version of a sense strand sequence of any one of the siRNAs disclosed in any of Tables 5-10. In some embodiments, the sense strand sequence comprises or consists of an siRNA with the sense strand sequence of a sense strand sequence of any one of the siRNAs disclosed in any of Tables 5-10, but with one or more additional or different modifications, or with a different modification pattern. In some embodiments, the sense strand sequence lacks the sequence modifications, or has different or additional sequence modifications, but otherwise is similar to a sequence described herein.

In some embodiments, the sense strand sequence comprises or consists of a sense strand sequence of any one of the siRNAs disclosed in Table 5, or an siRNA thereof having 1 or 2 nucleoside substitutions, additions, or deletions. In some embodiments, the sense strand sequence comprises or consists of a sense strand sequence of any one of the siRNAs disclosed in Table 5. In some embodiments, the sense strand sequence comprises or consists of a sense strand sequence of any one of the siRNAs disclosed in Table 5 where the relative ANGPTL expression in the table is below 1, or an siRNA thereof having 1 or 2 nucleoside substitutions, additions, or deletions. In some embodiments, the sense strand sequence comprises or consists of a sense strand sequence of any one of the siRNAs disclosed in Table 5 where the relative ANGPTL expression in the table is below 1. In some embodiments, the sense strand sequence comprises or consists of a sense strand sequence of any one of the siRNAs disclosed in Table 5 where the relative ANGPTL expression of the siRNA in the table is below the expression of the negative control siRNA in the table (e.g. below a relative expression level of 0.67), or an siRNA thereof having 1 or 2 nucleoside substitutions, additions, or deletions. In some embodiments, the sense strand sequence comprises or consists of a sense strand sequence of any one of the siRNAs disclosed in Table 5 where the relative ANGPTL expression of the siRNA in the table is below the expression of the negative control siRNA in the table (e.g. below a relative expression level of 0.67). In some embodiments, the sense strand sequence comprises or consists of a sense strand sequence of any one of the siRNAs disclosed in Table 5 where the relative ANGPTL expression in the table is below 0.5, or an siRNA thereof having 1 or 2 nucleoside substitutions, additions, or deletions. In some embodiments, the sense strand sequence comprises or consists of a sense strand sequence of any one of the siRNAs disclosed in Table 5 where the relative ANGPTL expression in the table is below 0.5. In some embodiments, the sense strand sequence comprises or consists of a sense strand sequence of any one of the siRNAs disclosed in Table 5 where the relative ANGPTL expression in the table is below 0.25, or an siRNA thereof having 1 or 2 nucleoside substitutions, additions, or deletions. In some embodiments, the sense strand sequence comprises or consists of a sense strand sequence of any one of the siRNAs disclosed in Table 5 where the relative ANGPTL expression in the table is below 0.25. In some embodiments, the sense strand sequence comprises or consists of an unmodified version of a sense strand sequence of any one of the siRNAs disclosed in Table 5. In some embodiments, the sense strand sequence comprises or consists of an siRNA with the sense strand sequence of a sense strand sequence of any one of the siRNAs disclosed in Table 5, but with one or more additional or different modifications, or with a different modification pattern. In some embodiments, the sense strand sequence lacks the sequence modifications, or has different or additional sequence modifications, but otherwise is similar to a sequence described herein.

In some embodiments, the sense strand sequence is incorporated into an siRNA that downregulates ANGPTL7. In some embodiments, the sense strand sequence comprises or consists of a sense strand sequence of any one of SEQ ID NOs: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212, or an siRNA thereof having 1 or 2 nucleoside substitutions, additions, or deletions. In some embodiments, the sense strand sequence comprises or consists of a sense strand sequence of any one of SEQ ID NOs: 11094, 11095, 11096, 11097, 11098, 11099, 11100, 11101, 11102, 11103, 11104, 11105, 11106, 11109, 11110, 11113, 11116, 11118, 11119, 11121, 11122, 11123, 11124, 11125, 11126, 11127, 11128, 11129, 11130, 11132, 11133, 11134, 11135, 11136, 11139, 11140, 11143, 11144, 11145, 11146, 11147, 11148, 11149, 11150, 11151, 11152, 11153, 11154, 11155, 11156, 11157, 11158, 11159, 11160, 11161, 11162, 11163, 11164, 11165, 11166, 11167, 11168, 11169, 11170, 11171, 11172, 11173, 11174, 11175, 11176, 11177, 11178, 11180, 11181, 11182, 11183, 11184, 11185, 11186, 11187, 11188, 11189, 11191, 11193, 11195, 11196, 11198, 11199, 11200, 11201, 11203, 11204, 11205, 11207, 11208, 11210, 11211, or 11212.

In some embodiments, the sense strand sequence comprises or consists of a sense strand sequence of any one of the siRNAs disclosed in Table 6, or an siRNA thereof having 1 or 2 nucleoside substitutions, additions, or deletions. In some embodiments, the sense strand sequence comprises or consists of a sense strand sequence of any one of the siRNAs disclosed in Table 6. In some embodiments, the sense strand sequence comprises or consists of a sense strand sequence of any one of the siRNAs disclosed in Table 6 where the relative ANGPTL expression in the table is below 1, or an siRNA thereof having 1 or 2 nucleoside substitutions, additions, or deletions. In some embodiments, the sense strand sequence comprises or consists of a sense strand sequence of any one of the siRNAs disclosed in Table 6 where the relative ANGPTL expression in the table is below 1. In some embodiments, the sense strand sequence comprises or consists of a sense strand sequence of any one of the siRNAs disclosed in Table 6 where the relative ANGPTL expression of the siRNA in the table is below the expression of the negative control siRNA in the table (e.g. below a relative expression level of 1.06), or an siRNA thereof having 1 or 2 nucleoside substitutions, additions, or deletions. In some embodiments, the sense strand sequence comprises or consists of a sense strand sequence of any one of the siRNAs disclosed in Table 6 where the relative ANGPTL expression of the siRNA in the table is below the expression of the negative control siRNA in the table (e.g. below a relative expression level of 1.06). In some embodiments, the sense strand sequence comprises or consists of a sense strand sequence of any one of the siRNAs disclosed in Table 6 where the relative ANGPTL expression in the table is below 0.5, or an siRNA thereof having 1 or 2 nucleoside substitutions, additions, or deletions. In some embodiments, the sense strand sequence comprises or consists of a sense strand sequence of any one of the siRNAs disclosed in Table 6 where the relative ANGPTL expression in the table is below 0.5. In some embodiments, the sense strand sequence comprises or consists of a sense strand sequence of any one of the siRNAs disclosed in Table 6 where the relative ANGPTL expression in the table is below 0.25, or an siRNA thereof having 1 or 2 nucleoside substitutions, additions, or deletions. In some embodiments, the sense strand sequence comprises or consists of a sense strand sequence of any one of the siRNAs disclosed in Table 6 where the relative ANGPTL expression in the table is below 0.25. In some embodiments, the sense strand sequence comprises or consists of an unmodified version of a sense strand sequence of any one of the siRNAs disclosed in Table 6. In some embodiments, the sense strand sequence comprises or consists of an siRNA with the sense strand sequence of a sense strand sequence of any one of the siRNAs disclosed in Table 6, but with one or more additional or different modifications, or with a different modification pattern. In some embodiments, the sense strand sequence lacks the sequence modifications, or has different or additional sequence modifications, but otherwise is similar to a sequence described herein.

In some embodiments, the sense strand sequence comprises or consists of a sense strand sequence of any one of the siRNAs disclosed in Table 7, or an siRNA thereof having 1 or 2 nucleoside substitutions, additions, or deletions. In some embodiments, the sense strand sequence comprises or consists of a sense strand sequence of any one of the siRNAs disclosed in Table 7. In some embodiments, the sense strand sequence comprises or consists of a sense strand sequence of any one of the siRNAs disclosed in Table 7 where the relative ANGPTL expression at 1 nM in the table is below 1, or an siRNA thereof having 1 or 2 nucleoside substitutions, additions, or deletions. In some embodiments, the sense strand sequence comprises or consists of a sense strand sequence of any one of the siRNAs disclosed in Table 7 where the relative ANGPTL expression at 1 nM in the table is below 1. In some embodiments, the sense strand sequence comprises or consists of a sense strand sequence of any one of the siRNAs disclosed in Table 7 where the relative ANGPTL expression at 1 nM of the siRNA in the table is below the expression of the negative control siRNA in the table (e.g. below a relative expression level of 0.66), or an siRNA thereof having 1 or 2 nucleoside substitutions, additions, or deletions. In some embodiments, the sense strand sequence comprises or consists of a sense strand sequence of any one of the siRNAs disclosed in Table 7 where the relative ANGPTL expression at 1 nM of the siRNA in the table is below the expression of the negative control siRNA in the table (e.g. below a relative expression level of 0.66). In some embodiments, the sense strand sequence comprises or consists of a sense strand sequence of any one of the siRNAs disclosed in Table 7 where the relative ANGPTL expression at 1 nM in the table is below 0.5, or an siRNA thereof having 1 or 2 nucleoside substitutions, additions, or deletions. In some embodiments, the sense strand sequence comprises or consists of a sense strand sequence of any one of the siRNAs disclosed in Table 7 where the relative ANGPTL expression at 1 nM in the table is below 0.5 (e.g. an siRNA with the sequence of ETD00245, ETD00247, or ETD00252). In some embodiments, the sense strand sequence comprises or consists of a sense strand sequence of any one of the siRNAs disclosed in Table 7 where the relative ANGPTL expression at 10 nM in the table is below 1, or an siRNA thereof having 1 or 2 nucleoside substitutions, additions, or deletions. In some embodiments, the sense strand sequence comprises or consists of a sense strand sequence of any one of the siRNAs disclosed in Table 7 where the relative ANGPTL expression at 10 nM in the table is below 1. In some embodiments, the sense strand sequence comprises or consists of an unmodified version of a sense strand sequence of any one of the siRNAs disclosed in Table 7. In some embodiments, the sense strand sequence comprises or consists of an siRNA with the sense strand sequence of a sense strand sequence of any one of the siRNAs disclosed in Table 7, but with one or more additional or different modifications, or with a different modification pattern. In some embodiments, the sense strand sequence lacks the sequence modifications, or has different or additional sequence modifications, but otherwise is similar to a sequence described herein.

In some embodiments, the sense strand sequence comprises or consists of a sense strand sequence of any one of the siRNAs disclosed in Table 8, or an siRNA thereof having 1 or 2 nucleoside substitutions, additions, or deletions. In some embodiments, the sense strand sequence comprises or consists of a sense strand sequence of any one of the siRNAs disclosed in Table 8. In some embodiments, the sense strand sequence comprises or consists of a sense strand sequence of any one of the siRNAs disclosed in Table 9, or an siRNA thereof having 1 or 2 nucleoside substitutions, additions, or deletions. In some embodiments, the sense strand sequence comprises or consists of a sense strand sequence of any one of the siRNAs disclosed in Table 9. In some embodiments, the sense strand sequence comprises or consists of a sense strand sequence of any one of the siRNAs disclosed in Table 10, or an siRNA thereof having 1 or 2 nucleoside substitutions, additions, or deletions. In some embodiments, the sense strand sequence comprises or consists of a sense strand sequence of any one of the siRNAs disclosed in Table 10. In some embodiments, the sense strand sequence lacks the sequence modifications, or has different or additional sequence modifications, but otherwise is similar to a sequence described herein.

In some embodiments, the sense strand sequence comprises or consists of a sense strand sequence of any one of the siRNAs disclosed in Table 11, or an siRNA thereof having 1 or 2 nucleoside substitutions, additions, or deletions. In some embodiments, the sense strand sequence comprises or consists of a sense strand sequence of any one of the siRNAs disclosed in Table 11. In some embodiments, the sense strand sequence comprises or consists of a sense strand sequence of any one of the siRNAs disclosed in Table 11 where the percent of the siRNA remaining at 4 hours in the table is at least 50%, or an siRNA thereof having 1 or 2 nucleoside substitutions, additions, or deletions. In some embodiments, the sense strand sequence comprises or consists of a sense strand sequence of any one of the siRNAs disclosed in Table 11 where the percent of the siRNA remaining at 4 hours in the table is at least 50%. In some embodiments, the sense strand sequence comprises or consists of a sense strand sequence of any one of the siRNAs disclosed in Table 11 where the percent of the siRNA remaining at 4 hours in the table is at least 75%, or an siRNA thereof having 1 or 2 nucleoside substitutions, additions, or deletions. In some embodiments, the sense strand sequence comprises or consists of a sense strand sequence of any one of the siRNAs disclosed in Table 11 where the percent of the siRNA remaining at 4 hours in the table is at least 75%. In some embodiments, the sense strand sequence comprises or consists of a sense strand sequence of any one of the siRNAs disclosed in Table 11 where the percent of the siRNA remaining at 24 hours in the table is at least 50%, or an siRNA thereof having 1 or 2 nucleoside substitutions, additions, or deletions. In some embodiments, the sense strand sequence comprises or consists of a sense strand sequence of any one of the siRNAs disclosed in Table 11 where the percent of the siRNA remaining at 24 hours in the table is at least 50%. In some embodiments, the sense strand sequence comprises or consists of a sense strand sequence of any one of the siRNAs disclosed in Table 11 where the percent of the siRNA remaining at 24 hours in the table is at least 75%, or an siRNA thereof having 1 or 2 nucleoside substitutions, additions, or deletions. In some embodiments, the sense strand sequence comprises or consists of a sense strand sequence of any one of the siRNAs disclosed in Table 11 where the percent of the siRNA remaining at 24 hours in the table is at least 75%. In some embodiments, the sense strand sequence comprises or consists of an unmodified version of a sense strand sequence of any one of the siRNAs disclosed in Table 11. In some embodiments, the sense strand sequence comprises or consists of an siRNA with the sense strand sequence of a sense strand sequence of any one of the siRNAs disclosed in Table 11, but with one or more additional or different modifications, or with a different modification pattern. In some embodiments, the sense strand sequence lacks the sequence modifications, or has different or additional sequence modifications, but otherwise is similar to a sequence described herein.

In some embodiments, the sense strand sequence comprises or consists of a sense strand sequence of any one of the siRNAs disclosed in Table 12, or an siRNA thereof having 1 or 2 nucleoside substitutions, additions, or deletions. In some embodiments, the sense strand sequence comprises or consists of a sense strand sequence of any one of the siRNAs disclosed in Table 12. In some embodiments, the sense strand sequence comprises or consists of a sense strand sequence of any one of the siRNAs disclosed in Table 13, or an siRNA thereof having 1 or 2 nucleoside substitutions, additions, or deletions. In some embodiments, the sense strand sequence comprises or consists of a sense strand sequence of any one of the siRNAs disclosed in Table 13. In some embodiments, the sense strand sequence lacks the sequence modifications, or has different or additional sequence modifications, but otherwise is similar to a sequence described herein.

In some embodiments, the sense strand sequence comprises or consists of the sequence of the sense strand of siRNA ETD00269, or an siRNA thereof having 1 or 2 nucleoside substitutions, additions, or deletions. In some embodiments, the sense strand sequence comprises or consists of the sequence of the sense strand of siRNA ETD00269. In some embodiments, the sense strand sequence comprises or consists of the sequence of the sense strand of siRNA ETD00270, or an siRNA thereof having 1 or 2 nucleoside substitutions, additions, or deletions. In some embodiments, the sense strand sequence comprises or consists of the sequence of the sense strand of siRNA ETD00270. In some embodiments, the sense strand sequence comprises or consists of the sequence of the sense strand of siRNA ETD00353, or an siRNA thereof having 1 or 2 nucleoside substitutions, additions, or deletions. In some embodiments, the sense strand sequence comprises or consists of the sequence of the sense strand of siRNA ETD00353. In some embodiments, the sense strand sequence comprises or consists of the sequence of the sense strand of siRNA ETD00356, or an siRNA thereof having 1 or 2 nucleoside substitutions, additions, or deletions. In some embodiments, the sense strand sequence comprises or consists of the sequence of the sense strand of siRNA ETD00356. In some embodiments, the sense strand sequence comprises or consists of the sequence of the sense strand of siRNA ETD00358, or an siRNA thereof having 1 or 2 nucleoside substitutions, additions, or deletions. In some embodiments, the sense strand sequence comprises or consists of the sequence of the sense strand of siRNA ETD00358. In some embodiments, the sense strand sequence comprises or consists of the sequence of the sense strand of siRNA ETD00370, or an siRNA thereof having 1 or 2 nucleoside substitutions, additions, or deletions. In some embodiments, the sense strand sequence comprises or consists of the sequence of the sense strand of siRNA ETD00370. In some embodiments, the sense strand sequence comprises or consists of the sequence of the sense strand of siRNA ETD00377, or an siRNA thereof having 1 or 2 nucleoside substitutions, additions, or deletions. In some embodiments, the sense strand sequence comprises or consists of the sequence of the sense strand of siRNA ETD00377. In some embodiments, the sense strand sequence comprises or consists of the sequence of the sense strand of siRNA ETD00378, or an siRNA thereof having 1 or 2 nucleoside substitutions, additions, or deletions. In some embodiments, the sense strand sequence comprises or consists of the sequence of the sense strand of siRNA ETD00378. In some embodiments, the sense strand sequence comprises or consists of the sequence of the sense strand of siRNA ETD00382, or an siRNA thereof having 1 or 2 nucleoside substitutions, additions, or deletions. In some embodiments, the sense strand sequence comprises or consists of the sequence of the sense strand of siRNA ETD00382. In some embodiments, the sense strand sequence comprises or consists of the sequence of SEQ ID NO: 11377, or an siRNA thereof having 1 or 2 nucleoside substitutions, additions, or deletions. In some embodiments, the sense strand sequence comprises or consists of the sequence of SEQ ID NO: 11377. In some embodiments, the sense strand sequence comprises or consists of the sequence of SEQ ID NO: 11378, or an siRNA thereof having 1 or 2 nucleoside substitutions, additions, or deletions. In some embodiments, the sense strand sequence comprises or consists of the sequence of SEQ ID NO: 11387. In some embodiments, the sense strand sequence lacks the sequence modifications, or has different or additional sequence modifications, but otherwise is similar to a sequence described herein.

In some embodiments, the antisense strand comprises a antisense strand sequence with one or more modifications or modification patterns. In some embodiments, the antisense strand sequence comprises or consists of sequence at least 75% identical to of any one of SEQ ID NOs: 11093-11212, at least 80% identical to of any one of SEQ ID NOs: 11093-11212, at least 85% identical to of any one of SEQ ID NOs: 11093-11212, at least 90% identical to of any one of SEQ ID NOs: 11093-11212, or at least 95% identical to of any one of SEQ ID NOs: 11093-11212. In some embodiments, the antisense strand sequence comprises or consists of the sequence of any one of SEQ ID NOs: 11093-11212, or a sequence thereof having 1, 2, 3, or 4 nucleoside substitutions, additions, or deletions. In some embodiments, the antisense strand sequence comprises or consists of the sequence of any one of SEQ ID NOs: 11093-11212, or a sequence thereof having 1 or 2 nucleoside substitutions, additions, or deletions. In some embodiments, the antisense strand sequence comprises or consists of the sequence of any one of SEQ ID NOs: 11093-11212. In some embodiments, the antisense strand sequence is an unmodified version of a antisense strand sequence described herein. In some embodiments, the antisense strand sequence has more or different sequence modifications than a antisense strand sequence described herein.

In some embodiments, the antisense strand sequence comprises or consists of sequence at least 75% identical to of any one of SEQ ID NOs: 11333-11354, at least 80% identical to of any one of SEQ ID NOs: 11333-11354, at least 85% identical to of any one of SEQ ID NOs: 11333-11354, at least 90% identical to of any one of SEQ ID NOs: 11333-11354, or at least 95% identical to of any one of SEQ ID NOs: 11333-11354. In some embodiments, the antisense strand sequence comprises or consists of the sequence of any one of SEQ ID NOs: 11333-11354, or a sequence thereof having 1, 2, 3, or 4 nucleoside substitutions, additions, or deletions. In some embodiments, the antisense strand sequence comprises or consists of the sequence of any one of SEQ ID NOs: 11333-11354, or a sequence thereof having 1 or 2 nucleoside substitutions, additions, or deletions. In some embodiments, the antisense strand sequence comprises or consists of the sequence of any one of SEQ ID NOs: 11333-11354. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of a antisense strand sequence of any one of the siRNAs disclosed in any of Tables 5-13, or an siRNA thereof having 1 or 2 nucleoside substitutions, additions, or deletions. In some embodiments, the antisense strand sequence comprises or consists of a antisense strand sequence of a antisense strand sequence of any one of the siRNAs disclosed in any of Tables 5-13. In some embodiments, the antisense strand sequence comprises or consists of a sequence at least 75% identical, at least 80% identical, at least 85% identical, at least 90% identical, or at least 95% identical to a antisense strand sequence of an siRNA in any of Tables 5-13.

In some embodiments, the antisense strand sequence comprises or consists of a antisense strand sequence of a antisense strand sequence of any one of the siRNAs disclosed in any of Tables 5-10, or an siRNA thereof having 1 or 2 nucleoside substitutions, additions, or deletions. In some embodiments, the antisense strand sequence comprises or consists of a antisense strand sequence of any one of the siRNAs disclosed in any of Tables 5-10. In some embodiments, the antisense strand sequence comprises or consists of a antisense strand sequence of any one of the siRNAs disclosed in any of Tables 5-10 where a relative ANGPTL expression in the table is below 1, or an siRNA thereof having 1 or 2 nucleoside substitutions, additions, or deletions. In some embodiments, the antisense strand sequence comprises or consists of a antisense strand sequence of any one of the siRNAs disclosed in any of Tables 5-10 where a relative ANGPTL expression in the table is below 1. In some embodiments, the antisense strand sequence comprises or consists of a antisense strand sequence of any one of the siRNAs disclosed in any of Tables 5-10 where a relative ANGPTL expression of the siRNA in the table is below the expression of a negative control in the table, or an siRNA thereof having 1 or 2 nucleoside substitutions, additions, or deletions. In some embodiments, the antisense strand sequence comprises or consists of a antisense strand sequence of any one of the siRNAs disclosed in any of Tables 5-10 where a relative ANGPTL expression of the siRNA in the table is below the expression of a negative control in the table. In some embodiments, the antisense strand sequence comprises or consists of a antisense strand sequence of any one of the siRNAs disclosed in any of Tables 5-10 where a relative ANGPTL expression in the table is below 0.5, or an siRNA thereof having 1 or 2 nucleoside substitutions, additions, or deletions. In some embodiments, the antisense strand sequence comprises or consists of a antisense strand sequence of any one of the siRNAs disclosed in any of Tables 5-10 where a relative ANGPTL expression in the table is below 0.5. In some embodiments, the antisense strand sequence comprises or consists of a antisense strand sequence of any one of the siRNAs disclosed in any of Tables 5-10 where a relative ANGPTL expression in the table is below 0.25, or an siRNA thereof having 1 or 2 nucleoside substitutions, additions, or deletions. In some embodiments, the antisense strand sequence comprises or consists of a antisense strand sequence of any one of the siRNAs disclosed in any of Tables 5-10 where a relative ANGPTL expression in the table is below 0.25. In some embodiments, the antisense strand sequence comprises or consists of an unmodified version of a antisense strand sequence of any one of the siRNAs disclosed in any of Tables 5-10. In some embodiments, the antisense strand sequence comprises or consists of an siRNA with the antisense strand sequence of a antisense strand sequence of any one of the siRNAs disclosed in any of Tables 5-10, but with one or more additional or different modifications, or with a different modification pattern. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of any one of the siRNAs disclosed in Table 5, or an siRNA thereof having 1 or 2 nucleoside substitutions, additions, or deletions. In some embodiments, the antisense strand sequence comprises or consists of a antisense strand sequence of any one of the siRNAs disclosed in Table 5. In some embodiments, the antisense strand sequence comprises or consists of a antisense strand sequence of any one of the siRNAs disclosed in Table 5 where the relative ANGPTL expression in the table is below 1, or an siRNA thereof having 1 or 2 nucleoside substitutions, additions, or deletions. In some embodiments, the antisense strand sequence comprises or consists of a antisense strand sequence of any one of the siRNAs disclosed in Table 5 where the relative ANGPTL expression in the table is below 1. In some embodiments, the antisense strand sequence comprises or consists of a antisense strand sequence of any one of the siRNAs disclosed in Table 5 where the relative ANGPTL expression of the siRNA in the table is below the expression of the negative control siRNA in the table (e.g. below a relative expression level of 0.67), or an siRNA thereof having 1 or 2 nucleoside substitutions, additions, or deletions. In some embodiments, the antisense strand sequence comprises or consists of a antisense strand sequence of any one of the siRNAs disclosed in Table 5 where the relative ANGPTL expression of the siRNA in the table is below the expression of the negative control siRNA in the table (e.g. below a relative expression level of 0.67). In some embodiments, the antisense strand sequence comprises or consists of a antisense strand sequence of any one of the siRNAs disclosed in Table 5 where the relative ANGPTL expression in the table is below 0.5, or an siRNA thereof having 1 or 2 nucleoside substitutions, additions, or deletions. In some embodiments, the antisense strand sequence comprises or consists of a antisense strand sequence of any one of the siRNAs disclosed in Table 5 where the relative ANGPTL expression in the table is below 0.5. In some embodiments, the antisense strand sequence comprises or consists of a antisense strand sequence of any one of the siRNAs disclosed in Table 5 where the relative ANGPTL expression in the table is below 0.25, or an siRNA thereof having 1 or 2 nucleoside substitutions, additions, or deletions. In some embodiments, the antisense strand sequence comprises or consists of a antisense strand sequence of any one of the siRNAs disclosed in Table 5 where the relative ANGPTL expression in the table is below 0.25. In some embodiments, the antisense strand sequence comprises or consists of an unmodified version of a antisense strand sequence of any one of the siRNAs disclosed in Table 5. In some embodiments, the antisense strand sequence comprises or consists of an siRNA with the antisense strand sequence of a antisense strand sequence of any one of the siRNAs disclosed in Table 5, but with one or more additional or different modifications, or with a different modification pattern. In some embodiments, the antisense strand sequence lacks the sequence modifications, or has different or additional sequence modifications, but otherwise is similar to a sequence described herein.

In some embodiments, the antisense strand sequence is incorporated into an siRNA that downregulates ANGPTL7. In some embodiments, the antisense strand sequence comprises or consists of a antisense strand sequence of any one of SEQ ID NOs: 11214, 11215, 11216, 11217, 11218, 11219, 11220, 11221, 11222, 11223, 11224, 11225, 11226, 11229, 11230, 11233, 11236, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332, or an siRNA thereof having 1 or 2 nucleoside substitutions, additions, or deletions. In some embodiments, the antisense strand sequence comprises or consists of a antisense strand sequence of any one of SEQ ID NOs: 11214, 11215, 11216, 11217, 11218, 11219, 11220, 11221, 11222, 11223, 11224, 11225, 11226, 11229, 11230, 11233, 11234, 11238, 11239, 11241, 11242, 11243, 11244, 11245, 11246, 11247, 11248, 11249, 11250, 11252, 11253, 11254, 11255, 11256, 11259, 11260, 11263, 11264, 11265, 11266, 11267, 11268, 11269, 11270, 11271, 11272, 11273, 11274, 11275, 11276, 11277, 11278, 11279, 11280, 11281, 11282, 11283, 11284, 11285, 11286, 11287, 11288, 11289, 11290, 11291, 11292, 11293, 11294, 11295, 11296, 11297, 11298, 11300, 11301, 11302, 11303, 11304, 11305, 11306, 11307, 11308, 11309, 11311, 11313, 11315, 11316, 11318, 11319, 11320, 11321, 11323, 11324, 11325, 11327, 11328, 11330, 11331, or 11332.

In some embodiments, the antisense strand sequence comprises or consists of a antisense strand sequence of any one of the siRNAs disclosed in Table 6, or an siRNA thereof having 1 or 2 nucleoside substitutions, additions, or deletions. In some embodiments, the antisense strand sequence comprises or consists of a antisense strand sequence of any one of the siRNAs disclosed in Table 6. In some embodiments, the antisense strand sequence comprises or consists of a antisense strand sequence of any one of the siRNAs disclosed in Table 6 where the relative ANGPTL expression in the table is below 1, or an siRNA thereof having 1 or 2 nucleoside substitutions, additions, or deletions. In some embodiments, the antisense strand sequence comprises or consists of a antisense strand sequence of any one of the siRNAs disclosed in Table 6 where the relative ANGPTL expression in the table is below 1. In some embodiments, the antisense strand sequence comprises or consists of a antisense strand sequence of any one of the siRNAs disclosed in Table 6 where the relative ANGPTL expression of the siRNA in the table is below the expression of the negative control siRNA in the table (e.g. below a relative expression level of 1.06), or an siRNA thereof having 1 or 2 nucleoside substitutions, additions, or deletions. In some embodiments, the antisense strand sequence comprises or consists of a antisense strand sequence of any one of the siRNAs disclosed in Table 6 where the relative ANGPTL expression of the siRNA in the table is below the expression of the negative control siRNA in the table (e.g. below a relative expression level of 1.06). In some embodiments, the antisense strand sequence comprises or consists of a antisense strand sequence of any one of the siRNAs disclosed in Table 6 where the relative ANGPTL expression in the table is below 0.5, or an siRNA thereof having 1 or 2 nucleoside substitutions, additions, or deletions. In some embodiments, the antisense strand sequence comprises or consists of a antisense strand sequence of any one of the siRNAs disclosed in Table 6 where the relative ANGPTL expression in the table is below 0.5. In some embodiments, the antisense strand sequence comprises or consists of a antisense strand sequence of any one of the siRNAs disclosed in Table 6 where the relative ANGPTL expression in the table is below 0.25, or an siRNA thereof having 1 or 2 nucleoside substitutions, additions, or deletions. In some embodiments, the antisense strand sequence comprises or consists of a antisense strand sequence of any one of the siRNAs disclosed in Table 6 where the relative ANGPTL expression in the table is below 0.25. In some embodiments, the antisense strand sequence comprises or consists of an unmodified version of a antisense strand sequence of any one of the siRNAs disclosed in Table 6. In some embodiments, the antisense strand sequence comprises or consists of an siRNA with the antisense strand sequence of a antisense strand sequence of any one of the siRNAs disclosed in Table 6, but with one or more additional or different modifications, or with a different modification pattern. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of any one of the siRNAs disclosed in Table 7, or an siRNA thereof having 1 or 2 nucleoside substitutions, additions, or deletions. In some embodiments, the antisense strand sequence comprises or consists of a antisense strand sequence of any one of the siRNAs disclosed in Table 7. In some embodiments, the antisense strand sequence comprises or consists of a antisense strand sequence of any one of the siRNAs disclosed in Table 7 where the relative ANGPTL expression at 1 nM in the table is below 1, or an siRNA thereof having 1 or 2 nucleoside substitutions, additions, or deletions. In some embodiments, the antisense strand sequence comprises or consists of a antisense strand sequence of any one of the siRNAs disclosed in Table 7 where the relative ANGPTL expression at 1 nM in the table is below 1. In some embodiments, the antisense strand sequence comprises or consists of a antisense strand sequence of any one of the siRNAs disclosed in Table 7 where the relative ANGPTL expression at 1 nM of the siRNA in the table is below the expression of the negative control siRNA in the table (e.g. below a relative expression level of 0.66), or an siRNA thereof having 1 or 2 nucleoside substitutions, additions, or deletions. In some embodiments, the antisense strand sequence comprises or consists of a antisense strand sequence of any one of the siRNAs disclosed in Table 7 where the relative ANGPTL expression at 1 nM of the siRNA in the table is below the expression of the negative control siRNA in the table (e.g. below a relative expression level of 0.66). In some embodiments, the antisense strand sequence comprises or consists of a antisense strand sequence of any one of the siRNAs disclosed in Table 7 where the relative ANGPTL expression at 1 nM in the table is below 0.5, or an siRNA thereof having 1 or 2 nucleoside substitutions, additions, or deletions. In some embodiments, the antisense strand sequence comprises or consists of a antisense strand sequence of any one of the siRNAs disclosed in Table 7 where the relative ANGPTL expression at 1 nM in the table is below 0.5 (e.g. an siRNA with the sequence of ETD00245, ETD00247, or ETD00252). In some embodiments, the antisense strand sequence comprises or consists of a antisense strand sequence of any one of the siRNAs disclosed in Table 7 where the relative ANGPTL expression at 10 nM in the table is below 1, or an siRNA thereof having 1 or 2 nucleoside substitutions, additions, or deletions. In some embodiments, the antisense strand sequence comprises or consists of a antisense strand sequence of any one of the siRNAs disclosed in Table 7 where the relative ANGPTL expression at 10 nM in the table is below 1. In some embodiments, the antisense strand sequence comprises or consists of an unmodified version of a antisense strand sequence of any one of the siRNAs disclosed in Table 7. In some embodiments, the antisense strand sequence comprises or consists of an siRNA with the antisense strand sequence of a antisense strand sequence of any one of the siRNAs disclosed in Table 7, but with one or more additional or different modifications, or with a different modification pattern. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of any one of the siRNAs disclosed in Table 8, or an siRNA thereof having 1 or 2 nucleoside substitutions, additions, or deletions. In some embodiments, the antisense strand sequence comprises or consists of a antisense strand sequence of any one of the siRNAs disclosed in Table 8. In some embodiments, the antisense strand sequence comprises or consists of a antisense strand sequence of any one of the siRNAs disclosed in Table 9, or an siRNA thereof having 1 or 2 nucleoside substitutions, additions, or deletions. In some embodiments, the antisense strand sequence comprises or consists of a antisense strand sequence of any one of the siRNAs disclosed in Table 9. In some embodiments, the antisense strand sequence comprises or consists of a antisense strand sequence of any one of the siRNAs disclosed in Table 10, or an siRNA thereof having 1 or 2 nucleoside substitutions, additions, or deletions. In some embodiments, the antisense strand sequence comprises or consists of a antisense strand sequence of any one of the siRNAs disclosed in Table 10. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of any one of the siRNAs disclosed in Table 11, or an siRNA thereof having 1 or 2 nucleoside substitutions, additions, or deletions. In some embodiments, the antisense strand sequence comprises or consists of a antisense strand sequence of any one of the siRNAs disclosed in Table 11. In some embodiments, the antisense strand sequence comprises or consists of a antisense strand sequence of any one of the siRNAs disclosed in Table 11 where the percent of the siRNA remaining at 4 hours in the table is at least 50%, or an siRNA thereof having 1 or 2 nucleoside substitutions, additions, or deletions. In some embodiments, the antisense strand sequence comprises or consists of a antisense strand sequence of any one of the siRNAs disclosed in Table 11 where the percent of the siRNA remaining at 4 hours in the table is at least 50%. In some embodiments, the antisense strand sequence comprises or consists of a antisense strand sequence of any one of the siRNAs disclosed in Table 11 where the percent of the siRNA remaining at 4 hours in the table is at least 75%, or an siRNA thereof having 1 or 2 nucleoside substitutions, additions, or deletions. In some embodiments, the antisense strand sequence comprises or consists of a antisense strand sequence of any one of the siRNAs disclosed in Table 11 where the percent of the siRNA remaining at 4 hours in the table is at least 75%. In some embodiments, the antisense strand sequence comprises or consists of a antisense strand sequence of any one of the siRNAs disclosed in Table 11 where the percent of the siRNA remaining at 24 hours in the table is at least 50%, or an siRNA thereof having 1 or 2 nucleoside substitutions, additions, or deletions. In some embodiments, the antisense strand sequence comprises or consists of a antisense strand sequence of any one of the siRNAs disclosed in Table 11 where the percent of the siRNA remaining at 24 hours in the table is at least 50%. In some embodiments, the antisense strand sequence comprises or consists of a antisense strand sequence of any one of the siRNAs disclosed in Table 11 where the percent of the siRNA remaining at 24 hours in the table is at least 75%, or an siRNA thereof having 1 or 2 nucleoside substitutions, additions, or deletions. In some embodiments, the antisense strand sequence comprises or consists of a antisense strand sequence of any one of the siRNAs disclosed in Table 11 where the percent of the siRNA remaining at 24 hours in the table is at least 75%. In some embodiments, the antisense strand sequence comprises or consists of an unmodified version of a antisense strand sequence of any one of the siRNAs disclosed in Table 11. In some embodiments, the antisense strand sequence comprises or consists of an siRNA with the antisense strand sequence of a antisense strand sequence of any one of the siRNAs disclosed in Table 11, but with one or more additional or different modifications, or with a different modification pattern. In some embodiments, the antisense strand sequence lacks the sequence modifications, or has different or additional sequence modifications, but otherwise is similar to a sequence described herein.

In some embodiments, the antisense strand sequence comprises or consists of a antisense strand sequence of any one of the siRNAs disclosed in Table 12, or an siRNA thereof having 1 or 2 nucleoside substitutions, additions, or deletions. In some embodiments, the antisense strand sequence comprises or consists of a antisense strand sequence of any one of the siRNAs disclosed in Table 12. In some embodiments, the antisense strand sequence comprises or consists of a antisense strand sequence of any one of the siRNAs disclosed in Table 13, or an siRNA thereof having 1 or 2 nucleoside substitutions, additions, or deletions. In some embodiments, the antisense strand sequence comprises or consists of a antisense strand sequence of any one of the siRNAs disclosed in Table 13. In some embodiments, the antisense strand sequence lacks the sequence modifications, or has different or additional sequence modifications, but otherwise is similar to a sequence described herein.

In some embodiments, the antisense strand sequence comprises or consists of the sequence of the antisense strand of siRNA ETD00269, or an siRNA thereof having 1 or 2 nucleoside substitutions, additions, or deletions. In some embodiments, the antisense strand sequence comprises or consists of the sequence of the antisense strand of siRNA ETD00269. In some embodiments, the antisense strand sequence comprises or consists of the sequence of the antisense strand of siRNA ETD00270, or an siRNA thereof having 1 or 2 nucleoside substitutions, additions, or deletions. In some embodiments, the antisense strand sequence comprises or consists of the sequence of the antisense strand of siRNA ETD00270. In some embodiments, the antisense strand sequence comprises or consists of the sequence of the antisense strand of siRNA ETD00353, or an siRNA thereof having 1 or 2 nucleoside substitutions, additions, or deletions. In some embodiments, the antisense strand sequence comprises or consists of the sequence of the antisense strand of siRNA ETD00353. In some embodiments, the antisense strand sequence comprises or consists of the sequence of the antisense strand of siRNA ETD00356, or an siRNA thereof having 1 or 2 nucleoside substitutions, additions, or deletions. In some embodiments, the antisense strand sequence comprises or consists of the sequence of the antisense strand of siRNA ETD00356. In some embodiments, the antisense strand sequence comprises or consists of the sequence of the antisense strand of siRNA ETD00358, or an siRNA thereof having 1 or 2 nucleoside substitutions, additions, or deletions. In some embodiments, the antisense strand sequence comprises or consists of the sequence of the antisense strand of siRNA ETD00358. In some embodiments, the antisense strand sequence comprises or consists of the sequence of the antisense strand of siRNA ETD00370, or an siRNA thereof having 1 or 2 nucleoside substitutions, additions, or deletions. In some embodiments, the antisense strand sequence comprises or consists of the sequence of the antisense strand of siRNA ETD00370. In some embodiments, the antisense strand sequence comprises or consists of the sequence of the antisense strand of siRNA ETD00377, or an siRNA thereof having 1 or 2 nucleoside substitutions, additions, or deletions. In some embodiments, the antisense strand sequence comprises or consists of the sequence of the antisense strand of siRNA ETD00377. In some embodiments, the antisense strand sequence comprises or consists of the sequence of the antisense strand of siRNA ETD00378, or an siRNA thereof having 1 or 2 nucleoside substitutions, additions, or deletions. In some embodiments, the antisense strand sequence comprises or consists of the sequence of the antisense strand of siRNA ETD00378. In some embodiments, the antisense strand sequence comprises or consists of the sequence of the antisense strand of siRNA ETD00382, or an siRNA thereof having 1 or 2 nucleoside substitutions, additions, or deletions. In some embodiments, the antisense strand sequence comprises or consists of the sequence of the antisense strand of siRNA ETD00382. In some embodiments, the antisense strand sequence comprises or consists of the sequence of the antisense strand of siRNA ETD00752, or an siRNA thereof having 1 or 2 nucleoside substitutions, additions, or deletions. In some embodiments, the antisense strand sequence comprises or consists of the sequence of the antisense strand of siRNA ETD00752. In some embodiments, the antisense strand sequence comprises or consists of the sequence of SEQ ID NO: 11379, or an siRNA thereof having 1 or 2 nucleoside substitutions, additions, or deletions. In some embodiments, the antisense strand sequence comprises or consists of the sequence of SEQ ID NO: 11379. In some embodiments, the antisense strand sequence lacks the sequence modifications, or has different or additional sequence modifications, but otherwise is similar to a sequence described herein.

Antisense Compounds

In one aspect, provided herein is an antisense compound or oligonucleotide for modulating the activity and/or expression of a target nucleic acid, e.g., ANGPTL7. In some embodiments, the antisense compound inhibits expression of ANGPTL7. In some cases, the antisense compound comprises a sequence at least about 80%, 85%, 90%, 95%, or 100% identical to a sequence selected from SEQ ID NOS: 4413-11084. In some cases, the antisense compound comprises a sequence at least about 80%, 85%, 90%, 95%, or 100% identical to SEQ ID NO: 11087.

In some embodiments, the antisense compound is specifically hybridizable to the target nucleic acid, where binding of the compound to the target nucleic acid interferes with the normal function of the target nucleic acid to cause, e.g., a loss of activity, and there is a sufficient degree of complementarity to avoid non-specific binding of the antisense compound to non-target nucleic acid sequences under conditions in which specific binding is desired. Such conditions include physiological conditions in the case of in vivo assays or therapeutic treatment, and conditions in which assays are performed in the case of in vitro assays.

In some embodiments, the antisense compounds include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, an antisense compound, whether DNA, RNA, chimeric, substituted etc, is specifically hybridizable when binding of the compound to the target DNA or RNA molecule interferes with the normal function of the target DNA or RNA, e.g., to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In some embodiments, targeting of ANGPTL7 includes without limitation, antisense sequences which are identified and expanded, using for example, PCR, hybridization etc., one or more of the sequences set forth as SEQ ID NOS: 4413-11084, and the like (e.g., oligonucleotides having at least about 80%, 85%, 90%, 95%, or 100% identity to a sequence selected from SEQ ID NOS: 4413-11084), to modulate the expression or function of ANGPTL7. In some embodiments, expression or function is down-regulated as compared to a control oligonucleotide that does not specifically hybridize to ANGPTL7.

In some embodiments, an antisense oligonucleotide comprises one or more modified nucleotides, shorter or longer fragments, modified bonds and the like. Examples of modified bonds or internucleotide linkages comprise phosphorothioate, phosphorodithioate or the like. In some embodiments, the nucleotides comprise a phosphorus derivative. The phosphorus derivative (or modified phosphate group) which may be attached to the sugar or sugar analog moiety in the modified oligonucleotides may be a monophosphate, diphosphate, triphosphate, alkylphosphate, alkanephosphate, phosphorothioate and the like.

In embodiments, oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule can be a multistep process. The process may begin with the identification of a target nucleic acid whose function is to be modulated. This target nucleic acid may be, for example, a cellular gene (or mRNA transcribed from the gene) whose expression is associated with a particular disorder or disease state. In some embodiments, the target nucleic acid encodes angiopoietin like 7 (ANGPTL7).

The targeting process may include determination of at least one target region, segment, or site within the target nucleic acid for the antisense interaction to occur such that the desired effect, e.g., modulation of expression, will result. In some embodiments, the term "region" is defined as a portion of the target nucleic acid having at least one identifiable structure, function, or characteristic. Within regions of target nucleic acids are segments. "Segments" may be defined as smaller or sub-portions of regions within a target nucleic acid. "Sites" may be defined as positions within a target nucleic acid.

In some embodiments, the antisense oligonucleotides bind to the natural antisense sequences of angiopoietin like 7 (ANGPTL7) and modulate the expression and/or function of ANGPTL7 (SEQ ID NO: 11085).

In some embodiments, the antisense oligonucleotides bind to one or more segments of angiopoietin like 7 (ANGPTL7) polynucleotides and modulate the expression and/or function of ANGPTL7. In some cases, the segments comprise at least five consecutive nucleotides of the ANGPTL7 sense or antisense polynucleotides.

Since the translation initiation codon is typically 5'-AUG (in transcribed mRNA molecules; 5-ATG in the corresponding DNA molecule), the translation initiation codon may be referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, in some cases, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In some embodiments, "start codon" and "translation initiation codon" refer to the codon or codons that are used in vivo to initiate translation of an mRNA transcribed from a gene encoding angiopoietin like 7, (ANGPTL7), regardless of the sequence(s) of such codons. In some cases, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

In some embodiments, the terms "start codon region" and "translation initiation codon region" refer to a portion of such an mRNA or gene that encompasses from about 25 to about 50 contiguous nucleotides in either direction (i.e., 5' or 3') from a translation initiation codon. In some cases, the terms "stop codon region" and "translation termination codon region" refer to a portion of such an mRNA or gene that encompasses from about 25 to about 50 contiguous nucleotides in either direction (i.e., 5' or 3D from a translation termination codon. Consequently, the "start codon region" (or "translation initiation codon region") and the "stop codon region" (or "translation termination codon region") are all regions that may be targeted effectively with the antisense compounds described herein.

The open reading frame (ORF) or "coding region," which refers to the region between the translation initiation codon and the translation termination codon, is also a region which may be targeted effectively. In some embodiments, a targeted region is the intragenic region encompassing the translation initiation or termination codon of the open reading frame (ORF) of a gene.

Another target region includes the 5' untranslated region (5'-UTR), which refers to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'-UTR), which refers to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5-most residue of the mRNA via a 5-5' triphosphate linkage. The 5' cap region of an mRNA is considered to include the 5' cap structure itself as well as the first 50 nucleotides adjacent to the cap site. Another target region is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In some embodiments, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In some embodiments, the antisense oligonucleotides bind to coding and/or non-coding regions of a target polynucleotide and modulate the expression and/or function of the target molecule.

In some embodiments, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In some embodiments, the types of variants described herein are also embodiments of target nucleic acids.

In some embodiments, the locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments. Additional target segments are readily identifiable by one having ordinary skill in the art in view of this disclosure.

Target segments 5-100 nucleotides in length comprising a stretch of at least five (5) consecutive nucleotides selected from within illustrative target segments are considered to be suitable for targeting as well.

In some embodiments, target segments can include DNA or RNA sequences that comprise at least the 5 consecutive nucleotides from the 5'-terminus of one of the target segments (the remaining nucleotides being a consecutive stretch of the same DNA or RNA beginning immediately upstream of the terminus of the target segment and continuing until the DNA or RNA contains about 5 to about 100 nucleotides). In some cases, target segments are represented by DNA or RNA sequences that comprise at least the 5 consecutive nucleotides from the 3'-terminus of one of the target segments (the remaining nucleotides being a consecutive stretch of the same DNA or RNA beginning immediately downstream of the 3'-terminus of the target segment and continuing until the DNA or RNA contains about 5 to about 100 nucleotides).

Once one or more target regions, segments or sites are identified, antisense compounds are chosen which are sufficiently complementary to the target, i.e., hybridize sufficiently well and with sufficient specificity, to give the desired effect.

Antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. In some cases, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like." In some (chimeric) embodiments, an antisense compound may contain both A- and B-form regions.

In some embodiments, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

In some embodiments, the "target segments" identified herein may be employed in a screen for additional compounds that modulate the expression of angiopoietin like 7 (ANGPTL7) polynucleotides. "Modulators" are those compounds that decrease or increase the expression of a nucleic acid molecule encoding ANGPTL7 and which comprise at least a 5-nucleotide portion that is complementary to a target segment. The screening method comprises the steps of contacting a target segment of a nucleic acid molecule encoding sense or natural antisense polynucleotides of ANGPTL7 with one or more candidate modulators, and selecting for one or more candidate modulators which decrease or increase the expression of a nucleic acid molecule encoding ANGPTL7 polynucleotides. Once it is shown that the candidate modulator or modulators are capable of modulating (e.g. either decreasing or increasing) the expression of a nucleic acid molecule encoding ANGPTL7 polynucleotides, the modulator may then be employed in further investigative studies of the function of ANGPTL7 polynucleotides, or for use as a research, diagnostic, or therapeutic agent.

The target segments may be also be combined with their respective complementary antisense compounds to form stabilized double-stranded (duplexed) oligonucleotides.

Such double stranded oligonucleotide moieties modulate target expression and regulate translation as well as RNA processing via an antisense mechanism. Moreover, the double-stranded moieties may be subject to chemical modifications. For example, such double-stranded moieties inhibit the target by the classical hybridization of antisense strand of the duplex to the target, thereby triggering enzymatic degradation of the target.

In some embodiments, an antisense oligonucleotide targets angiopoietin like 7 (ANGPTL7) polynucleotides (e.g. accession number NM_021146), variants, alleles, isoforms, homologs, mutants, derivatives, fragments and complementary sequences thereto. In some cases, the oligonucleotide is an antisense molecule.

In some embodiments, the target nucleic acid molecule is not limited to ANGPTL7 alone but extends to any of the isoforms, receptors, homologs and the like of ANGPTL7 molecules.

In some embodiments, the oligonucleotides are complementary to or bind to nucleic acid sequences of ANGPTL7 transcripts and modulate expression and/or function of ANGPTL7 molecules.

In some embodiments, oligonucleotides comprise sequences of at least 5 consecutive nucleotides of to modulate expression and/or function of ANGPTL7 molecules.

The polynucleotide targets comprise ANGPTL7, including family members thereof, variants of ANGPTL7; mutants of ANGPTL7, including SNPs; noncoding sequences of ANGPTL7; alleles of ANGPTL7; species variants, fragments and the like. In some cases, the oligonucleotide is an antisense molecule.

In some embodiments, the oligonucleotide targeting ANGPTL7 polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA). In some embodiments, the siRNA comprises one or more sequences selected from SEQ ID NOS: 1-4412. In some embodiments, the siRNA comprises a sequence comprising the reverse complement of a sequence selected from SEQ ID NOS: 1-4412. In some embodiments, the siRNA comprises a sequence having at least about 85%, 90%, or 95% homology to a sequence selected from SEQ ID NOS: 1-4412. In some embodiments, the siRNA comprises a sequence having at least about 85%, 90%, or 95% identity to a sequence selected from SEQ ID NOS: 1-4412.

In some embodiments, targeting of angiopoietin like 7 (ANGPTL7) polynucleotides, e.g. SEQ ID NO: 11085, modulate the expression or function of this target. In some embodiments, expression or function is down-regulated as compared to a control.

In some embodiments, targeting of angiopoietin like 7 (ANGPTL7) polynucleotides, e.g. SEQ ID NO 11086, modulate the expression or function of this target. In some embodiments, expression or function is down-regulated as compared to a control.

In some embodiments, provided are antisense compounds. These oligonucleotides can comprise one or more modified nucleotides, shorter or longer fragments, modified bonds and the like. In some embodiments, antisense compounds comprise sequences set forth as SEQ ID NOS: 4413-11084. In some cases, the antisense compound comprises a sequence at least about 80%, 85%, 90%, 95%, or 100% identical to SEQ ID NO: 11087.

In some embodiments, an antisense compound comprises one or more LNA nucleotides.

In some embodiments, an antisense compound comprises one or more UNA nucleotides.

In some embodiments, an antisense compound comprises one or more GNA nucleotides.

The antisense compounds can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound may comprise from 5 to about 80 nucleotides, and a double-stranded antisense compound (such as a dsRNA, for example) may comprise a sense and an antisense strand or portion of 5 to about 80 nucleotides in length. One of ordinary skill in the art will appreciate that this comprehends antisense portions of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range there within.

In some embodiments, the antisense compounds have antisense portions of 10 to 50 nucleotides in length. One having ordinary skill in the art will appreciate that this embodies oligonucleotides having antisense portions of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length.

In some embodiments, the antisense or oligonucleotide compounds have antisense portions of about 12 or 13 to 30 nucleotides in length. One having ordinary skill in the art will appreciate that this embodies antisense compounds having antisense portions of about 12, 13, 14, 15, 16, 17, 18, 19, 20, 21, 22, 23, 24, 25, 26, 27, 28, 29 or 30 nucleotides in length, or any range there within.

In some embodiments, the oligomeric compounds also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In some embodiments, the antisense oligonucleotides, such as for example, nucleic acid molecules set forth in SEQ ID NOS: 4413-11084 comprise one or more substitutions or modifications. In some embodiments, the nucleotides are substituted with locked nucleic acids (LNA). In some cases, the antisense compound comprises a sequence at least about 80%, 85%, 90%, 95%, or 100% identical to SEQ ID NO: 11087.

In some embodiments, the oligonucleotides target one or more regions of the nucleic acid molecules sense and/or antisense of coding and/or non-coding sequences associated with ANGPTL7 and the sequences set forth as SEQ ID NO: 11085.

In some embodiments, oligonucleotides disclosed herein are chimeric oligonucleotides. "Chimeric oligonucleotides" or "chimeras," are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In some embodiments, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide target pair, which is the temperature at which the oligonucleotide and target dissociate; dissociation is detected spectrophotometrically. The higher the Tm, the greater is the affinity of the oligonucleotide for the target.

Chimeric antisense compounds may be formed as composite structures of two or more oligonucleotides, modified oligonucleotides, oligonucleotides and/or oligonucleotides mimetics as described above. Such compounds may also be referred to as hybrids or gapmers.

In some embodiments, the composition comprises an oligonucleotide that inhibits the expression of ANGPTL7, wherein the oligonucleotide comprises an antisense oligonucleotide (ASO). In some embodiments, the ASO is 12-30 nucleosides in length. In some embodiments, the ASO is 14-30 nucleosides in length. In some embodiments, the ASO is at least about 10, 11, 12, 13, 14, 15, 15, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length.

In some embodiments, the composition comprises an oligonucleotide that inhibits the expression of ANGPTL7, wherein the oligonucleotide comprises an antisense oligonucleotide (ASO) about 12-30 nucleosides in length and comprising a nucleoside sequence comprising about 12-30 contiguous nucleosides of a full-length human ANGPTL7 mRNA sequence such as SEQ ID NO: 11085; wherein (i) the oligonucleotide comprises a modification comprising a modified nucleoside and/or a modified internucleoside linkage, and/or (ii) the composition comprises a pharmaceutically acceptable carrier.

In some embodiments, the composition comprises an oligonucleotide that inhibits the expression of ANGPTL7, wherein the oligonucleotide comprises an ASO about 12-30 nucleosides in length and comprising a nucleoside sequence comprising about 12-30 contiguous nucleosides of a full-length human ANGPTL7 mRNA sequence such as SEQ ID NO: 11086; wherein (i) the oligonucleotide comprises a modification comprising a modified nucleoside and/or a modified internucleoside linkage, and/or (ii) the composition comprises a pharmaceutically acceptable carrier.

In some embodiments, the composition comprises an oligonucleotide that inhibits the expression of ANGPTL7, wherein the oligonucleotide comprises an ASO. In some embodiments, the ASO comprises an ASO sequence. In some embodiments, the ASO sequence comprises or consists of the sequence of any one of SEQ ID NOs: 4413-11084, or a nucleic acid sequence thereof having 1, 2, 3, or 4 nucleoside substitutions, additions, or deletions. In some embodiments, the ASO sequence comprises or consists of the sequence of any one of SEQ ID NOs: 4413-11084, or a nucleic acid sequence thereof having 1 or 2 nucleoside substitutions, additions, or deletions. In some embodiments, the ASO sequence comprises or consists of the sequence of any one of SEQ ID NOs: 4413-11084. In some embodiments, the ASO sequence comprises or consists of the sequence of SEQ ID NO: 11087, or a nucleic acid sequence thereof having 1 or 2 nucleoside substitutions, additions, or deletions. In some embodiments, the ASO sequence comprises or consists of the sequence of SEQ ID NO: 11087. In some embodiments, the ASO comprises on or more modifications or modification patterns described herein.

Antisense Compound Modifications

In some embodiments, one or more nucleotides in an antisense compound are modified. The modifications described herein in reference to antisense compounds may be applicable to dsRNA agents or siRNAs.

In some embodiments, the region of the oligonucleotide which is modified comprises at least one nucleotide modified at the 2' position of the sugar, e.g., a 2'-0-alkyl, 2,-0-alkyl-0-alkyl or 2'-fluoro-modified nucleotide. In some embodiments, RNA modifications include 2'-fluoro, 2'-amino and 2' O-methyl modifications on the ribose of pyrimidines, abasic residues or an inverted base at the 3' end of the RNA. Such oligonucleotides may have a higher Tm (i.e., higher target binding affinity) than 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In some embodiments, the chimeric oligonucleotide is also modified to enhance nuclease resistance. Cells contain a variety of exo- and endo-nucleases which can degrade nucleic acids. A number of nucleotide and nucleoside modifications make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides modified to enhance their nuclease resistance survive intact for a longer time than unmodified oligonucleotides. A variety of oligonucleotide modifications have been demonstrated to enhance or confer nuclease resistance. In some cases, oligonucleotides contain at least one phosphorothioate modification. In some cases, oligonucleotide modifications which enhance target binding affinity are also, independently, able to enhance nuclease resistance.

Specific examples of some oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. In some cases, an oligonucleotide comprises a phosphorothioate backbone. In some cases, an oligonucleotide comprises heteroatom backbones, particularly CH2-NH-0-CH2, CH, ~N(CH3)-0~CH2 [known as a methylene(methylimino) or MM backbone], CH2-0~N (CH3)~CH2, CH2-N(CH3)-N(CH3)-CH2 and 0~N(CH3)~CH2-CH2 backbones, wherein the native phosphodiester backbone is represented as O—P—O—CH). In some cases, an oligonucleotide comprises a morpholino backbone structures. In some embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. In some cases, oligonucleotides comprise one of the following at the 2' position: OH, SH, SCH3, F, OCN, OCH3, OCH3 O(CH2)n CH3, O(CH2)n NH2 or O(CH2)n CH3 where n is from 1 to about 10; CI to CIO lower alkyl, alkoxyalkoxy, substituted lower alkyl, alkaryl or aralkyl; CI; Br; CN; CF3; OCF3; 0~, S—, or N-alkyl; 0-, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A non-limiting exemplary modification includes 2'-methoxyethoxy [2-0-CH2 CH2 OCH3, also known as 2'-0-(2-methoxyethyl)]. Other exemplary modifications include 2'-methoxy (2'-0~CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include nucleobase (often referred to as "base") modifications or substitutions. As used herein, "unmodified" or "natural" nucleotides include adenine (A), guanine (G), mymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl) adenine, 2-(aminoalklyamino)adenine or other heterosubstituted alkyladenines, 2-thiouracil, 2-tmothvmine, 5-bromouracil, 5-hydroxymethyluracil, 8-azaguanine, 7-deazaguanine, N6 (6-aminohexyl)adenine and 2,6-diaminopurine. A "universal" base, e.g., inosine, may be included. 5-Me-C substitutions increase nucleic acid duplex stability by 0.6-1.2° C. and are suitable base substitutions.

Another modification of the oligonucleotides involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyamine or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. Oligonucleotides may be chimeric oligonucleotides, e.g., as hereinbefore defined.

In some embodiments, the nucleic acid molecule is conjugated with a moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling VA) to synthesize fluorescently labeled, biotinylated or other modified oligonucleotides such as cholesterol-modified oligonucleotides.

In some embodiments, use of modifications such as the use of LNA monomers to enhance the potency, specificity and duration of action and broaden the routes of administration of oligonucleotides comprised of current chemistries such as MOE, ANA, FAN A, PS etc. This can be achieved by substituting some of the monomers in the current oligonucleotides by LNA monomers. The LNA modified oligonucleotide may have a size similar to the parent compound or may be larger or smaller. In some cases, such LNA-modified oligonucleotides contain less than about 70%, less than about 60%, or less than about 50% LNA monomers, and that their sizes are between about 5 and 25 nucleotides, or between about 12 and 20 nucleotides.

In some embodiments, modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3-5' linkages, 2-5' linked analogs of these, and those having inverted polarity wherein the adjacent pairs of nucleoside units are linked 3'-5' to 5'-3' or 2'-5' to 5'-2. Various salts, mixed salts and free acid forms are also included.

In some embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In some embodiments, both the sugar and the internucleoside linkage, i.e., the backbone, of the nucleotide units are replaced with novel groups while the base units are maintained for hybridization with the target nucleic acid. One such oligomeric compound, an oligonucleotide mimetic with excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

In some embodiments, the oligonucleotides comprise a heteroatom backbone, e.g., —CH2-NH-0-CH2-, —CH2-N (CH3)-0-CH2-known as a methylene (memylimino) or MMI backbone, —CH2-0-N(CH3)-CH2-, —CH2N(CH3)-N(CH3) CH2-, and -0-N(CH3)-CH2-CH2-, wherein the native phosphodiester backbone is represented as -0-P-0-CH2-0. In some embodiments, oligonucleotides comprise morpholino backbone structures.

Modified oligonucleotides may also contain one or more substituted sugar moieties. In some embodiments, oligonucleotides comprise one of the following at the 2' position: OH; F; 0-, S—, or N-alkyl; 0-, S—, or N-alkenyl; 0-, S- or N-alkynyl; or O alkyl-O-alkyl, wherein the alkyl, alkenyl and alkynyl may be substituted or unsubstituted C to CO alkyl or C2 to CO alkenyl and alkynyl. Non-limiting examples are O(CH2)n OmCH3, O(CH2)n, OCH3, O(CH2) nNH2, O(CH2)nCH3, O(CH2)n0NH2, and O(CH2n0N (CH2)nCH3)2 where n and m can be from 1 to about 10. In some embodiments, oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, 0CF3, SOCH3, SO2CH3, ON02, N02, N3, NH2, heterocycloalkyl, heterocycloalkaryl, ammoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. An exemplary modification comprises 2'-methoxyethoxy (2'-0-CH2CH20CH3, also known as 2'-0-(2-methoxyethyl) or 2'-MOE) i.e., an alkoxyalkoxy group. Another exemplary modification comprises 2'-dimethylaminooxyethoxy, i.e., a O(CH2)20N (CH3)2 group, also known as 2-DMAOE, as described in examples herein below, and 2'-dimemylaminoethoxyethoxy (also known as 2'-O-dimethylaminoethoxyethyl or 2'-DMAEOE), i.e., 2'-0-CH2-0-CH2-N(CH2)2.

Another exemplary modification comprises 2-methoxy (2-0 CH3), 2'-aminopropoxy (2'-0 CH2CH2CH2NH2) and 2-fluoro (2'-F) Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobut 1 moieties in place of the pentofuranosyl sugar.

Oligonucleotides may also comprise nucleobase (often referred to simply as "base") modifications or substitutions. In some embodiments, as used herein, "unmodified" or "natural" nucleotides comprise the purine bases adenine (A) and guanine (G), and the pyrimidine bases mymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazagnanine and 7-deazaadenine and 3-deazaguanine and 3-deazaadenine.

Certain nucleotides may be particularly useful for increasing the binding affinity of the oligomeric compounds. In some cases, these comprise 5-substituted pyrimidines, 6-azapyrirnidines and N-2, N-6 and 0-6 substituted purines, comprising 2-aminopropyladenine, 5-propynyluracil and/or 5-propynylcytosine. 5-methylcytosine substitutions increase nucleic acid duplex stability by 0.6-1.2° C., even more particularly when combined with 2'-Omethoxyethyl sugar modifications.

Another modification of the oligonucleotides involves chemically linking to the oligonucleotide one or more moieties or conjugates, which may enhance the activity, cellular distribution, or cellular uptake of the oligonucleotide. Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-0-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

In some embodiments, the composition comprises an oligonucleotide that inhibits the expression of ANGPTL7, wherein the oligonucleotide comprises an antisense oligonucleotide (ASO). In some embodiments, the ASO comprises modification pattern ASO1: 5'-nsnsnsnsnsdNsdNsdNsdNsdNsdNsdNsdNsdNsnsnsn snsn-3' (SEQ ID NO: 11380), wherein "dN" is any deoxynucleotide, "n" is a 2'O-methyl or 2'O-methoxyethyl-modified nucleoside, and "s" is a phosphorothioate linkage. In some embodiments, the ASO comprises modification pattern 1S, 2S, 3S, 4S, 5S, 1AS, 2AS, 3AS, or 4AS.

Ligands

A wide variety of entities can be coupled to the oligonucleotides described herein. In some embodiments, the entities are ligands, which are coupled, e.g., covalently, either directly or indirectly via an intervening tether. In some embodiments, a ligand is coupled to a dsRNA agent. In some embodiments, a ligand is coupled to an antisense compound.

In some embodiments, a ligand alters the distribution, targeting or lifetime of the molecule into which it is incorporated. In some embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhc-«Jamines, coumarins, and dyes. Groups that enhance the pharmacodynamic properties include groups that improve uptake, enhance resistance to degradation, and or strengthen sequence-specific hybridization with the target nucleic acid. Groups that enhance the pharmacokinetic properties include groups that improve uptake, distribution, metabolism or excretion of the compounds herein. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or Adamantane acetic acid, a palmityl moiety, or an octadecylamine or hexylamino-carbonyl-oxycholesterol moiety. Oligonucleotides may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzolhiadiazide, chlorothiazide, a diazepine, indomethicin, a barbiturate, a cephalosporin, a sulfa drug, an antidiabetic, an antibacterial or an antibiotic.

Some ligands can have endosomolytic properties. The endosomolytic ligands promote the lysis of the endosome and/or transport of the composition, or its components, from the endosome to the cytoplasm of the cell. The endosomolytic ligand may be a poly anionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/or transport of the composition, or its components, from the endosome to the cytoplasm of the cell. Exemplary endosomolytic ligands include the GALA peptide, the EALA peptide, and their derivatives. In some embodiments, the endosomolytic component may contain a chemical group (e.g., an amino acid) which will undergo a change in charge or protonation in response to a change in pH. The endosomolytic component may be linear or branched. Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an arginine-glycine-aspartic acid (RGD) peptide, an RGD peptide mimetic or an aptamer.

Additional examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g, cholesterol, cholic acid, adamantane acetic acid, 1-pyrene butyric acid, dihydrotestosterone, 1,3-Bis-0(hexadecyl)glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors.

They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-KB.

The ligand can be a substance, e.g., a drug, which can increase the uptake of the siRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example Exemplary ligands that would have such an effect include tumor necrosis factor alpha (TNF alpha), interleukin-1 beta, or gamma interferon.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL). In another aspect, the ligand is a cell-permeation agent, e.g., a helical cell-permeation agent. In some cases, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is may be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 3-50 amino acids long, e.g., about 3, 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In some cases, the peptide moiety can include a hydrophobic membrane translocation sequence (MTS). An exemplary hydrophobic MTS-containing peptide is RFGF derived from human fibroblast growth factor 4 and having the amino acid sequence AAVALLPAVLLALLAP (SEQ ID NO: 11390), an RFGF analogue (e.g., amino acid sequence AALLPVLLAAP (SEQ ID NO: 11391) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ, SEQ ID NO: 11392) and the Drosophila Antennapedia protein (RQIKIWFQNRRMKWK, SEQ ID NO: 11393) are capable of functioning as delivery peptides. A peptide or peptidomimetic can be encoded by a random sequence of DNA, such as a peptide identified from a phage-display library, or one-bead-one-compound (OBOC) combinatorial library. In some cases, the peptide or peptidomimetic tethered to an antisense oligonucleotide or siRNA agent via an incorporated monomer unit is a cell targeting peptide such as an arginine-glycine-aspartic acid (RGD)-peptide, or RGD mimic. A peptide moiety can range in length from about 3 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell. An RGD peptide can facilitate targeting of an siRNA agent to tumors of a variety of other tissues, including the lung, kidney, spleen, or liver. In some cases, the RGD peptide will facilitate targeting of an siRNA agent to the kidney. The RGD peptide may also be used to facilitate targeting of an siRNA agent to different cell types in the eye. RGD-binding integrins, such as the avb3 integrin pair, are expressed in trabecular meshwork, sclera, and ciliary body of the mouse anterior segment. The RGD peptide can be linear or cyclic, and can be modified, e.g., glycosylated or methylated to facilitate targeting to specific tissues. For example, a glycosylated RGD peptide can deliver an siRNA agent to a tumor cell expressing yB3. Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Exemplary conjugates of this type ligands that targets PECAM-1, VEGF, or other cancer gene, e.g., a cancer gene described herein. Cell binding ligands may be composed of multiple ligands (multivalency) to increase binding affinity. For example, more than one integrin-binding ligand may be combined. Without limiting the structures that bind to integrins, an example of a cyclic peptide RGD ligand is Cyclo(-Arg-Gly-Asp-D-Phe-Xaa) where Xaa is an amino acid with a sidechain that is amenable to conjugation. Naturally occurring examples of X include cysteine where a thiol is used for conjugation, lysine where an amine is used for conjugation. In addition, non-natural amino acids may have other functional groups such as alkynes, azides, maleimides for conjugation.

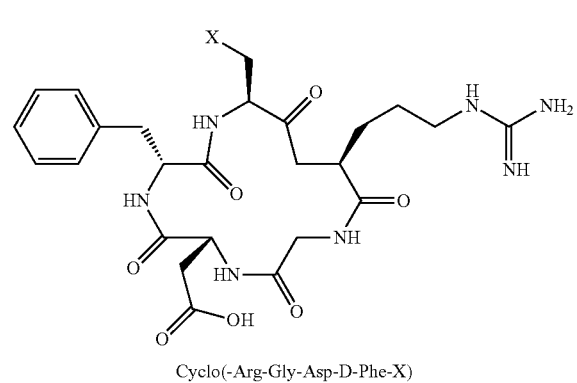

Cyclo(-Arg-Gly-Asp-D-Phe-X)

An example of a noncyclic, peptidomimetic is an amino benzoic acid derivative where in X is a site of conjugation.

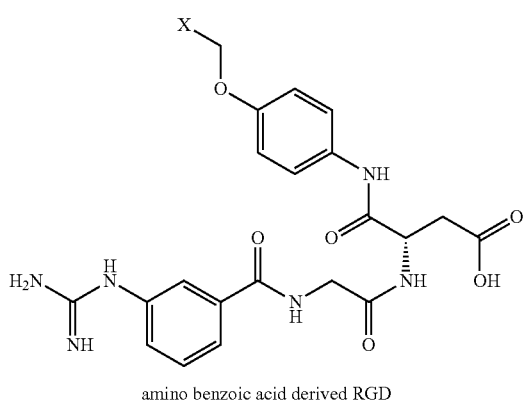

amino benzoic acid derived RGD

Some embodiments include an RGD ligand attached at either a 3' terminus or a 5' terminus. Some embodiments include an RGD ligand attached at a 3' terminus and a 5' terminus. In some embodiments, the RGD ligand comprises Cyclo(-Arg-Gly-Asp-D-Phe-Cys), Cyclo(-Arg-Gly-Asp-D-Phe-Lys), Cyclo(-Arg-Gly-Asp-D-Phe-azido), Cyclo(-Arg-Gly-Asp-D-Phe-alkynyl), amino benzoic acid-based RGD, or a combination thereof. In some embodiments, the RGD ligand is composed of 2, 3 or 4 RGD ligands. In some embodiments, the RGD is positioned on the sense strand. In some embodiments, the RGD is positioned at the 5' end of the sense strand. In some embodiments, the RGD is positioned at the 3' end of the sense strand. In some embodiments, the RGD is positioned on the antisense strand. In some embodiments, the RGD ligand is positioned at the 5' end of the antisense strand. In some embodiments, the RGD ligand is positioned at the 3' end of the antisense strand.

In some embodiments, a "cell permeation peptide" is capable of permeating a cell, e.g., a microbial cell, such as a bacterial or fungal cell, or a mammalian cell, such as a human cell. A microbial cell-permeating peptide can be, for example, an a-helical linear peptide (e.g., LL-37 or Ceropin PI), a disulfide bond-containing peptide (e.g., a-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen.

In some embodiments, a targeting peptide can be an amphipathic a-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H2A peptides, Xenopus peptides, esculentinis-1, and caerins. A number of factors may be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingo lipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable as ligands (e.g. as PK modulating ligands).

In addition, aptamers that bind serum components (e.g. serum proteins) are also amenable as PK modulating ligands.

When two or more ligands are present, the ligands can all have same properties, all have different properties or some ligands have the same properties while others have different properties. For example, a ligand can have targeting properties, have endosomolytic activity or have PK modulating properties. In some embodiments, all the ligands have different properties.

Ligands can be coupled to the oligonucleotides at various places, for example, 3'-end, 5'-end, and/or at an internal position. In some embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer is incorporated into the growing strand. For example, a monomer having, e.g., an amino-terminated tether (i.e., having no associated ligand), e.g., TAP-(CH2)nNH2 may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether. In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded siRNA agent contains a ligand conjugated to the sense strand. In some embodiments, a double-stranded siRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The F position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide. Linkers that conjugate the ligand to the nucleic acid include those discussed above. For example, the ligand can be one or more GalNAc (N-acetylglucosamine) derivatives attached through a bivalent or trivalent branched linker.

Cleavable Linking Groups

In some embodiments, an oligonucleotide compound or composition comprising an oligonucleotide compound comprises a cleavable linking group. In some cases a dsRNA agent comprises or is connected to a cleavable linking group. In some cases an antisense compound comprises or is connected to a cleavable linking group.

In some embodiments, a cleavable linking group is one which is sufficiently stable outside the cell, but which upon entry into a target cell is cleaved to release the two parts the linker is holding together. In some embodiments, the cleavable linking group is cleaved at least 10 times or more, or at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative agents. Generally, cleavage agents are more prevalent or found at higher levels or activities inside cells than in serum or blood.

Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a particular pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes. In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In some embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In some embodiments, candidate compounds are cleaved by at most 10% in the blood. In some embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are -0-P(0)(ORk)-0-, -0-P(S)(ORk)-0-, -0-P(S)(SRk)-0-, —S—P(0)(ORk)-0-, -0-P(0)(ORk)-S—, —S—P(0)(ORk)-S—, -0-P(S)(ORk)-S—, —S—P(S)(ORk)-0-, -0-P(0)(Rk)-0-, -0-P(S)(Rk)-0-, —S—P(0)(Rk)-0-, —S—P(S)(Rk)-0-, —S—P(0)(Rk)-S—, -0-P(S)(Rk)-S—. Some embodiments are -0-P(0)(OH)-0-, -0-P(S)(OH)-0-, -0-P(S)(SH)-0-, –S—P(0)(OH)-0-, -0-P(0)(OH)—S—, —S—P(0)(OH)—S—, -0-P(S)(OH)—S—, —S—P(S)(OH)-0-, —O—P(0)(H)-0-, -0-P(S)(H)-0-, —S—P(0)(H)-0-, —S—P(S)(H)-0-, —S—P(0)(H)—S—, -0-P(S)(H)—S—. An exemplary embodiment is -0-P(0)(OH)-0-. These candidates can be evaluated using methods analogous to those described above.

Acid Cleavable Linking Groups

Acid cleavable linking groups are linking groups that are cleaved under acidic conditions. In some embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—C(0)0, or —OC(O). An exemplary embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(0)0-, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(0)NHCHRBC(0)-, where RA and RB are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C5 and above (e.g., C5-C8) sugars; di- and trisaccharides include sugars having two or three monosaccharide units (e.g., C5-C8).

Nucleotide Mimics

In some embodiments, an oligonucleotide disclosed herein is a naked oligonucleotide. Naked oligonucleotides are defined as systems that contain no agents that are associated with the nucleic acid either covalently or non-covalently. The absence of any delivery vehicle may require that the oligonucleotide itself be sufficiently nuclease resistant, sufficiently long circulating and cell targeted. For small, solid-phase synthesized oligonucleotides such as those used in antisense oligonucleotides, RNAi, and innate immune stimulators, the use of nucleotide mimics may provide the required drug-like properties.

In some embodiments, an oligonucleotide of the present disclosure comprises nucleotides that replace phosphodiester group. The substitution of one non-bridging oxygen of a phosphodiester with a sulfur atom creates the phosphorothioate (PS) linkage. A PS bond creates a new stereocenter in the nucleotide and when synthesized under standard achiral conditions creates diastereomeric mixtures of Rp and Sp at the phosphorous atom.

There are other functional groups identified as replacements of the phosphodiester group in the oligonucleotide. Like phosphates and phosphorothioates, there are a variety of functional groups that are negatively charged such as phosphorodithioate (PS2) and thio-phosphoramidates. There are number of analogues that are uncharged such as phosphorodiamidate morpholino oligomer (PMO), peptide nucleic acid (PNA), phosphotriesters, and phosphonates. It is postulated that the uncharged analogues are not only nuclease resistant, but may also be more membrane permeable; however, the size and hydrophilicity of uncharged oligonucleotides still preclude their passive diffusion across membranes.

Morpholino oligos (PMOs) use a hydrolytically stable, uncharged phosphordiamidate functional group.

Peptide nucleic acids (PNAs) are—as their name suggests—based upon the amide functional group.

Enemas and intramuscular, intravitreal, intrathecal injections may be used for the administration of a variety of oligonucleotides with and without PS bonds.

In some embodiments, an oligonucleotide of the present disclosure comprises a nucleoside analogue that alters the structure of ribose. There are a variety of nucleotide mimics wherein the ribose or deoxyribose is modified to increase affinity for target and/or increase nuclease resistance. In some cases, there are modifications to all five positions of the ribose ring. In some cases, modifications are made to the 2' position of ribose.

In some embodiments, an oligonucleotide of the present disclosure comprises a modifications at the 1' position. In some cases, the oligonucleotide comprises a cytidine mimic that is designed to have increased affinity for guanosine bases due to hydrogen bonding through an aminoethyl group. In some cases, the oligonucleotide comprises a C-5 propynyl pyrimidines.

In some embodiments, an oligonucleotide of the present disclosure comprises a 2' modifications. Modifications of the hydroxyl group at the 2' position of ribose may be used to mimic the structure of the ribose ring while inhibiting ribonucleases that require the 2'OH group for hydrolysis of RNA. In some cases, the oligonucleotide comprises a 2'-O-Methyl ribonucleic acid that is naturally occurring and may increase binding affinity to RNA itself while being resistant to ribonuclease. In some cases, the oligonucleotide comprises a 2'-O-Methyl group. In some cases, the oligonucleotide comprises a 2'-O-Methoxyethyl(MOE) modification, which may mimic the ribonuclease resistance of O-methyl, attenuate protein-oligonucleotide interactions and have increased affinity for RNA.

In some embodiments, an oligonucleotide of the present disclosure comprises a 2'-deoxy-2'-fluoro (2'-F) analogue of nucleosides that adopt a C3'-endo conformation characteristic of the sugars in RNA helices.

In some embodiments, an oligonucleotide of the present disclosure comprises a 4'- and 5'-modifications, where alkoxy substituents at the 4' position of 2'deoxyribose mimic the conformation of ribose.

In some embodiments, an oligonucleotide of the present disclosure comprises a bicyclic 2'-4'-modification. There are a variety of ribose derivatives that lock the carbohydrate ring into the 3' endo conformation by the formation of bicyclic structures with a bridge between the 2' oxygen and the 4' position. The original bicyclic structure has a methylene bridging group and are termed locked nucleic acids (LNAs). The bicyclic structure "locks" the ribose into its preferred 3' endo conformation and increases base pairing affinity. Incorporation of LNAs into a DNA duplex can increase melting points up to 8° C. per LNA. Subsequently, a variety of bicyclic nucleotides have been developed such as Bridged Nucleic Acids (BNAs), Ethyl-bridged (ENAs), constrained ethyl (cEt) nucleic acids and tricyclic structures with varying affinity for target sites. LNAs can be incorporated into antagomirs, splice blocking oligonucleotides, either strand of an RNAi duplex; however, like other 3' endo conformers, LNAs are not substrates for RNAse H.

In some embodiments, an oligonucleotide of the present disclosure comprises an acyclic nucleic acid analog. In some cases, the analog comprises an alternative ribose ring structure. These include those in which the bond between 2' and 3' carbons in the ribose is absent, as well as those containing substitution of the ribose ring with a three-carbon backbone. Examples of acyclic nucleic acid analogs include unlocked nucleic acid (UNA) and glycol nucleic acids (GNA). Incorporation of these analogs reduce the melting temperature of the RNAi duplex and can be incorporated into either strand. Incorporation at the 5' end of the sense strand, or passenger strand, inhibits incorporation into this strand into RISC. Incorporation into the seed region of the antisense strand, or guide strand, can reduce off-target activity. Acyclic nucleic acid analogs may also increase resistance of the RNAi duplex to 3'-exonuclease activity.

In some embodiments, an oligonucleotide of the present disclosure comprises a modification patterns. Without being bound by theory, for RNAi duplexes, recognition by RISC requires RNA-like 3'-endo nucleotides and some patterns of RNA analogues. A pattern of alternating 2'-O-methyl groups may provide stability against nucleases, but not all permutations of alternating 2'-O-methyl are active RNAi agents. The fact that one may remove all 2'-hydroxy groups with alternating 2'-fluoro and 2'-O-methyl groups to produce duplexes that are resistant to nucleases and active in RNAi may suggest the 2'-hydroxy group is not absolutely required for activity, but that some sites in the RNAi duplex are sensitive to the added steric bulk of the methyl group.

Conjugated Oligonucleotides

Oligonucleotides may have groups conjugated via covalent bonds that prolong circulation, provide targeting to tissues and facilitate intracellular delivery.

In some embodiments, an oligonucleotide of the present disclosure is conjugated to polyethylene glycol (PEG), which may prevent clearance by two mechanisms: the increase in molecular weight above threshold for renal clearance and the prevention of non-specific interactions with extracellular surfaces and serum components. PEG may be incorporated into nucleic acid delivery vehicles by attachment to components that non-covalently associate with the nucleic acids, e.g. PEGylated lipids and polymers. PEG may also be directly conjugated to increase nucleic acid circulation times, decrease nonspecific interactions and alter biodistribution. In some cases, the targeting is passive and the potency of the nucleic may be compromised as PEG MW increases.

Another class of molecules that can be conjugated in order to increases circulation times is the attachment of lipophilic groups such as cholesterol or other lipophilic moiety with >12 carbons which interact with serum components such as albumen and lipoproteins thereby increasing circulation times and passive accumulation in the liver. In some cases, extensive PS modification increases circulation times through associations with serum components, with roughly 10 PS groups required for serum binding.

Formulations, Compositions, and Delivery

In some embodiments, the antisense oligonucleotide or dsRNA is administered in buffer.

In some embodiments, antisense oligonucleotide or dsRNA agent (sometimes referred to as siRNA) compounds described herein can be formulated for administration to a subject. A formulated antisense oligonucleotide or siRNA composition can assume a variety of states. In some examples, the composition is at least partially crystalline, uniformly crystalline, and/or anhydrous (e.g., less than 80, 50, 30, 20, or 10% water). In another example, the antisense oligonucleotide or siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the antisense oligonucleotide or siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

An antisense oligonucleotide or siRNA preparation can be formulated in combination with another agent, e.g., another therapeutic agent or an agent that stabilizes an antisense oligonucleotide or siRNA, e.g., a protein that complexes with siRNA to form an iRNP. Still other agents include chelators, e.g., EDTA (e.g., to remove divalent cations such as Mg2+), salts, RNAse inhibitors (e.g., a broad specificity RNAse inhibitor such as RNAsin) and so forth.

In some embodiments, the antisense oligonucleotide or siRNA preparation includes another antisense oligonucleotide or siRNA compound, e.g., a second siRNA that can mediate RNAi with respect to a second gene, or with respect to the same gene. Still other preparation can include at least 3, 5, ten, twenty, fifty, or a hundred or more different antisense oligonucleotide or siRNA species. Such siRNAs can mediate RNAi with respect to a similar number of different genes.

In some embodiments, the antisense oligonucleotide or siRNA preparation includes at least a second therapeutic agent (e.g., an agent other than a RNA or a DNA). For example, an antisense oligonucleotide or siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Liposomes

For ease of exposition the formulations, compositions and methods in this section are discussed largely with regard to unmodified antisense oligonucleotide or siRNA compounds. It may be understood, however, that these formulations, compositions and methods can be practiced with other antisense oligonucleotide or siRNA compounds, e.g., modified antisense oligonucleotide or siRNAs. An antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. In some embodiments, the term "liposome" refers to a vesicle with amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the antisense oligonucleotide or siRNA composition. The lipophilic material isolates the aqueous interior from an aqueous exterior, which typically does not include the antisense oligonucleotide or siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the antisense oligonucleotide or siRNA are delivered into the cell where the antisense oligonucleotide or siRNA can specifically bind to a target RNA. In some cases the liposomes are also specifically targeted, e.g., to direct the antisense oligonucleotide or siRNA to particular cell types.

A liposome containing an antisense oligonucleotide or siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The antisense oligonucleotide or siRNA preparation is then added to the micelles that include the lipid component. The cationic groups on the lipid interact with the antisense oligonucleotide or siRNA and condense around the antisense oligonucleotide or siRNA to form a liposome. After condensation, the detergent is removed, e.g., by dialysis, to yield a liposomal preparation of antisense oligonucleotide or siRNA.

If necessary a carrier compound that assists in condensation can be added during the condensation reaction, e.g., by controlled addition. For example, the carrier compound can be a polymer other than a nucleic acid {e.g., spermine or spermidine). pH can also be adjusted to favor condensation.

Commonly used techniques for preparing lipid aggregates of appropriate size for use as delivery vehicles include sonication and freeze-thaw plus extrusion. Microfluidization can be used when consistently small (50 to 200 nm) and relatively uniform aggregates are desired. These methods are readily adapted to packaging antisense oligonucleotide or siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs.

Nevertheless, some nucleic acid molecules are entrapped within the aqueous interior of these liposomes. pH-sensitive liposomes may be used to deliver DNA encoding the thymidine kinase gene to cell monolayers in culture where expression of the exogenous gene was detected in the target cells.

One type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver antisense oligonucleotide or siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated antisense oligonucleotide or siRNAs in their internal compartments from metabolism and degradation. Some considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA.

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Maryland) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis (oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that conjugate to a variety of moieties including, for example, carboxyspermine which may be conjugated to one of two types of lipids and includes compounds such as 5-carboxyspermylglycine dioctaoleoylamide ("DOGS") (TransfectamTM, Promega, Madison, Wisconsin) and dipalmitoylphosphatidylethanolamine 5-carboxyspermyl-amide ("DPPES").

Another cationic lipid conjugate includes derivatization of the lipid with cholesterol ("DC-Chol") which may be formulated into liposomes in combination with DOPE. Lipopolylysine, made by conjugating polylysine to DOPE, may be effective for transfection in the presence of serum. For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jo 11a, California) and Lipofectamine (DOSPA) (Life Technology, Inc., Gaithersburg, Maryland).

Liposomal formulations may be particularly suited for topical administration, and may present an advantage over other formulations. Such advantages include reduced side effects related to high systemic absorption of the administered drug, increased accumulation of the administered drug at the desired target, and the ability to administer antisense oligonucleotide or siRNA, into the skin. In some implementations, liposomes are used for delivering antisense oligonucleotide or siRNA to epidermal cells and also to enhance the penetration of antisense oligonucleotide or siRNA into dermal tissues, e.g., into skin. For example, the liposomes can be applied topically.

In some embodiments, non-ionic liposomal systems are used to deliver an oligonucleotide to the skin, e.g., using non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) may be used to deliver an oligonucleotide. Such formulations with antisense oligonucleotide or siRNA are useful for treating a dermatological disorder.

Liposomes that include antisense oligonucleotide or siRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include antisense oligonucleotide or siRNA can be delivered, for example, subcutaneously by infection in order to deliver antisense oligonucleotide or siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

In some embodiments, an oligonucleotide is formulated with a surfactant. Surfactants find wide application in formulations such as emulsions (including microemulsions) and liposomes (see above). In some embodiments, the antisense oligonucleotide or siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides a useful means for categorizing the different surfactants used in formulations.

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxy ethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfo succinates, and phosphates. The most important members of the anionic surfactant class are the alkyl sulfates and the soaps. If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Micelles and other Membranous Formulations

For ease of exposition the micelles and other formulations, compositions and methods in this section are discussed largely with regard to unmodified antisense oligonucleotide or siRNA compounds. It may be understood, however, that these micelles and other formulations, compositions and methods can be practiced with other antisense oligonucleotide or siRNA compounds, e.g., modified antisense oligonucleotide or siRNA compounds. The antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) composition can be provided as a micellar formulation. In some embodiments, "micelles" are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the antisense oligonucleotide or siRNA composition, an alkali metal Cs to C22 alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxy ethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. In some cases, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

Pharmaceutical Compositions

In some embodiments, the composition is a pharmaceutical composition. In some embodiments, the composition is sterile. In some embodiments, the composition further comprises a pharmaceutically acceptable carrier.

In some embodiments, the pharmaceutically acceptable carrier comprises water. In some embodiments, the pharmaceutically acceptable carrier comprises a buffer. In some embodiments, the pharmaceutically acceptable carrier comprises a saline solution. In some embodiments, the pharmaceutically acceptable carrier comprises water, a buffer, or a saline solution. In some embodiments, the composition comprises a liposome. In some embodiments, the pharmaceutically acceptable carrier comprises liposomes, lipids, nanoparticles, proteins, protein-antibody complexes, peptides, cellulose, nanogel, or a combination thereof.

The oligonucleotides disclosed herein may be formulated in a pharmaceutical composition. The specific concentrations of the oligonucleotide can be determined by experimentation.

For ease of exposition the particles, formulations, compositions and methods in this section are discussed largely with regard to antisense oligonucleotide or siRNA compounds. It may be understood, however, that these particles, formulations, compositions and methods can be practiced with modified antisense oligonucleotide or siRNA compounds. In some embodiments, an antisense oligonucleotide or siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

The antisense oligonucleotide or siRNA agents may be formulated for pharmaceutical use. Pharmaceutically acceptable compositions comprise a therapeutically-effective amount of one or more of the antisense oligonucleotide or dsRNA agents in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) inhalation; or (10) endotracheally.

In some embodiments, a "therapeutically-effective amount" is an amount of a compound, material, or composition comprising an oligonucleotide herein which is effective for producing some desired therapeutic effect in at least a sub-population of cells in an animal at a reasonable benefit/risk ratio applicable to any medical treatment.

In some embodiments, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage, or other relevant, form. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, from about 5 percent to about 70 percent, or from about 10 percent to about 30 percent.

In certain embodiments, a formulation comprises an excipient selected from the group consisting of cyclodextrins, celluloses, liposomes, micelle forming agents, e.g., bile acids, and polymeric carriers, e.g., polyesters and polyanhydrides; and a compound disclosed herein. In certain embodiments, an aforementioned formulation renders orally bio available a compound disclosed herein.

An agent preparation can be formulated in combination with another agent, e.g., another therapeutic agent or an agent that stabilizes an antisense oligonucleotide or siRNA, e.g., a protein that complexes with antisense oligonucleotide or siRNA to form particle. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound disclosed herein with the carrier and, optionally, one or more accessory ingredients. In general, the formulations are prepared by uniformly and intimately bringing into association a compound disclosed herein with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. In some cases, delayed absorption of a parenterally-administered drug form is accomplished by dissolving or suspending the drug in an oil vehicle.

The compounds disclosed herein may be formulated for administration in any convenient way for use in human or veterinary medicine, by analogy with other pharmaceuticals.

Further provided are pharmaceutical compositions of the oligonucleotide molecules described. These pharmaceutical compositions include salts of the above compounds, e.g., acid addition salts, for example, salts of hydrochloric, hydrobromic, acetic acid, and benzene sulfonic acid. These pharmaceutical formulations or pharmaceutical compositions can comprise a pharmaceutically acceptable carrier or diluent.

In some embodiments, pharmaceutical compositions (e.g. oligonucleotides and/or lipid nanoparticle formulations thereof) further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

In some embodiments, the siRNA and LNP compositions and formulations provided herein for use in pulmonary delivery further comprise one or more surfactants. Suitable surfactants or surfactant components for enhancing the uptake of the compositions include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

Gene Therapy Vector

In some embodiments, double-stranded RNAi agents or antisense oligonucleotides are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration, or by stereotactic injection. The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA agent and one that produces a transcript that includes the bottom strand of a dsRNA agent. When the templates are transcribed, the dsRNA agent is produced, and processed into siRNA agent fragments that mediate gene silencing.

Delivery Vehicles Based upon Complexation of Nucleic Acid

In some embodiments, complexation of oligonucleotide therapeutics with cationic agents inhibits nuclease from degrading the oligonucleotide by forming a steric barrier and by inhibiting nuclease binding by neutralizing anionic charge. The process of forming compact particles of nucleic acids from their extended chains is called condensation, which may be achieved by the addition of multiply-charged cationic species. Multiple positive charges can either be covalently attached to one another in a polycation or non-covalently associated with one another in a complex such as the surface of a cationic liposome. The resulting polycation-polyanion interaction is a colloidal dispersion where the nucleic acid particles vary in size and shape depending on the nucleic acid and the condensing cation. In general, the particles are greater than 20 nm in size, and—in the absence of agents to modulate surface charge such as polyethylene glycol (PEG)—have surface charges >20 mV.

The pharmacokinetics and biodistribution of nanoparticles are dependent upon their size and charge. Upon iv administration, large (>200 nm) and/or highly positively charged (surface charge >20 mV) are primarily distributed among endothelial tissues and macrophages in the liver and spleen and have a half-life of circulation less than 2 hours. Reduction in size (<100 nm) and surface charge (~0 mV) results increased circulation times. Local administration of positively charged polyplexes results in association with cells at site of application such as epithelial cells.

Strategies for Cytoplasmic Delivery

There are a variety of strategies to facilitate cytoplasmic delivery of oligonucleotides including endosomal buffering (i.e. proton sponge), titratable amphiphiles, cell penetrating peptides and masked membrane lytic polymers.

The mechanism of endosomal buffering (i.e. proton sponge) to facilitate endosomolysis relies on the ability of agents such as polyamines to buffer endosomal/lysosomal compartments. The resistance to acidification is postulated to result in increased osmotic pressure that results in lysis of the lysosomal compartment. Titratable amphiphiles are polymers/peptides whose structure is pH-dependent in such a way that at acidic pH they are hydrophobic and membrane disruptive. Typically, titratable amphiphiles are polyanionic polymers or peptides with carboxylic acids that become neutral and membrane disruptive upon acidification. Cell penetrating peptides (CPPs) are cationic peptides, with a high propensity of guanidinium groups, that enter cells without any apparent membrane lysis. Masked lytic polymers are membrane disruptive polymers whose membrane interactivity is attenuated by reversible covalent modification. Like titratable amphiphiles, the mechanism of endosomolysis by masked polymers relies on the use of amphipathic polymers whose ability to lyse membranes is controlled such that the activity is only functional in the acidic environment of the endosome/lysosome. In the case of titratable amphiphiles, the mechanism of control is a reversible protonation of carboxylic acids. In the case of masked polymers, the control of membrane activity is the irreversible cleavage of a group that inhibits membrane interactivity of the polymer.

Liposomal Delivery Systems

Nucleic acids entrapped in lipids (lipoplexes) are a common vehicle for the delivery of nucleic acids. Cationic lipids form electrostatic complexes between nucleic acid and lipids. In addition to the cationic lipids, there are typically neutral or anionic helper lipids which include unsaturated fatty acids and are postulated to assist in fusion between the lipoplex and the cellular membrane, and PEGylated lipids, which prevent aggregation during formulation and storage and non-specific interactions in vivo.

Lipids are water insoluble and nucleic acids are organic solvent insoluble. To mix these components in a controlled manner such that formulations are repeatable and relatively homogenous in size, detergents or water-miscible organic solvents such as ethanol are used. After formation of electrostatically-associated complexes, the amphipathic detergent or solvent is then removed by dialysis or solvent exchange. Depending on the components and the mixing procedure is possible to formulate lipoplexes that are well less than 100 nm.

Although the transfection efficiencies of lipoplexes are difficult to predict and optimization is empirical, there are a few design features identified to aid transfection efficiency in vivo: pH-sensitive cationic lipids, the use of unsaturation in the lipid chains and the hydrophobic-hydrophilic balance of PEG-lipids to balance circulation times and transfection efficiencies.

There is a correlation between the pKa of the amine groups of the cationic lipid, which is buffer in the range of the endosomal/lysosomal pathway (pH 4-7), and transfection ability. To synthesize lipids with such pKa values, lipids commonly have closely-spaced amines or imidazole groups. The effect of these weakly basic amine groups in the lipoplexes produces several attractive attributes that facilitate in vivo transfection: reduced surface charge at neutral pH thereby decreasing nonspecific interactions in vivo, increased surface charge in acid environment of endosomes and lysosomes thereby increasing electrostatic interactions with the cellular membrane in these compartments and providing buffering groups that can provide endosomolytic activity via the proton sponge mechanism.

Another common motif observed in cationic and helper lipids used in lipoplexes is the presence of unsaturation in their component fatty acids with oleic (18 carbon chain with one double bond) and linoleic (18 carbons with 2 double bonds) being very common. The incorporation of these groups increases fluidity of membranes, aids in the formation of fusogenic lipid structures and facilitates the release of cationic lipids from nucleic acids.

PEG-conjugated lipids are incorporated into lipoplexes to aid in the formation of nonaggregating small complexes and for the prevention of nonspecific interactions in vivo. Due to the hydrophilicity of PEG, their lipid conjugates are not permanently associated with lipoplexes and diffuse from the complexes with dilution and interaction with amphiphilic components in vivo. This loss of PEG shielding from the surface of the lipoplexes aids in transfection efficiency. In general, longer saturated fatty acid chains increase circulation while unsaturation and shorter chains decrease circulation.

A commonly invoked tumor targeting mechanism is the Enhanced Permeability and Retention (EPR) effect, which is when nanoparticles accumulate in tumor tissue much more than they do in normal tissues due to the leaky disorganized vasculature associated with tumor tissues and their lack of lymphatic drainage. EPR-based targeting requires long circulating particles.

Polymer Based Delivery Vehicles

Like lipoplexes, polymer-based transfection vehicles (polyplexes) provide nuclease protection and condensation of larger nucleic acids. Polyplexes are based upon cationic polymers that form electrostatic complexes with anionic nucleic acids. Polycations may be purely synthetic (such as polyethyleneimine), naturally occurring (such as histones, protamine, spermine and spermidine) or synthetic polymers based upon cationic amino acids such as ornithine, lysine and arginine.

Polycations form electrostatic complexes with polyanionic nucleic acids. The strength of the association is dependent upon the size of the nucleic acid and the size and charge density of the polycation.

There are three common strategies to improve the stability and surface charge of polyplexes to improve the circulation and targeting of ability of polyplexes: crosslinking of polycation, addition of a synthetic polyanion and conjugation of PEG.

Crosslinking, also called lateral stabilization and caging, is the formation of covalent polyamine-polyamine bonds after complexation/condensation of the nucleic acid. The crosslinking is accomplished by the addition of bifunctional, amine-reactive reagents that form a 3-D network of bonds around the nucleic acid, thereby making the polyplex resistant to displacement by salts and polyelectrolytes. The stability of the polyplexes is such that the nucleic acid is no longer active unless a mechanism of reversibility is introduced to allow for release of the nucleic acid. A common way to introduce reversibility is the use of disulfide-containing crosslinking reagent that can be reduced in the cytoplasm allowing release of nucleic acid therapeutic.

A common method to reduce the surface charge of a polyplex is the conjugation of PEG, a method commonly known as steric stabilization. The resulting PEG modified polyplexes have prolonged circulation in vivo. PEG modifications can be added to the size chains of polyamines— either before or after polyplex formation- or at the end of the polymer as a block copolymer of PEG and polycation.

Crosslinking and PEGylation are often combined to make stabilized polyplexes of reduced surface charge for systemic administration that can either be passively or actively targeted. As observed for lipoplexes, a variety of small molecule (such as GalNAc, RGD and folate) and biologic targeting ligands (such as transferrin and antibodies) may be conjugated to PEG-modified polyplexes for tissues selective targeting.

The most commonly used polymer for polyplexes- and the originator of the proton sponge mechanism—is polyethylenimine (PEI). PEI's high density of amine groups endows it with high charge density and a continuum of amine pKa's that buffer in the entire pH range of the endosome. The buffering capacity of PEI may be mimicked by the addition of weakly basic imidazole groups.

Oligonucleotide vehicle formulation. The solution conditions in which the oligonucleotide is dissolved, or its delivery vehicle is dispersed may play a role in its delivery. Hypotonic and hypertonic solution conditions may aid in cytoplasmic delivery for systemic and locally administration.

Methods and Routes for Administration

In embodiments disclosed herein, the accumulation and/or expression of ANGPTL7 may be suppressed or inhibited by at least 10%. In embodiments disclosed herein, the ocular tissue cell is conjunctiva, sclera, trabecular meshwork (TM) or cornea. In certain embodiments, the ocular tissue is TM, such as human TM. In certain embodiments, the TM cell that is the subject may be located in vivo in a mammal.

Embodiments disclosed herein also provide a method of treating glaucoma in a patient in need thereof comprising administering to the patient an oligonucleotide in an amount sufficient to suppress accumulation of ANGPTL7 in an ocular tissue cell, wherein the RNA is a double-stranded molecule with a first strand of RNA that is a ribonucleotide sequence that corresponds to a nucleotide sequence encoding ANGPTL7 and a second strand of RNA that is a ribonucleotide sequence that is complementary to the nucleotide sequence encoding ANGPTL7, wherein the first and the second ribonucleotide strands are complementary strands that hybridize to each other to form the double-stranded molecule, and wherein the double-stranded molecule suppresses accumulation of ANGPTL7 in the ocular tissue cell. In certain embodiments, the ocular tissue cell may be conjunctiva, sclera, trabecular meshwork (TM) or cornea. In certain embodiments, the glaucoma is an open-angle glaucoma. In certain embodiments, the expression of ANGPTL7 or certain ANGPTL7 transcripts are inhibited by at least 10%.

Embodiments disclosed herein provide a method of making and identifying an isolated ANGPTL7-specific RNA that inhibits or modulates ANGPTL7 expression in a cell involving (a) generating an RNA that is a double-stranded molecule with a first strand of RNA that is a ribonucleotide sequence that corresponds to a nucleotide sequence encoding ANGPTL7 and a second strand of RNA that is a ribonucleotide sequence that is complementary to the nucleotide sequence encoding ANGPTL7, wherein the first and the second ribonucleotide strands are complementary strands that hybridize to each other to form the double-stranded molecule, and wherein the double-stranded molecule suppresses or modulates accumulation of ANGPTL7 or certain ANPTL7 transcripts in an ocular tissue cell; and (b) screening the RNA to determine whether the RNA inhibits or modulates ANGPTL7 expression in a cell. In certain embodiments, the ocular tissue cell is conjunctiva, sclera, trabecular meshwork (TM) or cornea. The ANGPTL7 transcripts may be inhibited or modulated by at least 10%, or may be inhibited or modulated by at least 50%, or may be inhibited or modulated by at least 80%. In certain embodiments, the RNA is introduced by topical administration.

Conditions mediated by ANGPTL7 activity include, but are not limited to glaucoma (including, for example, primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma and absolute glaucoma), ocular hypertension, obesity, cancer, nevus sebaceous of Jadassohn, hepatitis C infection, osteoarthritis, keratoconus, fibrosis, hypoxia, abnormalities of lipid metabolism, oculocutaneous albinism, scleroderma, polymyositis, Crohn's disease, psoriasis, or rosacea. In some embodiments, the condition mediated by ANGPTL7 activity is an ocular condition. Ocular conditions include, but are not limited to, retinal artery occlusion, eyelid disease, panophthalmitis, ocular toxoplasmosis, angioid streaks, genetic eye tumor, retrobulbar hemorrhage, lacrimal gland adenoid cystic carcinoma, exfoliation syndrome, pharyngoconjunctival fever, takayasu arteritis, dry eye syndrome, macular holes, retinal vein occlusion, pterygium, vitreous body disease, ocular hypertension, retinopathy, cataract, ocular onchocerciasis, eye neoplasm, keratoconjunctivitis sicca, congenital nystagmus, genetic eye diseases, orbital myositis, glaucoma, optic neuritis, mixed cell uveal melanoma, uveitis, ocular tuberculosis, age-related macular degeneration, optic papillitis, eyelid neoplasm, ocular posterior capsular rupture, eye hemorrhage, eye injuries, ocular motility disease, corneal disease, acute retinal necrosis syndrome, eye infection, cycloplegia, microphthalmia, anterior uveitis, retinal drusen, diabetic eye disease, ocular foreign bodies, myopic macular degeneration, eye allergy, iritis, aniseikonia, retinal vasculitis, opsoclonus-myoclonus syndrome, ocular vascular disease, graves ophthalmopathy, lens disease, Sjogren syndrome, macular degeneration, or cytomegalovirus retinitis.

Routes of Delivery

A composition that includes an antisense oligonucleotide or dsRNA agent can be delivered to a subject by a variety of routes. Exemplary routes include: intravenous, subcutaneous, topical, rectal, anal, vaginal, nasal, endotracheally, inhalation, pulmonary, ocular.

In one embodiment, a patient is prophylactically or therapeutically administered an agent that reduces or modulates the expression of ANGPTL7. The inventive method may prevent or delay an increase in intraocular pressure, may reduce associated nerve loss, may confer protection on retinal sensory cells, etc. Administration may be by any ocular route. One example is topical application, with the ANGPTL7 reducing agent administered in a formulation of eye drops, cream, ointment, gel, salve, etc. Another example is intraocular injection with the ANGPTL7 reducing agent administered subconjunctivally, intravitreally, retrobulbarly, within the crystalline lens via piercing the lens capsule. Another example provides the ANGPTL7 reducing or modulating agent to the eye on or in a formulation such as a liposome, microsphere, microcapsule, biocompatible matrix, gel, polymer, nanoparticle, nanocapsule, etc. Another example provides the ANGPTL7 reducing or modulating agent on or in a device such as a device for transscleral delivery, or another intraocular device using, for example, iontophoresis or another type of release mechanism (controlled or not controlled), as known by one skilled in the art. Another example provides the ANGPTL7 reducing or modulating agent in conjunction with gene therapy, as known by one skilled in the art.

The antisense oligonucleotide or dsRNA agent can be incorporated into pharmaceutical compositions suitable for administration. Such compositions typically include one or more species of antisense oligonucleotide or dsRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In embodiments, the pharmaceutical compositions described herein can be formulated for oral, parental, intramuscular, transdermal, intravenous, inter-arterial, nasal, vaginal, sublingual, and subungual. Further, the route also includes, but is not limited to auricular, buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrachronchial, intrabursal, intracardiac, intracartilagenous, intracaudal, mtracavernous, intracavitary, intracerebral, intraci sternal, intracorneal, intracoronary, intracorporus cavernosum, intradermal, intradiscal, intraducatal, intraduodenal, intradural, intraepidermal, mtraesophageal, intragastric, intragingival, intraileal, intralesional, intralumical, intralymphatic, intramedullary, intrameningeal, intraocular, intraovarian, mtrapericardial, intraperitoneal, intrapleural, intrapulmonary, intrasinal, intrasynovial, intratendinous, intratesticular, intrathecal, intrathoracic, intratubular, intratumor, intratympanic, intrauterine, intravascular, intravenous bolus, intravenous drip, intraventricular, intravesical, intravitreal, iontophoresis, irrigation, laryngeal, nasal, nasogastric, occlusive dressing technique, ophthalmic, oropharyngeal, percutaneous, periarticular, peridural, periodontal, rectal, respirator}-, retrobulbar, soft tissue, subarachnoid, subconjunctival, subcutaneous, submucosal, topical, transmucosal, transplacental, transtracheal, transtympanic, ureteral, or urethal. In particular embodiments, the pharmaceutical compositions are formulated for intraocular administration, e.g., intravitreal, or topical.

The route and site of administration may be chosen to enhance targeting. For example, to target muscle cells, intramuscular injection into the muscles of interest would be a logical choice. Lung cells might be targeted by administering the antisense oligonucleotide or dsRNA agent in aerosol form.

Exemplary formulations for topical administration include those in which the antisense oligonucleotides or dsRNAs are in admixture with a topical delivery agent such as lipids, liposomes, fatty acids, fatty acid esters, steroids, chelating agents and surfactants. Exemplary lipids and liposomes include neutral (e.g. dioleoyl-phosphatidyl DOPE etlianolaniine, dimyristoylphosphatidyl choline DMPC, distearolyphosphatidyl choline) negative (e.g. dimyristoylphosphatidyl glycerol DMPG) and cationic (e.g. dioleoyltetramemylaminopropyl DOTAP and dioleoylphosphatidyl ethanolamine DOTMA).

For topical or other administration, antisense oligonucleotides or dsRNAs may be encapsulated within liposomes or may form complexes thereto, in particular to cationic liposomes. In some cases, antisense oligonucleotides or dsRNAs may be complexed to lipids, in particular to cationic lipids.

A topical formulation may be administered by any ophthalmogical vehicle, as know to one skilled in the art. Examples include, but are not limited to, eye droppers, satchels, applicators, etc. The amount and concentration of the formulation may depend upon the diluent, delivery system or device selected, clinical condition of the patient, side effects expected, stability of the compounds of the composition, presence and severity of other pathology, dosing frequency, active agent, etc.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Exemplary surfactants include fatty acids and or esters or salts thereof, bile acids and/or salts thereof. In some cases, penetration enhancers, for example, fatty acids salts are combined with bile acids salts. An exemplary combination is the sodium salt of lauric acid, capric acid and UDCA. Further penetration enhancers include polyoxyethylene-9-lauryl ether, polyoxyethylene-20-cetyl ether. Oligonucleotides may be delivered orally, in granular form including sprayed dried particles, or complexed to form micro or nanoparticles.

Compositions and formulations for pulmonary administration may include sterile aqueous solutions that may also contain buffers, diluents and other suitable additives such as, but not limited to, penetration enhancers, carrier compounds and other pharmaceutically acceptable carriers or excipients.

Dosage

In one aspect, provided is a method of administering an antisense oligonucleotide or dsRNA agent to a subject (e.g., a human subject). The method includes administering a unit dose of the antisense oligonucleotide or dsRNA agent that is 14-30 nucleotides (nt) long, for example, 21-23 nt, and is complementary to a target RNA (e.g., ANGPTL7), and optionally includes at least one 3' overhang 1-5 nucleotide long.

For topical administration, examples of concentrations that may be used include but are not limited to, less than 1 µg/mL, 1 µg/mL to 5 µg/mL, 5 µg/mL to 10 µg/mL, 10 µg/mL to 50 µg/mL, 50 µg/mL to 100 µg/mL, 100 µg/mL to 0.5 mg/mL, 0.5 mg/mL to 2.5 mg/mL, 1 mg/mL to 5 mg/mL, 5 mg/mL to 10 mg/mL, 10 mg/mL to 15 mg/mL, 15 mg/mL to 30 mg/mL, and greater than 30 mg/mL. For topical administration, examples of dosing regimens that may be used include but are not limited to, hourly, half-daily, daily, weekly, biweekly, monthly, quarterly, three times a year, twice a year, yearly, every two years, every three years, etc. Intervals between doses may be regular or varied. As one example, doses may be administered hourly or daily pre- and post-surgery for one week, for several weeks, or for several months, then may be administered twice a year or once a year until the desired reduction in intraocular pressure is achieved. As another example, doses may be administered daily or weekly pre- and/or post-surgery for one week, for several weeks, for several months, or for several years until the desired reduction in intraocular pressure achieved.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In some embodiments, the unit dose is not administered with a frequency {e.g., not a regular frequency). For example, the unit dose may be administered a single time.

In some embodiments, the effective dose is administered with other traditional therapeutic modalities. For example, a therapeutic agent useful for treating a disease or disorder affecting the eye.

In some embodiments, a subject is administered an initial dose and one or more maintenance doses of an antisense oligonucleotide or dsRNA agent. The maintenance dose or doses can be the same or lower than the initial dose, e.g., one-half less of the initial dose. A maintenance regimen can include treating the subject with a dose or doses ranging from 0.01 µg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days.

Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state is ablated, or if undesired side-effects are observed. The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

The antisense oligonucleotide or dsRNA agents can be administered to mammals, particularly large mammals such as nonhuman primates or humans in a number of ways.

In some embodiments, the administration of the antisense oligonucleotide or dsRNA agent is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, inhalation, pulmonary, intranasal, urethral or ocular. Administration can be provided by the subject or by another person, e.g., a health care provider. The medication can be provided in measured doses or in a dispenser which delivers a metered dose. Selected modes of delivery are discussed elsewhere herein.

Methods and Uses

Disclosed herein, in some embodiments, are methods of administering a composition described herein to a subject. Some embodiments relate to use a composition described herein, such as administering the composition to a subject. In some embodiments, the administration comprises an injection.

Some embodiments relate to a method of treating a disorder in a subject in need thereof. Some embodiments relate to use of a composition described herein in the method of treatment. Some embodiments include administering a composition described herein to a subject with the disorder.

In some embodiments, the administration treats the disorder in the subject. In some embodiments, the composition treats the disorder in the subject.

In some embodiments, the treatment comprises prevention, inhibition, or reversion of the disorder in the subject. Some embodiments relate to use of a composition described herein in the method of preventing, inhibiting, or reversing the disorder. Some embodiments relate to a method of preventing, inhibiting, or reversing a disorder a disorder in a subject in need thereof. Some embodiments include administering a composition described herein to a subject with the disorder. In some embodiments, the administration prevents, inhibits, or reverses the disorder in the subject. In some embodiments, the composition prevents, inhibits, or reverses the disorder in the subject.

Some embodiments relate to a method of preventing a disorder a disorder in a subject in need thereof. Some embodiments relate to use of a composition described herein in the method of preventing the disorder. Some embodiments include administering a composition described herein to a subject with the disorder. In some embodiments, the administration prevents the disorder in the subject. In some embodiments, the composition prevents the disorder in the subject.

Some embodiments relate to a method of inhibiting a disorder a disorder in a subject in need thereof. Some embodiments relate to use of a composition described herein in the method of inhibiting the disorder. Some embodiments include administering a composition described herein to a subject with the disorder. In some embodiments, the administration inhibits the disorder in the subject. In some embodiments, the composition inhibits the disorder in the subject.

Some embodiments relate to a method of reversing a disorder a disorder in a subject in need thereof. Some embodiments relate to use of a composition described herein in the method of reversing the disorder. Some embodiments include administering a composition described herein to a subject with the disorder. In some embodiments, the administration reverses the disorder in the subject. In some embodiments, the composition reverses the disorder in the subject.

In some embodiments, the administration comprises an injection. In some embodiments, the administration is to an eye. In some embodiments, the administration is intravenous.

Disorders

Some embodiments of the methods described herein include treating a disorder in a subject in need thereof. In some embodiments, the disorder is or includes a disorder with high ANGPTL7 expression. In some embodiments, the disorder is an eye disorder. In some embodiments, the disorder comprises a disorder associated with high intraocular pressure. In some embodiments, the disorder is glaucoma. In some embodiments, the glaucoma is a glaucoma subtype. In some embodiments, the glaucoma subtype is non-specific glaucoma. In some embodiments, the glaucoma subtype is primary open angle glaucoma (POAG). In some embodiments, the glaucoma subtype is primary angle closure glaucoma (PACG). In some embodiments, the glaucoma includes a glaucoma symptom. In some embodiments, the glaucoma symptom includes an intraocular pressure measurement. In some embodiments, the glaucoma symptom includes need for a glaucoma surgery. In some embodiments, the glaucoma symptom includes need for a glaucoma medication.

Subjects

Some embodiments of the methods described herein include treatment of a subject. Examples of subjects include vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is a dog. In some embodiments, the subject is a cat. In some embodiments, the subject is a cattle. In some embodiments, the subject is a mouse. In some embodiments, the subject is a rat. In some embodiments, the subject is a primate. In some embodiments, the subject is a monkey. In some embodiments, the subject is an animal, a mammal, a dog, a cat, cattle, a rodent, a mouse, a rat, a primate, or a monkey. In some embodiments, the subject is a human.

Baseline Measurements

Some embodiments of the methods described herein include obtaining a baseline measurement from a subject. For example, in some embodiments, a baseline measurement is obtained from the subject prior to treating the subject. In some embodiments, the baseline measurement comprises a baseline pressure measurement. In some embodiments, the baseline measurement is a baseline intraocular pressure measurement. In some embodiments, the baseline measurement is incidence of glaucoma. In some embodiments, the baseline measurement is incidence of a glaucoma subtype. In some embodiments, the baseline measurement is incidence of a glaucoma symptom.

In some embodiments, the baseline measurement is obtained by performing an assay such as an immunoassay, a colorimetric assay, or a fluorescence assay, on the sample obtained from the subject. In some embodiments, the baseline measurement is obtained by an immunoassay, a colorimetric assay, or a fluorescence assay. In some embodiments, the baseline measurement is obtained by PCR.

In some embodiments, the baseline measurement is a baseline ANGPTL7 protein measurement. In some embodiments, the baseline ANGPTL7 protein measurement comprises a baseline ANGPTL7 protein level. In some embodiments, the baseline ANGPTL7 protein level is indicated as a mass or percentage of ANGPTL7 protein per sample weight. In some embodiments, the baseline ANGPTL7 protein level is indicated as a mass or percentage of ANGPTL7 protein per sample volume. In some embodiments, the baseline ANGPTL7 protein level is indicated as a mass or percentage of ANGPTL7 protein per total protein within the sample. In some embodiments, the baseline ANGPTL7 protein measurement is a baseline circulating ANGPTL7 protein measurement. In some embodiments, the baseline ANGPTL7 protein measurement is obtained by an assay such as an immunoassay, a colorimetric assay, or a fluorescence assay.

In some embodiments, the baseline measurement is a baseline ANGPTL7 mRNA measurement. In some embodiments, the baseline ANGPTL7 mRNA measurement comprises a baseline ANGPTL7 mRNA level. In some embodiments, the baseline ANGPTL7 mRNA level is indicated as a mass or percentage of ANGPTL7 mRNA per sample weight. In some embodiments, the baseline ANGPTL7 mRNA level is indicated as a mass or percentage of ANGPTL7 mRNA per sample volume. In some embodiments, the baseline ANGPTL7 mRNA level is indicated as a mass or percentage of ANGPTL7 mRNA per total mRNA within the sample. In some embodiments, the baseline ANGPTL7 mRNA level is indicated as a mass or percentage of ANGPTL7 mRNA per total nucleic acids within the sample. In some embodiments, the baseline ANGPTL7 mRNA level is indicated relative to another mRNA level, such as an mRNA level of a housekeeping gene, within the sample. In some embodiments, the baseline ANGPTL7 mRNA measurement is obtained by an assay such as a polymerase chain reaction (PCR) assay. In some embodiments, the PCR comprises quantitative PCR (qPCR). In some embodiments, the PCR comprises reverse transcription of the ANGPTL7 mRNA.

Some embodiments of the methods described herein include obtaining a sample from a subject. In some embodiments, the baseline measurement is obtained in a sample obtained from the subject. In some embodiments, the sample is obtained from the subject prior to administration or treatment of the subject with a composition described herein. In some embodiments, a baseline measurement is obtained in a sample obtained from the subject prior to administering the composition to the subject. In some embodiments, the sample comprises ocular or eye tissue.

In some embodiments, the sample comprises a fluid. In some embodiments, the sample is a fluid sample. In some embodiments, the sample is a blood, plasma, or serum sample. In some embodiments, the fluid comprises an eye fluid. In some embodiments, the fluid comprises an intraocular fluid.

In some embodiments, the baseline measurement is obtained noninvasively. In some embodiments, the baseline measurement is obtained directly from the subject.

Effects

In some embodiments, the composition or administration of the composition affects a measurement such as a pressure measurement, an intraocular pressure measurement, incidence of glaucoma, incidence of a glaucoma subtype, or incidence of a glaucoma symptom, relative to the baseline measurement. In some embodiments, the measurement is an intraocular pressure measurement.

Some embodiments of the methods described herein include obtaining the measurement from a subject. For example, the measurement may be obtained from the subject after treating the subject. In some embodiments, the measurement is obtained in a second sample (such as a fluid or tissue sample described herein) obtained from the subject after the composition is administered to the subject. In some embodiments, the measurement is an indication that the disorder has been treated.

In some embodiments, the measurement is obtained by an assay as described herein. For example, the assay may comprise an immunoassay, a colorimetric assay, a fluorescence assay, or a PCR assay.

In some embodiments, the measurement is obtained within 1 week, within 2 weeks, within 3 weeks, within 1 month, within 2 months, within 3 months, within 6 months, within 1 year, within 2 years, within 3 years, within 4 years, or within 5 years after the administration of the composition. In some embodiments, the measurement is obtained after 1 week, after 2 weeks, after 3 weeks, after 1 month, after 2 months, after 3 months, after 6 months, after 1 year, after 2 years, after 3 years, after 4 years, or after 5 years, following the administration of the composition.

In some embodiments, the composition reduces the measurement relative to the baseline measurement. In some embodiments, the reduction is measured in a second tissue sample obtained from the subject after administering the composition to the subject. In some embodiments, the reduction is measured directly in the subject after administering the composition to the subject. In some embodiments, the measurement is decreased by about 2.5% or more, about 5% or more, or about 7.5% or more, relative to the baseline measurement. In some embodiments, the measurement is decreased by about 10% or more, relative to the baseline measurement. In some embodiments, the measurement is decreased by about 20% or more, about 30% or more, about 40% or more, about 50% or more, about 60% or more, about 70% or more, about 80% or more, about 90% or more, relative to the baseline measurement. In some embodiments, the measurement is decreased by no more than about 2.5%, no more than about 5%, or no more than about 7.5%, relative to the baseline measurement. In some embodiments, the measurement is decreased by no more than about 10%, relative to the baseline measurement. In some embodiments, the measurement is decreased by no more than about 20%, no more than about 30%, no more than about 40%, no more than about 50%, no more than about 60%, no more than about 70%, no more than about 80%, no more than about 90%, or no more than about 100% relative to the baseline measurement. In some embodiments, the measurement is decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the measurement is an ANGPTL7 protein measurement. In some embodiments, the ANGPTL7 protein measurement comprises an ANGPTL7 protein level. In some embodiments, the ANGPTL7 protein level is indicated as a mass or percentage of ANGPTL7 protein per sample weight. In some embodiments, the ANGPTL7 protein level is indicated as a mass or percentage of ANGPTL7 protein per sample volume. In some embodiments, the ANGPTL7 protein level is indicated as a mass or percentage of ANGPTL7 protein per total protein within the sample. In some embodiments, the ANGPTL7 protein measurement is a circulating ANGPTL7 protein measurement. In some embodiments, the baseline ANGPTL7 protein measurement is obtained by an assay such as an immunoassay, a colorimetric assay, or a fluorescence assay.

In some embodiments, the composition reduces the ANGPTL7 protein measurement relative to the baseline ANGPTL7 protein measurement. In some embodiments, the composition reduces circulating ANGPTL7 protein levels relative to the baseline ANGPTL7 protein measurement. In some embodiments, the composition reduces tissue ANGPTL7 protein levels (such as ocular ANGPTL7 protein levels) relative to the baseline ANGPTL7 protein measurement. In some embodiments, the reduced ANGPTL7 protein levels are measured in a second sample obtained from the subject after administering the composition to the subject.

In some embodiments, the ANGPTL7 protein measurement is decreased by about 2.5% or more, about 5% or more, or about 7.5% or more, relative to the baseline ANGPTL7 protein measurement. In some embodiments, the ANGPTL7 protein measurement is decreased by about 10% or more, relative to the baseline ANGPTL7 protein measurement. In some embodiments, the ANGPTL7 protein measurement is decreased by about 20% or more, about 30% or more, about 40% or more, about 50% or more, about 60% or more, about 70% or more, about 80% or more, about 90% or more, or about 100% or more relative to the baseline ANGPTL7 protein measurement. In some embodiments, the ANGPTL7 protein measurement is decreased by no more than about 2.5%, no more than about 5%, or no more than about 7.5%, relative to the baseline ANGPTL7 protein measurement. In some embodiments, the ANGPTL7 protein measurement is decreased by no more than about 10%, relative to the baseline ANGPTL7 protein measurement. In some embodiments, the ANGPTL7 protein measurement is decreased by no more than about 20%, no more than about 30%, no more than about 40%, no more than about 50%, no more than about 60%, no more than about 70%, no more than about 80%, no more than about 90%, or no more than about 100% relative to the baseline ANGPTL7 protein measurement. In some embodiments, the ANGPTL7 protein measurement is decreased by 2.5%, 5%, 7.5%, 19%, 20%, 30%, 40%, 50%, 60%, 70%, 80%, 90%, 100%, or by a range defined by any of the two aforementioned percentages.

In some embodiments, the measurement is an ANGPTL7 mRNA measurement. In some embodiments, the ANGPTL7 mRNA measurement comprises an ANGPTL7 mRNA level. In some embodiments, the ANGPTL7 mRNA level is indicated as a mass or percentage of ANGPTL7 mRNA per sample weight. In some embodiments, the ANGPTL7 mRNA level is indicated as a mass or percentage of ANGPTL7 mRNA per sample volume. In some embodiments, the ANGPTL7 mRNA level is indicated as a mass or percentage of ANGPTL7 mRNA per total mRNA within the sample. In some embodiments, the ANGPTL7 mRNA level is indicated as a mass or percentage of ANGPTL7 mRNA per total nucleic acids within the sample. In some embodiments, the ANGPTL7 mRNA level is indicated relative to another mRNA level, such as an mRNA level of a house-keeping gene, within the sample. In some embodiments, the ANGPTL7 mRNA measurement is obtained by an assay such as a PCR assay. In some embodiments, the PCR comprises qPCR. In some embodiments, the PCR comprises reverse transcription of the ANGPTL7 mRNA.

In some embodiments, the composition reduces the ANGPTL7 mRNA measurement relative to the baseline ANGPTL7 mRNA measurement. In some embodiments, the ANGPTL7 mRNA measurement is obtained in a second sample obtained from the subject after administering the composition to the subject. In some embodiments, the composition reduces ANGPTL7 mRNA levels relative to the baseline ANGPTL7 mRNA levels. In some embodiments, the reduced ANGPTL7 mRNA levels are measured in a second sample obtained from the subject after administering the composition to the subject. In some embodiments, the second sample is an ocular sample.

In some embodiments, the ANGPTL7 mRNA measurement is reduced by about 2.5% or more, about 5% or more, or about 7.5% or more, relative to the baseline ANGPTL7 mRNA measurement. In some embodiments, the ANGPTL7 mRNA measurement is decreased by about 10% or more, relative to the baseline ANGPTL7 mRNA measurement. In some embodiments, the ANGPTL7 mRNA measurement is decreased by about 20% or more, about 30% or more, about 40% or more, about 50% or more, about 60% or more, about 70% or more, about 80% or more, about 90% or more, or about 100% or more relative to the baseline ANGPTL7 mRNA measurement. In some embodiments, the ANGPTL7 mRNA measurement is decreased by no more than about 2.5%, no more than about 5%, or no more than about 7.5%, relative to the baseline ANGPTL7 mRNA measurement. In some embodiments, the ANGPTL7 mRNA measurement is decreased by no more than about 10%, relative to the baseline ANGPTL7 mRNA measurement. In some embodiments, the ANGPTL7 mRNA measurement is decreased by no more than about 20%, no more than about 30%, no more than about 40%, no more than about 50%, no more than about 60%, no more than about 70%, no more than about 80%, no more than about 90%, or no more than about 100% relative to the baseline ANGPTL7 mRNA measurement. In some embodiments, the ANGPTL7 mRNA measurement is decreased by 2.5%, 5%, 7.5%, 10%, 20%, 30%, 40%, 50%, 60%, 70%, 80%, 90%, 100%, or by a range defined by any of the two aforementioned percentages.

Methods of Inhibiting or Modulating Expression of the Target Gene

Embodiments also relate to methods for inhibiting the expression of a target gene. The method comprises the step of administering the antisense oligonucleotide or dsRNA agents in any of the preceding embodiments, in an amount sufficient to inhibit expression of the target gene. In some embodiments, the target gene is ANGPTL7. Another aspect relates to a method of modulating the expression of a target gene in a cell, comprising providing to said cell an antisense oligonucleotide or dsRNA agent. In some embodiments, the target gene is ANGPTL7. In some embodiments, the antisense oligonucleotide or dsRNA agent described herein is modified.

The present disclosure provides vitro and in vivo methods for treatment of a disease or disorder in a mammal by downregulating or silencing the transcription and/or translation of a target gene or gene transcript of interest. In some embodiments, the method comprises introducing an antisense oligonucleotide or dsRNA agent that silences expression (e.g., mRNA and/or protein levels) of a target sequence into a cell by contacting the cell with a modified antisense oligonucleotide or dsRNA agent described herein. In some embodiments, the method comprises in vivo delivery of an antisense oligonucleotide or dsRNA agent that silences expression of a target sequence by administering to a mammal a modified antisense oligonucleotide or dsRNA described herein. Administration of the antisense oligonucleotide or dsRNA can be by any route known in the art, such as, e.g., oral, intranasal, inhalation, intravenous, intraperitoneal, intramuscular, intra-articular, intralesional, intratracheal, endotracheal, subcutaneous, or intradermal. In some cases, delivery is by respiratory tract administration. In some embodiments, the target sequence is ANGPTL7.

In certain embodiments, the antisense oligonucleotide or dsRNA agent comprises a carrier system, e.g., to deliver the antisense oligonucleotide or dsRNA agent into a cell of a mammal. Non-limiting examples of carrier systems include nucleic acid-lipid particles, liposomes, micelles, virosomes, nucleic acid complexes, and mixtures thereof. In certain instances, the antisense oligonucleotide or dsRNA molecule is complexed with a lipid such as a cationic lipid to form a lipoplex. In certain instances, the antisense oligonucleotide or dsRNA agent is complexed with a polymer such as a cationic polymer (e.g., polyethylenimine (PEI)) to form a polyplex. The antisense oligonucleotide or dsRNA agent may also be complexed with cyclodextrin or a polymer thereof. In some embodiments, the antisense oligonucleotide or dsRNA agent is encapsulated in a nucleic acid-lipid particle.

Assessing Up-Regulation or Inhibition of Gene or Transcript Expression

Transfer of an exogenous nucleic acid into a host cell or organism can be assessed by directly detecting the presence of the nucleic acid in the cell or organism. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense or dsRNA modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non-coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides or dsRNA would be assayed by modulation of the reporter gene. Reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Lac), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

ANGPTL7 protein and mRNA expression can be assayed using for example, immunoassays such as the ELISA to measure protein levels.

In some embodiments, ANGPTL7 expression (e.g., mRNA or protein) in a sample (e.g., cells or tissues in vivo or in vitro) treated using an antisense oligonucleotide or dsRNA agent is evaluated by comparison with ANGPTL7 expression in a control sample. For example, expression of the protein or nucleic acid can be compared using a mock-treated or untreated sample. In some cases, comparison with a sample treated with a control antisense oligonucleotide (e.g., one having an altered or different sequence) can be made depending on the information desired. In some embodiments, a difference in the expression of the ANGPTL7 protein or nucleic acid in a treated vs. an untreated sample can be compared with the difference in expression of a different nucleic acid (including any standard deemed appropriate by the researcher, e.g., a house-keeping gene) in a treated sample vs. an untreated sample.

Observed differences can be expressed as desired, e.g., in the form of a ratio or fraction, for use in a comparison with control. In embodiments, the level of ANGPTL7 mRNA or protein, in a sample treated with an antisense oligonucleotide or dsRNA, is increased or decreased by about 1.25-fold to about 10-fold or more relative to an untreated sample or a sample treated with a control nucleic acid. In embodiments, the level of ANGPTL7 mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds disclosed herein can be utilized for diagnostics, therapeutics, and prophylaxis, and as research reagents and components of kits. Furthermore, antisense oligonucleotides or dsRNA, which inhibit gene expression may be used to elucidate the function of particular genes or to distinguish between functions of various members of a biological pathway.

For use in kits and diagnostics and in various biological systems, the compounds disclosed herein, either alone or in combination with other compounds or therapeutics, may be useful as tools in differential and/or combinatorial analyses to elucidate expression patterns of a portion or the entire complement of genes expressed within cells and tissues.

In some embodiments, the term "biological system" or "system" is any organism, cell, cell culture or tissue that expresses, or is made competent to express products of the angiopoietin like 7 (ANGPTL7) genes. These include, but are not limited to, humans, transgenic animals, cells, cell cultures, tissues, xenografts, transplants and combinations thereof.

As one non limiting example, expression patterns within cells or tissues treated with one or more antisense compounds or dsRNAs are compared to control cells or tissues not treated with antisense compounds or dsRNAs and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

In some embodiments, the compounds disclosed herein are useful for research and diagnostics, because these compounds hybridize to nucleic acids encoding angiopoietin like 7 (ANGPTL7). For example, oligonucleotides that hybridize with such efficiency and under such conditions as disclosed herein as to be effective ANGPTL7 modulators are effective primers or probes under conditions favoring gene amplification or detection, respectively. These primers and probes are useful in methods requiring the specific detection of nucleic acid molecules encoding ANGPTL7 and in the amplification of said nucleic acid molecules for detection or for use in further studies of ANGPTL7. Hybridization of the antisense oligonucleotides, particularly the primers and probes, with a nucleic acid encoding ANGPTL7 can be detected, e.g., by conjugation of an enzyme to the oligonucleotide, radiolabeling of the oligonucleotide, or any other suitable detection means. Kits using such detection means for detecting the level of ANGPTL7 in a sample may also be prepared.

The specificity and sensitivity of antisense and sRNA are also harnessed for therapeutic uses. For therapeutics, an animal, e.g., a human, suspected of having a disease or disorder which can be treated by modulating the expression of ANGPTL7 polynucleotides is treated by administering oligonucleotide compounds disclosed herein. For example, in one non-limiting embodiment, the methods comprise the step of administering to the animal in need of treatment, a therapeutically effective amount of ANGPTL7 modulator. The ANGPTL7 modulators disclosed herein effectively modulate the activity of the ANGPTL7 or modulate the expression of the ANGPTL7 protein. In some embodiments, the activity or expression of ANGPTL7 in an animal is inhibited or modulated by about 10% as compared to a control. The control may be an oligonucleotide that does not specifically hybridize to ANGPTL7. In some cases, the activity or expression of ANGPTL7 in an animal is inhibited or modulated by about 30%. In some cases, the activity or expression of ANGPTL7 in an animal is inhibited or modulated by 50% or more. Thus, the oligomeric compounds may modulate expression of angiopoietin like 7 (ANGPTL7) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control. The reduction of or modulation in the expression of angiopoietin like 7, (ANGPTL7) may be measured in serum, blood, adipose tissue, liver or any other body fluid, tissue or organ of the animal. In some cases, the cells contained within said fluids, tissues or organs being analyzed contain a nucleic acid molecule encoding ANGPTL7 peptides and or the ANGPTL7 protein itself.

Drug Discovery

The compounds disclosed herein can also be applied in the areas of drug discovery and target validation. The compounds and target segments identified herein may be used in drug discovery efforts to elucidate relationships that exist between angiopoietin like 7 (ANGPTL7) polynucleotides and a disease state, phenotype, or condition. These methods include detecting or modulating ANGPTL7 polynucleotides comprising contacting a sample, tissue, cell, or organism with the compounds disclosed herein, measuring the nucleic acid or protein level of ANGPTL7 polynucleotides and/or a related phenotypic or chemical endpoint at some time after treatment, and optionally comparing the measured value to a non-treated sample or sample treated with a further compound disclosed herein. These methods can also be performed in parallel or in combination with other experiments to determine the function of unknown genes for the process of target validation or to determine the validity of a particular gene product as a target for treatment or prevention of a particular disease, condition, or phenotype.

This disclosure is further illustrated by the following examples, which should not be construed as further limiting. The contents of all references, pending patent applications and published patents, cited throughout this application are hereby expressly incorporated by reference.

Embodiments

Some embodiments include one or more of the following:
1. An RNA interference (RNAi) agent capable of inhibiting or modulating the expression of angiopoietin like 7 (ANGPTL7), wherein the RNAi agent comprises a double-stranded RNA (dsRNA) comprising a sense strand and an antisense strand, each strand having 14 to 30 nucleotides.
2. The RNAi agent of embodiment 1, wherein the dsRNA has a length of 17-30 nucleotide pairs.
3. The RNAi agent of embodiment 1 or embodiment 2, wherein the sense strand and antisense strand each have 17-30 nucleotides.
4. The RNAi agent of any of embodiments 1-3, wherein the sense strand comprises a sequence at least about 80%, 85%, 90%, 95%, or 100% identical to a sequence selected from SEQ ID NOS: 1-4412.
5. The RNAi agent of any of embodiments 1-4, wherein the antisense strand comprises a sequence at least about 80%, 85%, 90%, 95%, or 100% identical to the reverse complement of the sense strand.
6. The RNAi agent of any of embodiments 1-5, wherein the antisense strand comprises a sequence at least about 80%, 85%, 90%, 95%, or 100% identical to a sequence selected from SEQ ID NOS: 1-4412.
7. The RNAi agent of any of embodiments 1-3, wherein the sequence of the sense strand comprises SEQ ID NO: 11089 and the sequence of the antisense strand comprises SEQ ID NO: 11090.
8. The RNAi agent of any of embodiments 1-7, comprising one or more nucleotide modifications selected from the group consisting of LNA, HNA, CeNA, 2'-methoxyethyl, 2'-0-alkyl, 2'-0-allyl, 2'-C-allyl, 2'-fluoro, and 2'-deoxy.
9. The RNAi agent of any of embodiments 1-8, wherein the nucleotides are modified with either 2'-OCH$_3$ or 2'-F.
10. The RNAi agent of any of embodiments 1-9, further comprising at least one ligand.
11. The RNAi agent of any of embodiments 1-10, comprising one or more nucleotide modifications selected from the group consisting of 2'-0-methyl nucleotide, 2'-deoxyfluoro nucleotide, 2'-O—N-methylacetamido (2'-0-NMA) nucleotide, a 2'-0-dimethylaminoethoxyethyl (2'-0-DMAEOE) nucleotide, 2'-0-aminopropyl (2'-0-AP) nucleotide, and 2'-ara-F.
12. The RNAi agent of any of embodiments 1-11, further comprising at least one phosphorothioate or methylphosphonate internucleotide linkage.
13. The RNAi agent of any of embodiments 1-12, wherein the nucleotide at the 1 position of the 5'-end of the antisense strand of the dsRNA is selected from the group consisting of A, dA, dU, U, and dT.
14. The RNAi agent of any of embodiments 1-13, wherein the base pair at the 1 position of the 5'-end of the dsRNA is an AU base pair.
15. An RNA interference (RNAi) agent capable of inhibiting or modulating the expression of ANGPTL7, wherein the RNAi agent comprises a double-stranded RNA (dsRNA) comprising a sense strand and an antisense strand, each of the strands having 14 to 30 nucleotides, wherein the sense strand contains at least two motifs of three identical modifications on three consecutive nucleotides, a first of said sense strand motifs occurring at a cleavage site in the sense strand and a second of said sense strand motifs occurring at a different region of the sense strand that is separated from the first sense strand motif by at least one nucleotide; and wherein the antisense strand contains at least two motifs of three identical modifications on three consecutive nucleotides, a first of said antisense strand motifs occurring at or near the cleavage site in the antisense strand and a second of said antisense strand motifs occurring at a different region of the antisense strand that is separated from the first antisense strand motif by at least one nucleotide; wherein the modification in the first antisense strand motif is different than the modification in the second antisense strand motif.
16. The RNAi agent of embodiment 15, wherein at least one of the nucleotides occurring in the first sense strand motif forms a base pair with one of the nucleotides in the first antisense strand motif.
17. The RNAi agent of embodiment 15 or embodiment 16, wherein the dsRNA has 17-30 nucleotide base pairs.
18. The RNAi agent of embodiment 17, wherein the dsRNA has 17-19 nucleotide base pairs.
19. The RNAi agent of any of embodiments 15-18, wherein each strand has 17-23 nucleotides.
20. The RNAi agent of any of embodiments 15-19, wherein the modifications on the nucleotides of the sense strand and/or antisense strand are selected from the group consisting of LNA, HNA, CeNA, 2'-methoxyethyl, 2'-0-alkyl, 2'-0-allyl, 2'-C-allyl, 2'-fluoro, 2'-deoxy, and combinations thereof.
21. The RNAi agent of any of embodiments 15-20, wherein the modifications on the nucleotides of the sense strand and/or antisense strand are 2'-OCH3 or 2'-F.
22. The RNAi agent of any of embodiments 15-21, further comprising a ligand attached to the 3' end of the sense strand.
23. An RNA interference (RNAi) agent capable of inhibiting or modulating the expression of ANGPTL7, wherein the RNAi agent comprises a double-stranded RNA (dsRNA) comprising a sense strand and an antisense strand, each of the strands having 14 to 30 nucleotides, wherein the sense strand contains at least one motif of three 2'-F modifications on three consecutive nucleotides, one of said motifs occurring at or near the cleavage site in the sense strand; and wherein the antisense strand contains at least one motif of three 2'-0-methyl modifications on three consecutive nucleotides, one of said motifs occurring at or near the cleavage site in the antisense strand.
24. The RNAi agent of embodiment 23, wherein the sense strand comprises a sequence at least about 80%, 85%, 90%, 95%, or 100% identical to a sequence selected from SEQ ID NOS: 1-4412.
25. The RNAi agent of embodiment 23 or embodiment 24, wherein the antisense strand comprises a sequence at least about 80%, 85%, 90%, 95%, or 100% identical to the reverse complement of the sense strand.
26. The RNAi agent of any of embodiments 23-25, wherein the antisense strand comprises a sequence at least about 80%, 85%, 90%, 95%, or 100% identical to a sequence selected from SEQ ID NOS: 1-4412.
27. A method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length, wherein said at least one antisense oligonucleotide has at least 50% sequence identity to a reverse complement of a polynucleotide comprising 5 to 30 consecutive nucleotides within nucleotides 1 to 2224 of SEQ ID NO: 11085; thereby modulating a function of and/or the expression of the angiopoietin like 7 (ANGPTL7) polynucleotide in patient cells or tissues, in vivo or in vitro.
28. A method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length, wherein said antisense oligonucleotide has at least 50% sequence identity to an antisense oligonucleotide to the angiopoietin like 7 (ANGPTL7) polynucleotide; thereby modulating a function of and/or the expression of the angiopoietin like 7 (ANGPTL7) polynucleotide in patient cells or tissues, in vivo or in vitro.
29. A method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide that targets a region of a natural antisense oligonucleotide of the angiopoietin like 7 (ANGPTL7) polynucleotide; thereby modulating a function of and/or the expression of the angiopoietin like 7 (ANGPTL7) polynucleotide in patient cells or tissues, in vivo or in vitro.
30. A method of modulating a function of and/or the expression of an angiopoietin like 7 (ANGPTL7) polynucleotide in patient cells or tissues, in vivo or in vitro, the method comprising: contacting said cells or tissues with at least one antisense oligonucleotide 5 to 30 nucleotides in length; thereby modulating a function of and/or the expression of the ANGPTL7 polynucleotide in patient cells or tissues, in vivo or in vitro.
31. The method of any one of embodiments 27-29, wherein the at least one antisense oligonucleotide comprises SEQ ID NO: 11087.
32. The method of embodiment 30, wherein the at least one antisense oligonucleotide comprises a sequence selected from SEQ ID NOS: 4413-11084.
33. The method of any one of embodiments 27-29, wherein the at least one antisense oligonucleotide comprises a sequence at least about 80%, 85%, 90%, 95% identical to SEQ ID SEQ ID NOS: 4413-11084.
34. The method of any of embodiments 27-33, wherein a function of and/or the expression of the angiopoietin like 7 (ANGPTL7) is increased in vivo or in vitro with respect to a control oligonucleotide that does not target or specifically hybridize to ANGPTL7.
35. The method of any of embodiments 27-33, wherein a function of and/or the expression of the angiopoietin like 7 (ANGPTL7) is decreased in vivo or in vitro with respect to a control oligonucleotide that does not target or specifically hybridize to ANGPTL7.
36. The method of any of embodiments 27-35, wherein the at least one antisense oligonucleotide targets a natural antisense sequence of an angiopoietin like 7 (ANGPTL7) polynucleotide.
37. The method of any of embodiments 27-36, wherein the at least one antisense oligonucleotide targets a nucleic acid sequence comprising coding and/or non-coding nucleic acid sequences of an angiopoietin like 7 (ANGPTL7) polynucleotide.
38. The method of any of embodiments 27-37, wherein the at least one antisense oligonucleotide targets overlapping and/or non-overlapping sequences of an angiopoietin like 7 (ANGPTL7) polynucleotide.
39. The method of any of embodiments 27-38, wherein the at least one antisense oligonucleotide comprises one or more modifications.
40. The method of embodiment 39, wherein the one or more modifications is selected from: at least one modified sugar moiety, at least one modified internucleoside linkage, at least one modified nucleotide, and combinations thereof.

41. The method of embodiment 39, wherein the one or more modifications comprise at least one modified sugar moiety selected from: a 2'-0-methoxyethyl modified sugar moiety, a 2'-methoxy modified sugar moiety, a 2'-0-alkyl modified sugar moiety, a bicyclic sugar moiety, and combinations thereof.

42. The method of embodiment 39, wherein the one or more modifications comprise at least one modified internucleoside linkage selected from: a phosphorothioate, 2'-Omethoxyethyl (MOE), 2'-fluoro, alkylphosphonate, phosphorodithioate, alkylphosphonothioate, phosphoramidate, carbamate, carbonate, phosphate triester, acetamidate, carboxymethyl ester, and combinations thereof 43. The method of embodiment 39, wherein the one or more modifications comprise at least one modified nucleotide selected from: a peptide nucleic acid (PNA), a locked nucleic acid (LNA), an arabin-nucleic acid (FANA), an analogue, a derivative, and combinations thereof.

44. A method of modulating a function of and/or the expression of an angiopoietin like 7 (ANGPTL7) gene in mammalian cells or tissues, in vivo or in vitro, the method comprising: contacting said cells or tissues with at least one short interfering RNA (siRNA) oligonucleotide 5 to 30 nucleotides in length, said at least one siRNA oligonucleotide being specific for an antisense polynucleotide of an angiopoietin like 7 (ANGPTL7) polynucleotide, wherein said at least one siRNA oligonucleotide has at least 50% sequence identity to a complementary sequence of at least about five consecutive nucleic acids of the antisense and/or sense nucleic acid molecule of the angiopoietin like 7 (ANGPTL7) polynucleotide; thereby modulating a function of and or the expression of angiopoietin like 7, (ANGPTL7) in mammalian cells or tissues in vivo or in vitro.

45. The method of embodiment 44, wherein said oligonucleotide has at least 80% sequence identity to a sequence of at least about five consecutive nucleic acids that is complementary to the antisense and/or sense nucleic acid molecule of the angiopoietin like 7 (ANGPTL7) polynucleotide.

46. The method of embodiment 44 or embodiment 45, wherein the at least one siRNA oligonucleotide comprises a sequence selected from SEQ ID NOS: 1-4412.

47. The method of embodiment 44 or embodiment 45, wherein the at least one siRNA oligonucleotide comprises a sequence at least about 80%, 85%, 90%, 95%, or 100% identical to a sequence selected from SEQ ID NOS: 1-4412.

48. A method of modulating a function of and/or the expression of angiopoietin like 7, (ANGPTL7) in mammalian cells or tissues, in vivo or in vitro, the method comprising: contacting said cells or tissues with at least one antisense oligonucleotide of about 5 to 30 nucleotides in length, the antisense oligonucleotide specific for noncoding and/or coding sequences of a sense and/or natural antisense strand of an angiopoietin like 7 (ANGPTL7) polynucleotide, wherein said at least one antisense oligonucleotide has at least 50% sequence identity to at least one nucleic acid sequence set forth as 1 to 2224 of SEQ ID NO: 11085 or its complement; thereby modulating the function and/or expression of the angiopoietin like 7 (AGNPTL7) in mammalian cells or tissues, in vivo or in vitro.

49. The method of embodiment 48, wherein the at least one antisense oligonucleotide comprises a sequence selected from SEQ ID NOS: 4413-11084.

50. The method of embodiment 48, wherein the at least one antisense oligonucleotide comprises a sequence at least about 80%, 85%, 90%, 95% identical to SEQ ID NOS: 4413-11084.

51. A synthetic, modified oligonucleotide comprising at least one modification wherein the at least one modification is selected from: at least one modified sugar moiety; at least one modified internucleotide linkage; at least one modified nucleotide, and combinations thereof; wherein said oligonucleotide is an antisense compound which hybridizes to and modulates the function and/or expression of an angiopoietin like 7 (ANGPTL7) polynucleotide in vivo or in vitro as compared to a control oligonucleotide that does not specifically hybridize to the ANGPTL7 polynucleotide.

52. The oligonucleotide of embodiment 51, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

53. The oligonucleotide of embodiment 52, wherein said oligonucleotide comprises at least one phosphorothioate internucleotide linkage.

54. The oligonucleotide of embodiment 52, wherein said oligonucleotide comprises a backbone of phosphorothioate internucleotide linkages.

55. The oligonucleotide of embodiment 52, wherein the oligonucleotide comprises at least one modified nucleotide, said modified nucleotide selected from: a peptide nucleic acid, a locked nucleic acid (LNA), and an analogue, derivative, and a combination thereof.

56. The oligonucleotide of embodiment 51, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

57. The oligonucleotide of embodiment 51, wherein the oligonucleotide comprises a plurality of modifications, wherein said modifications comprise modified nucleotides selected from: peptide nucleic acids, locked nucleic acids (LNA), and analogues, derivatives, and a combination thereof 58. The oligonucleotide of embodiment 51, wherein the oligonucleotide comprises at least one modified sugar moiety selected from: a 2'-O-methoxyethyl modified sugar moiety, a 2'-methoxy modified sugar moiety, a 2-O-alkyl modified sugar moiety, a bicyclic sugar moiety, and a combination thereof.

59. The oligonucleotide of embodiment 51, wherein the oligonucleotide comprises a plurality of modifications, wherein said modifications comprise modified sugar moieties selected from: a 2'-0-methoxyethyl modified sugar moiety, a 2-methoxy modified sugar moiety, a 2'-0-alkyl modified sugar moiety, a bicyclic sugar moiety, and a combination thereof.

60. The oligonucleotide of embodiment 51, wherein the oligonucleotide is of at least about 5 to 30 nucleotides in length and hybridizes to an antisense and/or sense strand of an angiopoietin like 7 (ANGPTL7) polynucleotide, wherein said oligonucleotide has at least about 20% sequence identity to a complementary sequence of at least about five consecutive nucleic acids of the antisense and/or sense coding and/or noncoding nucleic acid sequences of the angiopoietin like 7 (ANGPTL7) polynucleotide.

61. The oligonucleotide of embodiment 51, wherein the oligonucleotide has at least about 80% sequence identity to a complementary sequence of at least about five consecutive nucleic acids of the antisense and or sense coding and/or noncoding nucleic acid sequence of the angiopoietin like 7 (ANGPTL7) polynucleotide.

62. The oligonucleotide of embodiment 51, wherein said oligonucleotide hybridizes to and modulates expression and/or function of at least one angiopoietin like 7 (ANGPTL7) polynucleotide, in vivo or in vitro, as compared to the control oligonucleotide.

63. The oligonucleotide of embodiment 51, wherein the oligonucleotide comprises the sequence set forth as SEQ ID NO: 11087.

64. The oligonucleotide of any one of embodiments 51-63, wherein the at least one antisense oligonucleotide comprises SEQ ID NOS: 4413-11084.

65. The oligonucleotide of any one of embodiments 51-63, wherein the at least one antisense oligonucleotide comprises a sequence at least about 80%, 85%, 90%, or 95% identical to SEQ ID NOS: 4413-11084.

66. A composition comprising one or more oligonucleotides specific for one or more angiopoietin like 7 (ANGPTL7) polynucleotides, said one or more oligonucleotides comprising an antisense sequence, complementary sequence, allele, homolog, isoform, variant, derivative, mutant, or fragment of the ANGPTL7 polynucleotide, or a combination thereof.

67. The composition of embodiment 66 wherein the one or more oligonucleotides have at least about 40% sequence identity as compared to the nucleotide sequence set forth as SEQ ID NO: 11087.

68. The composition of embodiment 66 or embodiment 67, wherein the oligonucleotide comprises the nucleotide sequence set forth as SEQ ID NO: 11087.

69. The composition of embodiment 66, wherein the one or more oligonucleotides comprises a sequence selected from SEQ ID NOS: 1-4412.

70. The composition of embodiment 66, wherein the one or more oligonucleotides comprises a sequence at least about 80%, 85%, 90%, 95%, or 100% identical to a sequence selected from SEQ ID NOS: 1-4412.

71. The composition of any of embodiments 66-70, wherein the one or more oligonucleotides comprises one or more modifications or substitutions.

72. The composition of embodiment 71, wherein the one or more modifications are selected from: phosphorothioate, methylphosphonate, peptide nucleic acid, locked nucleic acid (LNA) molecules, and combinations thereof.

73. A method of preventing or treating a disease associated with at least one angiopoietin like 7 (ANGPTL7) polynucleotide and/or at least one encoded product thereof, the method comprising: administering to a subject in need thereof a therapeutically effective dose of at least one antisense oligonucleotide that binds to a natural antisense sequence of said at least one angiopoietin like 7 (ANGPTL7) polynucleotide and modulates expression of said at least one angiopoietin like 7 (ANGPTL7) polynucleotide; thereby preventing or treating the disease associated with the at least one angiopoietin like 7 (ANGPTL7) polynucleotide and or at least one encoded product thereof.

74. A method of preventing or treating a disease associated with at least one angiopoietin like 7 (ANGPTL7) polynucleotide and/or at least one encoded product thereof, the method comprising: administering to a subject in need thereof a therapeutically effective dose of at least one antisense oligonucleotide that binds to a natural sense sequence of said at least one angiopoietin like 7 (ANGPTL7) polynucleotide and modulates expression of said at least one angiopoietin like 7 (ANGPTL7) polynucleotide; thereby preventing or treating the disease associated with the at least one angiopoietin like 7 (ANGPTL7) polynucleotide and or at least one encoded product thereof.

75. The method of embodiment 73 or embodiment 74, wherein a disease associated with the at least one angiopoietin like 7 (ANGPTL7) polynucleotide is selected from: a disease or disorder associated with abnormal function and/or expression of ANGPTL7, a disease or disorder associated with optic nerve damage, a disease or disorder associated with intraocular pressure, a degenerative retinal disease or disorder, an inflammatory eye disease or disorder, an allergic eye disease or disorder, a disease or disorder associated with degeneration or inflammation of the joints, a disease or disorder associated with abnormal lipid metabolism, cancer, Alzheimer's disease, dementia, stroke and brain ischemia.

76. The method of embodiment 75, wherein the disease or disorder associated with optic nerve damage comprises primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma, absolute glaucoma, ocular hypertension, or a combination thereof 77. The method of embodiment 75, wherein the disease or disorder associated with degeneration or inflammation of the joints comprises osteoarthritis, osteoarthrosis or a combination thereof.

78. The method of embodiment 75, wherein the cancer is selected from lung cancer, epidermoid carcinoma, breast cancer, or a combination thereof.

79. A method of identifying and selecting at least one oligonucleotide for in vivo administration comprising: identifying at least one oligonucleotide comprising at least five consecutive nucleotides which are complementary to ANGPTL7 or to a polynucleotide that is antisense to ANGPTL7; measuring the thermal melting point of a hybrid of an antisense oligonucleotide and the ANGPTL7 or the polynucleotide that is antisense to the ANGPTL7 under stringent hybridization conditions; and selecting at least one oligonucleotide for in vivo administration based on the information obtained.

80. A method of treating a disease or condition mediated by ANGPTL7, the method comprising administering to a subject in need thereof an oligonucleotide comprising a sequence at least about 80%, 85%, 90%, 95%, or 100% identical to a sequence selected from SEQ ID NOS: 1-4412.

81. The method of embodiment 80, wherein the oligonucleotide comprises a sequence selected from SEQ ID NOS: 1-4412.
82. The method of embodiment 80 or embodiment 81, wherein the target is ANGPTL7.
83. The method of any of embodiments 80-82, wherein the disease or condition comprises glaucoma (including, primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma and absolute glaucoma), ocular hypertension, optic neuropathy or a combination thereof
84. The method of any of embodiments 80-83, wherein the oligonucleotide comprises dsRNA.
85. The method of embodiment 84, wherein the oligonucleotide comprises a sequence at least about 80%, 85%, 90%, 95%, or 100% identical to a sequence selected from SEQ ID NOS: 1-4412.
86. The method of any of embodiments 80-83, wherein the oligonucleotide comprises a sequence at least about 80%, 85%, 90%, 95%, or 100% identical to SEQ ID NOS: 4413-11084.
87. A method of treating one or more disorders of the eye in a subject in need thereof comprising editing an ANGPTL7 gene in the subject wherein the one or more disorders of the eye comprises glaucoma or ocular hypertension.
88. The method of embodiment 87, wherein the editing of the ANGPTL7 gene comprises administering CRISPR/cas9 to the subject.
89. The method of embodiment 88, wherein the CRISPR/cas9 targets the ANGPTL7 gene.
90. The method of embodiment 88, wherein the CRISPR/cas9 edits the ANGPTL7 gene to a loss of function mutation.
91. The method of embodiment 90, wherein the loss of function mutation comprises a premature stop mutation.
92. The method of embodiment 91, wherein the premature stop mutation occurs at amino acid position 177 according to the human protein sequence numbering.
93. The method of embodiment 88, wherein the CRISPR/cas9 edits the ANGPTL7 gene to a missense mutation.
94. The method of embodiment 93, wherein the missense mutation comprises a glutamine to histidine mutation.
95. The method of embodiment 94, wherein the glutamine to histidine mutation occurs at amino acid position 175 according to the human protein sequence numbering.
96. The method of embodiment 88, wherein the CRISPR/cas9 is delivered systemically to the subject.
97. The method of embodiment 88, wherein the CRISPR/cas9 is delivered locally to the subject.
98. The method of embodiment 97, wherein the CRISPR/cas9 is delivered locally to the eye of the subject.
99. The method of embodiment 88, wherein the editing of the ANGPTL7 gene is efficacious in treating the one or more disorders of the eye.
100. The method of embodiment 99, wherein the one or more disorders of the eye is glaucoma.
101. The method of embodiment 99, wherein the subject has ocular hypertension.
102. The method of embodiment 101, wherein imaging from the subject ocular hypertension demonstrates optic nerve damage.
103. The method of embodiment 87, wherein the subject has received a first line treatment comprised of topical ocular prostaglandin analogues, beta-adrenergic blockers, alpha-adrenergic agonists, and carbonic anhydrase inhibitors for the one or more disorders of the eye.
104. The method of embodiment 87, wherein the editing of the ANGPTL7 gene causes a reduction in or modulation of the production of the gene product of ANGPTL7 in the subject.
105. The method of embodiment 87, wherein the editing of the ANGPTL7 gene causes a reduction in the subject of intraocular pressure.
106. A composition comprising CRISPR/cas9 that targets ANGPTL7 that is efficacious in treating glaucoma or ocular hypertension.
107. The composition of embodiment 106, wherein the CRISPR/cas9 edits the ANGPTL7 gene to a loss of function mutation.
108. The composition of embodiment 107, wherein the loss of function mutation comprises a premature stop mutation.
109. The composition of embodiment 108, wherein the premature stop mutation occurs at amino acid position 177 according to the human protein sequence numbering.
110. The composition of embodiment 106, wherein the CRISPR/cas9 edits the ANGPTL7 gene to a missense mutation.
111. The composition of embodiment 110, wherein the missense mutation comprises a glutamine to histidine mutation.
112. The composition of embodiment 111, wherein the glutamine to histidine mutation occurs at amino acid position 175 according to the human protein sequence numbering.
113. A pharmaceutical composition comprising an siRNA molecule comprising a sense strand and an antisense strand, which targets SEQ ID NO. 11086 and when introduced to an eye of a patient in an effective amount reduces intraocular pressure of the eye; and a pharmaceutically acceptable carrier.
114. The pharmaceutical composition of embodiment 113, wherein the siRNA molecule reduces intraocular pressure by at least 5%, at least 10%, at least 15%, at least 20%, at least 25%, at least 30% relative to a pre-treatment value of intraocular pressure in the eye of the patient.
115. The pharmaceutical composition of embodiment 113, wherein the pharmaceutical composition is formulated for topical administration to the eye.
116. The pharmaceutical composition of any of embodiments 113-115, wherein the siRNA has a length of 17-30 nucleotide pairs.
117. The pharmaceutical composition of any of embodiments 113-115, wherein the sense strand and antisense strand each have 17-30 nucleotides.
118. The pharmaceutical composition of any of embodiments 113-115, wherein the sense strand and antisense strand each have 21 nucleotides.
119. The pharmaceutical composition of any of embodiments 113-117, wherein the sense strand comprises a sequence at least about 80%, 85%, 90%, 95%, or 100% identical to a sequence selected from SEQ ID NOS: 1-4412.

120. The pharmaceutical composition of any of embodiments 113-118, wherein the antisense strand comprises a sequence at least about 80%, 85%, 90%, 95%, or 100% identical to the reverse complement of the sense strand.

121. The pharmaceutical composition of any of embodiments 113-119, wherein the antisense strand comprises a sequence at least about 80%, 85%, 90%, 95%, or 100% identical to a sequence selected from SEQ ID NOS: 1-4412.

122. The pharmaceutical composition of any of embodiments 113-116, wherein the sequence of the sense strand comprises SEQ ID NO: 11089 and the sequence of the antisense strand comprises SEQ ID NO: 11090.

123. The pharmaceutical composition of any of embodiments 113-121, comprising a modified internucleoside linkage.

124. The pharmaceutical composition of embodiment 123, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.

125. The pharmaceutical composition of embodiment 124, wherein the modified internucleoside linkage comprises one or more phosphorothioate linkages.

126. The pharmaceutical composition of embodiment 125, wherein the one or more phosphorothioate linkages is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 phosphorothioate linkages.

127. The pharmaceutical composition of embodiment 124 or embodiment 125, wherein the sense strand of the siRNA comprises one or more phosphorothioate linkages.

128. The pharmaceutical composition of embodiment 127, wherein the one or more phosphorothioate linkages of the sense strand is about 1, 2, 3, 4, 5, 6, 7, 8, 9, 10, 11, 12, 13, 14, 15, 16, 17, 18, 19, 20, or 21 phosphorothioate linkages.

129. The pharmaceutical composition of embodiment 128, wherein the one or more phosphorothioate linkages of the sense strand is about 1, 2, 3, 4, or 5 phosphorothioate linkages.

130. The pharmaceutical composition of embodiment 129, wherein the one or more phosphorothioate linkages of the sense strand is about 4 phosphorothioate linkages.

131. The pharmaceutical composition of any one of embodiments 127-130, wherein the sense strand comprises a phosphorothioate linkage between the first nucleoside and the second nucleoside of the sense strand, in a 5' to 3' direction.

132. The pharmaceutical composition of any one of embodiments 127-131, wherein the sense strand comprises a phosphorothioate linkage between the second nucleoside and the third nucleoside of the sense strand, in a 5' to 3' direction.

133. The pharmaceutical composition of any one of embodiments 127-132, wherein the sense strand comprises a phosphorothioate linkage between the nineteenth nucleoside and the twentieth nucleoside of the sense strand, in a 5' to 3' direction.

134. The pharmaceutical composition of any one of embodiments 127-133, wherein the sense strand comprises a phosphorothioate linkage between the twentieth nucleoside and the twenty-first nucleoside of the sense strand, in a 5' to 3' direction.

135. The pharmaceutical composition of any one of embodiments 124-134, wherein the antisense strand of the siRNA comprises one or more phosphorothioate linkages.

136. The pharmaceutical composition of embodiment 135, wherein the one or more phosphorothioate linkages of the antisense strand is about 1, 2, 3, 4, 5, 6, 7, 8, 9, 10, 11, 12, 13, 14, 15, 16, 17, 18, 19, 20, or 21 phosphorothioate linkages.

137. The pharmaceutical composition of embodiment 136, wherein the one or more phosphorothioate linkages of the antisense strand is about 1, 2, 3, 4, or 5 phosphorothioate linkages.

138. The pharmaceutical composition of embodiment 137, wherein the one or more phosphorothioate linkages of the antisense strand is about 4 phosphorothioate linkages.

139. The pharmaceutical composition of any one of embodiments 135-138, wherein the antisense strand comprises a phosphorothioate linkage between the first nucleoside and the second nucleoside of the antisense strand, in a 5' to 3' direction.

140. The pharmaceutical composition of any one of embodiments 135-139, wherein the antisense strand comprises a phosphorothioate linkage between the second nucleoside and the third nucleoside of the antisense strand, in a 5' to 3' direction.

141. The pharmaceutical composition of any one of embodiments 135-140, wherein the antisense strand comprises a phosphorothioate linkage between the nineteenth nucleoside and the twentieth nucleoside of the sense strand, in a 5' to 3' direction.

142. The pharmaceutical composition of any one of embodiments 135-141, wherein the antisense strand comprises a phosphorothioate linkage between the twentieth nucleoside and the twenty-first nucleoside of the sense strand, in a 5' to 3' direction.

143. The pharmaceutical composition of any one of embodiments 113-142, comprising a modified nucleoside.

144. The pharmaceutical composition of embodiment 143, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

145. The pharmaceutical composition of embodiment 144, wherein the modified nucleoside comprises a of 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

146. The pharmaceutical composition of embodiment 144, wherein the modified nucleoside comprises one or more 2'fluoro modified nucleosides.

147. The pharmaceutical composition of embodiment 146, wherein the one or more 2' fluoro modified nucleosides is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 2' fluoro modified nucleosides.

148. The pharmaceutical composition of embodiment 145 or embodiment 146, wherein the sense strand of the siRNA comprises one or more 2' fluoro modified nucleosides.

149. The pharmaceutical composition of embodiment 148, wherein the one or more 2' fluoro modified nucleosides of the sense strand is about 1, 2, 3, 4, 5, 6, 7, 8, 9, 10, 11, 12, 13, 14, 15, 16, 17, 18, 19, 20, or 21 2' fluoro modified nucleosides.

150. The pharmaceutical composition of embodiment 149, wherein the one or more 2' fluoro modified nucleosides of the sense strand is about eleven 2' fluoro modified nucleosides.

151. The pharmaceutical composition of embodiment 149, wherein the one or more 2' fluoro modified nucleosides of the sense strand is about four 2' fluoro modified nucleosides.

152. The pharmaceutical composition of embodiment 149, wherein the one or more 2' fluoro modified nucleosides of the sense strand is about three 2' fluoro modified nucleosides.

153. The pharmaceutical composition of any one of embodiments 148-152, wherein the first nucleoside of the sense strand comprises the 2' fluoro modified nucleoside, in a 5' to 3' direction.

154. The pharmaceutical composition of any one of embodiments 148-153, wherein the third nucleoside of the sense strand comprises the 2' fluoro modified nucleoside, in a 5' to 3' direction.

155. The pharmaceutical composition of any one of embodiments 148-154, wherein the fifth nucleoside of the sense strand comprises the 2' fluoro modified nucleoside, in a 5' to 3' direction.

156. The pharmaceutical composition of any one of embodiments 148-155, wherein the seventh nucleoside of the sense strand comprises the 2' fluoro modified nucleoside, in a 5' to 3' direction.

157. The pharmaceutical composition of any one of embodiments 148-156, wherein the eighth nucleoside of the sense strand comprises the 2' fluoro modified nucleoside, in a 5' to 3' direction.

158. The pharmaceutical composition of any one of embodiments 148-157, wherein the ninth nucleoside of the sense strand comprises the 2' fluoro modified nucleoside, in a 5' to 3' direction.

159. The pharmaceutical composition of any one of embodiments 148-158, wherein the eleventh nucleoside of the sense strand comprises the 2' fluoro modified nucleoside, in a 5' to 3' direction.

160. The pharmaceutical composition of any one of embodiments 148-159, wherein the thirteenth nucleoside of the sense strand comprises the 2' fluoro modified nucleoside, in a 5' to 3' direction.

161. The pharmaceutical composition of any one of embodiments 148-160, wherein the fifteenth nucleoside of the sense strand comprises the 2' fluoro modified nucleoside, in a 5' to 3' direction.

162. The pharmaceutical composition of any one of embodiments 148-161, wherein the seventeenth nucleoside of the sense strand comprises the 2' fluoro modified nucleoside, in a 5' to 3' direction.

163. The pharmaceutical composition of any one of embodiments 148-162, wherein the nineteenth nucleoside of the sense strand comprises the 2' fluoro modified nucleoside, in a 5' to 3' direction.

164. The pharmaceutical composition of any one of embodiments 148-163, wherein the fifth, seventh, and ninth nucleosides of the sense strand comprises the 2' fluoro modified nucleoside, in a 5' to 3' direction.

165. The pharmaceutical composition of any one of embodiments 148-164, comprising the pattern fN-Z1-fN-Z2-fN, wherein fN comprises the 2' fluoro modified nucleoside and Z1 and Z2 are independently a 2' 0-methyl modified nucleoside or a 2' fluoro modified nucleoside.

166. The pharmaceutical composition of embodiment 165, wherein the fN-Z1-fN-Z2-fN corresponds to nucleosides five to nine of the sense strand, in a 5' to 3' direction.

167. The pharmaceutical composition of any one of embodiments 148-166, wherein the sense strand comprises at least two contiguous 2' fluoro modified nucleosides.

168. The pharmaceutical composition of embodiment 167, wherein the at least two contiguous 2' fluoro modified nucleosides is two contiguous 2' fluoro modified nucleosides.

169. The pharmaceutical composition of embodiment 168, wherein the at least two contiguous 2' fluoro modified nucleosides is three contiguous 2' fluoro modified nucleosides.

170. The pharmaceutical composition of any one of embodiments 145-169, wherein the antisense strand of the siRNA comprises one or more 2' fluoro modified nucleosides.

171. The pharmaceutical composition of embodiment 170, wherein the one or more 2' fluoro modified nucleosides of the antisense strand is about 1, 2, 3, 4, 5, 6, 7, 8, 9, 10, 11, 12, 13, 14, 15, 16, 17, 18, 19, 20, or 21 2' fluoro modified nucleosides.

172. The pharmaceutical composition of embodiment 171, wherein the one or more 2' fluoro modified nucleosides of the antisense strand is about eight 2' fluoro modified nucleosides.

173. The pharmaceutical composition of embodiment 171, wherein the one or more 2' fluoro modified nucleosides of the antisense strand is about six 2' fluoro modified nucleosides.

174. The pharmaceutical composition of embodiment 171, wherein the one or more 2' fluoro modified nucleosides of the antisense strand is about five 2' fluoro modified nucleosides.

175. The pharmaceutical composition of embodiment 171, wherein the one or more 2' fluoro modified nucleosides of the antisense strand is about four 2' fluoro modified nucleosides.

176. The pharmaceutical composition of any one of embodiments 170-175, wherein the second nucleoside of the antisense strand comprises the 2' fluoro modified nucleoside, in a 5' to 3' direction.

177. The pharmaceutical composition of any one of embodiments 170-176, wherein the fourth nucleoside of the antisense strand comprises the 2' fluoro modified nucleoside, in a 5' to 3' direction.

178. The pharmaceutical composition of any one of embodiments 170-177, wherein the sixth nucleoside of the antisense strand comprises the 2' fluoro modified nucleoside, in a 5' to 3' direction.

179. The pharmaceutical composition of any one of embodiments 170-178, wherein the eighth nucleoside of the antisense strand comprises the 2' fluoro modified nucleoside, in a 5' to 3' direction.

180. The pharmaceutical composition of any one of embodiments 170-179, wherein the ninth nucleoside of the antisense strand comprises the 2' fluoro modified nucleoside, in a 5' to 3' direction.

181. The pharmaceutical composition of any one of embodiments 170-180, wherein the tenth nucleoside of the antisense strand comprises the 2' fluoro modified nucleoside, in a 5' to 3' direction.

182. The pharmaceutical composition of any one of embodiments 170-181, wherein the fourteenth nucleoside of the antisense strand comprises the 2' fluoro modified nucleoside, in a 5' to 3' direction.

183. The pharmaceutical composition of any one of embodiments 170-182, wherein the sixteenth nucleoside of the antisense strand comprises the 2' fluoro modified nucleoside, in a 5' to 3' direction.

184. The pharmaceutical composition of any one of embodiments 170-183, wherein the eighteenth nucleoside of the antisense strand comprises the 2' fluoro modified nucleoside, in a 5' to 3' direction.

185. The pharmaceutical composition of any one of embodiments 170-184, wherein the second and fourteenth nucleosides of the antisense strand comprises the 2' fluoro modified nucleoside, in a 5' to 3' direction.

186. The pharmaceutical composition of any one of embodiments 170-185, wherein the second, sixth, fourteenth, and sixteenth nucleosides of the antisense strand comprises the 2' fluoro modified nucleoside, in a 5' to 3' direction.

187. The pharmaceutical composition of any one of embodiments 170-186, comprising the pattern Z3-fN-Z4-fN, wherein fN comprises the 2' fluoro modified nucleoside and Z3 and Z4 are independently a 2' O-methyl modified nucleoside or a 2' fluoro modified nucleoside.

188. The pharmaceutical composition of embodiment 187, wherein the Z3-fN-Z4-fN corresponds to nucleosides thirteen to sixteen of the antisense strand, in a 5' to 3' direction.

189. The pharmaceutical composition of any one of embodiments 143-188, wherein the modified nucleoside comprises a 2' O-alkyl modified nucleoside.

190. The pharmaceutical composition of embodiment 189, wherein the 2'-O-alkyl modified nucleoside comprises one or more 2' O-methyl modified nucleosides.

191. The pharmaceutical composition of embodiment 190, wherein the one or more 2' O-methyl modified nucleosides is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 2' O-methyl modified nucleosides.

192. The pharmaceutical composition of any one of embodiments 189-191, wherein the sense strand of the siRNA comprises one or more 2' O-methyl modified nucleosides.

193. The pharmaceutical composition of embodiment 192, wherein the one or more 2' O-methyl modified nucleosides of the sense strand is about 1, 2, 3, 4, 5, 6, 7, 8, 9, 10, 11, 12, 13, 14, 15, 16, 17, 18, 19, 20, or 21 2' O-methyl modified nucleosides.

194. The pharmaceutical composition of embodiment 193, wherein the one or more 2' O-methyl modified nucleosides of the sense strand is about ten 2' O-methyl modified nucleosides.

195. The pharmaceutical composition of embodiment 193, wherein the one or more 2' O-methyl modified nucleosides of the sense strand is about seventeen 2' O-methyl modified nucleosides.

196. The pharmaceutical composition of embodiment 193, wherein the one or more 2' O-methyl modified nucleosides of the sense strand is about eighteen 2' O-methyl modified nucleosides.

197. The pharmaceutical composition of any one of embodiments 192-196, wherein the first nucleoside of the sense strand comprises the 2' O-methyl modified nucleoside, in a 5' to 3' direction.

198. The pharmaceutical composition of any one of embodiments 192-197, wherein the second nucleoside of the sense strand comprises the 2' O-methyl modified nucleoside, in a 5' to 3' direction.

199. The pharmaceutical composition of any one of embodiments 192-198, wherein the third nucleoside of the sense strand comprises the 2' O-methyl modified nucleoside, in a 5' to 3' direction.

200. The pharmaceutical composition of any one of embodiments 192-199, wherein the fourth nucleoside of the sense strand comprises the 2' O-methyl modified nucleoside, in a 5' to 3' direction.

201. The pharmaceutical composition of any one of embodiments 192-200, wherein the sixth nucleoside of the sense strand comprises the 2' O-methyl modified nucleoside, in a 5' to 3' direction.

202. The pharmaceutical composition of any one of embodiments 192-201, wherein the eighth nucleoside of the sense strand comprises the 2' O-methyl modified nucleoside, in a 5' to 3' direction.

203. The pharmaceutical composition of any one of embodiments 192-202, wherein the tenth nucleoside of the sense strand comprises the 2' O-methyl modified nucleoside, in a 5' to 3' direction.

204. The pharmaceutical composition of any one of embodiments 192-203, wherein the eleventh nucleoside of the sense strand comprises the 2' O-methyl modified nucleoside, in a 5' to 3' direction.

205. The pharmaceutical composition of any one of embodiments 192-204, wherein the twelfth nucleoside of the sense strand comprises the 2' O-methyl modified nucleoside, in a 5' to 3' direction.

206. The pharmaceutical composition of any one of embodiments 192-205, wherein the thirteenth nucleoside of the sense strand comprises the 2' O-methyl modified nucleoside, in a 5' to 3' direction.

207. The pharmaceutical composition of any one of embodiments 192-206, wherein the fourteenth nucleoside of the sense strand comprises the 2' O-methyl modified nucleoside, in a 5' to 3' direction.

208. The pharmaceutical composition of any one of embodiments 192-207, wherein the fifteenth nucleoside of the sense strand comprises the 2' O-methyl modified nucleoside, in a 5' to 3' direction.

209. The pharmaceutical composition of any one of embodiments 192-208, wherein the sixteenth nucleoside of the sense strand comprises the 2' O-methyl modified nucleoside, in a 5' to 3' direction.

210. The pharmaceutical composition of any one of embodiments 192-209, wherein the seventeenth nucleoside of the sense strand comprises the 2' O-methyl modified nucleoside, in a 5' to 3' direction.

211. The pharmaceutical composition of any one of embodiments 192-210, wherein the eighteenth nucleoside of the sense strand comprises the 2' O-methyl modified nucleoside, in a 5' to 3' direction.

212. The pharmaceutical composition of any one of embodiments 192-211, wherein the nineteenth nucleoside of the sense strand comprises the 2' O-methyl modified nucleoside, in a 5' to 3' direction.
213. The pharmaceutical composition of any one of embodiments 192-212, wherein the twentieth nucleoside of the sense strand comprises the 2' O-methyl modified nucleoside, in a 5' to 3' direction.
214. The pharmaceutical composition of any one of embodiments 192-213, wherein the twenty-first nucleoside of the sense strand comprises the 2' O-methyl modified nucleoside, in a 5' to 3' direction.
215. The pharmaceutical composition of any one of embodiments 192-214, wherein the second, fourth, sixth, tenth, twelfth, fourteenth, and sixteenth, eighteenth, twentieth, and twenty-first nucleosides of the sense strand comprises the 2' O-methyl modified nucleoside, in a 5' to 3' direction.
216. The pharmaceutical composition of any one of embodiments 192-215, comprising the pattern mN-Z5-mN-Z6, wherein mN comprises the 2' O-methyl modified nucleoside and Z5 and Z6 are independently a 2' O-methyl modified nucleoside or a 2' fluoro modified nucleoside.
217. The pharmaceutical composition of embodiment 216, wherein the mN-Z5-mN-Z6-mN corresponds to nucleosides four to seven of the sense strand, in a 5' to 3' direction.
218. The pharmaceutical composition of embodiment 216 or embodiment 217, wherein Z5 is the 2' fluoro modified nucleoside.
219. The pharmaceutical composition of embodiment 216 or embodiment 217, wherein Z5 is the 2' O-methyl modified nucleoside.
220. The pharmaceutical composition of any one of embodiments 216-219, wherein Z6 is the 2' fluoro modified nucleoside.
221. The pharmaceutical composition of any one of embodiments 216-219, wherein Z6 is the 2' O-methyl modified nucleoside.
222. The pharmaceutical composition of any one of embodiments 192-221, comprising the pattern mN-Z5-mN-Z6-mN, wherein mN comprises the 2' O-methyl modified nucleoside and Z5 and Z6 are independently a 2' O-methyl modified nucleoside or a 2' fluoro modified nucleoside.
223. The pharmaceutical composition of embodiment 222, wherein the mN-Z5-mN-Z6-mN corresponds to nucleosides two to six of the sense strand, in a 5' to 3' direction.
224. The pharmaceutical composition of embodiment 222, wherein the mN-Z5-mN-Z6-mN corresponds to nucleosides ten to fourteen of the sense strand, in a 5' to 3' direction.
225. The pharmaceutical composition of embodiment 222, wherein the mN-Z5-mN-Z6-mN corresponds to nucleosides twelve to sixteen of the sense strand, in a 5' to 3' direction.
226. The pharmaceutical composition of embodiment 222, wherein the mN-Z5-mN-Z6-mN corresponds to nucleosides fourteen to eighteen of the sense strand, in a 5' to 3' direction.
227. The pharmaceutical composition of embodiment 222, wherein the mN-Z5-mN-Z6-mN corresponds to nucleosides sixteen to twenty of the sense strand, in a 5' to 3' direction.
228. The pharmaceutical composition of any one of embodiments 192-227, comprising the pattern mN-Z5-mN-Z6-mN-Z7-mN, wherein Z7 is a 2' O-methyl modified nucleoside or a 2' fluoro modified nucleoside.
229. The pharmaceutical composition of embodiment 228, wherein the mN-Z5-mN-Z6-mN-Z7-mN corresponds to nucleosides ten to sixteen of the sense strand, in a 5' to 3' direction.
230. The pharmaceutical composition of embodiment 228, wherein the mN-Z5-mN-Z6-mN-Z7-mN corresponds to nucleosides twelve to eighteen of the sense strand, in a 5' to 3' direction.
231. The pharmaceutical composition of embodiment 228, wherein the mN-Z5-mN-Z6-mN-Z7-mN corresponds to nucleosides fourteen to twenty of the sense strand, in a 5' to 3' direction.
232. The pharmaceutical composition of any one of embodiments 192-231, comprising the pattern mN-Z5-mN-Z6-mN-Z7-mN-Z8-mN, wherein Z8 is a 2' O-methyl modified nucleoside or a 2' fluoro modified nucleoside.
233. The pharmaceutical composition of embodiment 232, wherein the mN-Z5-mN-Z6-mN-Z7-mN-Z8-mN corresponds to nucleosides ten to eighteen of the sense strand, in a 5' to 3' direction.
234. The pharmaceutical composition of embodiment 232, wherein the mN-Z5-mN-Z6-mN-Z7-mN-Z8-mN corresponds to nucleosides twelve to twenty of the sense strand, in a 5' to 3' direction.
235. The pharmaceutical composition of any one of embodiments 192-234, comprising the pattern mN-Z5-mN-Z6-mN-Z7-mN-Z8-mN-Z9-mN, wherein Z9 is a 2' O-methyl modified nucleoside or a 2' fluoro modified nucleoside.
236. The pharmaceutical composition of embodiment 235, wherein the mN-Z5-mN-Z6-mN-Z7-mN-Z8-mN-Z9-mN corresponds to nucleosides ten to twenty of the sense strand, in a 5' to 3' direction.
237. The pharmaceutical composition of any one of embodiments 192-236, wherein the sense strand comprises at least two contiguous 2' O-methyl modified nucleosides.
238. The pharmaceutical composition of embodiment 237, wherein the at least two contiguous 2' O-methyl modified nucleosides is three contiguous 2' O-methyl modified nucleosides.
239. The pharmaceutical composition of embodiment 237, wherein the at least two contiguous 2' O-methyl modified nucleosides is four contiguous 2' O-methyl modified nucleosides.
240. The pharmaceutical composition of embodiment 237, wherein the at least two contiguous 2' O-methyl modified nucleosides is five contiguous 2' O-methyl modified nucleosides.
241. The pharmaceutical composition of embodiment 237, wherein the at least two contiguous 2' O-methyl modified nucleosides is six contiguous 2' O-methyl modified nucleosides.
242. The pharmaceutical composition of embodiment 237, wherein the at least two contiguous 2' O-methyl modified nucleosides is seven contiguous 2' O-methyl modified nucleosides.
243. The pharmaceutical composition of embodiment 237, wherein the at least two contiguous 2' O-methyl modified nucleosides is eight contiguous 2' O-methyl modified nucleosides.

244. The pharmaceutical composition of embodiment 237, wherein the at least two contiguous 2' O-methyl modified nucleosides is nine contiguous 2' O-methyl modified nucleosides.

245. The pharmaceutical composition of embodiment 237, wherein the at least two contiguous 2' O-methyl modified nucleosides is ten contiguous 2' O-methyl modified nucleosides.

246. The pharmaceutical composition of embodiment 237, wherein the at least two contiguous 2' O-methyl modified nucleosides is eleven contiguous 2' O-methyl modified nucleosides.

247. The pharmaceutical composition of embodiment 237, wherein the at least two contiguous 2' O-methyl modified nucleosides is twelve contiguous 2' O-methyl modified nucleosides.

248. The pharmaceutical composition of any one of embodiments 189-247, wherein the antisense strand of the siRNA comprises one or more 2' O-methyl modified nucleosides.

249. The pharmaceutical composition of embodiment 248, wherein the one or more 2' O-methyl modified nucleosides of the antisense strand is about 1, 2, 3, 4, 5, 6, 7, 8, 9, 10, 11, 12, 13, 14, 15, 16, 17, 18, 19, 20, or 21 2' O-methyl modified nucleosides.

250. The pharmaceutical composition of embodiment 249, wherein the one or more 2' O-methyl modified nucleosides of the antisense strand is about thirteen 2' O-methyl modified nucleosides.

251. The pharmaceutical composition of embodiment 249, wherein the one or more 2' O-methyl modified nucleosides of the antisense strand is about fifteen 2' O-methyl modified nucleosides.

252. The pharmaceutical composition of embodiment 249, wherein the one or more 2' O-methyl modified nucleosides of the antisense strand is about seventeen 2' O-methyl modified nucleosides.

253. The pharmaceutical composition of any one of embodiments 249-252, wherein the first nucleoside of the antisense strand comprises the 2' O-methyl modified nucleoside, in a 5' to 3' direction.

254. The pharmaceutical composition of any one of embodiments 249-253, wherein the third nucleoside of the antisense strand comprises the 2' O-methyl modified nucleoside, in a 5' to 3' direction.

255. The pharmaceutical composition of any one of embodiments 249-254, wherein the fourth nucleoside of the antisense strand comprises the 2' O-methyl modified nucleoside, in a 5' to 3' direction.

256. The pharmaceutical composition of any one of embodiments 249-255, wherein the fifth nucleoside of the antisense strand comprises the 2' O-methyl modified nucleoside, in a 5' to 3' direction.

257. The pharmaceutical composition of any one of embodiments 249-256, wherein the seventh nucleoside of the antisense strand comprises the 2' O-methyl modified nucleoside, in a 5' to 3' direction.

258. The pharmaceutical composition of any one of embodiments 249-257, wherein the eighth nucleoside of the antisense strand comprises the 2' O-methyl modified nucleoside, in a 5' to 3' direction.

259. The pharmaceutical composition of any one of embodiments 249-258, wherein the ninth nucleoside of the antisense strand comprises the 2' O-methyl modified nucleoside, in a 5' to 3' direction.

260. The pharmaceutical composition of any one of embodiments 249-259, wherein the tenth nucleoside of the antisense strand comprises the 2' O-methyl modified nucleoside, in a 5' to 3' direction.

261. The pharmaceutical composition of any one of embodiments 249-260, wherein the eleventh nucleoside of the antisense strand comprises the 2' O-methyl modified nucleoside, in a 5' to 3' direction.

262. The pharmaceutical composition of any one of embodiments 249-261, wherein the twelfth nucleoside of the antisense strand comprises the 2' O-methyl modified nucleoside, in a 5' to 3' direction.

263. The pharmaceutical composition of any one of embodiments 249-262, wherein the thirteenth nucleoside of the antisense strand comprises the 2' O-methyl modified nucleoside, in a 5' to 3' direction.

264. The pharmaceutical composition of any one of embodiments 249-263, wherein the fifteenth nucleoside of the antisense strand comprises the 2' O-methyl modified nucleoside, in a 5' to 3' direction.

265. The pharmaceutical composition of any one of embodiments 249-264, wherein the seventeenth nucleoside of the antisense strand comprises the 2' O-methyl modified nucleoside, in a 5' to 3' direction.

266. The pharmaceutical composition of any one of embodiments 249-265, wherein the eighteenth nucleoside of the antisense strand comprises the 2' O-methyl modified nucleoside, in a 5' to 3' direction.

267. The pharmaceutical composition of any one of embodiments 249-266, wherein the nineteenth nucleoside of the antisense strand comprises the 2' O-methyl modified nucleoside, in a 5' to 3' direction.

268. The pharmaceutical composition of any one of embodiments 249-267, wherein the twentieth nucleoside of the antisense strand comprises the 2' O-methyl modified nucleoside, in a 5' to 3' direction.

269. The pharmaceutical composition of any one of embodiments 249-268, wherein the twenty-first nucleoside of the antisense strand comprises the 2' O-methyl modified nucleoside, in a 5' to 3' direction.

270. The pharmaceutical composition of any one of embodiments 249-269, wherein the first, third, fifth, seventh, eleventh, twelfth, thirteenth, fifteenth, seventeenth, nineteenth, twentieth, and twenty-first nucleosides of the antisense strand comprises the 2' O-methyl modified nucleoside, in a 5' to 3' direction.

271. The pharmaceutical composition of any one of embodiments 249-270, wherein the antisense strand comprises at least two contiguous 2' O-methyl modified nucleosides.

272. The pharmaceutical composition of embodiment 271, wherein the at least two contiguous 2' O-methyl modified nucleosides is three contiguous 2' O-methyl modified nucleosides.

273. The pharmaceutical composition of embodiment 271, wherein the at least two contiguous 2' O-methyl modified nucleosides is four contiguous 2' O-methyl modified nucleosides.

274. The pharmaceutical composition of embodiment 271, wherein the at least two contiguous 2' O-methyl modified nucleosides is five contiguous 2' O-methyl modified nucleosides.

275. The pharmaceutical composition of embodiment 271, wherein the at least two contiguous 2' O-methyl modified nucleosides is six contiguous 2' O-methyl modified nucleosides.

276. The pharmaceutical composition of embodiment 271, wherein the at least two contiguous 2' O-methyl modified nucleosides is seven contiguous 2' O-methyl modified nucleosides.

277. The pharmaceutical composition of any one of embodiments 248-276, wherein the antisense strand comprises a first sequence comprising at least two contiguous 2' O-methyl modified nucleosides and a second sequence comprising at least two contiguous 2' O-methyl modified nucleosides.

278. The pharmaceutical composition of embodiment 277, wherein the first sequence comprises at least three contiguous 2' O-methyl modified nucleosides, and the second sequence comprises at least three contiguous 2' O-methyl modified nucleosides.

279. The pharmaceutical composition of embodiment 277, wherein the first sequence comprises three contiguous 2' O-methyl modified nucleosides, and the second sequence comprises three contiguous 2' O-methyl modified nucleosides.

280. The pharmaceutical composition of embodiment 277, wherein the first sequence comprises four contiguous 2' O-methyl modified nucleosides, and the second sequence comprises five contiguous 2' O-methyl modified nucleosides.

281. The pharmaceutical composition of embodiment 277, wherein the first sequence comprises seven contiguous 2' O-methyl modified nucleosides, and the second sequence comprises five contiguous 2' O-methyl modified nucleosides.

282. The pharmaceutical composition of embodiment 277, wherein the first sequence comprises at least four contiguous 2' O-methyl modified nucleosides.

283. The pharmaceutical composition of embodiment 277, wherein the first sequence comprises at least five contiguous 2' O-methyl modified nucleosides.

284. The pharmaceutical composition of embodiment 277, wherein the first sequence comprises at least six contiguous 2' O-methyl modified nucleosides.

285. The pharmaceutical composition of embodiment 277, wherein the first sequence comprises at least seven contiguous 2' O-methyl modified nucleosides.

286. The pharmaceutical composition of any one of embodiments 282-285, wherein the second sequence comprises at least four contiguous 2' O-methyl modified nucleosides.

287. The pharmaceutical composition of any one of embodiments 282-285, wherein the second sequence comprises at least five contiguous 2' O-methyl modified nucleosides.

288. The pharmaceutical composition of any one of embodiments 282-285, wherein the second sequence comprises at least six contiguous 2' O-methyl modified nucleosides.

289. The pharmaceutical composition of any one of embodiments 282-285, wherein the second sequence comprises at least seven contiguous 2' O-methyl modified nucleosides.

290. The pharmaceutical composition of any one of embodiments 113-289, wherein the sense strand comprises a ribose.

291. The pharmaceutical composition of embodiment 290, wherein the sense strand comprises about 1, 2, 3, 4, 5, 6, 7, 8, 9, 10, 11, 12, 13, 14, 15, 16, 17, 18, 19, 20, or 21 ribose.

292. The pharmaceutical composition of embodiment 290 or embodiment 291, wherein the first nucleoside of the sense strand comprises the ribose, in a 5' to 3' direction.

293. The pharmaceutical composition of any one of embodiments 290-292, wherein the second nucleoside of the sense strand comprises the ribose, in a 5' to 3' direction.

294. The pharmaceutical composition of any one of embodiments 290-293, wherein the third nucleoside of the sense strand comprises the ribose, in a 5' to 3' direction.

295. The pharmaceutical composition of any one of embodiments 290-294, wherein the fourth nucleoside of the sense strand comprises the ribose, in a 5' to 3' direction.

296. The pharmaceutical composition of any one of embodiments 290-295, wherein the fifth nucleoside of the sense strand comprises the ribose, in a 5' to 3' direction.

297. The pharmaceutical composition of any one of embodiments 290-296, wherein the sixth nucleoside of the sense strand comprises the ribose, in a 5' to 3' direction.

298. The pharmaceutical composition of any one of embodiments 290-297, wherein the seventh nucleoside of the sense strand comprises the ribose, in a 5' to 3' direction.

299. The pharmaceutical composition of any one of embodiments 290-298, wherein the eighth nucleoside of the sense strand comprises the ribose, in a 5' to 3' direction.

300. The pharmaceutical composition of any one of embodiments 290-299, wherein the ninth nucleoside of the sense strand comprises the ribose, in a 5' to 3' direction.

301. The pharmaceutical composition of any one of embodiments 290-300, wherein the tenth nucleoside of the sense strand comprises the ribose, in a 5' to 3' direction.

302. The pharmaceutical composition of any one of embodiments 290-301, wherein the eleventh nucleoside of the sense strand comprises the ribose, in a 5' to 3' direction.

303. The pharmaceutical composition of any one of embodiments 290-302, wherein the twelfth nucleoside of the sense strand comprises the ribose, in a 5' to 3' direction.

304. The pharmaceutical composition of any one of embodiments 290-303, wherein the thirteenth nucleoside of the sense strand comprises the ribose, in a 5' to 3' direction.

305. The pharmaceutical composition of any one of embodiments 290-304, wherein the fourteenth nucleoside of the sense strand comprises the ribose, in a 5' to 3' direction.

306. The pharmaceutical composition of any one of embodiments 290-305, wherein the fifteenth nucleoside of the sense strand comprises the ribose, in a 5' to 3' direction.

307. The pharmaceutical composition of any one of embodiments 290-306, wherein the sixteenth nucleoside of the sense strand comprises the ribose, in a 5' to 3' direction.

308. The pharmaceutical composition of any one of embodiments 290-307, wherein the seventeenth nucleoside of the sense strand comprises the ribose, in a 5' to 3' direction.

309. The pharmaceutical composition of any one of embodiments 290-308, wherein the eighteenth nucleoside of the sense strand comprises the ribose, in a 5' to 3' direction.
310. The pharmaceutical composition of any one of embodiments 290-309, wherein the nineteenth nucleoside of the sense strand comprises the ribose, in a 5' to 3' direction.
311. The pharmaceutical composition of any one of embodiments 290-310, wherein the twentieth nucleoside of the sense strand comprises the ribose, in a 5' to 3' direction.
312. The pharmaceutical composition of any one of embodiments 290-311, wherein the twenty-first nucleoside of the sense strand comprises the ribose, in a 5' to 3' direction.
313. The pharmaceutical composition of any one of embodiments 113-312, wherein the antisense strand comprises a ribose.
314. The pharmaceutical composition of embodiment 313, wherein the antisense strand comprises about 1, 2, 3, 4, 5, 6, 7, 8, 9, 10, 11, 12, 13, 14, 15, 16, 17, 18, 19, 20, or 21 ribose.
315. The pharmaceutical composition of embodiment 313 or embodiment 314, wherein the first nucleoside of the antisense strand comprises the ribose, in a 5' to 3' direction.
316. The pharmaceutical composition of any one of embodiments 313-315, wherein the second nucleoside of the antisense strand comprises the ribose, in a 5' to 3' direction.
317. The pharmaceutical composition of any one of embodiments 313-316, wherein the third nucleoside of the antisense strand comprises the ribose, in a 5' to 3' direction.
318. The pharmaceutical composition of any one of embodiments 313-317, wherein the fourth nucleoside of the antisense strand comprises the ribose, in a 5' to 3' direction.
319. The pharmaceutical composition of any one of embodiments 313-318, wherein the fifth nucleoside of the antisense strand comprises the ribose, in a 5' to 3' direction.
320. The pharmaceutical composition of any one of embodiments 313-319, wherein the sixth nucleoside of the antisense strand comprises the ribose, in a 5' to 3' direction.
321. The pharmaceutical composition of any one of embodiments 313-320, wherein the seventh nucleoside of the antisense strand comprises the ribose, in a 5' to 3' direction.
322. The pharmaceutical composition of any one of embodiments 313-321, wherein the eighth nucleoside of the antisense strand comprises the ribose, in a 5' to 3' direction.
323. The pharmaceutical composition of any one of embodiments 313-322, wherein the ninth nucleoside of the antisense strand comprises the ribose, in a 5' to 3' direction.
324. The pharmaceutical composition of any one of embodiments 313-323, wherein the tenth nucleoside of the sense antisense comprises the ribose, in a 5' to 3' direction.
325. The pharmaceutical composition of any one of embodiments 313-324, wherein the eleventh nucleoside of the antisense strand comprises the ribose, in a 5' to 3' direction.
326. The pharmaceutical composition of any one of embodiments 313-325, wherein the twelfth nucleoside of the antisense strand comprises the ribose, in a 5' to 3' direction.
327. The pharmaceutical composition of any one of embodiments 313-326, wherein the thirteenth nucleoside of the antisense strand comprises the ribose, in a 5' to 3' direction.
328. The pharmaceutical composition of any one of embodiments 313-327, wherein the fourteenth nucleoside of the antisense strand comprises the ribose, in a 5' to 3' direction.
329. The pharmaceutical composition of any one of embodiments 313-328, wherein the fifteenth nucleoside of the antisense strand comprises the ribose, in a 5' to 3' direction.
330. The pharmaceutical composition of any one of embodiments 313-329, wherein the sixteenth nucleoside of the antisense strand comprises the ribose, in a 5' to 3' direction.
331. The pharmaceutical composition of any one of embodiments 313-330, wherein the seventeenth nucleoside of the antisense strand comprises the ribose, in a 5' to 3' direction.
332. The pharmaceutical composition of any one of embodiments 313-331, wherein the eighteenth nucleoside of the antisense strand comprises the ribose, in a 5' to 3' direction.
333. The pharmaceutical composition of any one of embodiments 313-332, wherein the nineteenth nucleoside of the antisense strand comprises the ribose, in a 5' to 3' direction.
334. The pharmaceutical composition of any one of embodiments 313-333, wherein the twentieth nucleoside of the antisense strand comprises the ribose, in a 5' to 3' direction.
335. The pharmaceutical composition of any one of embodiments 313-334, wherein the twenty-first nucleoside of the antisense strand comprises the ribose, in a 5' to 3' direction.
336. The pharmaceutical composition of any one of embodiments 113-335, further comprising a lipid attached at either 3' or 5' terminus.
337. The pharmaceutical composition of embodiment 336, wherein the lipid comprises cholesterol, myristoyl, palmitoyl, stearoyl, lithocholoyl, docosanoyl, docosahexaenoyl, myristyl, palmityl stearyl, α-tocopherol, or a combination thereof.
338. The pharmaceutical composition of embodiment 336 or embodiment 337, wherein the lipid comprises a first lipid on the sense strand and a second lipid on the antisense strand.
339. The pharmaceutical composition of any one of embodiments 336-338, wherein the lipid is positioned on the sense strand.
340. The pharmaceutical composition of embodiment 339, wherein the lipid is positioned at the 5' end of the sense strand.
341. The pharmaceutical composition of embodiment 339, wherein the lipid is positioned at the 3' end of the sense strand.
342. The pharmaceutical composition of any one of embodiments 336-341, wherein the lipid is positioned on the antisense strand.
343. The pharmaceutical composition of embodiment 342, wherein the lipid is positioned at the 5' end of the antisense strand.

344. The pharmaceutical composition of embodiment 342, wherein the lipid is positioned at the 3' end of the antisense strand.

345. The pharmaceutical composition of any one of embodiments 113-344, wherein the sense strand and the antisense strand form a double-stranded RNA duplex.

346. The pharmaceutical composition of embodiment 345, wherein the double-stranded RNA duplex comprises from about 14 to about 30 nucleosides.

347. The pharmaceutical composition of embodiment 346, wherein the double-stranded RNA duplex comprises from about 17 to about 30 nucleosides.

348. The pharmaceutical composition of embodiment 347, wherein the double-stranded RNA duplex comprises about 21 nucleosides.

349. The pharmaceutical composition of any one of embodiments 345-348, wherein the double-stranded RNA duplex comprises at least one base pair.

350. The pharmaceutical composition of embodiment 349, wherein the first base pair of the double-stranded RNA duplex is an AU base pair.

351. The pharmaceutical composition of any one of embodiments 113-350, wherein the sense strand comprises pattern 1S: 5' fN s mN s fN-mN-fN-mN-fN-fN-fN-mN-fN-mN-fN-mN-fN-mN-fN-mN-fN s mN s mN 3' (SEQ ID NO: 11381), wherein "fN" is a 2' fluoro-modified nucleoside, "mN" is a 2' O-methyl modified nucleoside, "-" is a phosphodiester, and "s" is a phosphorothioate.

352. The pharmaceutical composition of any one of embodiments 113-350, wherein the sense strand comprises pattern 2S: 5' mN s mN s mN-mN-fN-mN-fN-fN-fN-mN-mN-mN-mN-mN-mN-mN-mN-mN s mN s mN 3' (SEQ ID NO: 11382), wherein "fN" is a 2' fluoro-modified nucleoside, "mN" is a 2' O-methyl modified nucleoside, "-" is a phosphodiester, and "s" is a phosphorothioate.

353. The pharmaceutical composition of any one of embodiments 113-350, wherein the sense strand comprises pattern 3S: 5' mN s mN s mN-mN-fN-mN-fN-mN-fN-mN-mN-mN-mN-mN-mN-mN-mN-mN s mN s mN 3' (SEQ ID NO: 11383), wherein "fN" is a 2' fluoro-modified nucleoside, "mN" is a 2' O-methyl modified nucleoside, "-" is a phosphodiester, and "s" is a phosphorothioate.

354. The pharmaceutical composition of any one of embodiments 113-350, wherein the sense strand comprises pattern 4S: 5' fN s mN s fN-mN-fN-mN-fN-fN-fN-mN-fN-mN-fN-mN-fN-mN-fN-mN-fN s mN s mN-N-Lipid 3' (SEQ ID NO: 11384), wherein "fN" is a 2' fluoro-modified nucleoside, "mN" is a 2' O-methyl modified nucleoside, "-" is a phosphodiester, "s" is a phosphorothioate, and N comprises one or more nucleosides.

355. The pharmaceutical composition of embodiment 354, wherein the one or more nucleosides is three nucleosides.

356. The pharmaceutical composition of embodiment 354 or 355, wherein each of the one or more nucleosides independently comprise a ribose or deoxyribose.

357. The pharmaceutical composition of any one of embodiments 113-350, wherein the sense strand comprises pattern 5S: 5' mN s mN s mN-mN-fN-mN-fN-fN-fN-mN-mN-mN-mN-mN-mN-mN-mN-mN s mN s mN-N-Lipid 3' (SEQ ID NO: 11385), wherein "fN" is a 2' fluoro-modified nucleoside, "mN" is a 2' O-methyl modified nucleoside, "-" is a phosphodiester, "s" is a phosphorothioate, and N comprises one or more nucleosides.

358. The pharmaceutical composition of embodiment 357, wherein the one or more nucleosides is three nucleosides.

359. The pharmaceutical composition of embodiment 357 or 358, wherein each of the one or more nucleosides independently comprise a ribose or deoxyribose.

360. The pharmaceutical composition of any one of embodiments 113-359, wherein the antisense strand comprises pattern 1AS: 5' mN s fN s mN-fN-mN-fN-mN-fN-mN-fN-mN-mN-mN-fN-mN-fN-mN-fN-mN s mN s mN 3' (SEQ ID NO: 11386), wherein "fN" is a 2' fluoro-modified nucleoside, "mN" is a 2' O-methyl modified nucleoside, "-" is a phosphodiester, and "s" is a phosphorothioate.

361. The pharmaceutical composition of any one of embodiments 113-359, wherein the antisense strand comprises pattern 2AS: 5' mN s fN s mN-mN-mN-fN-mN-fN-fN-mN-mN-mN-mN-fN-mN-fN-mN-mN-mN s mN s mN 3' (SEQ ID NO: 11387), wherein "fN" is a 2' fluoro-modified nucleoside, "mN" is a 2' O-methyl modified nucleoside, "-" is a phosphodiester, and "s" is a phosphorothioate.

362. The pharmaceutical composition of any one of embodiments 113-359, wherein the antisense strand comprises pattern 3AS: 5' mN s fN s mN-mN-mN-fN-mN-mN-mN-mN-mN-mN-mN-fN-mN-fN-mN-mN-mN s mN s mN 3' (SEQ ID NO: 11388), wherein "fN" is a 2' fluoro-modified nucleoside, "mN" is a 2' O-methyl modified nucleoside, "-" is a phosphodiester, and "s" is a phosphorothioate.

363. The pharmaceutical composition of any one of embodiments 113-359, wherein the antisense strand comprises pattern 4AS: 5' mN s fN s mN-fN-mN-fN-mN-mN-mN-mN-mN-mN-mN-fN-mN-fN-mN-mN-mN s mN s mN 3' (SEQ ID NO: 11389), wherein "fN" is a 2' fluoro-modified nucleoside, "mN" is a 2' O-methyl modified nucleoside, "-" is a phosphodiester, and "s" is a phosphorothioate.

364. The pharmaceutical composition of any one of embodiments 113-350, wherein the sense strand comprises pattern 1S and the antisense strand comprises pattern 1AS.

365. The pharmaceutical composition of any one of embodiments 113-350, wherein the sense strand comprises pattern 2S and the antisense strand comprises pattern 2AS.

366. The pharmaceutical composition of any one of embodiments 113-350, wherein the sense strand comprises pattern 3S and the antisense strand comprises pattern 3AS.

367. The pharmaceutical composition of any one of embodiments 113-350, wherein the sense strand comprises pattern 4S and the antisense strand comprises pattern 4AS.

368. A method of treating an eye disease or disorder comprising administering to the eye of a patient in need thereof a short interfering nucleic acid molecule (siRNA) that targets a portion of mRNA encoding ANGPTL7, wherein the siRNA comprises a double-stranded nucleic acid region comprising a sense strand and an antisense strand, and wherein there is greater than 90% sequence identity or greater than 90% sequence complementarity between said double-stranded nucleic acid region of siRNA and the portion of mRNA encoding ANGPTL7 that is targeted by the siRNA.
369. The method of embodiment 368, wherein the eye disease or disorder is characterized by increased intraocular pressure.
370. The method of embodiment 368 or embodiment 369, wherein the siRNA is administered to the eye of the patient in an effective amount that reduces IOP in the eye of the patient.
371. The method of embodiment 370, wherein the siRNA molecule reduces intraocular pressure by at least 5%, at least 10%, at least 15%, at least 20%, at least 25%, at least 30% relative to a pre-treatment value of intraocular pressure in the eye of the patient.
372. The method of any of embodiments 368-371, wherein the siRNA is formulated for topical administration to the eye.
373. The method of any of embodiments 368-372, wherein the eye disease or disorder comprises glaucoma.
374. The method of embodiment 373, wherein the glaucoma is selected from the group consisting of optic nerve damage comprises primary open-angle glaucoma, primary angle-closure glaucoma, normal-tension glaucoma, pigmentary glaucoma, exfoliation glaucoma, juvenile glaucoma, congenital glaucoma, inflammatory glaucoma, phacogenic glaucoma, glaucoma secondary to intraocular hemorrhage, traumatic glaucoma, neovascular glaucoma, drug-induced glaucoma, toxic glaucoma, and absolute glaucoma.
375. The method of embodiment 374, wherein the eye disease or disorder is selected from the group consisting a disease or disorder associated with optic nerve damage, a disease or disorder associated with intraocular pressure, a degenerative retinal disease or disorder, an inflammatory eye disease or disorder, an allergic eye disease or disorder.
376. The method of any of embodiments 368-375, wherein the siRNA has a length of 17-30 nucleotide pairs.
377. The method of any of embodiments 368-376, wherein the sense strand and antisense strand each have 17-30 nucleotides.
378. The method of any of embodiments 368-377, wherein the sense strand comprises a sequence at least about 80%, 85%, 90%, 95%, or 100% identical to a sequence selected from SEQ ID NOS: 1-4412.
379. The method of any of embodiments 368-378, wherein the antisense strand comprises a sequence at least about 80%, 85%, 90%, 95%, or 100% identical to the reverse complement of the sense strand.
380. The method of any of embodiments 368-379, wherein the antisense strand comprises a sequence at least about 80%, 85%, 90%, 95%, or 100% identical to a sequence selected from SEQ ID NOS: 1-4412.
381. The method of any of embodiments 368-380, wherein the sequence of the sense strand comprises SEQ ID NO: 11089 and the sequence of the antisense strand comprises SEQ ID NO: 11090.
382. The method of any of embodiments 368-381, comprising a modified internucleoside linkage.
383. The method of embodiment 382, wherein the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof.
384. The method of embodiment 383, wherein the modified internucleoside linkage comprises one or more phosphorothioate linkages.
385. The method of embodiment 384, wherein the one or more phosphorothioate linkages is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 phosphorothioate linkages.
386. The method of embodiment 384 or embodiment 385, wherein the sense strand of the siRNA comprises one or more phosphorothioate linkages.
387. The method of embodiment 386, wherein the one or more phosphorothioate linkages of the sense strand is about 1, 2, 3, 4, 5, 6, 7, 8, 9, 10, 11, 12, 13, 14, 15, 16, 17, 18, 19, 20, or 21 phosphorothioate linkages.
388. The method of embodiment 387, wherein the one or more phosphorothioate linkages of the sense strand is about 1, 2, 3, 4, or 5 phosphorothioate linkages.
389. The method of embodiment 388, wherein the one or more phosphorothioate linkages of the sense strand is about 4 phosphorothioate linkages.
390. The method of any one of embodiments 382-389, wherein the sense strand comprises a phosphorothioate linkage between the first nucleoside and the second nucleoside of the sense strand, in a 5' to 3' direction.
391. The method of any one of embodiments 382-390, wherein the sense strand comprises a phosphorothioate linkage between the second nucleoside and the third nucleoside of the sense strand, in a 5' to 3' direction.
392. The method of any one of embodiments 382-391, wherein the sense strand comprises a phosphorothioate linkage between the nineteenth nucleoside and the twentieth nucleoside of the sense strand, in a 5' to 3' direction.
393. The method of any one of embodiments 382-392, wherein the sense strand comprises a phosphorothioate linkage between the twentieth nucleoside and the twenty-first nucleoside of the sense strand, in a 5' to 3' direction.
394. The method of any one of embodiments 384-393, wherein the antisense strand of the siRNA comprises one or more phosphorothioate linkages.
395. The method of embodiment 394, wherein the one or more phosphorothioate linkages of the antisense strand is about 1, 2, 3, 4, 5, 6, 7, 8, 9, 10, 11, 12, 13, 14, 15, 16, 17, 18, 19, 20, or 21 phosphorothioate linkages.
396. The method of embodiment 395, wherein the one or more phosphorothioate linkages of the antisense strand is about 1, 2, 3, 4, or 5 phosphorothioate linkages.
397. The method of embodiment 396, wherein the one or more phosphorothioate linkages of the antisense strand is about 4 phosphorothioate linkages.
398. The method of any one of embodiments 394-397, wherein the antisense strand comprises a phosphorothioate linkage between the first nucleoside and the second nucleoside of the antisense strand, in a 5' to 3' direction.
399. The method of any one of embodiments 394-398, wherein the antisense strand comprises a phosphorothioate linkage between the second nucleoside and the third nucleoside of the antisense strand, in a 5' to 3' direction.
400. The method of any one of embodiments 394-399, wherein the antisense strand comprises a phosphorothioate linkage between the nineteenth nucleoside and the twentieth nucleoside of the sense strand, in a 5' to 3' direction.

401. The method of any one of embodiments 394-400, wherein the antisense strand comprises a phosphorothioate linkage between the twentieth nucleoside and the twenty-first nucleoside of the sense strand, in a 5' to 3' direction.

402. The method of any one of embodiments 368-401, comprising a modified nucleoside.

403. The method of embodiment 402, wherein the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-O-allyl, 2'-fluoro, or 2'-deoxy, or a combination thereof.

404. The method of embodiment 403, wherein the modified nucleoside comprises a of 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof.

405. The method of embodiment 403, wherein the modified nucleoside comprises one or more 2'fluoro modified nucleosides.

406. The method of embodiment 405, wherein the one or more 2' fluoro modified nucleosides is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 2' fluoro modified nucleosides.

407. The method of embodiment 405 or embodiment 406, wherein the sense strand of the siRNA comprises one or more 2' fluoro modified nucleosides.

408. The method of embodiment 407, wherein the one or more 2' fluoro modified nucleosides of the sense strand is about 1, 2, 3, 4, 5, 6, 7, 8, 9, 10, 11, 12, 13, 14, 15, 16, 17, 18, 19, 20, or 21 2' fluoro modified nucleosides.

409. The method of embodiment 408, wherein the one or more 2' fluoro modified nucleosides of the sense strand is about eleven 2' fluoro modified nucleosides.

410. The method of embodiment 408, wherein the one or more 2' fluoro modified nucleosides of the sense strand is about four 2' fluoro modified nucleosides.

411. The method of embodiment 408, wherein the one or more 2' fluoro modified nucleosides of the sense strand is about three 2' fluoro modified nucleosides.

412. The method of any one of embodiments 407-411, wherein the first nucleoside of the sense strand comprises the 2' fluoro modified nucleoside, in a 5' to 3' direction.

413. The method of any one of embodiments 407-412, wherein the third nucleoside of the sense strand comprises the 2' fluoro modified nucleoside, in a 5' to 3' direction.

414. The method of any one of embodiments 407-413, wherein the fifth nucleoside of the sense strand comprises the 2' fluoro modified nucleoside, in a 5' to 3' direction.

415. The method of any one of embodiments 407-414, wherein the seventh nucleoside of the sense strand comprises the 2' fluoro modified nucleoside, in a 5' to 3' direction.

416. The method of any one of embodiments 407-415, wherein the eighth nucleoside of the sense strand comprises the 2' fluoro modified nucleoside, in a 5' to 3' direction.

417. The method of any one of embodiments 407-416, wherein the ninth nucleoside of the sense strand comprises the 2' fluoro modified nucleoside, in a 5' to 3' direction.

418. The method of any one of embodiments 407-417, wherein the eleventh nucleoside of the sense strand comprises the 2' fluoro modified nucleoside, in a 5' to 3' direction.

419. The method of any one of embodiments 407-418, wherein the thirteenth nucleoside of the sense strand comprises the 2' fluoro modified nucleoside, in a 5' to 3' direction.

420. The method of any one of embodiments 407-419, wherein the fifteenth nucleoside of the sense strand comprises the 2' fluoro modified nucleoside, in a 5' to 3' direction.

421. The method of any one of embodiments 407-420, wherein the seventeenth nucleoside of the sense strand comprises the 2' fluoro modified nucleoside, in a 5' to 3' direction.

422. The method of any one of embodiments 407-421, wherein the nineteenth nucleoside of the sense strand comprises the 2' fluoro modified nucleoside, in a 5' to 3' direction.

423. The method of any one of embodiments 407-422, wherein the fifth, seventh, and ninth nucleosides of the sense strand comprises the 2' fluoro modified nucleoside, in a 5' to 3' direction.

424. The method of any one of embodiments 407-423, comprising the pattern fN-Z1-fN-Z2-fN, wherein fN comprises the 2' fluoro modified nucleoside and Z1 and Z2 are independently a 2' O-methyl modified nucleoside or a 2' fluoro modified nucleoside.

425. The method of embodiment 424, wherein the fN-Z1-fN-Z2-fN corresponds to nucleosides five to nine of the sense strand, in a 5' to 3' direction.

426. The method of any one of embodiments 407-425, wherein the sense strand comprises at least two contiguous 2' fluoro modified nucleosides.

427. The method of embodiment 426, wherein the at least two contiguous 2' fluoro modified nucleosides is two contiguous 2' fluoro modified nucleosides.

428. The method of embodiment 426, wherein the at least two contiguous 2' fluoro modified nucleosides is three contiguous 2' fluoro modified nucleosides.

429. The method of any one of embodiments 405-428, wherein the antisense strand of the siRNA comprises one or more 2' fluoro modified nucleosides.

430. The method of embodiment 429, wherein the one or more 2' fluoro modified nucleosides of the antisense strand is about 1, 2, 3, 4, 5, 6, 7, 8, 9, 10, 11, 12, 13, 14, 15, 16, 17, 18, 19, 20, or 21 2' fluoro modified nucleosides.

431. The method of embodiment 430, wherein the one or more 2' fluoro modified nucleosides of the antisense strand is about eight 2' fluoro modified nucleosides.

432. The method of embodiment 430, wherein the one or more 2' fluoro modified nucleosides of the antisense strand is about six 2' fluoro modified nucleosides.

433. The method of embodiment 430, wherein the one or more 2' fluoro modified nucleosides of the antisense strand is about five 2' fluoro modified nucleosides.

434. The method of embodiment 430, wherein the one or more 2' fluoro modified nucleosides of the antisense strand is about four 2' fluoro modified nucleosides.

435. The method of any one of embodiments 429-434, wherein the second nucleoside of the antisense strand comprises the 2' fluoro modified nucleoside, in a 5' to 3' direction.
436. The method of any one of embodiments 429-435, wherein the fourth nucleoside of the antisense strand comprises the 2' fluoro modified nucleoside, in a 5' to 3' direction.
437. The method of any one of embodiments 429-436, wherein the sixth nucleoside of the antisense strand comprises the 2' fluoro modified nucleoside, in a 5' to 3' direction.
438. The method of any one of embodiments 429-437, wherein the eighth nucleoside of the antisense strand comprises the 2' fluoro modified nucleoside, in a 5' to 3' direction.
439. The method of any one of embodiments 429-438, wherein the ninth nucleoside of the antisense strand comprises the 2' fluoro modified nucleoside, in a 5' to 3' direction.
440. The method of any one of embodiments 429-439, wherein the tenth nucleoside of the antisense strand comprises the 2' fluoro modified nucleoside, in a 5' to 3' direction.
441. The method of any one of embodiments 429-440, wherein the fourteenth nucleoside of the antisense strand comprises the 2' fluoro modified nucleoside, in a 5' to 3' direction.
442. The method of any one of embodiments 429-441, wherein the sixteenth nucleoside of the antisense strand comprises the 2' fluoro modified nucleoside, in a 5' to 3' direction.
443. The method of any one of embodiments 429-442, wherein the eighteenth nucleoside of the antisense strand comprises the 2' fluoro modified nucleoside, in a 5' to 3' direction.
444. The method of any one of embodiments 429-443, wherein the second and fourteenth nucleosides of the antisense strand comprises the 2' fluoro modified nucleoside, in a 5' to 3' direction.
445. The method of any one of embodiments 429-444, wherein the second, sixth, fourteenth, and sixteenth nucleosides of the antisense strand comprises the 2' fluoro modified nucleoside, in a 5' to 3' direction.
446. The method of any one of embodiments 429-445, comprising the pattern Z3-fN-Z4-fN, wherein fN comprises the 2' fluoro modified nucleoside and Z3 and Z4 are independently a 2' O-methyl modified nucleoside or a 2' fluoro modified nucleoside.
447. The method of embodiment 446, wherein the Z3-fN-Z4-fN corresponds to nucleosides thirteen to sixteen of the antisense strand, in a 5' to 3' direction.
448. The method of any one of embodiments 404-447, wherein the modified nucleoside comprises a 2' O-alkyl modified nucleoside.
449. The method of embodiment 448, wherein the 2' O-alkyl modified nucleoside comprises one or more 2' O-methyl modified nucleosides.
450. The method of embodiment 449, wherein the one or more 2' O-methyl modified nucleosides is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 2' O-methyl modified nucleosides.
451. The method of any one of embodiments 448-450, wherein the sense strand of the siRNA comprises one or more 2' O-methyl modified nucleosides.
452. The method of embodiment 451, wherein the one or more 2' O-methyl modified nucleosides of the sense strand is about 1, 2, 3, 4, 5, 6, 7, 8, 9, 10, 11, 12, 13, 14, 15, 16, 17, 18, 19, 20, or 21 2' O-methyl modified nucleosides.
453. The method of embodiment 452, wherein the one or more 2' O-methyl modified nucleosides of the sense strand is about ten 2' O-methyl modified nucleosides.
454. The method of embodiment 452, wherein the one or more 2' O-methyl modified nucleosides of the sense strand is about seventeen 2' O-methyl modified nucleosides.
455. The method of embodiment 452, wherein the one or more 2' O-methyl modified nucleosides of the sense strand is about eighteen 2' O-methyl modified nucleosides.
456. The method of any one of embodiments 449-455, wherein the first nucleoside of the sense strand comprises the 2' O-methyl modified nucleoside, in a 5' to 3' direction.
457. The method of any one of embodiments 449-456, wherein the second nucleoside of the sense strand comprises the 2' O-methyl modified nucleoside, in a 5' to 3' direction.
458. The method of any one of embodiments 449-457, wherein the third nucleoside of the sense strand comprises the 2' O-methyl modified nucleoside, in a 5' to 3' direction.
459. The method of any one of embodiments 449-458, wherein the fourth nucleoside of the sense strand comprises the 2' O-methyl modified nucleoside, in a 5' to 3' direction.
460. The method of any one of embodiments 449-459, wherein the sixth nucleoside of the sense strand comprises the 2' O-methyl modified nucleoside, in a 5' to 3' direction.
461. The method of any one of embodiments 449-460, wherein the eighth nucleoside of the sense strand comprises the 2' O-methyl modified nucleoside, in a 5' to 3' direction.
462. The method of any one of embodiments 449-461, wherein the tenth nucleoside of the sense strand comprises the 2' O-methyl modified nucleoside, in a 5' to 3' direction.
463. The method of any one of embodiments 449-462, wherein the eleventh nucleoside of the sense strand comprises the 2' O-methyl modified nucleoside, in a 5' to 3' direction.
464. The method of any one of embodiments 449-463, wherein the twelfth nucleoside of the sense strand comprises the 2' O-methyl modified nucleoside, in a 5' to 3' direction.
465. The method of any one of embodiments 449-464, wherein the thirteenth nucleoside of the sense strand comprises the 2' O-methyl modified nucleoside, in a 5' to 3' direction.
466. The method of any one of embodiments 449-465, wherein the fourteenth nucleoside of the sense strand comprises the 2' O-methyl modified nucleoside, in a 5' to 3' direction.
467. The method of any one of embodiments 449-466, wherein the fifteenth nucleoside of the sense strand comprises the 2' O-methyl modified nucleoside, in a 5' to 3' direction.

468. The method of any one of embodiments 449-467, wherein the sixteenth nucleoside of the sense strand comprises the 2' O-methyl modified nucleoside, in a 5' to 3' direction.

469. The method of any one of embodiments 449-468, wherein the seventeenth nucleoside of the sense strand comprises the 2' O-methyl modified nucleoside, in a 5' to 3' direction.

470. The method of any one of embodiments 449-469, wherein the eighteenth nucleoside of the sense strand comprises the 2' O-methyl modified nucleoside, in a 5' to 3' direction.

471. The method of any one of embodiments 449-470, wherein the nineteenth nucleoside of the sense strand comprises the 2' O-methyl modified nucleoside, in a 5' to 3' direction.

472. The method of any one of embodiments 449-471, wherein the twentieth nucleoside of the sense strand comprises the 2' O-methyl modified nucleoside, in a 5' to 3' direction.

473. The method of any one of embodiments 449-472, wherein the twenty-first nucleoside of the sense strand comprises the 2' O-methyl modified nucleoside, in a 5' to 3' direction.

474. The method of any one of embodiments 449-473, wherein the second, fourth, sixth, tenth, twelfth, fourteenth, and sixteenth, eighteenth, twentieth, and twenty-first nucleosides of the sense strand comprises the 2' O-methyl modified nucleoside, in a 5' to 3' direction.

475. The method of any one of embodiments 449-474, comprising the pattern mN-Z5-mN-Z6, wherein mN comprises the 2' O-methyl modified nucleoside and Z5 and Z6 are independently a 2' O-methyl modified nucleoside or a 2' fluoro modified nucleoside.

476. The method of embodiment 475, wherein the mN-Z5-mN-Z6-mN corresponds to nucleosides four to seven of the sense strand, in a 5' to 3' direction.

477. The method of embodiment 475 or embodiment 476, wherein Z5 is the 2' fluoro modified nucleoside.

478. The method of embodiment 475 or embodiment 476, wherein Z5 is the 2' O-methyl modified nucleoside.

479. The method of any one of embodiments 475-478, wherein Z6 is the 2' fluoro modified nucleoside.

480. The method of any one of embodiments 475-478, wherein Z6 is the 2' O-methyl modified nucleoside.

481. The method of any one of embodiments 449-480, comprising the pattern mN-Z5-mN-Z6-mN, wherein mN comprises the 2' O-methyl modified nucleoside and Z5 and Z6 are independently a 2' O-methyl modified nucleoside or a 2' fluoro modified nucleoside.

482. The method of embodiment 481, wherein the mN-Z5-mN-Z6-mN corresponds to nucleosides two to six of the sense strand, in a 5' to 3' direction.

483. The method of embodiment 481, wherein the mN-Z5-mN-Z6-mN corresponds to nucleosides ten to fourteen of the sense strand, in a 5' to 3' direction.

484. The method of embodiment 481, wherein the mN-Z5-mN-Z6-mN corresponds to nucleosides twelve to sixteen of the sense strand, in a 5' to 3' direction.

485. The method of embodiment 481, wherein the mN-Z5-mN-Z6-mN corresponds to nucleosides fourteen to eighteen of the sense strand, in a 5' to 3' direction.

486. The method of embodiment 481, wherein the mN-Z5-mN-Z6-mN corresponds to nucleosides sixteen to twenty of the sense strand, in a 5' to 3' direction.

487. The method of any one of embodiments 449-486, comprising the pattern mN-Z5-mN-Z6-mN-Z7-mN, wherein Z7 is a 2' O-methyl modified nucleoside or a 2' fluoro modified nucleoside.

488. The method of embodiment 487, wherein the mN-Z5-mN-Z6-mN-Z7-mN corresponds to nucleosides ten to sixteen of the sense strand, in a 5' to 3' direction.

489. The method of embodiment 488, wherein the mN-Z5-mN-Z6-mN-Z7-mN corresponds to nucleosides twelve to eighteen of the sense strand, in a 5' to 3' direction.

490. The method of embodiment 488, wherein the mN-Z5-mN-Z6-mN-Z7-mN corresponds to nucleosides fourteen to twenty of the sense strand, in a 5' to 3' direction.

491. The method of any one of embodiments 449-490, comprising the pattern mN-Z5-mN-Z6-mN-Z7-mN-Z8-mN, wherein Z8 is a 2' O-methyl modified nucleoside or a 2' fluoro modified nucleoside.

492. The method of embodiment 491, wherein the mN-Z5-mN-Z6-mN-Z7-mN-Z8-mN corresponds to nucleosides ten to eighteen of the sense strand, in a 5' to 3' direction.

493. The method of embodiment 491, wherein the mN-Z5-mN-Z6-mN-Z7-mN-Z8-mN corresponds to nucleosides twelve to twenty of the sense strand, in a 5' to 3' direction.

494. The method of any one of embodiments 449-493, comprising the pattern mN-Z5-mN-Z6-mN-Z7-mN-Z8-mN-Z9-mN, wherein Z9 is a 2' O-methyl modified nucleoside or a 2' fluoro modified nucleoside.

495. The method of embodiment 494, wherein the mN-Z5-mN-Z6-mN-Z7-mN-Z8-mN-Z9-mN corresponds to nucleosides ten to twenty of the sense strand, in a 5' to 3' direction.

496. The method of any one of embodiments 449-495, wherein the sense strand comprises at least two contiguous 2' O-methyl modified nucleosides.

497. The method of embodiment 496, wherein the at least two contiguous 2' O-methyl modified nucleosides is three contiguous 2' O-methyl modified nucleosides.

498. The method of embodiment 496, wherein the at least two contiguous 2' O-methyl modified nucleosides is four contiguous 2' O-methyl modified nucleosides.

499. The method of embodiment 496, wherein the at least two contiguous 2' O-methyl modified nucleosides is five contiguous 2' O-methyl modified nucleosides.

500. The method of embodiment 496, wherein the at least two contiguous 2' O-methyl modified nucleosides is six contiguous 2' O-methyl modified nucleosides.

501. The method of embodiment 496, wherein the at least two contiguous 2' O-methyl modified nucleosides is seven contiguous 2' O-methyl modified nucleosides.

502. The method of embodiment 496, wherein the at least two contiguous 2' O-methyl modified nucleosides is eight contiguous 2' O-methyl modified nucleosides.

503. The method of embodiment 496, wherein the at least two contiguous 2' O-methyl modified nucleosides is nine contiguous 2' O-methyl modified nucleosides.

504. The method of embodiment 496, wherein the at least two contiguous 2' O-methyl modified nucleosides is ten contiguous 2' O-methyl modified nucleosides.

505. The method of embodiment 496, wherein the at least two contiguous 2' O-methyl modified nucleosides is eleven contiguous 2' O-methyl modified nucleosides.

506. The method of embodiment 496, wherein the at least two contiguous 2' O-methyl modified nucleosides is twelve contiguous 2' O-methyl modified nucleosides.

507. The method of any one of embodiments 449-506, wherein the antisense strand of the siRNA comprises one or more 2' O-methyl modified nucleosides.

508. The method of embodiment 507, wherein the one or more 2' O-methyl modified nucleosides of the antisense strand is about 1, 2, 3, 4, 5, 6, 7, 8, 9, 10, 11, 12, 13, 14, 15, 16, 17, 18, 19, 20, or 21 2' O-methyl modified nucleosides.

509. The method of embodiment 508, wherein the one or more 2' O-methyl modified nucleosides of the antisense strand is about thirteen 2' O-methyl modified nucleosides.

510. The method of embodiment 508, wherein the one or more 2' O-methyl modified nucleosides of the antisense strand is about fifteen 2' O-methyl modified nucleosides.

511. The method of embodiment 508, wherein the one or more 2' O-methyl modified nucleosides of the antisense strand is about seventeen 2' O-methyl modified nucleosides.

512. The method of any one of embodiments 507-511, wherein the first nucleoside of the antisense strand comprises the 2' O-methyl modified nucleoside, in a 5' to 3' direction.

513. The method of any one of embodiments 507-512, wherein the third nucleoside of the antisense strand comprises the 2' O-methyl modified nucleoside, in a 5' to 3' direction.

514. The method of any one of embodiments 507-513, wherein the fourth nucleoside of the antisense strand comprises the 2' O-methyl modified nucleoside, in a 5' to 3' direction.

515. The method of any one of embodiments 507-514, wherein the fifth nucleoside of the antisense strand comprises the 2' O-methyl modified nucleoside, in a 5' to 3' direction.

516. The method of any one of embodiments 507-515, wherein the seventh nucleoside of the antisense strand comprises the 2' O-methyl modified nucleoside, in a 5' to 3' direction.

517. The method of any one of embodiments 507-516, wherein the eighth nucleoside of the antisense strand comprises the 2' O-methyl modified nucleoside, in a 5' to 3' direction.

518. The method of any one of embodiments 507-517, wherein the ninth nucleoside of the antisense strand comprises the 2' O-methyl modified nucleoside, in a 5' to 3' direction.

519. The method of any one of embodiments 507-518, wherein the tenth nucleoside of the antisense strand comprises the 2' O-methyl modified nucleoside, in a 5' to 3' direction.

520. The method of any one of embodiments 507-519, wherein the eleventh nucleoside of the antisense strand comprises the 2' O-methyl modified nucleoside, in a 5' to 3' direction.

521. The method of any one of embodiments 507-520, wherein the twelfth nucleoside of the antisense strand comprises the 2' O-methyl modified nucleoside, in a 5' to 3' direction.

522. The method of any one of embodiments 507-521, wherein the thirteenth nucleoside of the antisense strand comprises the 2' O-methyl modified nucleoside, in a 5' to 3' direction.

523. The method of any one of embodiments 507-522, wherein the fifteenth nucleoside of the antisense strand comprises the 2' O-methyl modified nucleoside, in a 5' to 3' direction.

524. The method of any one of embodiments 507-523, wherein the seventeenth nucleoside of the antisense strand comprises the 2' O-methyl modified nucleoside, in a 5' to 3' direction.

525. The method of any one of embodiments 507-524, wherein the eighteenth nucleoside of the antisense strand comprises the 2' O-methyl modified nucleoside, in a 5' to 3' direction.

526. The method of any one of embodiments 507-525, wherein the nineteenth nucleoside of the antisense strand comprises the 2' O-methyl modified nucleoside, in a 5' to 3' direction.

527. The method of any one of embodiments 507-526, wherein the twentieth nucleoside of the antisense strand comprises the 2' O-methyl modified nucleoside, in a 5' to 3' direction.

528. The method of any one of embodiments 507-527, wherein the twenty-first nucleoside of the antisense strand comprises the 2' O-methyl modified nucleoside, in a 5' to 3' direction.

529. The method of any one of embodiments 507-528, wherein the first, third, fifth, seventh, eleventh, twelfth, thirteenth, fifteenth, seventeenth, nineteenth, twentieth, and twenty-first nucleosides of the antisense strand comprises the 2' O-methyl modified nucleoside, in a 5' to 3' direction.

530. The method of any one of embodiments 507-529, wherein the antisense strand comprises at least two contiguous 2' O-methyl modified nucleosides.

531. The method of embodiment 530, wherein the at least two contiguous 2' O-methyl modified nucleosides is three contiguous 2' O-methyl modified nucleosides.

532. The method of embodiment 530, wherein the at least two contiguous 2' O-methyl modified nucleosides is four contiguous 2' O-methyl modified nucleosides.

533. The method of embodiment 530, wherein the at least two contiguous 2' O-methyl modified nucleosides is five contiguous 2' O-methyl modified nucleosides.

534. The method of embodiment 530, wherein the at least two contiguous 2' O-methyl modified nucleosides is six contiguous 2' O-methyl modified nucleosides.

535. The method of embodiment 530, wherein the at least two contiguous 2' O-methyl modified nucleosides is seven contiguous 2' O-methyl modified nucleosides.

536. The method of any one of embodiments 507-535, wherein the antisense strand comprises a first sequence comprising at least two contiguous 2' O-methyl modified nucleosides and a second sequence comprising at least two contiguous 2' O-methyl modified nucleosides.

537. The method of embodiment 536, wherein the first sequence comprises at least three contiguous 2' O-methyl modified nucleosides, and the second sequence comprises at least three contiguous 2' O-methyl modified nucleosides.

538. The method of embodiment 536, wherein the first sequence comprises three contiguous 2' O-methyl modified nucleosides, and the second sequence comprises three contiguous 2' O-methyl modified nucleosides.

539. The method of embodiment 536, wherein the first sequence comprises four contiguous 2' O-methyl modified nucleosides, and the second sequence comprises five contiguous 2' O-methyl modified nucleosides.

540. The method of embodiment 536, wherein the first sequence comprises seven contiguous 2' O-methyl modified nucleosides, and the second sequence comprises five contiguous 2' O-methyl modified nucleosides.
541. The method of embodiment 536, wherein the first sequence comprises at least four contiguous 2' O-methyl modified nucleosides.
542. The method of embodiment 536, wherein the first sequence comprises at least five contiguous 2' O-methyl modified nucleosides.
543. The method of embodiment 536, wherein the first sequence comprises at least six contiguous 2' O-methyl modified nucleosides.
544. The method of embodiment 536, wherein the first sequence comprises at least seven contiguous 2' O-methyl modified nucleosides.
545. The method of any one of embodiments 541-544, wherein the second sequence comprises at least four contiguous 2' O-methyl modified nucleosides.
546. The method of any one of embodiments 541-544, wherein the second sequence comprises at least five contiguous 2' O-methyl modified nucleosides.
547. The method of any one of embodiments 511-544, wherein the second sequence comprises at least six contiguous 2' O-methyl modified nucleosides.
548. The method of any one of embodiments 511-544, wherein the second sequence comprises at least seven contiguous 2' O-methyl modified nucleosides.
549. The method of any one of embodiments 368-548, wherein the sense strand comprises a ribose.
550. The method of embodiment 549, wherein the sense strand comprises about 1, 2, 3, 4, 5, 6, 7, 8, 9, 10, 11, 12, 13, 14, 15, 16, 17, 18, 19, 20, or 21 ribose.
551. The method of embodiment 549 or embodiment 550, wherein the first nucleoside of the sense strand comprises the ribose, in a 5' to 3' direction.
552. The method of any one of embodiments 549-551, wherein the second nucleoside of the sense strand comprises the ribose, in a 5' to 3' direction.
553. The method of any one of embodiments 549-552, wherein the third nucleoside of the sense strand comprises the ribose, in a 5' to 3' direction.
554. The method of any one of embodiments 549-553, wherein the fourth nucleoside of the sense strand comprises the ribose, in a 5' to 3' direction.
555. The method of any one of embodiments 549-554, wherein the fifth nucleoside of the sense strand comprises the ribose, in a 5' to 3' direction.
556. The method of any one of embodiments 549-555, wherein the sixth nucleoside of the sense strand comprises the ribose, in a 5' to 3' direction.
557. The method of any one of embodiments 549-556, wherein the seventh nucleoside of the sense strand comprises the ribose, in a 5' to 3' direction.
558. The method of any one of embodiments 549-557, wherein the eighth nucleoside of the sense strand comprises the ribose, in a 5' to 3' direction.
559. The method of any one of embodiments 549-558, wherein the ninth nucleoside of the sense strand comprises the ribose, in a 5' to 3' direction.
560. The method of any one of embodiments 549-559, wherein the tenth nucleoside of the sense strand comprises the ribose, in a 5' to 3' direction.
561. The method of any one of embodiments 549-560, wherein the eleventh nucleoside of the sense strand comprises the ribose, in a 5' to 3' direction.
562. The method of any one of embodiments 549-561, wherein the twelfth nucleoside of the sense strand comprises the ribose, in a 5' to 3' direction.
563. The method of any one of embodiments 549-562, wherein the thirteenth nucleoside of the sense strand comprises the ribose, in a 5' to 3' direction.
564. The method of any one of embodiments 549-563, wherein the fourteenth nucleoside of the sense strand comprises the ribose, in a 5' to 3' direction.
565. The method of any one of embodiments 549-564, wherein the fifteenth nucleoside of the sense strand comprises the ribose, in a 5' to 3' direction.
566. The method of any one of embodiments 549-565, wherein the sixteenth nucleoside of the sense strand comprises the ribose, in a 5' to 3' direction.
567. The method of any one of embodiments 549-566, wherein the seventeenth nucleoside of the sense strand comprises the ribose, in a 5' to 3' direction.
568. The method of any one of embodiments 549-567, wherein the eighteenth nucleoside of the sense strand comprises the ribose, in a 5' to 3' direction.
569. The method of any one of embodiments 549-568, wherein the nineteenth nucleoside of the sense strand comprises the ribose, in a 5' to 3' direction.
570. The method of any one of embodiments 549-569, wherein the twentieth nucleoside of the sense strand comprises the ribose, in a 5' to 3' direction.
571. The method of any one of embodiments 549-570, wherein the twenty-first nucleoside of the sense strand comprises the ribose, in a 5' to 3' direction.
572. The method of any one of embodiments 368-571, wherein the antisense strand comprises a ribose.
573. The method of embodiment 572, wherein the antisense strand comprises about 1, 2, 3, 4, 5, 6, 7, 8, 9, 10, 11, 12, 13, 14, 15, 16, 17, 18, 19, 20, or 21 ribose.
574. The method of embodiment 572 or embodiment 573, wherein the first nucleoside of the antisense strand comprises the ribose, in a 5' to 3' direction.
575. The method of any one of embodiments 572-574, wherein the second nucleoside of the antisense strand comprises the ribose, in a 5' to 3' direction.
576. The method of any one of embodiments 572-575, wherein the third nucleoside of the antisense strand comprises the ribose, in a 5' to 3' direction.
577. The method of any one of embodiments 572-576, wherein the fourth nucleoside of the antisense strand comprises the ribose, in a 5' to 3' direction.
578. The method of any one of embodiments 572-577, wherein the fifth nucleoside of the antisense strand comprises the ribose, in a 5' to 3' direction.
579. The method of any one of embodiments 572-578, wherein the sixth nucleoside of the antisense strand comprises the ribose, in a 5' to 3' direction.
580. The method of any one of embodiments 572-579, wherein the seventh nucleoside of the antisense strand comprises the ribose, in a 5' to 3' direction.
581. The method of any one of embodiments 572-580, wherein the eighth nucleoside of the antisense strand comprises the ribose, in a 5' to 3' direction.
582. The method of any one of embodiments 572-581, wherein the ninth nucleoside of the antisense strand comprises the ribose, in a 5' to 3' direction.
583. The method of any one of embodiments 572-582, wherein the tenth nucleoside of the sense antisense comprises the ribose, in a 5' to 3' direction.

584. The method of any one of embodiments 572-583, wherein the eleventh nucleoside of the antisense strand comprises the ribose, in a 5' to 3' direction.

585. The method of any one of embodiments 572-584, wherein the twelfth nucleoside of the antisense strand comprises the ribose, in a 5' to 3' direction.

586. The method of any one of embodiments 572-585, wherein the thirteenth nucleoside of the antisense strand comprises the ribose, in a 5' to 3' direction.

587. The method of any one of embodiments 572-586, wherein the fourteenth nucleoside of the antisense strand comprises the ribose, in a 5' to 3' direction.

588. The method of any one of embodiments 572-587, wherein the fifteenth nucleoside of the antisense strand comprises the ribose, in a 5' to 3' direction.

589. The method of any one of embodiments 572-588, wherein the sixteenth nucleoside of the antisense strand comprises the ribose, in a 5' to 3' direction.

590. The method of any one of embodiments 572-589, wherein the seventeenth nucleoside of the antisense strand comprises the ribose, in a 5' to 3' direction.

591. The method of any one of embodiments 572-590, wherein the eighteenth nucleoside of the antisense strand comprises the ribose, in a 5' to 3' direction.

592. The method of any one of embodiments 572-591, wherein the nineteenth nucleoside of the antisense strand comprises the ribose, in a 5' to 3' direction.

593. The method of any one of embodiments 572-592, wherein the twentieth nucleoside of the antisense strand comprises the ribose, in a 5' to 3' direction.

594. The method of any one of embodiments 572-593, wherein the twenty-first nucleoside of the antisense strand comprises the ribose, in a 5' to 3' direction.

595. The method of any one of embodiments 368-594, further comprising a lipid attached at either 3' or 5' terminus.

596. The method of embodiment 595, wherein the lipid comprises cholesterol, myristoyl, palmitoyl, stearoyl, lithocholoyl, docosanoyl, docosahexaenoyl, myristyl, palmityl stearyl, α-tocopherol, or a combination thereof.

597. The method of embodiment 595 or embodiment 596, wherein the lipid comprises a first lipid on the sense strand and a second lipid on the antisense strand.

598. The method of any one of embodiments 595-597, wherein the lipid is positioned on the sense strand.

599. The method of embodiment 598, wherein the lipid is positioned at the 5' end of the sense strand.

600. The method of embodiment 598, wherein the lipid is positioned at the 3' end of the sense strand.

601. The method of any one of embodiments 595-600, wherein the lipid is positioned on the antisense strand.

602. The method of embodiment 601, wherein the lipid is positioned at the 5' end of the antisense strand.

603. The method of embodiment 601, wherein the lipid is positioned at the 3' end of the antisense strand.

604. The method of any one of embodiments 368-594, further comprising an arginine-glycine-aspartic acid (RGD) ligand attached at a 3' terminus and/or a 5' terminus.

605. The method of any one of embodiments 368-603, further comprising an RGD ligand attached at either a 3' terminus or a 5' terminus.

606. The method of embodiment 604 or 605, wherein the RGD ligand comprises Cyclo(-Arg-Gly-Asp-D-Phe-Cys), Cyclo(-Arg-Gly-Asp-D-Phe-Lys), Cyclo(-Arg-Gly-Asp-D-Phe-azido), Cyclo(-Arg-Gly-Asp-D-Phe-alkynyl), amino benzoic acid-based RGD, or a combination thereof.

607. The method of embodiment 604 or embodiment 605, wherein the RGD ligand is composed of 2, 3 or 4 RGD ligands.

608. The method of any one of embodiments 604-607, wherein the RGD is positioned on the sense strand.

609. The method of embodiment 608, wherein the RGD is positioned at the 5' end of the sense strand.

610. The method of embodiment 608, wherein the RGD is positioned at the 3' end of the sense strand.

611. The method of any one of embodiments 604-607, wherein the RGD is positioned on the antisense strand.

612. The method of embodiment 611, wherein the RGD ligand is positioned at the 5' end of the antisense strand.

613. The method of embodiment 611, wherein the RGD ligand is positioned at the 3' end of the antisense strand.

614. The method of any one of embodiments 368-613, wherein the sense strand and the antisense strand form a double-stranded RNA duplex.

615. The method of embodiment 614, wherein the double-stranded RNA duplex comprises from about 14 to about 30 nucleosides.

616. The method of embodiment 614, wherein the double-stranded RNA duplex comprises from about 17 to about 30 nucleosides.

617. The method of embodiment 614, wherein the double-stranded RNA duplex comprises about 21 nucleosides.

618. The method of any one of embodiments 614-617, wherein the double-stranded RNA duplex comprises at least one base pair.

619. The method of embodiment 618, wherein the first base pair of the double-stranded RNA duplex is an AU base pair.

620. The method of any one of embodiments 368-614, wherein the sense strand comprises pattern 1S: 5' fN s mN s fN-mN-fN-mN-fN-fN-fN-mN-fN-mN-fN-mN-fN-mN-fN-mN-fN s mN s mN 3' (SEQ ID NO: 11381), wherein "fN" is a 2' fluoro-modified nucleoside, "mN" is a 2' O-methyl modified nucleoside, "-" is a phosphodiester, and "s" is a phosphorothioate.

621. The method of any one of embodiments 368-614, wherein the sense strand comprises pattern 2S: 5' mN s mN s mN-mN-fN-mN-fN-fN-fN-mN-mN-mN-mN-mN-mN-mN-mN-mN-mN s mN s mN 3' (SEQ ID NO: 11382), wherein "fN" is a 2' fluoro-modified nucleoside, "mN" is a 2' O-methyl modified nucleoside, "-" is a phosphodiester, and "s" is a phosphorothioate.

622. The method of any one of embodiments 368-614, wherein the sense strand comprises pattern 3S: 5' mN s mN s mN-mN-fN-mN-fN-mN-fN-mN-mN-mN-mN-mN-mN-mN-mN-mN-mN s mN s mN 3' (SEQ ID NO: 11383), wherein "fN" is a 2' fluoro-modified nucleoside, "mN" is a 2' O-methyl modified nucleoside, "-" is a phosphodiester, and "s" is a phosphorothioate.

623. The method of any one of embodiments 368-614, wherein the sense strand comprises pattern 4S: 5' fN s mN s fN-mN-fN-mN-fN-fN-fN-mN-fN-mN-fN-mN-fN-mN-fN-mN-fN s mN s mN-N-Lipid 3' (SEQ ID NO: 11384), wherein "fN" is a 2' fluoro-modified nucleoside, "mN" is a 2' O-methyl modified nucleoside, "-" is a phosphodiester, "s" is a phosphorothioate, and N comprises one or more nucleosides.

624. The method of embodiment 623, wherein the one or more nucleosides is three nucleosides.

625. The method of embodiment 623 or 624, wherein each of the one or more nucleosides independently comprise a ribose or deoxyribose.
626. The method of any one of embodiments 368-619, wherein the sense strand comprises pattern 5S: 5' mN s mN s mN-mN-fN-mN-fN-fN-fN-mN-mN-mN-mN-mN-mN-mN-mN-mN-mN s mN s mN-N-Lipid 3' (SEQ ID NO: 11385), wherein "fN" is a 2' fluoro-modified nucleoside, "mN" is a 2' O-methyl modified nucleoside, "-" is a phosphodiester, "s" is a phosphorothioate, and N comprises one or more nucleosides.
627. The method of embodiment 626, wherein the one or more nucleosides is three nucleosides.
628. The method of embodiment 626 or 627, wherein each of the one or more nucleosides independently comprise a ribose or deoxyribose.
629. The method of any one of embodiments 368-628, wherein the antisense strand comprises pattern 1AS: 5' mN s fN s mN-fN-mN-fN-mN-fN-mN-fN-mN-mN-mN-fN-mN-fN-mN-fN-mN s mN s mN 3' (SEQ ID NO: 11386), wherein "fN" is a 2' fluoro-modified nucleoside, "mN" is a 2' O-methyl modified nucleoside, "-" is a phosphodiester, and "s" is a phosphorothioate.
630. The method of any one of embodiments 368-628, wherein the antisense strand comprises pattern 2AS: 5' mN s fN s mN-mN-mN-fN-mN-fN-fN-mN-mN-mN-mN-fN-mN-fN-mN-mN-mN s mN s mN 3' (SEQ ID NO: 11387), wherein "fN" is a 2' fluoro-modified nucleoside, "mN" is a 2' O-methyl modified nucleoside, "-" is a phosphodiester, and "s" is a phosphorothioate.
631. The method of any one of embodiments 368-628, wherein the antisense strand comprises pattern 3AS: 5' mN s fN s mN-mN-mN-fN-mN-mN-mN-mN-mN-mN-mN-fN-mN-fN-mN-mN-mN s mN s mN 3' (SEQ ID NO: 11388), wherein "fN" is a 2' fluoro-modified nucleoside, "mN" is a 2' O-methyl modified nucleoside, "-" is a phosphodiester, and "s" is a phosphorothioate.
632. The method of any one of embodiments 368-628, wherein the antisense strand comprises pattern 4AS: 5' mN s fN s mN-fN-mN-fN-mN-mN-mN-mN-mN-mN-mN-fN-mN-mN-mN-mN-mN s mN s mN 3' (SEQ ID NO: 11389), wherein "fN" is a 2' fluoro-modified nucleoside, "mN" is a 2' O-methyl modified nucleoside, "-" is a phosphodiester, and "s" is a phosphorothioate.
633. The method of any one of embodiments 368-619, wherein the sense strand comprises pattern 1S and the antisense strand comprises pattern 1 AS.
634. The method of any one of embodiments 368-619, wherein the sense strand comprises pattern 2S and the antisense strand comprises pattern 2AS.
635. The method of any one of embodiments 368-619, wherein the sense strand comprises pattern 3S and the antisense strand comprises pattern 3AS.
636. The method of any one of embodiments 368-619, wherein the sense strand comprises pattern 4S and the antisense strand comprises pattern 4AS.

EXAMPLES

The following non-limiting examples serve to illustrate selected embodiments. It will be appreciated that variations in proportions and alternatives in elements of the components shown will be apparent to those skilled in the art and are within the scope of embodiments presented herein.

Example 1. Association of ANGPTL7 Protein Altering Variants with IOP and Glaucoma Applicant evaluated approximately 30,000,000 imputed variants in ~350,000 individuals from the UK Biobank cohort for associations with glaucoma and glaucoma-relevant phenotypes, including non-specific glaucoma, primary open angle glaucoma (POAG), primary angle closure glaucoma (PACG), glaucoma surgery, glaucoma medication use, and intraocular pressure (IOP) (see Table 1). Elevated IOP is a primary causal feature and risk factor for glaucoma.

TABLE 1

Case Definitions and Case and Control Counts for Evaluated Phenotypes

| Trait | Case Definition | Case # | Control # |
|---|---|---|---|
| Glaucoma | Hospital diagnosis of glaucoma OR glaucoma surgery or meds OR self-reported history of glaucoma in a nurse-led interview | 6896 | 328209 |
| ICD Glaucoma POAG | Hospital diagnosis of primary open angle glaucoma | 836 | 328209 |
| ICD Glaucoma PACG | Hospital diagnosis of primary angle closed glaucoma | 571 | 328209 |
| Glaucoma Surgery | Hospital procedure for glaucoma | 1229 | 328209 |
| Glaucoma Medication | Use of prostaglandin analogs, alpha agonists, carbonic anhydrase inhibitors, and beta blockers used to treat glaucoma | 2131 | 328209 |
| IOP | intra-ocular pressure measure | 70107 | NA |

Associations were observed between a rare missense variant (rs28991009; minor allele frequency ~0.0073) within ANGPTL7 and glaucoma and related traits (see Table 2). The major allele of this variant (chr1-11253684-G, hg19) encodes for a glutamine and the minor allele (chr1-11253684-T, hg19) a histidine at amino acid position 175 of the full length ANGPTL7 protein (Gln175His; Q175H). Carriers of the minor allele of this variant had about half the risk of glaucoma as non-carriers (p=4×10^-5; OR=0.61). ICD defined subtypes of POAG (p=0.04; OR=0.0.44) and PACG (p=0.08; OR=0.42) demonstrated similar protection. Odds of glaucoma medication use (p=0.04; OR=0.66) and glaucoma surgery (p=0.03; OR=0.50) were also reduced, and an association with reduced IOP was observed (p=2×10^-13; beta=−0.21).

TABLE 2

Association of ANGPTL7 Variant rs28991009 with Glaucoma and Related Traits

| Trait | Variant | Effect Size | P |
|---|---|---|---|
| Glaucoma | rs28991009 | 0.61 (OR) | 4.07E−05 |
| ICD Glaucoma POAG | rs28991009 | 0.44 (OR) | 0.04 |
| ICD Glaucoma PACG | rs28991009 | 0.42 (OR) | 0.08 |
| Glaucoma Surgery | rs28991009 | 0.50 (OR) | 0.03 |
| Glaucoma Medication | rs28991009 | 0.66 (OR) | 0.04 |
| IOP | rs28991009 | −0.21 (Beta) | 1.95E−13 |

Next, we performed a gene burden test utilizing all protein altering variants in ANGPTL7. Gene burden tests are used to aggregate rare variants in a gene by functional class that are too rare to be tested individually. Though imputation of array genotypes has improved significantly with the availability of large reference datasets consisting of haplotypes observed in whole genome sequencing studies, imputation of very rare variants remains challenging and can be inaccurate. For this reason, we conducted the burden test using all directly genotyped protein altering variants in ANGPTL7, resulting in inclusion of the Q175H missense variant (MAF=0.0073; rs28991009), an R140H missense variant (MAF=0.0024; rs28991002), a G136R missense variant (MAF=0.0005; rs200058074) and an R177Ter stop gain variant (MAF=0.0004; rs143435072). Individuals carrying predicted ANGPTL7 protein altering variants had a significantly lower IOP when compared to non-carriers (p=1.01E-17; beta=−0.20) (Table 3). The burden result was driven by the Q175H, R140H and R177Ter variants; the G136R variant was not associated with IOP (Table 3).

TABLE 3

Association of ANGPTL7 Protein Altering Variants with IOP

| RSID | Function | AAF | REF | ALT | BETA (95% CI) | P |
|---|---|---|---|---|---|---|
| rs28991009 | Missense (Q175H) | 7.27E-03 | G | T | −0.22 (−0.27, −0.16) | 2.72E-14 |
| rs28991002 | Missense (R140H) | 2.36E-03 | G | A | −0.17 (−0.27, −0.08) | 4.63E-04 |
| rs143435072 | Stop gain (R177Ter) | 3.81E-04 | C | T | −0.39 (−0.64, −0.14) | 2.00E-03 |
| rs200058074 | Missense (G136R) | 5.06E-04 | A | G | 0.02 (−0.19, 0.24) | 0.84 |
| Burden | NA | 1.05E-02 | NA | NA | −0.20 (−0.25, −0.15) | 1.01E-17 |

The protective (i.e. IOP-lowering) associations with Q175H and R140H were directionally consistent with the predicted loss of function variant R177Ter; in other words, the minor allele of all three variants was associated with decreased IOP. By inference, these data indicate that loss of function (LOF) of ANGPTL7 protects against the development of ocular hypertension and glaucoma. Accordingly, in some cases therapeutic inhibition or modulation of ANGPTL7 may be an effective genetically-informed method of treatment for these diseases.

Example 2. Protective (i.e. IOP-Lowering) Variants in ANGPTL7 Result in Less Secreted ANGPTL7 Protein Pre-mRNA or protein-coding sequence (CDS) expression constructs encoding for wild type, Q175H, R140H and R177Ter proteins were generated (FIG. 1). The pre-mRNA or CDS of the protein coding transcript (ENST00000376819) of ANGPTL7 was cloned into a pcDNA3.1(+) vector driven by a CMV promoter. Note that the pre-mRNA constructs contained exons, introns, and 5' and 3' UTRs, while the CDS constructs contained only exons. The purpose in utilizing pre-mRNA constructs is that they allow for evaluation of alternatively spliced transcripts. Empty vector and a GFP tagged vector were used as controls. For Q175H (rs28991009) expression constructs, the T allele replaces the G allele at DNA sequence position chr1:11253684 (human genome build 37). This creates a Gln175His amino acid substitution in the ANGPTL7 protein. For R140H (rs28991002) expression constructs, the A allele replaces the G allele at DNA position chr1:11252369 (human genome build 37). For R177Ter (rs143435072) expression constructs, the T allele replaces the C allele at DNA sequence position chr1:11253688 (human genome build 37). This creates an Arg177Ter premature stop codon.

Figure 2:
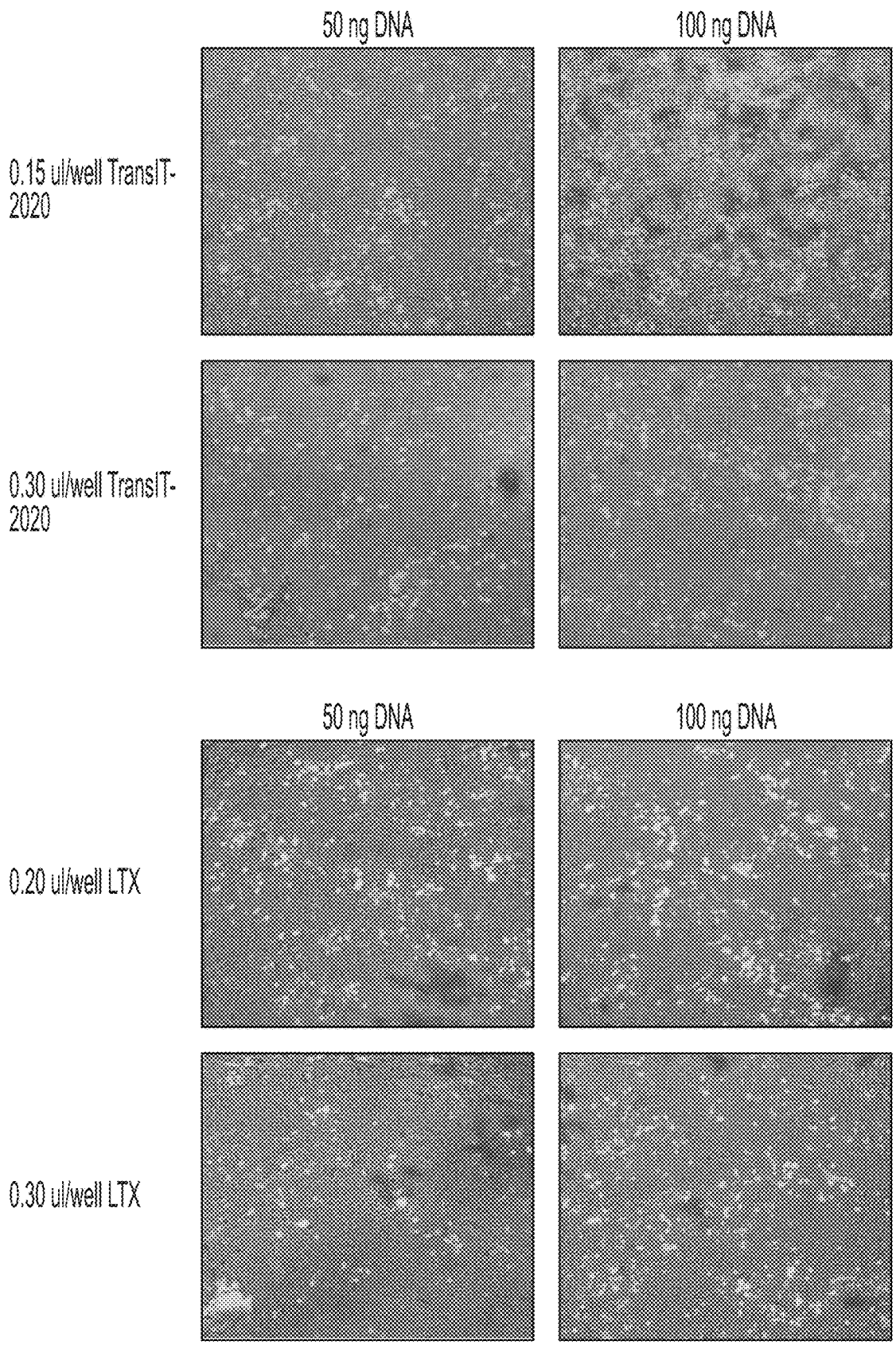
FIG. 2 shows fluorescent microscopy images of HEK293 cells transfected with a pcDNA3.1(+) GFP vector.
Figure 3:
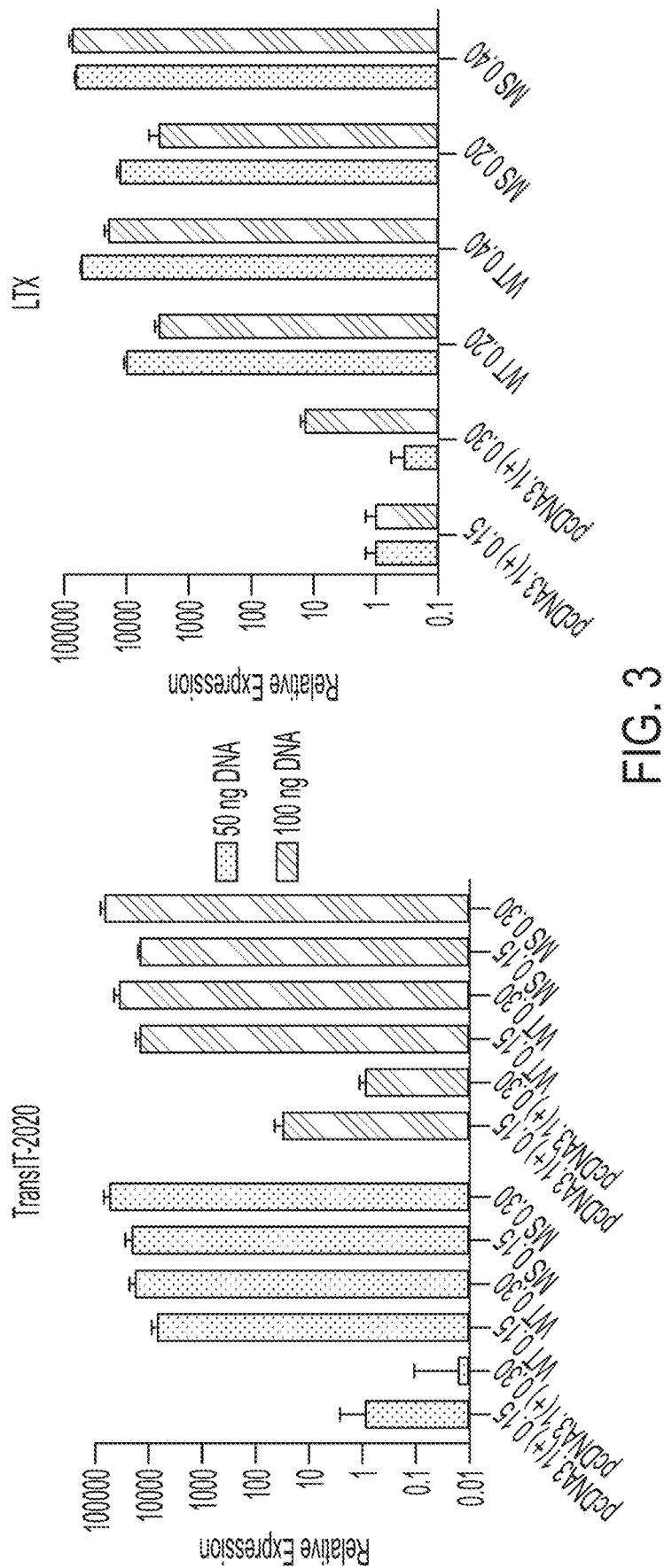
FIG. 3 shows results of qPCR measuring ANGPTL7 mRNA expression in HEK293 cells transfected with the WT and Q175H pre-mRNA expression constructs.

Transfections of HEK293 cells were optimized using the GFP-tagged and ANGPTL7 WT and Q175H pre-mRNA constructs. Briefly, HEK293 cells were plated at 10,000 cells/well in a 96-well plate in complete growth media and grown for 48 hours followed by a media change. Cells were then transfected with 50 ng or 100 ng of plasmid DNA and 0.15 ul/well or 0.30 ul/well of TransIT-2020 or 0.20 ul/well or 0.40 ul/well Lipofectamine LTX reagents. Cells were incubated for 60 hours, and then either imaged for GFP fluorescence (see FIG. 2) or harvested with Cells-to-Ct reagent and qPCR used to assess ANGPTL7 expression (see FIG. 3). The GFP vector transfection confirmed high transfection efficiency with TransIT-2020 reagent and the qPCR assay confirmed that both the wild-type and Q175H constructs produce ANGPTL7.

Figure 4:
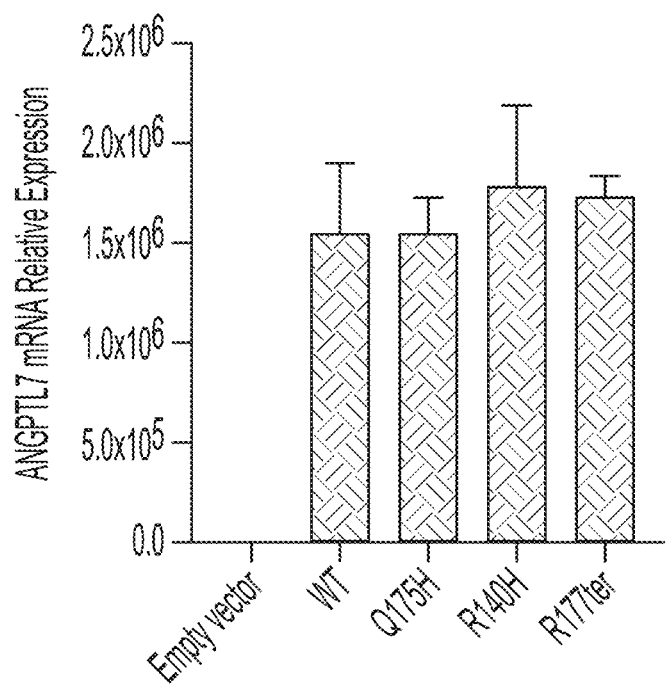
FIG. 4 shows results of qPCR measuring ANGPTL7 mRNA expression in HEK293 cells transfected with the WT, Q175H, R140H and R177Ter pre-mRNA expression constructs.

To evaluate, in parallel, the effects of the Q175H, R140H and R177Ter IOP-lowering variants on mRNA and protein expression levels, wild-type and variant constructs were transiently transfected and expressed in HEK293 cells. ANGPTL7 mRNA expression in empty vector transfected HEK293 cells was negligible, while expression from the plasmid constructs was robust and equivalent between the wild-type and variant (Q175H, R140H and R177Ter) transfected cells (FIG. 4).

Figure 5:
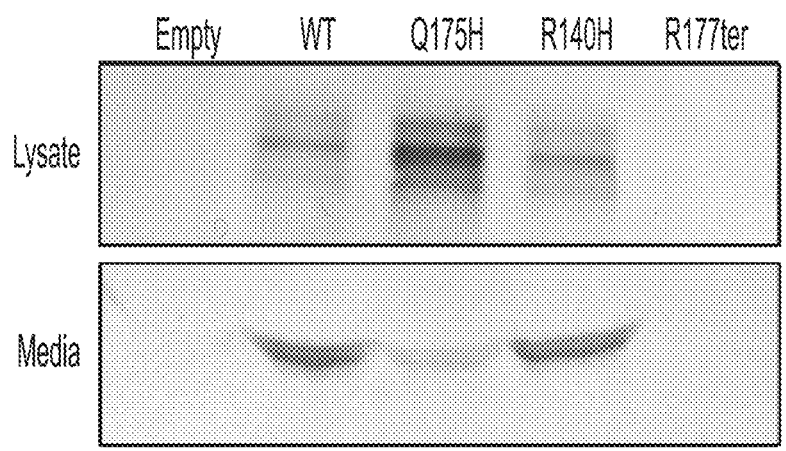
FIG. 5 includes an image of a western blot of ANGPTL7 in HEK293 cells transfected with the WT, Q175H, R140H and R177Ter pre-mRNA expression constructs.

Cell lysates and media from transfected cells were assayed to evaluate intracellular and secreted ANGPTL7 protein by Western blot (FIG. 5). In empty vector transfected HEK293 cells, ANGPTL7 was not detectable by Western blot. In cells transfected with the Q175H construct, ANGPTL7 was markedly reduced in the medium and increased in the cell lysate, suggesting a secretion defect. No protein was detected in lysates or media from cells transfected with the R177Ter construct, in spite of mRNA levels that are equivalent to wild type, suggesting degradation at the protein level rather than nonsense mediated decay. There was no apparent difference between wild type and R140H in either secreted or intracellular protein abundance by Western blot.

Figure 6:
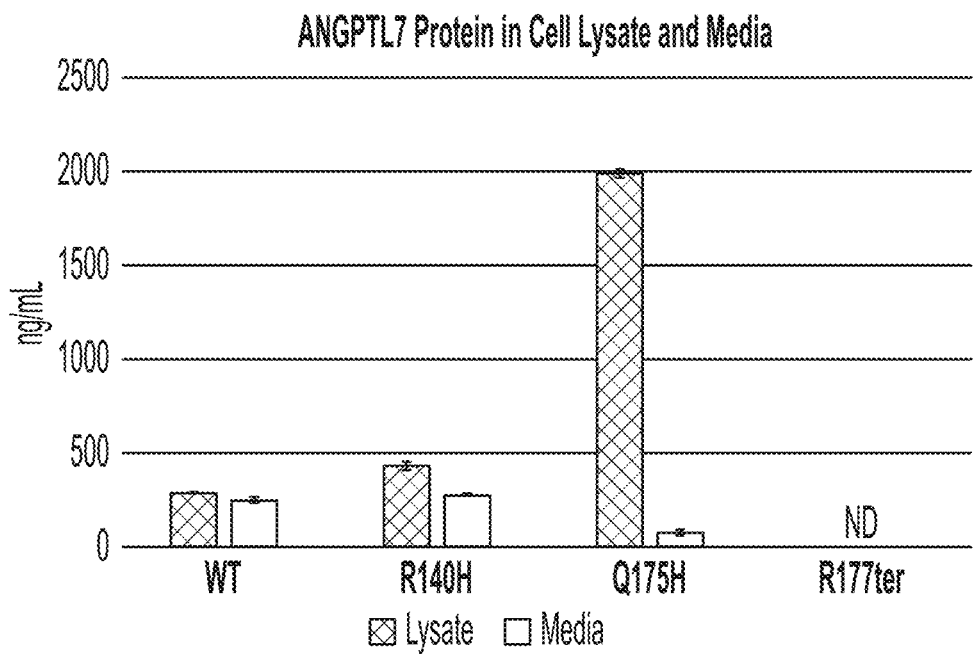
FIG. 6 includes results of an ELISA assay measuring ANGPTL7 protein expression in HEK293 cells transfected with the WT, Q175H, R140H and R177Ter pre-mRNA expression constructs.
Figure 7:
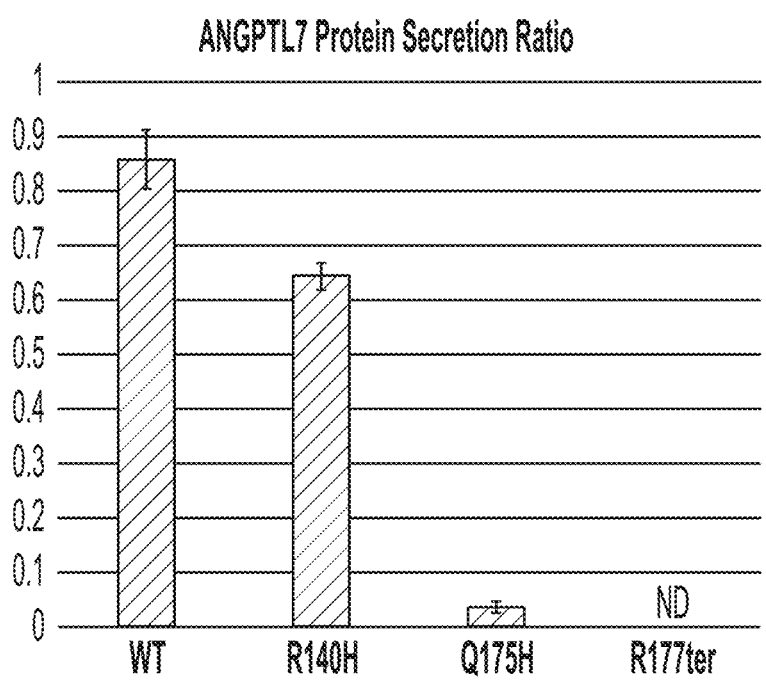
FIG. 7 shows the ratio of secreted vs. intracellular protein (as measured by ELISA) in HEK293 cells transfected with the WT, Q175H, R140H and R177Ter pre-mRNA expression constructs.

Western blot results were validated using a quantitative ELISA assay (FIG. 6). Q175H protein was 6.8-fold more abundant in the cell lysate compared to wild-type, whereas the wild-type protein was 3.3-fold more abundant in the media. This results in a heavily skewed ratio of protein in the media versus lysate when comparing wild-type and Q175H missense protein (~22:1 ratio) (FIG. 7). The R140H protein demonstrated a lower secretion ratio than wild type, though this difference was modest. Protein was below the ELISA limit of detection in both the media and cell lysate for cells transfected with the R177Ter construct, consistent with the Western blot results.

Figure 8:
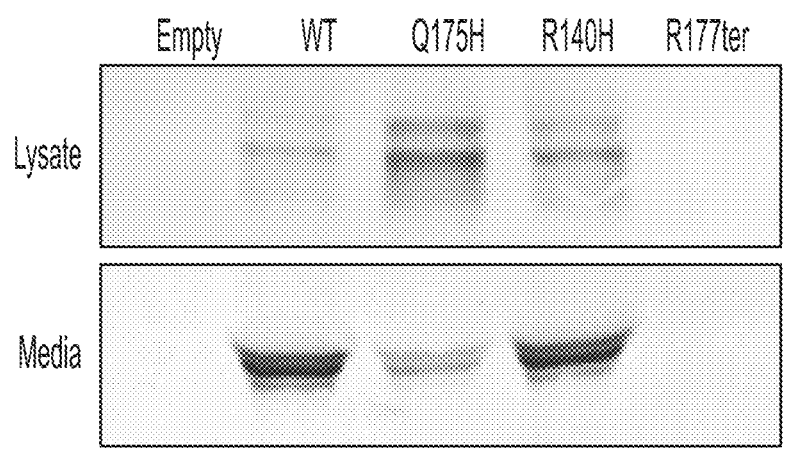
FIG. 8 includes an image of a western blot of ANGPTL7 in HEK293 cells transfected with the WT, Q175H, R140H and R177Ter CDS expression constructs.

Similar experiments were performed using CDS constructs rather than pre-mRNA constructs, and results were equivalent to those for the pre-mRNA constructs, as demonstrated by Western Blot (FIG. 8).

Therefore, experimental evaluation of ANGPTL7 proteins demonstrates that genetic variants in ANGPTL7 that are observed to lower IOP and protect from ocular hypertension and glaucoma result in reduced intracellular and/or extracellular ANGPTL7 protein, thereby confirming utility of inhibiting or modulating ANGPTL7 for treatment of these diseases.

Example 3. Verification of a Predicted Noncoding ANGPTL7 Transcript

Figure 9:
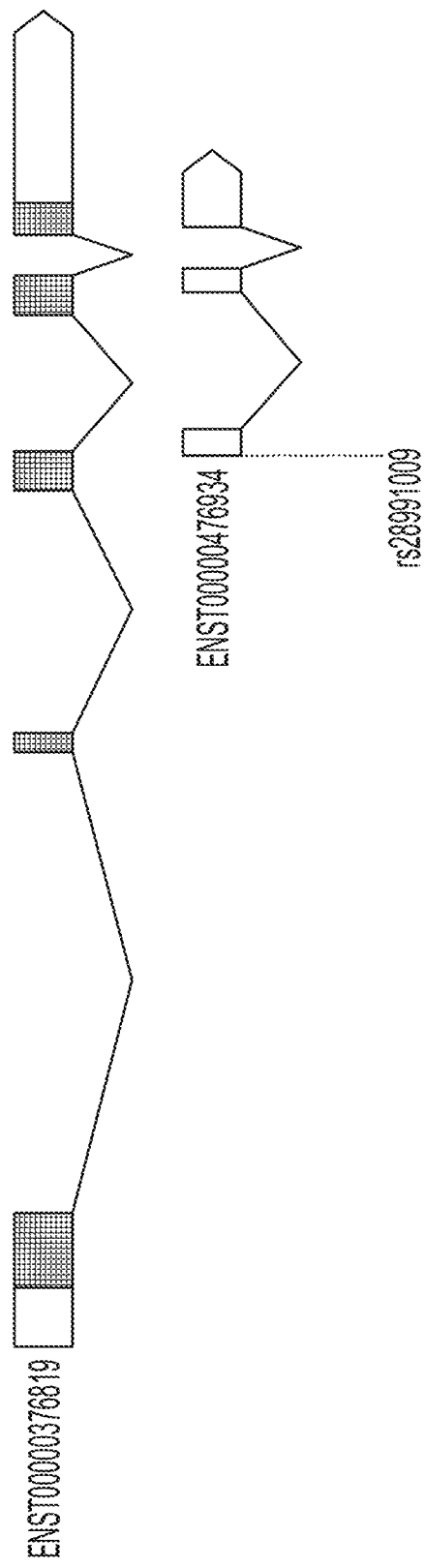
FIG. 9 shows protein coding and noncoding ANGPTL7 transcripts and the relative location of the Q175H missense variant.

ANGPTL7 has two database annotated RNA transcripts, the canonical protein coding transcript (ENST00000376819) and a noncoding transcript (ENST00000476934) (FIG. 9). The protein coding transcript is comprised of five exons encoding for a 346aa protein. The noncoding transcript is comprised of three noncoding exons, the first of which starts within the third exon of the protein coding transcript. The noncoding transcript is a less well annotated transcript with weak support in the Ensembl database. Of note, the rs28991009 (Q175H) variant is located at the first nucleotide position of the noncoding transcript. This suggests possible involvement of this variant in the generation of the noncoding transcript and another possible mechanism, in addition to the secretion defect discovered by the applicant, by which the Q175H missense variant or other variants could result in loss of functional protein.

Figure 10:
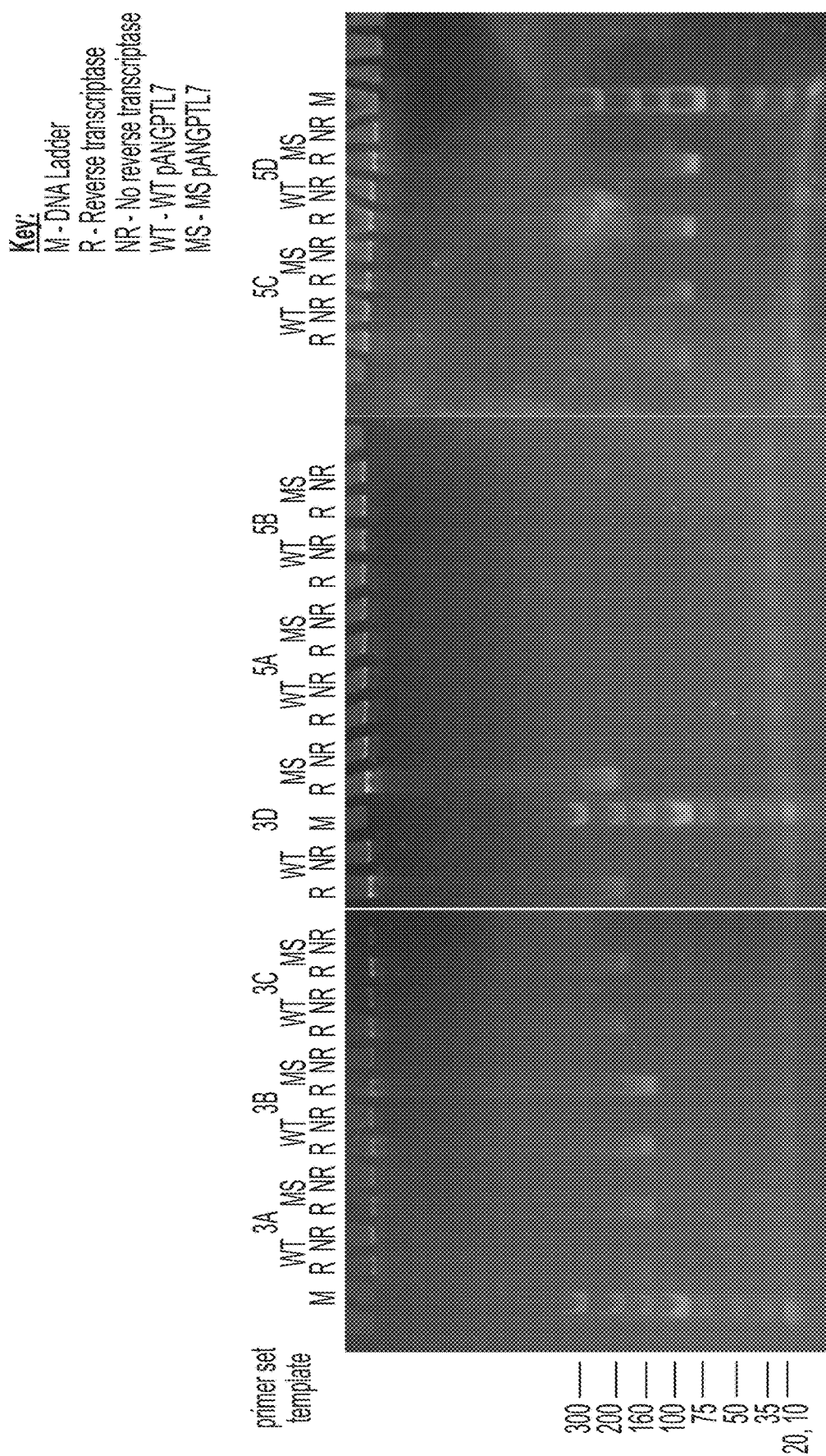
FIG. 10 shows an agarose gel with transcript-specific PCR products from HEK293 cells transfected with WT and Q175H pre-mRNA expression constructs.

A number of PCR primers were designed to detect, in a non-quantitative PCR assay, the protein coding and noncoding ANGPTL7 transcripts from HEK293 cells transfected with the wild type and Q175H variant pre-mRNA constructs. These pre-mRNA constructs allow for generation of alternatively spliced transcripts, if such transcripts exist. Briefly, HEK293 cells were transfected with 50 ng of the wild type or 50 ng of the Q175H pre-mRNA constructs. cDNA was prepared from these transfected cells and was used as template material in a 32-cycle PCR reaction whose products were then run on an agarose gel. The expected amplicon lengths from the various PCR primer combinations are given in Table 4. Both WT and alternatively spliced ANGPTL7 transcripts were produced from both the WT and Q175H ANGPTL7 pre-mRNA constructs in transfected HEK-293 cells (FIG. 10). Note that the relative abundance of these transcripts cannot be determined from this PCR assay.

Figure 11:
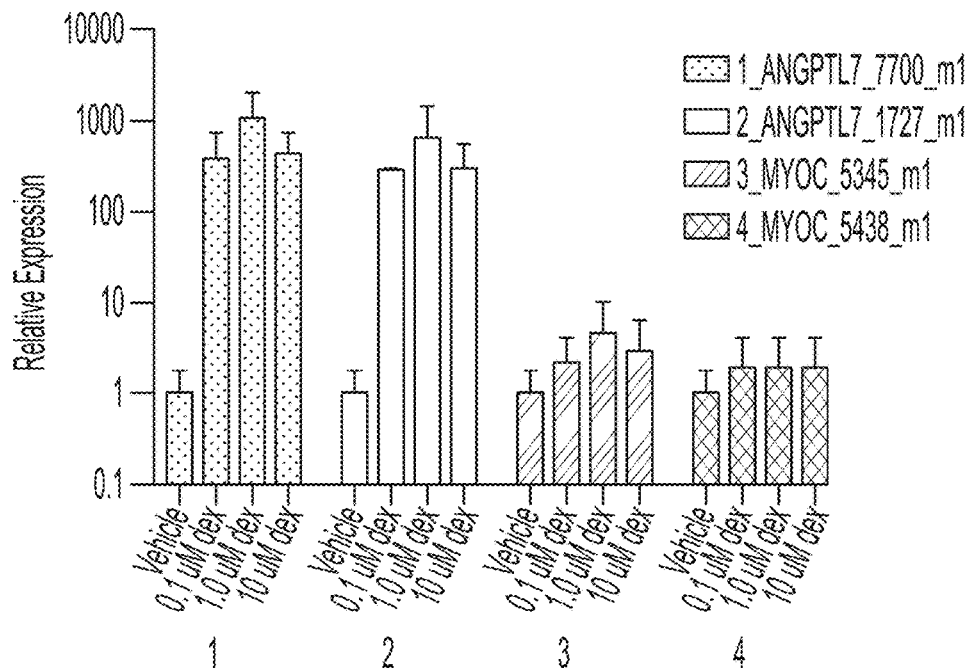
FIG. 11 shows ANGPTL7 and MYOC expression in dexamethasone induced HTM cells.
Figure 12:
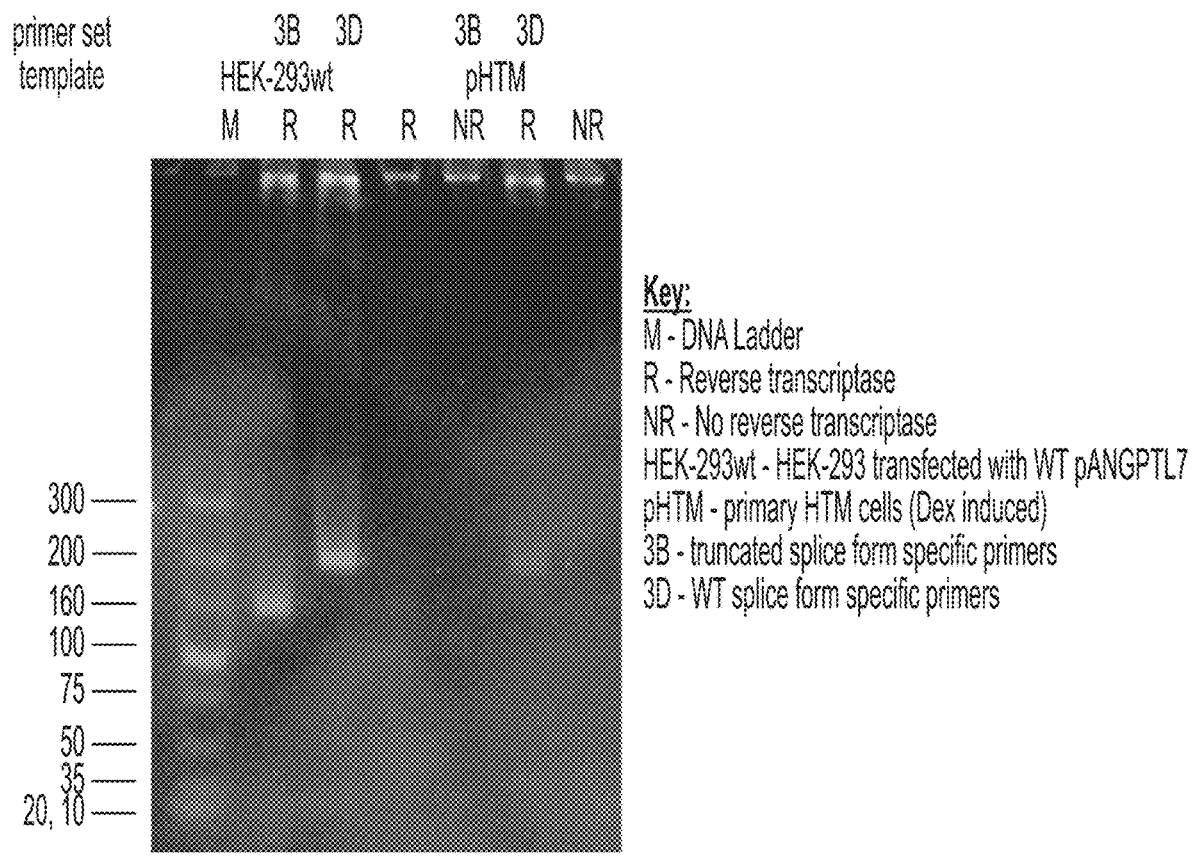
FIG. 12 shows an agarose gel with transcript-specific PCR products from dexamethasone induced primary HTM cells.

Next, primary human trabecular meshwork (HTM) cells were plated at 25,000 cells/well in 24-well plates in complete HTM growth medium and grown overnight. Cells were treated with dexamethasone or vehicle (100% EtOH) for 5 days, then cDNA was harvested with Cells-to-Ct kit and assayed by qPCR with probes for ANGPTL7 and MYOC (FIG. 11). Strong induction of ANGPTL7 and MYOC was observed. Next, cDNA from dexamethasone induced pHTM cells was used as a template in transcript specific PCR reactions using a subset of the primers used above (Table 4). PCR products indicate that the protein coding transcript is present in dexamethasone induced pHTM cells, and that the noncoding or alternatively spliced transcript form is also likely present (but near the limit of detection) using this assay (see FIG. 12).

Therefore, evaluation of native transcripts in pHTM cells as well as evaluation of transcripts arising from pre-mRNA plasmid constructs transfected in HEK293 cells have demonstrated the existence of alternatively spliced ANGPTL7 transcripts consistent with the existence of the putative ANGPLT7 noncoding transcript and suggests a potential mechanism of disease risk modulation.

Example 4. Using CRISPR Knock-Ins to Determine that Protein Altering Variants in ANGPTL7 Alter Transcript and/or Protein Abundance ANGPTL7 CRISPR knock-ins are created for the rs28991009 (Q175H), rs28991002 (R140H) and rs143435072 (R177Ter) variants in immortalized human trabecular meshwork cells (iHTMs). For rs28991009 knock-in creation, the T allele replaces the G allele at position chr1:11253684 (human genome build 37). This creates a Gln175His amino acid substitution in the ANGPTL7 protein. For rs28991002 knock-in creation, the A allele replaces the G allele at position chr1:11252369 (human genome build 37). For rs143435072 knock-in creation, the T allele replaces the C allele at position chr1:11253688 (human genome build 37). This creates an Arg177Ter premature stop codon.

Knock-in and wild type iHTM cells are used to demonstrate that the protein altering variants in ANGPTL7 result in secretion defects, or alterations in coding and/or noncoding transcript abundance, or alterations in protein abundance, thereby resulting in loss of functional ANGPTL7 protein.

TABLE 4

Primers Sets and Expected Amplicons for Detection of the Protein Coding (WT) and Noncoding (Trunc) Transcripts

| Primer Set | Splice Form | WT mRNA | WT pre-mRNA | Truncated mRNA | Truncated pre-mRNA |
|---|---|---|---|---|---|
| Set 3B (ET P00011/26) | Trunc | 2 MM at 3' 26 | 2 MM at 3' 26 | 142 bp | 3 MM at 3' 26 |
| Set 3C (ET P00011/27) | WT | 208 bp | 894 bp | 2 MM at 3' 27 | 3 MM at 3' 27 |
| Set 3D (ET P00011/28) | WT | 209 bp | 895 bp | 2 MM at 3' 28 | 3 MM at 3' 28 |
| Set 5A (ET P00015/25) | Trunc | 2 MM at 3' 25 | 2 MMat 3' 25, 1 MM 15 | 2 MM at 3' 15 | 3 MM at 3' 25, 1 MM 15 |
| Set 5B (ET P00015/26) | Trunc | 2 MM at 3' 26 | 2 MM at 3' 26, 1 MM 15 | 2 MM at 3' 15 | 3 MM at 3' 26, 1 MM 15 |
| Set 5C (ET P00015/27) | WT | 97 bp | 1 MM at 3' 15 | 2 MM at 3' 27, 15 | 3 MM at 3' 27, 1 MM 15 |
| Set 5D (ET P00015/28) | WT | 98 bp | 1 MM at 3' 15 | 2 MM at 3' 28, 15 | 3 MM at 3' 28, 1 MM 15 |

Knock-in and wild-type iHTM cells are grown to confluency and then serially passaged in complete IMEM media supplemented with 10% FBS until growing well. Cells are plated in 24-well plates and left untreated or treated with DEX. DEX (Sigma) stock solution is prepared by adding absolute ethanol to the commercial vial obtaining a final concentration of 0.1 mM and kept at 4° C. The DEX stock solution of 0.1 µM is diluted 1000× (100 nM final concentration) in IMEM media before use. Parallel wells receive IMEM medium containing the drug vehicle under the same conditions. Seventy-two hours after treatment cells are harvested with Cells-to-Ct reagent.

qPCR is performed using the ABI Prism 7900HT Fast Real-Time PCR System (ThermoFisher, Carlsbad, CA). Amplification by PCR is performed according to the manufacturer's protocols (ThermoFisher). Primers and probes for the ANGPTL7 protein coding (ENST00000376819) and noncoding (ENST00000476934) transcripts are used to quantitate the relative abundance of protein coding and noncoding transcript arising from the WT, Q175H, R140H and Arg177Ter knock-in iHTM cells.

Gene expression of extracellular matrix and glaucoma related genes are also evaluated from this same experiment using the same qPCR system. These genes include myocilin (MYOC), collagens type I and V (COL1A1 and COL5A1), versican (VCAN) and fibronectin (FN1). The composition and quality of the extracellular matrix in which human trabecular meshwork cells are embedded is directly relevant to the aqueous humor outflow and glaucoma disease pathology.

Northern blots are also performed to quantitate the relative abundance of protein coding and noncoding transcript arising from WT, Q175H, R140H and Arg177Ter knock-in iHTM cells. Knock-in and wild-type iHTM cells are grown to confluency and then serially passaged in complete IMEM media supplemented with 10% FBS until growing well. Cells are plated in 24-well plates and left untreated or treated with DEX. Parallel wells receive IMEM medium containing the drug vehicle under the same conditions. Seventy-two hours after treatment total RNA is extracted for Northern blot using a probe which captures both the protein coding and noncoding ANGPTL7 transcripts.

Western blots are also performed to quantitate the relative abundance of ANGPTL7 protein arising from WT, Q175H, R140H and Arg177Ter knock-in iHTM cells. Knock-in and wild-type iHTM cells are grown to confluency and then serially passaged in complete IMEM media supplemented with 10% FBS until growing well. Cells are plated in 24-well plates and left untreated or treated with DEX. Parallel wells receive IMEM medium containing the drug vehicle under the same conditions. Seventy-two hours after treatment cells are trypsinized and cell lysates prepared using a RIPA buffer. Cell lysates and cell culture supernatants are used to perform Western blots using an ANGPTL7 antibody (Abcam) and a GAPDH antibody (Abcam) as a loading control. The Western blot of lysates and supernatants is used to determine if the missense variant modulates ANGPTL7 protein abundance or ANGPTL7 protein secretion.

Example 5. Using Human Cells with Known Genotypes to Determine that Protein Altering Variants in ANGPTL7 Alter Transcript and/or Protein Abundance Human EBV-transformed lymphoblastoid cell lines (LCL) from donors that are known heterozygous or homozygous carriers of the minor alleles of rs28991009 (Q175H), rs28991002 (R140H) and rs143435072 (R177Ter) are acquired. A subset of the cells from each donor are transformed to induced pluripotent stem cells and further differentiated to primary human trabecular meshwork cells (pHTM).

LCL and pHTM cells from variant carriers are compared to non-carriers and are used to demonstrate that the protein altering variants in ANGPTL7 result in secretion defects, or alterations in coding and/or noncoding transcript abundance, or alterations in protein abundance, thereby resulting in loss of functional ANGPTL7 protein. LCL and pHTM cells are grown to confluency and then serially passaged in complete IMEM media supplemented with 10% FBS until growing well. Cells are plated in 24-well plates and left untreated or treated with DEX. DEX (Sigma) stock solution is prepared by adding absolute ethanol to the commercial vial obtaining a final concentration of 0.1 mM and kept at 4° C. The DEX stock solution of 0.1 µM is diluted 1000× (100 nM final concentration) in IMEM media before use. Parallel wells receive IMEM medium containing the drug vehicle under the same conditions. Seventy-two hours after treatment cells are harvested with Cells-to-Ct reagent.

qPCR is performed using the ABI Prism 7900HT Fast Real-Time PCR System (ThermoFisher, Carlsbad, CA). Amplification by PCR is performed according to the manufacturer's protocols (ThermoFisher). Primers and probes for the ANGPTL7 protein coding (ENST00000376819) and noncoding (ENST00000476934) transcripts are used to quantitate the relative abundance of protein coding and noncoding transcript in LCL and pHTM cells from donors.

Gene expression of extracellular matrix and glaucoma related genes are also evaluated from this same experiment using the same qPCR system. These genes include myocilin (MYOC), collagens type I and V (COL1A1 and COL5A1), versican (VCAN) and fibronectin (FN1). The composition and quality of the extracellular matrix in which human trabecular meshwork cells are embedded is directly relevant to the aqueous humor outflow and glaucoma disease pathology.

Northern blots are also performed to quantitate the relative abundance of protein coding and noncoding transcript in LCL and pHTM donor-derived cells. LCL and pHTM cells are grown to confluency and then serially passaged in complete IMEM media supplemented with 10% FBS until growing well. Cells are plated in 24-well plates and left untreated or treated with DEX. Parallel wells receive IMEM medium containing the drug vehicle under the same conditions. Seventy-two hours after treatment total RNA is extracted for Northern blot using a probe which captures both the protein coding and noncoding ANGPTL7 transcripts.

Western blots are also performed to quantitate the relative abundance of ANGPTL7 protein arising in LCL and pHTM donor-derived cells. LCL and pHTM cells are grown to confluency and then serially passaged in complete IMEM media supplemented with 10% FBS until growing well. Cells are plated in 24-well plates and left untreated or treated with DEX. Parallel wells receive IMEM medium containing the drug vehicle under the same conditions. Seventy-two hours after treatment cells are trypsinized and cell lysates prepared using a RIPA buffer. Cell lysates and cell culture supernatants are used to perform Western blots using an ANGPTL7 antibody (Abcam) and a GAPDH antibody (Abcam) as a loading control. The Western blot of lysates and supernatants is used to determine if the missense variant modulates ANGPTL7 protein abundance or ANGPTL7 protein secretion.

Example 6. RNA Synthesis and Duplex Annealing

1. Oligonucleotide Synthesis:

All oligonucleotides are synthesized on an AKTA oligopilot synthesizer or an ABI 394 synthesizer. Commercially available controlled pore glass solid support (dT-CPG, 500A, Prime Synthesis) and RNA phosphoramidites with standard protecting groups, 5'-0-dimethoxytrityl N6-benzoyl-2'-t-butyldimethylsilyl-adenosine-3'-O—N,N'-diisopropyl-2-cyanoethylphosphoramidite, 5'-0-dimethoxytrityl-N4-acetyl-2'-t-butyldimethylsilyl-cytidine-3'-0-N,N'-diisopropyl-2-cyanoethylphosphoramidite, 5'-0-dimethoxytrityl-N2~isobutryl-2'-t-butyldimethylsilyl-guanosine-3'-O—N,N'-diisopropyl-2-cyanoethylphosphoramidite, and 5-0-dimethoxytrityl-2'-t-butyldimethylsilyl-uridine-3'-0-N,N'-diisopropyl-2-cyanoethylphosphoramidite (Pierce Nucleic Acids Technologies) are used for the oligonucleotide synthesis unless otherwise specified. The 2'-F phosphoramidites, 5'-O-dimethoxytrityl-N4-acetyl-2'-fluro-cytidine-3'-0-N,N'-diisopropyl-2-cyanoethylphosphoramidite and 5'-O-dimethoxytrityl-2'-fluro-uridine-3'-0-N,N'-diisopropyl-2-cyanoethylphosphoramidite are purchased from (Promega). All phosphoramidites are used at a concentration of 0.2M in acetonitrile (CH3CN) except for guanosine which is used at 0.2M concentration in 10% THF/ANC (v/v). Coupling/ recycling time of 16 minutes is used. The activator is 5-ethyl thiotetrazole (0.75M, American International Chemicals), for the PO-oxidation Iodine/Water/Pyridine is used and the PS-oxidation PADS (2%>) in 2,6-lutidine/ACN (1:1 v/v) is used.

2. Deprotection-I (Nucleobase Deprotection)

After completion of synthesis, the support is transferred to a 100 ml glass bottle (VWR). The oligonucleotide is cleaved from the support with simultaneous deprotection of base and phosphate groups with 80 mL of a mixture of ethanolic ammonia [ammonia:ethanol (3:1)] for 6.5 h at 55° C. The bottle is cooled briefly on ice and then the ethanolic ammonia mixture is filtered into a new 250 ml bottle. The CPG is washed with 2×40 mL portions of ethanol/water (1:1 v/v). The volume of the mixture is then reduced to ~30 ml by roto-vap. The mixture is then frozen on dry ice and dried under vacuum on a speed vac.

3. Deprotection-II (Removal of 2' TBDMS Group)

The dried residue is resuspended in 26 ml of triethylamine, triethylamine trihydro fluoride (TEA.3HF) or pyridine-HF and DMSO (3:4:6) and heated at 60° C. for 90 minutes to remove the tert-butyldimethylsilyl (TBDMS) groups at the 2' position. The reaction is then quenched with 50 ml of 20 mM sodium acetate and pH adjusted to 6.5, and stored in freezer until purification.

4. Analysis

The oligonucleotides are analyzed by high-performance liquid chromatography (HPLC) prior to purification and selection of buffer and column depends on nature of the sequence and or conjugated ligand.

5. HPLC Purification

The ligand conjugated oligonucleotides are purified reverse phase preparative HPLC. The unconjugated oligonucleotides are purified by anion-exchange HPLC on a TSK gel column packed in house. The buffers are 20 mM sodium phosphate (pH 8.5) in 10% CH3CN (buffer A) and 20 mM sodium phosphate (pH 8.5) in 10% CH3CN, 1M NaBr (buffer B). Fractions containing full-length oligonucleotides are pooled, desalted, and lyophilized. Approximately 0.15 OD of desalted oligonucleotides are diluted in water to 150 µï and then pipetted in special vials for CGE and LC/MS analysis.

Compounds are finally analyzed by LC-ESMS and CGE.

6. siRNA Preparation

For the preparation of siRNA, equimolar amounts of sense and antisense strand are heated in 1×PBS at 95° C. for 5 min and slowly cooled to room temperature.

Integrity of the duplex is confirmed by HPLC analysis.

Example 7. Selection of Sequences in Order to Identify Therapeutic siRNAs to Modulate Expression of the ANGPTL7 mRNA Screening sets were defined based by bioinformatic analysis. The therapeutic siRNA molecule has to target human ANGPTL7 as well as the ANGPTL7 sequence of at least one toxicology-relevant species, in this case, the non-human primates (NHP) rhesus and cynomolgus monkeys. The key drivers for the design of the screening set were predicted specificity of the siRNAs against the transcriptome of the relevant species as well as cross-reactivity between species. Predicted specificity in human, rhesus monkey, cynomolgus monkey, mouse, rat and dog was determined for sense (S) and antisense (AS) strand. These were assigned a "specificity score" which considers the likelihood of unintended downregulation of any other transcript by full or partial complementarity of an siRNA strand (up to 4 mismatches within positions 2-18) as well as the number and positions of mismatches. Thus, the predicted most likely off-target(s) for antisense and sense strand of each siRNA can be identified. In addition, the number of potential off-targets is used as an additional specificity factor in the specificity score. It is preferable to identify siRNAs with high specificity and a low number of predicted off-targets.

In addition to selecting siRNA sequences with high sequence specificity to ANGPTL7 mRNA, siRNA sequences within the seed region were analyzed for similarity to seed regions of known miRNAs. siRNAs can function in a miRNA like manner via base-pairing with complementary sequences within the 3'-UTR of mRNA molecules. The complementarity typically encompasses the 5'-bases at positions 2-7 of the miRNA (seed region). In order to circumvent siRNAs to act via functional miRNA binding sites, siRNA strands are avoided that contain natural miRNA seed regions. Seed regions identified in miRNAs from human, mouse, rat, rhesus monkey, dog, rabbit and pig are referred to as "conserved". Combining the "specificity score" with miRNA seed analysis yields the "specificity category". This is divided into categories 1-4, with 1 having the highest specificity and 4 having the lowest specificity. Each strand of the siRNA is assigned to a specificity category.

Species cross-reactivity was assessed for human, cynomolgus monkey, rhesus monkey, mouse, rat, dog, and rabbit. The analysis was based on a canonical siRNA design using 19 bases and 17 bases (without considering positions 1 and 19) for cross-reactivity. Full match as well as single mismatch analysis was included.

Analysis of the human Single Nucleotide Polymorphism (SNP) database (NCBI-DB-SNP) to identify siRNAs targeting regions with known SNPs was also carried out in order to identify siRNAs that may be non-functional in individuals containing the SNP. Information regarding the positions of SNPs within the target sequence as well as minor allele frequency (MAF) in case data was obtained in this analysis.

Initial analysis of the relevant ANGPTL7 mRNA sequence revealed few sequences can be identified that fulfil the specificity requirements and at the same time target ANGPTL7 mRNA in all relevant species. Therefore, it was decided to design independent screening subsets for the therapeutic siRNAs.

All siRNAs in these subsets recognize the human ANGPTL7 sequence, as a human cell culture system was selected for determination of in vitro activity. Therefore, all siRNAs in these subsets can be used to target human ANGPTL7 in a therapeutic setting.

The number of 19mer sequences that can be derived from human ANGPTL7 mRNA (NM_021146.4) without consideration of specificity or species cross-reactivity is 2,206 (sense strand SEQ ID NOS: 1-2206). This set would encompass all possible ANGPTL7 siRNA sequences.

Prioritizing sequences for target specificity, species cross-reactivity, miRNA seed region sequences and SNPs as described above yields siRNA subset A. This subset is composed of 207 siRNAs with sense strand SEQ ID NOS: 7, 39, 42, 92, 93, 94, 95, 98, 99, 103, 112, 113, 114, 115, 117, 118, 119, 120, 124, 125, 127, 206, 207, 227, 257, 271, 272, 480, 487, 488, 489, 490, 491, 492, 493, 497, 498, 499, 501, 579, 583, 584, 587, 588, 592, 593, 594, 596, 598, 600, 601, 602, 603, 604, 605, 606, 629, 630, 634, 636, 637, 642, 645, 646, 649, 652, 657, 658, 739, 740, 741, 742, 743, 751, 756, 804, 813, 817, 819, 845, 846, 849, 852, 871, 872, 873, 874, 875, 876, 878, 879, 881, 905, 906, 907, 908, 915, 916, 917, 918, 919, 920, 923, 943, 944, 948, 952, 953, 958, 960, 974, 976, 977, 979, 982, 983, 984, 985, 986, 988, 989, 990, 991, 992, 993, 997, 1000, 1001, 1002, 1003, 1004, 1009, 1011, 1016, 1020, 1021, 1085, 1086, 1087, 1088, 1092, 1094, 1097, 1105, 1107, 1131, 1132, 1133, 1134, 1138, 1140, 1197, 1198, 1199, 1201, 1202, 1260, 1262, 1263, 1264, 1424, 1425, 1427, 1429, 1430, 1434, 1435, 1436, 1438, 1460, 1463, 1524, 1525, 1527, 1528, 1530, 1532, 1533, 1537, 1538, 1539, 1541, 1639, 1640, 1654, 1691, 1692, 1693, 1694, 1762, 1764, 1765, 1794, 1795, 1796, 1797, 1798, 1968, 1969, 2030, 2085, 2087, 2089, 2091, 2095, 2099, and 2192.

The siRNAs in siRNA subset A has the following characteristics:
1. Cross-reactivity: With 19mer in human ANGPTL7 mRNA, with 17mer/19mer in NHP ANGPTL7
2. Specificity category: For human and NHP: —AS2 or better, SS3 or better miRNA seeds: AS+SS strand: —seed region not conserved in human, mouse, and rat and not present in >4 species
3. Off-target frequency: ≤20 human off-targets matched with 2 mismatches by antisense strand
4. SNPs: siRNA target sites do not harbor SNPs with a MAF≥1% (pos. 2-18)

The siRNA sequences in siRNA subset A can further be selected for more stringent specificity to yield siRNA subset B. SiRNA subset B is composed of 173 siRNAs with sense strand SEQ ID NOS: 7, 39, 92, 93, 94, 95, 98, 99, 112, 113, 114, 115, 117, 118, 119, 120, 124, 125, 127, 207, 257, 271, 272, 487, 488, 489, 490, 491, 492, 493, 497, 498, 499, 501, 579, 583, 587, 588, 593, 594, 596, 598, 600, 601, 602, 603, 604, 605, 606, 629, 630, 634, 636, 637, 642, 645, 646, 649, 652, 739, 740, 741, 742, 743, 804, 813, 817, 845, 849, 852, 871, 872, 873, 874, 875, 876, 878, 879, 881, 905, 906, 907, 908, 915, 916, 917, 918, 919, 920, 923, 944, 952, 953, 958, 960, 974, 976, 977, 979, 982, 984, 985, 989, 990, 991, 992, 993, 997, 1000, 1001, 1002, 1003, 1004, 1009, 1016, 1021, 1085, 1086, 1087, 1088, 1092, 1094, 1097, 1105, 1107, 1131, 1132, 1133, 1134, 1138, 1140, 1197, 1198, 1199, 1201, 1202, 1262, 1263, 1424, 1425, 1427, 1429, 1430, 1434, 1435, 1436, 1460, 1463, 1524, 1525, 1527, 1528, 1530, 1532, 1533, 1537, 1538, 1539, 1541, 1639, 1654, 1691, 1692, 1764, 1765, 1794, 1795, 1796, 1797, 1798, 1968, 2091, and 2095.

The siRNAs in siRNA subset B has the following characteristics:
1. Cross-reactivity: With 19mer in human ANGPTL7 mRNA, with 17mer/19mer in NHP ANGPTL7
2. Specificity category: For human and NHP: -AS2 or better, SS3 or better miRNA seeds: AS+SS strand: —seed region not conserved in human, mouse, and rat and not present in >4 species
3. Off-target frequency: ≤15 human off-targets matched with 2 mismatches by antisense strand
4. SNPs: siRNA target sites do not harbor SNPs with a MAF ≥1% (pos. 2-18)

The siRNA sequences in siRNA subset B can further be selected for absence of seed regions in the AS strand that are identical to a seed region of known human miRNA to yield siRNA subset C. SiRNA subset C is composed of 120 siRNAs with sense strand SEQ ID NOS: 7, 39, 92, 94, 113, 114, 115, 117, 118, 119, 120, 127, 207, 257, 271, 272, 488, 489, 490, 498, 499, 501, 579, 587, 588, 593, 594, 596, 600, 601, 605, 606, 629, 630, 636, 642, 645, 646, 739, 740, 741, 742, 743, 813, 845, 849, 871, 872, 873, 878, 879, 881, 905, 906, 907, 908, 916, 917, 918, 919, 952, 958, 976, 979, 982, 984, 989, 990, 991, 992, 993, 1000, 1002, 1003, 1004, 1009, 1016, 1087, 1088, 1092, 1094, 1097, 1105, 1107, 1131, 1132, 1133, 1134, 1198, 1199, 1201, 1202, 1262, 1424, 1427, 1434, 1435, 1463, 1524, 1525, 1527, 1528, 1530, 1532, 1533, 1537, 1538, 1541, 1639, 1691, 1692, 1764, 1765, 1794, 1796, 1797, 1798, 1968, 2091, and 2095.

The siRNAs in siRNA subset C has the following characteristics:
1. Cross-reactivity: With 19mer in human ANGPTL7 mRNA, with 17mer/19mer in NHP ANGPTL7
2. Specificity category: For human and NHP: -AS2 or better, SS3 or better miRNA seeds: AS+SS strand: —seed region not conserved in human, mouse, and rat and not present in >4 species. AS strand: —seed region not identical to seed region of known human miRNA
3. Off-target frequency: ≤15 human off-targets matched with 2 mismatches by antisense strand
4. SNPs: siRNA target sites do not harbor SNPs with a MAF≥1% (pos. 2-18)

The siRNA sequences in siRNA subset C can also be selected for absence of seed regions in the AS or S strands that are identical to a seed region of known human miRNA to yield siRNA subset D. SiRNA subset D is composed of 90 siRNAs with sense strand SEQ ID NOS: 92, 113, 115, 119, 120, 127, 488, 490, 499, 579, 587, 588, 592, 593, 594, 600, 601, 605, 606, 630, 642, 657, 658, 740, 742, 743, 813, 846, 871, 872, 878, 881, 905, 907, 916, 917, 918, 919, 943, 948, 958, 979, 982, 983, 984, 989, 990, 991, 992, 1000, 1002, 1003, 1004, 1016, 1020, 1087, 1088, 1097, 1105, 1107, 1131, 1132, 1133, 1134, 1199, 1202, 1260, 1262, 1264, 1427, 1435, 1438, 1463, 1524, 1525, 1527, 1528, 1532, 1538, 1541, 1639, 1692, 1762, 1765, 1794, 1797, 1968, 2030, 2095, and 2192.

The siRNAs in siRNA subset D has the following characteristics:
1. Cross-reactivity: With 19mer in human ANGPTL7 mRNA, with 17mer/19mer in NHP ANGPTL7

2. Specificity category: For human and NHP: -AS2 or better, SS3 or better miRNA seeds: AS+SS strand: —seed region not conserved in human, mouse, and rat and not present in >4 species. AS+SS strand: —seed region not identical to seed region of known human miRNA
3. Off-target frequency: ≤20 human off-targets matched with 2 mismatches by antisense strand
4. SNPs: siRNA target sites do not harbor SNPs with a MAF ≥1% (pos. 2-18)

The siRNA sequences in siRNA subset D can further be selected for more stringent specificity to yield siRNA subset E. SiRNA subset E is composed of 76 siRNAs with sense strand SEQ ID NOS: 92, 113, 115, 119, 120, 127, 488, 490, 499, 579, 587, 588, 593, 594, 600, 601, 605, 606, 630, 642, 740, 742, 743, 813, 871, 872, 878, 881, 905, 907, 916, 917, 918, 919, 958, 979, 982, 984, 989, 990, 991, 992, 1000, 1002, 1003, 1004, 1016, 1087, 1088, 1097, 1105, 1107, 1131, 1132, 1133, 1134, 1199, 1202, 1262, 1427, 1435, 1463, 1524, 1525, 1527, 1528, 1532, 1538, 1541, 1639, 1692, 1765, 1794, 1797, 1968, and 2095.

The siRNAs in siRNA subset E has the following characteristics:
1. Cross-reactivity: With 19mer in human ANGPTL7 mRNA, with 17mer/19mer in NHP ANGPTL7
2. Specificity category: For human and NHP: -AS2 or better, SS3 or better miRNA seeds: AS+SS strand: —seed region not conserved in human, mouse, and rat and not present in >4 species. AS+SS strand: —seed region not identical to seed region of known human miRNA
3. Off-target frequency: ≤15 human off-targets matched with 2 mismatches by antisense strand
4. SNPs: siRNA target sites do not harbor SNPs with a MAF ≥1% (pos. 2-18)

Example 8. siRNA or Antisense Oligonucleotide (ASO)-Mediated Modulation of ANGPTL7 Expression in Primary Human Trabecular Meshwork Cells (pHTMs) in the Presence and Absence of Dexamethasone (DEX)

In this experiment, siRNA or ASO inhibition of ANGPTL7 is performed in primary human trabecular meshwork cells, to evaluate the efficacy of knockdown of ANGPTL7 and the effect of this on extracellular matrix and glaucoma related genes including myocilin (MYOC), collagens type I and V (COL1A1 and COL5A1), versican (VCAN) and fibronectin (FN1). The composition and quality of the extracellular matrix in which human trabecular meshwork cells are embedded is directly relevant to the aqueous humor outflow and glaucoma disease pathology.

Primary HTM cells are grown to confluency and then serially passaged in complete IMEM media supplemented with 10% FBS until passage 4. Cells are then transfected in a 24-well plate with a non-targeting control or ANGPTL7 targeting siRNA. The ANGPTL7 siRNA has the following sequence: sense strand 5' GUACAACUGCUGCACA-GACUU 3' (SEQ ID NO:11089), antisense strand 5' GUCU-GUGCAGCAGUUGUACUU 3' (SEQ ID NO: 11090). The non-targeting control siRNA has the following sequence: sense strand 5' GUUGUACAGCAUGCGGAGAUU 3' (SEQ ID NO:11091), antisense strand 5' UCUCCG-CAUGCUGUACAACUU 3' (SEQ ID NO: 11092). In parallel, cells are transfected in a 24-well plate with a non-targeting control ASO or ANGPTL7 ASO. The ANGPTL7 ASO has the following sequence: 5' mTsmTsmGsmTsm-AsdCsdCsdAsdGsdTsdAsdGsdCsdCs-dAsmCsmCsmTsmTsmT 3' (SEQ ID NO:11087). The non-targeting control ASO has the following sequence: 5' mTsmCsmTsmAsmAsdCsdCsdGsdAsdGsdCsdTsdGsd-AsdTsmGsmGsmAsmCsmT 3' (SEQ ID NO:11088). Briefly, transfections are performed using TransIT TKO (Mirus) following the manufacturer's recommended protocol. For each well receiving siRNA, 1 ul siRNA (10 uM stock), 2.5 ul TransIT-TKO, and 50 ul OptiMEM are mixed, incubated at room temperature for 30 minutes, and added dropwise to each well containing cells and 1 mL complete IMEM media. For each well receiving ASO, 1 ul ASO (1 mM stock), 2.5 ul TransIT-TKO, and 50 ul OptiMEM are mixed, incubated at room temperature for 30 minutes, and added dropwise to each well containing cells and 1 mL complete IMEM media.

Twenty-four hours after transfection, media is changed and HTM cells are treated with DEX for 48 hours in the presence of serum. DEX (Sigma) stock solution is prepared by adding absolute ethanol to the commercial vial obtaining a final concentration of 0.1 mM and kept at 4° C. The DEX stock solution of 0.1 µM is diluted 1000× (100 nM final concentration) in IMEM media before use. Parallel wells receive IMEM medium containing the drug vehicle under the same conditions. At the end of each treatment, cells are washed two times with PBS, lysed with 350 µL guanidine thiocyanate buffer and processed for RNA extraction.

Total RNA is reverse transcribed to cDNA using a First-Strand III cDNA Synthesis kit. Normalized cDNA quantification is carried out by real-time TaqMan PCR using fluorescently labeled TaqMan probes/primers sets of selected genes (ANGPTL7, MYOC, COL1A1, COL5A1, VCAN, FN1, and PPIA). Reactions are carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula $2^{-\Delta\Delta C_T}$, where $C_T$ is the cycle at threshold (automatic measurement), $\Delta C_T$ is $C_T$ of the assayed gene minus $C_T$ of the endogenous control (PPIA), and $\Delta\Delta C_T$ is the $\Delta C_T$ of the normalized assayed gene in the treated sample minus the $\Delta C_T$ of the same gene in the untreated one (calibrator).

Example 9. siRNA-Mediated Modulation of ANGPTL7 in a Mouse Model of Dexamethasone-Induced Ocular Hypertension/Glaucoma In this experiment, the glucocorticoid-induced mouse model of glaucoma is used to evaluate the effect of siRNA inhibition of ANGPTL7 on IOP. C57BL/6J mice that receive weekly periocular conjunctival fornix (CF) injections of a dexamethasone-21-acetate (Dex-Ac) formulation develop relatively rapid and significant elevation of IOP that is correlated with reduced conventional outflow facility, similar to glaucomatous disease in human patients.

Three routes of delivery are evaluated for siRNA inhibition of ANGPTL7. These include (1) intracameral injection (2) intravitreal injection and (3) topical delivery administered in eye drops.

Adult (6-8 months old) C57BL/6J mice are obtained from the Jackson Laboratory (Bar Harbor, ME). The animals are kept in environmentally controlled rooms under specific pathogen-free conditions (temperature, 20-26° C.); humidity, 30-70%) with a 12-hour light-dark cycle for 2 weeks before use. Food and water are available ad libitum. All animals are used in accordance with animal care guidelines.

Mice are divided into 9 groups. All treatments are applied to both eyes. Group A (n=4) is an untreated group. Group B (n=4) is a group treated with weekly periocular injections of Dex-Ac (four total treatments). Group C (n=4) is a group treated with vehicle. Group D (n=4) is treated with Dex-Ac and an ANGPTL7 targeting siRNA via intracameral injection into the anterior chamber. Group E (n=4) is treated with Dex-Ac and a non-targeting control siRNA via intracameral injection into the anterior chamber. Group F (n=4) is treated with Dex-Ac and an ANGPTL7 targeting siRNA via intravitreal injection into the posterior chamber. Group G (n=4) is treated with Dex-Ac and a non-targeting control siRNA via intravitreal injection into the posterior chamber. Group H (n=4) is treated with Dex-Ac and an ANGPTL7 targeting siRNA via topical administration of an eye drop. Group I (n=4) is treated with Dex-Ac and a non-targeting control siRNA via topical administration of an eye drop.

The ANGPTL7 siRNA has the following sequence: sense strand 5' GUACAACUGCUGCACAGACUU 3' (SEQ ID NO:11089), antisense strand 5' GUCUGUGCAGCAGUU-GUACUU 3' (SEQ ID NO: 11090). Some preferred siRNA sequences may include any one of ETD00342 (sense strand 5' CfsasAfaGfgUfGfGfcUfaCfuGfgUfaAfsusu 3' SEQ ID NO: 11172, antisense strand 5' usUfsaCfcAfgUfaGfccaCf-cUfuUfgsusu 3' SEQ ID NO: 11292), ETD00343 (sense strand 5' AfsasGfgUfgGfCfUfaCfuGfgUfaCfaAfsusu 3' SEQ ID NO: 11173, antisense strand 5' usUfsgUfaCfcAfgU-fagcCfaCfcUfususu 3' SEQ ID NO: 11293), ETD00344 (sense strand 5' GfsusGfgCfuAfCfUfgGfuAfcA-faCfuAfsusu 3' SEQ ID NO: 11174, antisense strand 5' usAfsgUfuGfuAfcCfaguAfgCfcAfcsusu 3' SEQ ID NO: 11294), ETD00345 (sense strand 5' UfsgsGfuAfcA-fAfCfuGfcUfgCfaCfaAfsusu 3' SEQ ID NO: 11175, antisense strand 5' usUfsgUfgCfaGfcAfguuGfuAfcCfasusu 3' SEQ ID NO: 11295) or ETD00346 (sense strand 5' GfsusAfcAfaCfUfUfgGfcUfgCfaCfaGfaAfsusu 3' SEQ ID NO: 11176, antisense strand 5' usUfscUfgUfgCfaGfcagU-fuGfuAfcsusu 3' SEQ ID NO: 11296). Some embodiments include any one of ETD00342, ETD00343, ETD00344, ETD00345, or ETD00346, but without the modification patterns of any of SEQ ID NOs: 11172-11176 or 11292-11296, or with different modifications or modification patterns than those SEQ ID NOs. A hydrophobic moiety, such as cholesterol, may also be attached to the siRNA. A ligand that binds to receptors on the cell surface, such as RGD to integrins, may also be attached to the siRNA. Hydrophobic groups may be combined with cell-targeting ligands to increase cellular uptake. The non-targeting control siRNA has the following sequence: sense strand 5' GUUGUACAG-CAUGCGGAGAUU 3' (SEQ ID NO: 11091), antisense strand 5' UCUCCGCAUGCUGUACAACUU 3' (SEQ ID NO: 11092).

For periocular injection of Dex-Ac or vehicle, a 32-gauge needle with a Hamilton glass microsyringe (25-µL volume; Hamilton Company, Reno, NV) is used. The lower eyelid is retracted, and the needle is inserted through the CF. Dex-Ac or vehicle suspension (20 µL) is injected immediately under the CF over the course of 10 to 15 seconds. The needle is then withdrawn. The procedure is performed on both eyes of each animal (each animal receives either Dex-Ac in both eyes or vehicle in both eyes). Mice are treated with Dex-Ac or vehicle once per week until the end of the study.

For intracameral injections, a topical anesthetic (tetracaine hydrochloride 0.5%, Bausch & Lomb) is applied to the eye. 1 ug of siRNA or scrambled control in vehicle is injected using a 36G beveled needle mounted on a 10 µl microsyringe. An UltraMicroPump II (World precision instrument's UMP2 and UMC4) is used to precisely control the volume of injection. The needle is entered at the limbus and care is taken not to traumatize the iris or the lens. Mice with injury to iris or lens are excluded from the study. As the needle is withdrawn after injection, a cotton tip applicator is applied for about 1 minute to prevent aqueous reflux.

For intravitreal injection, a 33-gauge needle with a glass microsyringe (10-µL volume; Hamilton Company) is used. The eye is proptosed, and the needle is inserted through the equatorial sclera and inserted into the vitreous chamber at an angle of approximately 45 degrees, taking care to avoid touching the posterior part of the lens or the retina. 10 ug of siRNA or scrambled control in vehicle is injected into the vitreous over the course of 1 minute. The needle is then left in place for a further 30 seconds (to facilitate mixing), before being rapidly withdrawn.

The study length is 32 days. Oligonucleotide treatment (siRNA or scrambled controls) occurs on days 0 and 14. Dex-Ac treatment occurs once weekly on days 7, 14, 21 and 28 Animals are euthanized and tissues harvested on day 32.

IOP is measured on days 0, 14 and 28, just prior to any treatment. Mice from each group are anaesthetized using intraperitoneal injection (0.1 µL) of ketamine (100 mg/kg) and xylazine (9 mg/kg). One mouse is anaesthetized at a time and IOP is measured as soon as the mouse fails to respond to touch. All care is taken to ensure that the mice are in a similar level of anesthesia when the IOP measurements are made. To measure the IOP, a handheld tonometer (Tono-Lab, Colonial Medical Supply, Franconia, NH) is used.

Mice are euthanized on day 32. Both eyes from each animal will be harvested and dissected along the equator, and the anterior hemisphere placed in RNAlater. Total RNA is extracted from homogenized tissue and reverse transcribed to cDNA using a First-Strand III cDNA Synthesis kit. Normalized cDNA quantification is carried out by real-time TaqMan PCR using fluorescently labeled TaqMan probes/primers sets of selected genes (ANGPTL7, MYOC, COL1A1, COL5A1, VCAN, FN1, and PPIA). Reactions are carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula $2^{-\Delta\Delta C_T}$, where $C_T$ is the cycle at threshold (automatic measurement), $\Delta C_T$ is $C_T$ of the assayed gene minus $C_T$ of the endogenous control (PPIA), and $\Delta\Delta C_T$ is the $\Delta C_T$ of the normalized assayed gene in the treated sample minus the $\Delta C_T$ of the same gene in the untreated one (calibrator).

Example 10. Antisense Oligonucleotide (ASO)-Mediated Modulation of ANGPTL7 in a Mouse Model of Dexamethasone-Induced Ocular Hypertension/Glaucoma In this experiment, the glucocorticoid-induced mouse model of glaucoma is used to evaluate the effect of ASO inhibition of ANGPTL7 on IOP. C57BL/6J mice that receive weekly periocular conjunctival fornix (CF) injections of a dexamethasone-21-acetate (Dex-Ac) formulation develop relatively rapid and significant elevation of IOP that is correlated with reduced conventional outflow facility, similar to glaucomatous disease in human patients.

Three routes of delivery are evaluated for ASO inhibition of ANGPTL7. These include (1) intracameral injection (2) intravitreal injection and (3) topical delivery administered in eye drops.

Adult (6-8 months old) C57BL/6J mice are obtained from the Jackson Laboratory (Bar Harbor, ME). The animals are kept in environmentally controlled rooms under specific pathogen-free conditions (temperature, 20-26° C.); humidity, 30-70%) with a 12-hour light-dark cycle for 2 weeks before use. Food and water are available ad libitum. All animals are used in accordance with animal care guidelines.

Mice are divided into 9 groups. All treatments are applied to both eyes. Group A (n=4) is an untreated group. Group B (n=4) is a group treated with weekly periocular injections of Dex-Ac (four total treatments). Group C (n=4) is a group treated with vehicle. Group D (n=4) is treated with Dex-Ac and an ANGPTL7 targeting ASO via intracameral injection into the anterior chamber. Group E (n=4) is treated with Dex-Ac and a non-targeting control ASO via intracameral injection into the anterior chamber. Group F (n=4) is treated with Dex-Ac and an ANGPTL7 targeting ASO via intravitreal injection into the posterior chamber. Group G (n=4) is treated with Dex-Ac and a non-targeting control ASO via intravitreal injection into the posterior chamber. Group H (n=4) is treated with Dex-Ac and an ANGPTL7 targeting ASO via topical administration of an eye drop. Group I (n=4) is treated with Dex-Ac and a non-targeting control ASO via topical administration of an eye drop.

The ANGPTL7 ASO has the following sequence: 5' mTsmTsmGsmTsmAsdCsdCsdAsdGsdTsdAsdGsdCsdCsdAsmCsmCsmTsmTsmT 3' (SEQ ID NO: 11087). The non-targeting control ASO has the following sequence: 5' mTsmCsmTsmAsmAsdCsdCsdGsdAsdGsdCsdTsdGsdAsdTsmGsmGsmAsmCsmT 3' (SEQ ID NO: 11088). A hydrophobic moiety, such as cholesterol, may also be attached to the ASO. A ligand that binds to receptors on the cell surface, such as RGD to integrins, may also be attached to the ASO. Hydrophobic groups may be combined with cell-targeting ligands to increase cellular uptake.

For periocular injection of Dex-Ac or vehicle, a 32-gauge needle with a Hamilton glass microsyringe (25-µL volume; Hamilton Company, Reno, NV) is used. The lower eyelid is retracted, and the needle is inserted through the CF. Dex-Ac or vehicle suspension (20 µL) is injected immediately under the CF over the course of 10 to 15 seconds. The needle is then withdrawn. The procedure is performed on both eyes of each animal (each animal receives either Dex-Ac in both eyes or vehicle in both eyes). Mice are treated with Dex-Ac or vehicle once per week until the end of the study.

For intracameral injections, a topical anesthetic (tetracaine hydrochloride 0.5%, Bausch & Lomb) is applied to the eye. 10 ug of ASO or scrambled control in vehicle is injected using a 36G beveled needle mounted on a 10 µl microsyringe. An UltraMicroPump II (World precision instrument's UMP2 and UMC4) is used to precisely control the volume of injection. The needle is entered at the limbus and care is taken not to traumatize the iris or the lens. Mice with injury to iris or lens are excluded from the study. As the needle is withdrawn after injection, a cotton tip applicator is applied for about 1 minute to prevent aqueous reflux.

For intravitreal injection, a 33-gauge needle with a glass microsyringe (10-µL volume; Hamilton Company) is used. The eye is proptosed, and the needle is inserted through the equatorial sclera and inserted into the vitreous chamber at an angle of approximately 45 degrees, taking care to avoid touching the posterior part of the lens or the retina. 10 ug of ASO or scrambled control in vehicle is injected into the vitreous over the course of 1 minute. The needle is then left in place for a further 30 seconds (to facilitate mixing), before being rapidly withdrawn.

The study length is 32 days. Oligonucleotide treatment (ASO or scrambled controls) occurs on days 0 and 14. Dex-Ac treatment occurs once weekly on days 7, 14, 21 and 28 Animals are euthanized and tissues harvested on day 32.

IOP is measured on days 0, 14 and 28, just prior to any treatment. Mice from each group are anaesthetized using intraperitoneal injection (0.1 µl) of ketamine (100 mg/kg) and xylazine (9 mg/kg). One mouse is anaesthetized at a time and IOP is measured as soon as the mouse fails to respond to touch. All care is taken to ensure that the mice are in a similar level of anesthesia when the IOP measurements are made. To measure the IOP, a handheld tonometer (Tono-Lab, Colonial Medical Supply, Franconia, NH) is used.

Mice are euthanized on day 32. Both eyes from each animal will be harvested and dissected along the equator, and the anterior hemisphere placed in RNAlater. Total RNA is extracted from homogenized tissue and reverse transcribed to cDNA using a First-Strand III cDNA Synthesis kit. Normalized cDNA quantification is carried out by real-time TaqMan PCR using fluorescently labeled TaqMan probes/primers sets of selected genes (ANGPTL7, MYOC, COL1A1, COL5A1, VCAN, FN1, and PPIA). Reactions are carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula $2^{-\Delta\Delta C_T}$, where $C_T$ is the cycle at threshold (automatic measurement), $\Delta C_T$ is $C_T$ of the assayed gene minus $C_T$ of the endogenous control (PPIA), and $\Delta\Delta C_T$ is the $\Delta C_T$ of the normalized assayed gene in the treated sample minus the $\Delta C_T$ of the same gene in the untreated one (calibrator).

Example 11. siRNA or Antisense Oligonucleotide (ASO)-Mediated Modulation of ANGPTL7 in a Mouse Model of Spontaneous Glaucoma In this experiment, the DBA/2J mouse model of glaucoma is used to evaluate the effect of siRNA or ASO inhibition of ANGPTL7 on IOP. DBA/J2 mice develop age related IOP increases and retinal nerve damage characteristic of human disease. DBA/2J mice normally demonstrate peak IOP elevation at 8 months of age.

Adult mice from inbred strains DBA/2J are obtained from the Jackson Laboratory (Bar Harbor, ME). The animals are kept in environmentally controlled rooms under specific pathogen-free conditions (temperature, 20-26° C.); humidity, 30-70%) with a 12-hour light-dark cycle for 2 weeks before use. Food and water are available ad libitum. All animals are used in accordance with animal care guidelines.

Experiments are performed on 6-month-old mice. Mice are divided into six groups. Group A (n=4) is an untreated control group. Group B (n=4) is treated with ANGPTL7 targeting siRNA via intraocular/intracameral injection into the anterior chamber. Group C (n=4) is treated with a non-targeting control siRNA via intraocular injection into the anterior chamber. Group D (n=4) is treated with ANGPTL7 targeting ASO via intraocular injection into the anterior chamber. Group E (n=4) is treated with a non-targeting control ASO via intraocular injection into the anterior chamber. Group F (n=4) is treated with vehicle.

The ANGPTL7 siRNA has the following sequence: sense strand 5' GUACAACUGCUGCACAGACUU 3' (SEQ ID NO:11089), antisense strand 5' GUCUGUGCAGCAGUU-GUACUU 3' (SEQ ID NO: 11090). The non-targeting control siRNA has the following sequence: sense strand 5' GUUGUACAGCAUGCGGAGAUU 3' (SEQ ID NO: 11091), antisense strand 5' UCUCCGCAUGCUGUA-CAACUU 3' (SEQ ID NO: 11092). Some preferred siRNA sequences may include any one of ETD00342 (sense strand 5' CfsasAfaGfgUfGfGfcUfaCfuGfgUfaAfsusu 3' SEQ ID NO: 11172, antisense strand 5' usUfsaCfcAfgUfaGfccaCf-cUfuUfgsusu 3' SEQ ID NO: 11292), ETD00343 (sense strand 5' AfsasGfgUfgGfCfUfaCfuGfgUfaCfaAfsusu 3' SEQ ID NO: 11173, antisense strand 5' usUfsgUfaCfcAfgU-fagcCfaCfcUfususu 3' SEQ ID NO: 11293), ETD00344 (sense strand 5' GfsusGfgCfuAfCfUfgGfuAfcA-faCfuAfsusu 3' SEQ ID NO: 11174, antisense strand 5' usAfsgUfuGfuAfcCfaguAfgCfcAfcsusu 3' SEQ ID NO: 11294), ETD00345 (sense strand 5' UfsgsGfuAfcA-fAfCfuGfcUfgCfaCfaAfsusu 3' SEQ ID NO: 11175, antisense strand 5' usUfsgUfgCfaGfcAfguuGfuAfcCfasusu 3' SEQ ID NO: 11295) or ETD00346 (sense strand 5' GfsusAfcAfaCfUfGfcUfgCfaCfaGfaAfsusu 3' SEQ ID NO: 11176, antisense strand 5' usUfscUfgUfgCfaGfcagU-fuGfuAfcsusu 3' SEQ ID NO: 11296). Some embodiments include any one of ETD00342, ETD00343, ETD00344, ETD00345, or ETD00346, but without the modification patterns of any of SEQ ID NOs: 11172-11176 or 11292-11296, or with different modifications or modification patterns than those SEQ ID NOs. A hydrophobic moiety, such as cholesterol, may also be attached to the siRNA. A ligand that binds to receptors on the cell surface, such as RGD to integrins, may also be attached to the siRNA. Hydrophobic groups may be combined with cell-targeting ligands to increase cellular uptake.

The ANGPTL7 ASO has the following sequence: 5' mTsmTsmGsmTsmAsdCsdCsdAsdGsdTsdAsdGsdCsd-dAsmCsmCsmTsmTsmT 3' (SEQ ID NO: 11087). The non-targeting control ASO has the following sequence: 5' mTsmCsmTsmAsmAsdCsdCsdGsdAsdGsdCsdTsdGsd-AsdTsmGsmGsmAsmCsmT 3' (SEQ ID NO: 11088). A hydrophobic moiety, such as cholesterol, could also be attached to the ASO. A ligand that binds to receptors on the cell surface, such as RGD to integrins, may also be attached to the ASO. Hydrophobic groups may be combined with cell-targeting ligands to increase cellular uptake.

For intracameral injections, a topical anesthetic (tetracaine hydrochloride 0.5%, Bausch & Lomb) is applied to the desired eye. 10 ug of siRNA or ASO in a 1 ul of vehicle is injected using a 36G beveled needle mounted on a 10 μl microsyringe. An UltraMicroPump II (World precision instrument's UMP2 and UMC4) is used to precisely control the volume of injection. The needle is entered at the limbus and care is taken not to traumatize the iris or the lens. Mice with injury to iris or lens are excluded from the study. As the needle is withdrawn after injection, a cotton tip applicator is applied for about 1 minute to prevent aqueous reflux.

IOP is measured a day prior to injections, and also measured at two, four, six- and eight-weeks post-injection. Mice from each group are anaesthetized using intraperitoneal injection (0.1 μL) of ketamine (100 mg/kg) and xylazine (9 mg/kg). One mouse is anaesthetized at a time and IOP is measured as soon as the mouse fails to respond to touch. All care is taken to ensure that the mice are in a similar level of anesthesia when the IOP measurements are made. To measure the IOP, a handheld tonometer (TonoLab, Colonial Medical Supply, Franconia, NH) is used.

Mice are euthanized after the final, eight-week IOP measurements. Trabecular meshwork tissue is dissected out of the enucleated eyes under a dissecting microscope and prepared for RNA extraction. Total RNA is reverse transcribed to cDNA using a First-Strand III cDNA Synthesis kit. Normalized cDNA quantification is carried out by real-time TaqMan PCR using fluorescently labeled TaqMan probes/primers sets of selected genes (ANGPTL7, MYOC, COL1A1, COL5A1, VCAN, FN1, and PPIA). Reactions are carried out in 20 μL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula $2^{-\Delta\Delta C_T}$, where $C_T$ is the cycle at threshold (automatic measurement), $\Delta C_T$ is $C_T$ of the assayed gene minus $C_T$ of the endogenous control (PPIA), and $\Delta\Delta C_T$ is the $\Delta C_T$ of the normalized assayed gene in the treated sample minus the $\Delta C_T$ of the same gene in the untreated one (calibrator).

Example 12. Chemically Modified ANGPTL7 siRNAs

The siRNAs targeting ANGPTL7 can be synthesized with chemical modifications with the sense strand having the pattern 5' NfsnsNfnNfnNfNfNfnNfnNfnNfnNfnNfsnsn 3' (Modification pattern 1S, SEQ ID NO: 11381) and the antisense strand having the pattern nsNfsnNfnNfnNfnNfnnnNfnNfnNfnsnsn 3' (Modification pattern 1AS, SEQ ID NO: 11386). "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand. Some siRNAs that may include these chemical modifications comprise sequences of any of SEQ ID NOs: 11093-11376.

The siRNAs targeting ANGPTL7 can also be synthesized with chemical modifications with the sense strand having the pattern of modifications 5' nsnsnnNfnNfNfNfnnnnnnnnnnnsnsn (SEQ ID NO: 11382) and antisense strand having the pattern of modifications 5' nsNfsnnnNfnnnnnnnNfnNfnnnsnsn 3' (SEQ ID NO: 11388). "N" can be any nucleoside (for example ribose, deoxyribose, or derivatives thereof), "Nf" is a 2' fluoro-modified nucleoside, "n" is a 2' O-methyl modified nucleoside, and "s" is a phosphorothioate linkage. In addition, adenosine can be placed at position 19 in the sense strand and uridine at position 1 in the antisense strand.

Example 13. Screening ANGPTL7 siRNAs for Activity in Human Cells in Culture

Chemically modified ANGPTL7 siRNAs cross reactive for human and non-human primate and derived from sequences in siRNA subset C were assayed for ANGPTL7 mRNA knockdown activity in cells in culture. ARPE-19 (ATCC® CRL-2302™) cells were seeded in 96-well tissue culture plates at a cell density of 7,500 cells per well in DMEM:F12 (ATCC Catalog No. 30-2006) supplemented with 10% fetal bovine serum and incubated overnight in a water-jacketed, humidified incubator at 37° C. in an atmosphere composed of air plus 5% carbon dioxide. The ANGPTL7 siRNAs were individually transfected into ARPE-19 cells in duplicate wells at 10 nM final concentration using 0.3 μL Lipofectamine RNAiMax (Fisher) per well. Silencer Select Negative Control #1 (ThermoFisher, Catalog #4390843) was transfected at 10 nM final concentration as a control. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL7 mRNA from each well was measured in triplicate by real-time qPCR on an Applied Biosystems 7500 Fast Real-Time PCR machine using TaqMan Gene Expression Assay for human ANGPTL7 (ThermoFisher, assay #Hs00221727_m1). The level of PPIA mRNA was measured using TaqMan Gene Expression Assay (ThermoFisher, assay #Hs99999904_m1) and used to determine relative ANGPTL7 mRNA levels in each well using the delta-delta Ct method. All data were normalized to relative ANGPTL7 mRNA levels in untreated ARPE-19 cells. Results are shown in Table 5.

TABLE 5

Knockdown Activity of ANGPLT7-Specific siRNAs at 10 nM in Human ARPE-19 Cells

| siRNA name | Sense Strand (SEQ ID NO) | Antisense Strand (SEQ ID NO) | Relative ANGPTL7 Expression |
|---|---|---|---|
| Untreated Cells | — | — | 1.00 |
| Negative Control siRNA | — | — | 0.67 |
| ETD00263 | 11093 | 11213 | 0.72 |
| ETD00264 | 11094 | 11214 | 0.34 |
| ETD00265 | 11095 | 11215 | 0.33 |
| ETD00266 | 11096 | 11216 | 0.26 |
| ETD00267 | 11097 | 11217 | 0.24 |
| ETD00268 | 11098 | 11218 | 0.29 |
| ETD00269 | 11099 | 11219 | 0.18 |
| ETD00270 | 11100 | 11220 | 0.09 |
| ETD00271 | 11101 | 11221 | 0.23 |
| ETD00272 | 11102 | 11222 | 0.22 |
| ETD00273 | 11103 | 11223 | 0.19 |
| ETD00274 | 11104 | 11224 | 0.09 |
| ETD00275 | 11105 | 11225 | 0.14 |
| ETD00276 | 11106 | 11226 | 0.18 |
| ETD00277 | 11107 | 11227 | 0.77 |
| ETD00278 | 11108 | 11228 | 0.58 |
| ETD00279 | 11109 | 11229 | 0.26 |
| ETD00280 | 11110 | 11230 | 0.15 |
| ETD00281 | 11111 | 11231 | 1.64 |
| ETD00282 | 11112 | 11232 | 0.95 |
| ETD00283 | 11113 | 11233 | 0.29 |
| ETD00284 | 11114 | 11234 | 0.54 |
| ETD00285 | 11115 | 11235 | 0.53 |
| ETD00286 | 11116 | 11236 | 0.16 |
| ETD00287 | 11117 | 11237 | 0.80 |
| ETD00288 | 11118 | 11238 | 0.14 |
| ETD00289 | 11119 | 11239 | 0.22 |
| ETD00290 | 11120 | 11240 | 0.60 |
| ETD00291 | 11121 | 11241 | 0.20 |
| ETD00292 | 11122 | 11242 | 0.34 |
| ETD00293 | 11123 | 11243 | 0.25 |
| ETD00294 | 11124 | 11244 | 0.18 |
| ETD00295 | 11125 | 11245 | 0.07 |
| ETD00296 | 11126 | 11246 | 0.06 |
| ETD00297 | 11127 | 11247 | 0.16 |
| ETD00298 | 11128 | 11248 | 0.14 |
| ETD00299 | 11129 | 11249 | 0.33 |
| ETD00300 | 11130 | 11250 | 0.49 |
| ETD00301 | 11131 | 11251 | 0.60 |
| ETD00302 | 11132 | 11252 | 0.17 |
| ETD00303 | 11133 | 11253 | 0.37 |
| ETD00304 | 11134 | 11254 | 0.27 |
| ETD00305 | 11135 | 11255 | 0.36 |
| ETD00306 | 11136 | 11256 | 0.30 |
| ETD00307 | 11137 | 11257 | 0.77 |
| ETD00308 | 11138 | 11258 | 0.93 |
| ETD00309 | 11139 | 11259 | 0.31 |
| ETD00310 | 11140 | 11260 | 0.37 |
| ETD00311 | 11141 | 11261 | 0.84 |
| ETD00312 | 11142 | 11262 | 1.69 |
| ETD00313 | 11143 | 11263 | 0.13 |
| ETD00314 | 11144 | 11264 | 0.24 |
| ETD00315 | 11145 | 11265 | 0.11 |
| ETD00316 | 11146 | 11266 | 0.16 |
| ETD00317 | 11147 | 11267 | 0.14 |
| ETD00318 | 11148 | 11268 | 0.21 |
| ETD00319 | 11149 | 11269 | 0.27 |
| ETD00320 | 11150 | 11270 | 0.11 |
| ETD00321 | 11151 | 11271 | 0.14 |
| ETD00322 | 11152 | 11272 | 0.08 |
| ETD00323 | 11153 | 11273 | 0.32 |
| ETD00324 | 11154 | 11274 | 0.44 |
| ETD00325 | 11155 | 11275 | 0.17 |
| ETD00326 | 11156 | 11276 | 0.18 |
| ETD00327 | 11157 | 11277 | 0.34 |
| ETD00328 | 11158 | 11278 | 0.17 |
| ETD00329 | 11159 | 11279 | 0.08 |
| ETD00330 | 11160 | 11280 | 0.11 |
| ETD00331 | 11161 | 11281 | 0.08 |
| ETD00332 | 11162 | 11282 | 0.17 |
| ETD00333 | 11163 | 11283 | 0.31 |
| ETD00334 | 11164 | 11284 | 0.41 |
| ETD00335 | 11165 | 11285 | 0.06 |
| ETD00336 | 11166 | 11286 | 0.22 |
| ETD00337 | 11167 | 11287 | 0.12 |
| ETD00338 | 11168 | 11288 | 0.19 |
| ETD00339 | 11169 | 11289 | 0.17 |
| ETD00340 | 11170 | 11290 | 0.18 |
| ETD00341 | 11171 | 11291 | 0.13 |
| ETD00342 | 11172 | 11292 | 0.13 |
| ETD00343 | 11173 | 11293 | 0.32 |
| ETD00344 | 11174 | 11294 | 0.22 |
| ETD00345 | 11175 | 11295 | 0.37 |
| ETD00346 | 11176 | 11296 | 0.14 |
| ETD00347 | 11177 | 11297 | 0.20 |
| ETD00348 | 11178 | 11298 | 0.20 |
| ETD00349 | 11179 | 11299 | 0.65 |
| ETD00350 | 11180 | 11300 | 0.34 |
| ETD00351 | 11181 | 11301 | 0.13 |
| ETD00352 | 11182 | 11302 | 0.11 |
| ETD00353 | 11183 | 11303 | 0.11 |
| ETD00354 | 11184 | 11304 | 0.14 |
| ETD00355 | 11185 | 11305 | 0.13 |
| ETD00356 | 11186 | 11306 | 0.10 |
| ETD00357 | 11187 | 11307 | 0.38 |
| ETD00358 | 11188 | 11308 | 0.05 |
| ETD00359 | 11189 | 11309 | 0.11 |
| ETD00360 | 11190 | 11310 | 2.23 |
| ETD00361 | 11191 | 11311 | 0.42 |
| ETD00362 | 11192 | 11312 | 0.61 |
| ETD00363 | 11193 | 11313 | 0.48 |
| ETD00364 | 11194 | 11314 | 0.65 |
| ETD00365 | 11195 | 11315 | 0.24 |
| ETD00366 | 11196 | 11316 | 0.38 |
| ETD00367 | 11197 | 11317 | 0.77 |
| ETD00368 | 11198 | 11318 | 0.16 |
| ETD00369 | 11199 | 11319 | 0.11 |
| ETD00370 | 11200 | 11320 | 0.43 |
| ETD00371 | 11201 | 11321 | 0.35 |
| ETD00372 | 11202 | 11322 | 0.79 |
| ETD00373 | 11203 | 11323 | 0.45 |
| ETD00374 | 11204 | 11324 | 0.34 |
| ETD00375 | 11205 | 11325 | 0.15 |
| ETD00376 | 11206 | 11326 | 0.64 |
| ETD00377 | 11207 | 11327 | 0.29 |
| ETD00378 | 11208 | 11328 | 0.17 |
| ETD00379 | 11209 | 11329 | 0.56 |
| ETD00380 | 11210 | 11330 | 0.36 |
| ETD00381 | 11211 | 11331 | 0.42 |
| ETD00382 | 11212 | 11332 | 0.19 |

"—" untreated ARPE-19 cells;
Negative Control siRNA,
Silencer Select Negative Control #1

A subset of the ANGPTL7 siRNA at were tested in a second screen for activity at 1 nM concentration using ARPE-19 cells and the transfection procedures as described above. Results are shown in Table 6.

TABLE 6

Knockdown Activity of ANGPLT7-Specific siRNAs at 1 nM in Human ARPE-19 Cell

| siRNA name | Sense Strand (SEQ ID NO) | Antisense Strand (SEQ ID NO) | Relative ANGPTL7 Expression |
|---|---|---|---|
| Untreated Cells | — | — | 1.00 |
| Negative Control siRNA | — | — | 1.06 |
| ETD00269 | 11100 | 11220 | 0.16 |
| ETD00270 | 11143 | 11263 | 0.19 |
| ETD00273 | 11161 | 11281 | 0.27 |
| ETD00276 | 11183 | 11303 | 0.21 |
| ETD00280 | 11186 | 11306 | 0.28 |
| ETD00286 | 11188 | 11308 | 0.43 |
| ETD00291 | 11099 | 11219 | 0.47 |
| ETD00294 | 11103 | 11223 | 0.41 |
| ETD00297 | 11106 | 11226 | 0.45 |
| ETD00302 | 11110 | 11230 | 0.13 |
| ETD00313 | 11116 | 11236 | 0.34 |
| ETD00316 | 11121 | 11241 | 0.31 |
| ETD00318 | 11124 | 11244 | 0.42 |
| ETD00325 | 11127 | 11247 | 0.50 |
| ETD00326 | 11132 | 11252 | 0.67 |
| ETD00328 | 11146 | 11266 | 0.49 |
| ETD00331 | 11148 | 11268 | 0.39 |
| ETD00332 | 11155 | 11275 | 1.09 |
| ETD00338 | 11156 | 11276 | 0.96 |
| ETD00339 | 11158 | 11278 | 0.27 |
| ETD00340 | 11162 | 11282 | 0.31 |
| ETD00347 | 11168 | 11288 | 0.46 |
| ETD00348 | 11169 | 11289 | 0.45 |
| ETD00353 | 11170 | 11290 | 0.53 |
| ETD00356 | 11177 | 11297 | 0.21 |
| ETD00358 | 11178 | 11298 | 0.31 |
| ETD00368 | 11198 | 11318 | 0.48 |
| ETD00375 | 11205 | 11325 | 0.44 |
| ETD00378 | 11208 | 11328 | 0.51 |
| ETD00382 | 11212 | 11332 | 0.28 |

"—" untreated ARPE-19 cells;
Negative Control siRNA,
Silencer Select Negative Control #1

Example 14. Screening ANGPTL7 siRNAs for Activity in Mouse Cells in Culture

It can be advantageous to possess ANGPTL7 siRNAs that are cross-reactive for human and rodent species. Chemically modified ANGPTL7 siRNAs derived from those that are predicted to be cross-reactive for human and mouse ANGPTL7 were assayed for ANGPTL7 mRNA knockdown activity in mouse cells in culture. C166 (ATCC® CRL-2581™) cells were seeded in 96-well tissue culture plates at a cell density of 10,000 cells per well in DMEM supplemented with 10% fetal bovine serum and incubated overnight in a water-jacketed, humidified incubator at 37° C. in an atmosphere composed of air plus 5% carbon dioxide. The ANGPTL7 siRNAs were individually transfected into C166 cells in duplicate wells at 1 nM and 10 nM final concentration using 0.3 µL Lipofectamine RNAiMax (Fisher) per well. Silencer Select Negative Control #1 (ThermoFisher, Catalog #4390843) was transfected at 10 nM final concentration as a control. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL7 mRNA from each well was measured in triplicate by real-time qPCR on an Applied Biosystems 7500 Fast Real-Time PCR machine using TaqMan Gene Expression Assay for mouse ANGPTL7 (ThermoFisher, assay #Mm00480431_m1). The level of PPIA mRNA was measured using TaqMan Gene Expression Assay (ThermoFisher, assay #Mm02342430_g1) and used to determine relative ANGPTL7 mRNA levels in each well using the delta-delta Ct method. All data were normalized to relative ANGPTL7 mRNA levels in untreated C166 cells. Results are shown in Table 7. In some embodiments, an oligonucleotide such as an siRNA described herein, that targets human ANGPTL7 is cross-reactive with human, NHP, mouse, rat, and/or dog ANGPTL7 (e.g. any one of ETD00342-ETD00346, or a version thereof with different sequence modifications, or without sequence modifications).

TABLE 7

Knockdown Activity of ANGPLT7-Specific siRNAs at 1 nM and 10 nM in Mouse C166 cells

| siRNA name | Sense Strand (SEQ ID NO) | Antisense Strand (SEQ ID NO) | Relative ANGPTL7 Expression | |
|---|---|---|---|---|
| | | | 1 nM siRNA | 10 nM siRNA |
| Untreated Cells | — | — | 1.00 | — |
| Negative Control siRNA | — | — | 0.66 | — |
| ETD00241 | 11333 | 11355 | 1.04 | 0.92 |
| ETD00242 | 11334 | 11356 | 0.71 | 0.78 |
| ETD00243 | 11335 | 11357 | 0.85 | 0.83 |
| ETD00244 | 11336 | 11358 | 0.54 | 0.79 |
| ETD00245 | 11337 | 11359 | 0.43 | 0.71 |
| ETD00246 | 11338 | 11360 | 0.59 | 0.83 |
| ETD00247 | 11339 | 11361 | 0.35 | 0.76 |
| ETD00248 | 11340 | 11362 | 0.93 | 0.90 |
| ETD00249 | 11341 | 11363 | 0.67 | 0.90 |
| ETD00250 | 11342 | 11364 | 0.77 | 0.89 |
| ETD00251 | 11343 | 11365 | 0.52 | 0.82 |
| ETD00252 | 11344 | 11366 | 0.44 | 0.77 |
| ETD00253 | 11345 | 11367 | 0.82 | 0.81 |
| ETD00254 | 11346 | 11368 | 0.94 | 0.87 |
| ETD00255 | 11347 | 11369 | 0.76 | 0.83 |
| ETD00256 | 11348 | 11370 | 0.89 | 0.91 |
| ETD00257 | 11349 | 11371 | 0.52 | 0.92 |
| ETD00258 | 11350 | 11372 | 0.89 | 0.94 |
| ETD00259 | 11351 | 11373 | 0.70 | 0.91 |
| ETD00260 | 11352 | 11374 | 0.52 | 0.92 |
| ETD00261 | 11353 | 11375 | 0.55 | 0.89 |
| ETD00262 | 11354 | 11376 | 0.78 | 0.95 |

"—" untreated C166 cells;
Negative Control siRNA,
Silencer Select Negative Control #1

Example 15. Determining the IC50 of ANGPTL7 siRNAs in Human ARPE-19 Cells

The IC50 values for knockdown of ANGPTL7 mRNA by select ANGPTL7 siRNAs were determined in ARPE-19 cells. The ETD00269, ETD00270, ETD00353, ETD00356, ETD00358, ETD00370, ETD00377, ETD00378 and ETD00382 siRNAs were assayed individually at 3 nM, 1 nM, 0.3 nM, 0.1 nM and 0.03 nM. A subset of siRNAs was also assayed at 0.01 nM. The ARPE-19 (ATCC® CRL-2302™) cells were seeded in 96-well tissue culture plates at a cell density of 7,500 cells per well in DMEM supplemented with 10% fetal bovine serum and incubated overnight in a water-jacketed, humidified incubator at 37° C. in an atmosphere composed of air plus 5% carbon dioxide. The ANGPTL7 siRNAs were individually transfected into ARPE-19 cells in triplicate wells using 0.3 µL Lipofectamine RNAiMax (Fisher) per well. Silencer Select Negative Control #1 (ThermoFisher, Catalog #4390843) was transfected at 0.03 and 3 nM final concentration as a control. After incubation for 48 hours at 37° C., total RNA was harvested from each well and cDNA prepared using TaqMan® Fast Advanced Cells-to-CT™ Kit (ThermoFisher, Catalog #A35374) according to the manufacturer's instructions. The level of ANGPTL7 mRNA from each well was measured in triplicate by real-time qPCR on an Applied Biosystems 7500 Fast Real-Time PCR machine using TaqMan Gene Expression Assay for human ANGPTL7 (ThermoFisher, assay #Hs00221727_m1). The level of PPIA mRNA was measured using TaqMan Gene Expression Assay (ThermoFisher, assay #Hs99999904_m1) and used to determine relative ANGPTL7 mRNA levels in each well using the delta-delta Ct method. All data were normalized to relative ANGPTL7 mRNA levels in untreated ARPE-19 cells. Curve fit was accomplish using the [inhibitor] vs. response (three parameters) function in GraphPad Prism software. Results are shown in Table 8, Table 9, and Table 10.

TABLE 8

IC50 Values of ETD00269, ETD00270, ETD00358 and ETD00382 ANGPTL7 siRNAs

| siRNA | [siRNA] | Relative ANGPTL7 mRNA Levels | IC50 |
|---|---|---|---|
| — | — | 1.000 | ND |
| Negative Control siRNA | 3 nM | 0.713 | ND |
|  | 0.03 nM | 0.712 | ND |
| ETD00269 | 3 nM | 0.156 | 0.23 |
|  | 1 nM | 0.649 |  |
|  | 0.3 nM | 0.849 |  |
|  | 0.1 nM | 1.469 |  |
|  | 0.03 nM | 1.808 |  |
| ETD00270 | 3 nM | 0.305 | 0.044 |
|  | 1 nM | 0.445 |  |
|  | 0.3 nM | 0.225 |  |
|  | 0.1 nM | 0.720 |  |
|  | 0.03 nM | 0.907 |  |
| ETD00358 | 3 nM | 0.129 | 0.15 |
|  | 1 nM | 0.140 |  |
|  | 0.3 nM | 0.553 |  |
|  | 0.1 nM | 0.936 |  |
|  | 0.03 nM | 1.292 |  |
| ETD00382 | 3 nM | 0.316 | 0.28 |
|  | 1 nM | 0.492 |  |
|  | 0.3 nM | 0.229 |  |
|  | 0.1 nM | 0.205 |  |
|  | 0.03 nM | 0.206 |  |

TABLE 9

IC50 Values of ETD00353 and ETD00356 ANGPTL7 siRNAs

| siRNA | [siRNA] | Relative ANGPTL7 mRNA Levels | IC50 |
|---|---|---|---|
| — | — | 1.000 | ND |
| Negative Control siRNA | 3 nM | 1.487 | ND |
|  | 0.03 nM | 0.188 | ND |
| ETD00353 | 3 nM | 0.383 | 1.52 |
|  | 1 nM | 0.772 |  |
|  | 0.3 nM | 1.140 |  |
|  | 0.1 nM | 1.423 |  |
|  | 0.03 nM | 1.257 |  |
|  | 0.01 nM | 1.424 |  |
| ETD00356 | 3 nM | 0.107 | 0.12 |
|  | 1 nM | 0.152 |  |
|  | 0.3 nM | 0.294 |  |
|  | 0.1 nM | 0.712 |  |

TABLE 9-continued

IC50 Values of ETD00353 and ETD00356 ANGPTL7 siRNAs

| siRNA | [siRNA] | Relative ANGPTL7 mRNA Levels | IC50 |
|---|---|---|---|
|  | 0.03 nM | 0.793 |  |
|  | 0.01 nM | 1.073 |  |

TABLE 10

IC50 Values of ETD00370, ETD00377 and ETD00378 ANGPTL7 siRNAs

| siRNA | [siRNA] | Relative ANGPTL7 mRNA Levels | IC50 |
|---|---|---|---|
| — | — | 1.000 | ND |
| Negative Control siRNA | 0.03 nM | 1.951 | ND |
|  | 3 nM | 1.579 | ND |
| ETD00370 | 3 nM | 0.251 | 0.49 |
|  | 1 nM | 0.589 |  |
|  | 0.3 nM | 0.990 |  |
|  | 0.1 nM | 1.736 |  |
|  | 0.03 nM | 1.566 |  |
| ETD00377 | 3 nM | 0.358 | 2.64 |
|  | 1 nM | 0.462 |  |
|  | 0.3 nM | 0.476 |  |
|  | 0.1 nM | 0.548 |  |
|  | 0.03 nM | 1.361 |  |
| ETD00378 | 3 nM | 0.281 | 0.17 |
|  | 1 nM | 0.575 |  |
|  | 0.3 nM | 1.037 |  |
|  | 0.1 nM | 1.570 |  |
|  | 0.03 nM | 1.816 |  |

Example 16. Assessing the Extent of Nuclease Resistance of ANGPTL7 siRNAs

Resistance of select ANGPTL7 siRNAs to nuclease digestion was assessed by incubating the siRNAs in rat liver tritosomes. Each siRNA (7 ng/μL final concentration) was placed into a PCR tube containing a cocktail prepared on ice containing 1× catabolic buffer (Xenotech, Catalog #K5200, Lot #18-1-0698), 0.5× rat tritosomes (Xenotech, Catalog #R0610. LT, Lot #1610405), 0.1 U/μL porcine intestinal heparin (Zageno, Catalog #H3149-10KU). An aliquot was removed, an equal volume of 50 mM EDTA was added, and the sample placed at −80° C. This sample was designated as the 0 hr timepoint. The remainder of the reaction was placed in an Eppendorf Mastercycler Gradient and incubated at 37° C. After incubation for 4 and 24 hours, an aliquot was removed from the reaction and stopped by addition of an equal volume of 50 mM EDTA and placed at −80° C. until analysis by gel electrophoresis. All samples were then thawed on ice and 6×DNA Gel Loading Dye (ThermoFisher Catalog #R0611) was added to 1× final concentration. 20 μL of each sample was loaded onto a 20% polyacrylamide TBE gel (ThermoFisher, Catalog #EC63155BOX). Electrophoresis was carried out at a constant 100V for 75 minutes in an XCell SureLock Mini-Cell Electrophoresis System (ThermoFisher) using 1×TBE (Tris/boric/EDTA) (Fisher, Catalog #FERB52) as the tank buffer. The siRNA was visualized by staining the gel with a 1:10,000 dilution of SYBR Gold (ThermoFisher, Catalog #S-11494) in TBE for 15 minutes at room temperature with rocking. The gel was washed with 1×TBE for 15 minutes and then placed on a FotoPrep1 UV transilluminator (Fotodyne). The gel was imaged using the camera app set on MONO on an iPhone 6s with a yellow gel filter (Neewer) placed over the lens. Band intensity was measured using NIH ImageJ using the "Analyze: Gels" function. The remaining siRNA percent was normalized to the value obtained at the 0 hr timepoint for that siRNA. Results are shown in Table 11. By using this assay, we were able to determine that some siRNAs are more resistant to nuclease digestion with more remaining intact over time compared with other siRNAs with the same modification pattern.

TABLE 11

Resistance of ANGPTL7 siRNAs to Nucleases Present in Rat Liver Tritosomes

| siRNA | Timepoint (hr) | % remaining |
|---|---|---|
| ETD00269 | 0 | 100% |
|  | 4 | 109% |
|  | 24 | 69% |
| ETD00270 | 0 | 100% |
|  | 4 | 69% |
|  | 24 | 47% |
| ETD00276 | 0 | 100% |
|  | 4 | 103% |
|  | 24 | 78% |
| ETD00302 | 0 | 100% |
|  | 4 | 68% |
|  | 24 | 26% |
| ETD00353 | 0 | 100% |
|  | 4 | 75% |
|  | 24 | 34% |
| ETD00356 | 0 | 100% |
|  | 4 | 66% |
|  | 24 | 29% |
| ETD00358 | 0 | 100% |
|  | 4 | 89% |
|  | 24 | 48% |
| ETD00382 | 0 | 100% |
|  | 4 | 126% |
|  | 24 | 64% |
| ETD00370 | 0 | 100% |
|  | 4 | 97% |
|  | 24 | 55% |
| ETD00374 | 0 | 100% |
|  | 4 | 54% |
|  | 24 | 2% |
| ETD00377 | 0 | 100% |
|  | 4 | 92% |
|  | 24 | 49% |
| ETD00378 | 0 | 100% |
|  | 4 | 87% |
|  | 24 | 55% |
| ETD00381 | 0 | 100% |
|  | 4 | 54% |
|  | 24 | 5% |

Example 17. siRNA-Mediated Knockdown of ANGPTL7 Expression in Primary Human Trabecular Meshwork Cells in the Presence of Dexamethasone In this experiment, primary human trabecular meshwork cells exposed to dexamethasone were treated with a siRNA targeting ANGPTL7. Primary HTM cells (Cell Applications Catalog #634-05a) were grown to confluency in high-glucose DMEM (Cytiva cat #SH30243.01) supplemented with 10% FBS (Gemini Bio Catalog #900-108) in a water-jacketed, humidified incubator at 37° C. in an atmosphere composed of air plus 5% carbon dioxide. The cells were harvested with Trypsin/EDTA (PromoCell Catalog #C-41010), resuspended in DMEM+10% FBS at a cell density of 200,000 cells/mL, then seeded in 24-well tissue culture plates at 20,000 cells/well. Once the cells reached 80% confluency, the media was replaced and cells were serum starved in DMEM for 24 hrs in a water-jacketed, humidified incubator at 37° C. in an atmosphere composed of air plus 5% carbon dioxide. Next, 5 uL of dexamethasone (Sigma Catalog #D4902-100 MG) prepared at 50 uM was added to the wells to give a final concentration of 500 nM and the plates incubated an additional 24 hours. This was designated Day 0. On Day 1, the media was replaced with 0.5 mL DMEM, 0.5 mL DMEM containing 1 uM negative control siRNA (Accell Non-targeting Control siRNA #2, Dharmacon Catalog #D-001910-02-20) or 0.5 mL DMEM containing 1 uM ETD00752 targeting ANGPTL7. The ANGPTL7 siRNA ETD00752 has a TEG-cholesterol moiety attached to the 3' end of the sense strand and is derived from ETD00356. ETD00752 includes the following sequences: sense strand 5' AfsusAfuGfuAfCfCfaAf-gGfaUfgUfuAfsusu[Chol-TEG] 3' (SEQ ID NO: 11377), antisense strand 5' usAfsaCfaUfcCfuUfgguAfcAfuAfususu 3' (SEQ ID NO: 11306). On Day 2, Day 4 and Day 6, 5 uL of 50 uM dexamethasone was added to all wells. On Day 3 and Day 5, media was replaced with 0.5 mL of fresh DMEM, 0.5 mL fresh DMEM containing 1 uM negative control siRNA (Accell Non-targeting Control siRNA #2, Dharmacon #D-001910-02-20) or 0.5 mL fresh DMEM containing 1 uM ETD00752 targeting ANGPTL7 in the appropriate wells. Controls also included cells that did not receive siRNA or dexamethsone.

On Day 8, media was collected for quantitation of ANGPTL7 protein by ELISA (RayBio® Human ANGPTL7 ELISA Kit Catalog #ELH-ANGPTL7-1) according to the manufacturer's instructions. Total RNA was harvested from the cells and cDNA prepared using TaqMan® Fast Advanced Cells-to-CT™ Kit (ThermoFisher, Catalog #A35374) according to the manufacturer's instructions. The level of ANGPTL7 mRNA from cells in each well was measured in triplicate by real-time qPCR on an Applied Biosystems 7500 Fast Real-Time PCR machine using TaqMan Gene Expression Assay for human ANGPTL7 (ThermoFisher, assay #Hs00221727_m1). The level of PPIA mRNA was measured using TaqMan Gene Expression Assay (ThermoFisher, assay #Hs99999904_m1) and used to determine relative ANGPTL7 mRNA levels from cells in each well using the delta-delta Ct method. All data were normalized to relative ANGPTL7 mRNA levels in cells treated with dexamethasone alone. Results are shown in Table 12. Results indicate primary HTM cells treated with dexamethasone have much higher levels of ANGPTL7 mRNA and ANGPTL7 protein than cells that have not been treated with dexamethasone. In addition, primary HTM cells exposed to dexamethasone and treated with ETD00752 had much lower levels of ANGPTL7 mRNA and ANGPTL7 protein than cells that had not been treated with ETD00752 or had been treated with the Accell Non-targeting Control siRNA #2.

TABLE 12

Induction of ANGPTL7 Expression by Dexamethasone and Knockdown of ANGPTL7 expression by ETD00752 in Primary HTM Cells

| siRNA name | Relative ANGPTL7 mRNA | ANGPTL7 Protein (ng/uL) |
|---|---|---|
| Cells with dexamethasone | 1.00 | 15.7 |
| Accell Non-targeting Control siRNA #2 | 0.44 | 8.1 |
| ETD00752 | 0.021 | 1.6 |
| Cells without dexamethasone | 0.027 | 1.9 |

Example 18. siRNA-Mediated Knockdown of ANGPTL7 Expression in a 3D In Vitro Model of Glaucoma In the human eye, homeostatic intraocular pressure (IOP) is maintained by formation and drainage of the aqueous humor, primarily through the human trabecular meshwork (HTM). Approximately, 70-90% of the aqueous humor is drained through this tissue and it is believed that a decrease in outflow through the TM leads to elevated IOP. An in vitro 3D HTM model (3D-HTM™) that recapitulates the biological and physiological characteristics of the HTM has been established by the contract research organization Glauconix. The following study was performed using 3D-HTM™ in order to provide proof of concept of siRNA-mediated knockdown of ANGPTL7 in an in vitro model system of glaucoma.

The 3D-HTM™ constructs were cultured in 10% FBS-IMEM using primary donor trabecular meshwork cells over a two-week period. Once the 3D-HTM™ constructs were ready, they were placed in 6.7% FBS-IMEM for 24 h prior to the treatments. Treatments included the following: On Day 0, media was replaced with fresh 6.7% FBS medium containing 500 nM dexamethasone. On Day 3, the media was replaced with fresh 6.7% FBS medium containing 500 nM dexamethasone. On Day 4, the media was replaced with fresh 6.7% FBS medium without dexamethasone and transfected with siRNA. The siRNAs used in this study were ETD00153, ETD00353 and ETD00356. ETD00153 is an siRNA that does not target ANGPTL7 and functioned as a negative control siRNA. ETD00153 has the following sequences: sense strand 5' UfsgsUfgGfcCfCfGfcAfcGfgGfgCfaAfsusu 3' (SEQ ID NO: 11378), antisense strand 5' usUfsgCfcCfcGfuGfcggGfcCfaCfasusu 3' (SEQ ID NO: 11379). ETD00353 and ETD00356 are siRNAs that target ANGPTL7. ETD00353 has the following sequences: sense strand 5' CfsasUfgGfaUfCfUfaCfcUfaCfuCfcAfsusu 3' (SEQ ID NO: 11183), antisense strand 5' usGfsgAfgUf-aGfgUfagaUfcCfaUfgsusu 3' (SEQ ID NO: 11303). ETD00356 has the following sequences: sense strand 5' AfsusAfuGfAfCfCfaAfgGfaUfgUfuAfsusu 3' (SEQ ID NO:11186), antisense strand 5' usAfsaCfaUfcCfuUfg-guAfcAfuAfususu 3' (SEQ ID NO: 11306). Transfection was accomplished using Targefect-RAW (Targeting Systems, Catalog #RAW-01). Transfection complexes were prepared on ice. First, 100 nM siRNA from 100 µM stock was added to 4.5 g/L DMEM without antibiotics and the tubes were flicked 12 times to accomplish mixing. Next, a volume of targefect that was $\frac{1}{50}^{th}$ of the total volume of the mixture was added to the diluted siRNA and the tubes were flicked 12 times to accomplish mixing. To this a volume of the virofect enhancer reagent that was $\frac{1}{25}^{th}$ of the total volume of the mixture was added. The tubes were flicked 12 times to accomplish mixing. The mixture was then incubated at 37° C. for 25 minutes to allow the formation of the transfection complexes. Complete medium (10% pFBS DMEM with antibiotics) was then added to the transfection complexes at double the volume of the complex. For example, if the volume of the complexes was 0.5 mL, 1 mL of complete medium was added. Next, 225 µL of the complex plus complete medium mixture was added to the appropriate wells. On Day 5, dexamethasone was added to 500 nM without changing the media. On Day 6, the media was replaced with fresh media containing 6.7% FBS without dexamethasone and the wells receiving siRNA were transfected a second time using the protocol for the first transfection described above. On Day 7, dexamethasone was added to 500 nM without changing the media.

On Day 8, Total RNA was harvested from the cells using the RNAeasy Plus Mini kit (Qiagen, Catalog #74134) according to the manufacturer's instructions. The cDNA was prepared from 500 ng of total RNA using the Maxima first strand synthesis kit (ThermoFisher Catalog #K1642) according to the manufacturer's instructions. The level of ANGPTL7 mRNA from cells in each well was measured in triplicate by real-time qPCR on an Applied Biosystems 7500 Fast Real-Time PCR machine using TaqMan Gene Expression Assay for human ANGPTL7 (ThermoFisher, assay #Hs00221727 ml). The level of PPIA mRNA was measured using TaqMan Gene Expression Assay (ThermoFisher, assay #Hs99999904_ml) and used to determine relative ANGPTL7 mRNA levels from cells in each well using the delta-delta Ct method. All data were normalized to relative ANGPTL7 mRNA levels in cells treated with dexamethasone alone. Results are shown in Table 13. Results indicate 3D-HTM™ cells exposed to dexamethasone and transfected with siRNAs ETD00353 or ETD00356 had much lower levels of ANGPTL7 mRNA than 3D-HTM™ cells not receiving siRNA or those that had been transfected with the negative control siRNA ETD00153.

TABLE 13 siRNA-mediated Knockdown of ANGPTL7 expression in 3D-HTMTM cells

| siRNA name | Relative ANGPTL7 mRNA |
| --- | --- |
| 3D-HTM ™ cells with dexamethasone | 1.00 |
| ETD00153 | 0.95 |
| ETD00353 | 0.54 |
| ETD00356 | 0.31 |

SEQUENCE INFORMATION

Some embodiments include one or more nucleic acid sequences from the non-limiting examples in the following table:

TABLE 14

Sequences

| SEQ ID NO: | Description |
| --- | --- |
| 1-4412 | ANGPTL7 siRNA oligonucleotide sequences |
| 4413-11084 | ANGPTL7 antisense oligonucleotide sequences |
| 11085 | Full-length ANGPTL7 human mRNA (GenBank Acc. # NM_021146.4) |
| 11086 | Full-length ANGPTL7 human pre-mRNA (NC_000001.11 (11189289..11195981) |
| 11087 | Antisense oligonucleotide targeting ANGPTL7 (e.g. human, NHP, mouse, rat, dog) |
| 11088 | Non-targeting control antisense oligonucleotide |
| 11089 | Sense strand oligonucleotide targeting ANGPTL7 (e.g. human, NHP, mouse, rat, dog) |

TABLE 14-continued

Sequences

| SEQ ID NO: | Description |
|---|---|
| 11090 | Antisense strand oligonucleotide targeting ANGPTL7 (e.g. human, NHP, mouse, rat, dog) |
| 11091 | Sense strand non-targeting (control) oligonucleotide |
| 11092 | Antisense strand non-targeting (control) oligonucleotide |
| 11093-11332 | Modified human ANGPT7 siRNA sequences |
| 11333-11376 | Modified human ANGPT7 siRNA sequences that are cross-reactive with mouse |
| 11377 | ETD00752 sense strand |
| 11378 | ETD00153 sense strand |
| 11379 | ETD00153 antisense strand |
| 11380 | ASO modification pattern |
| 11381 | Modification pattern 1S |
| 11382 | Modification pattern 2S |
| 11383 | Modification pattern 3S |
| 11384 | Modification pattern 4S |
| 11385 | Modification pattern 5S |
| 11386 | Modification pattern 1AS |
| 11387 | Modification pattern 2AS |
| 11388 | Modification pattern 3AS |
| 11389 | Modification pattern 4AS |
| 11390-11393 | Peptide moieties |

SEQUENCE LISTING

The patent contains a lengthy sequence listing. A copy of the sequence listing is available in electronic form from the USPTO web site (https://seqdata.uspto.gov/?pageRequest=docDetail&DocID=US12378556B2). An electronic copy of the sequence listing will also be available from the USPTO upon request and payment of the fee set forth in 37 CFR 1.19(b)(3).

We claim:

1. A method of treating an ocular disorder in a subject in need thereof, comprising administering to the subject a composition comprising an oligonucleotide that targets Angiopoietin like 7 (ANGPTL7) and when administered to a cell decreases expression of ANGPTL7, wherein the oligonucleotide comprises a small interfering RNA (siRNA) comprising a sense strand and an antisense strand, wherein the sense strand comprises an oligonucleotide sequence of SEQ ID NOs: 948, 1424, 1541, or 2091 in which at least one internucleoside linkage is modified and at least one nucleoside is modified, or an oligonucleotide sequence comprising 1 or 2 nucleoside substitutions, additions, or deletions of SEQ ID NOs: 948, 1424, 1541, or 2091 in which at least one internucleoside linkage is modified and at least one nucleoside is modified, and wherein the antisense strand comprises an oligonucleotide sequence of SEQ ID NOs: 3154, 3630, 3747, or 4297 in which at least one internucleoside linkage is modified and at least one nucleoside is modified, or an oligonucleotide sequence comprising 1 or 2 nucleoside substitutions, additions, or deletions of SEQ ID NOs: 3154, 3630, 3747, or 4297 in which at least one internucleoside linkage is modified and at least one nucleoside is modified, wherein the ocular disorder comprises glaucoma or ocular hypertension, and wherein the administering to the subject the composition comprises administering the composition to the subject by an ocular route.

2. The method of claim 1, wherein the at least one nucleoside that is modified comprises a 2'-fluoro modified nucleoside.

3. The method of claim 1, wherein the at least one nucleoside that is modified comprises a 2'-O-methyl modified nucleoside.

4. The method of claim 1, wherein the oligonucleotide comprises 15-23 modified nucleosides.

5. The method of claim 4, wherein the 15-23 modified nucleosides comprise 2'-fluoro modified nucleosides and 2'-O-methyl modified nucleosides.

6. The method of claim 1, wherein the at least one internucleoside linkage that is modified comprises a phosphorothioate linkage.

7. The method of claim 1, wherein the oligonucleotide comprises a lipid attached at a 3' or 5' terminus of the oligonucleotide.

8. The method of claim 7, wherein the lipid comprises cholesterol, myristoyl, palmitoyl, stearoyl, lithocholoyl, docosanoyl, docosahexaenoyl, myristyl, palmityl stearyl, or α-tocopherol, or a combination thereof.

9. The method of claim 8, wherein the lipid is attached to the 3' terminus of the sense strand.

10. The method of claim 9, wherein the lipid comprises cholesterol.

11. The method of claim 1, wherein the sense strand comprises an oligonucleotide sequence of SEQ ID NO: 11186 and the antisense strand comprises an oligonucleotide sequence of SEQ ID NO: 11306.

12. The method of claim 1, wherein the sense strand comprises an oligonucleotide sequence of SEQ ID NO: 11211 and the antisense strand comprises an oligonucleotide sequence of SEQ ID NO: 11331.

13. The method of claim 1, wherein the sense strand comprises an oligonucleotide sequence of SEQ ID NO: 948 and modification pattern 1S, and the antisense strand comprises an oligonucleotide sequence of SEQ ID NO: 3154 and modification pattern 1AS.

14. The method of claim 1, wherein the composition further comprises a pharmaceutically acceptable excipient.

15. The method of claim 1, wherein the composition decreases intraocular pressure in an eye of the subject relative to a baseline intraocular pressure measurement obtained from the subject prior to administering the composition to the subject.

16. The method of claim 15, wherein the composition decreases intraocular pressure in the eye of the subject by at least 10% relative to the baseline intraocular pressure measurement obtained from the subject prior to administering the composition to the subject.

17. The method of claim 1, wherein the ocular route comprises topical administration or intraocular injection.

18. The method of claim 17, wherein the topical administration comprises a formulation of eye drops, cream, ointment, gel, or salve.

19. The method of claim 17, wherein the intraocular injection comprises a subconjunctival, periocular, periocular conjunctival fornix, intravitreal, intracameral, or retrobulbar injection.

\* \* \* \* \*